(12) United States Patent
Nara et al.

(10) Patent No.: US 7,538,224 B2
(45) Date of Patent: *May 26, 2009

(54) HSP90 FAMILY PROTEIN INHIBITORS

(75) Inventors: Shinji Nara, Sunto-gun (JP); Hiroshi Nakagawa, Sunto-gun (JP); Yutaka Kanda, Tokyo (JP); Takayuki Nakashima, Sunto-gun (JP); Shiro Soga, Rockville, MD (US); Jiro Kajita, Sunto-gun (JP); Jun-ichi Saito, Sunto-gun (JP); Yukimasa Shiotsu, Sunto-gun (JP); Shiro Akinaga, Sunto-gun (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/561,415

(22) PCT Filed: Jun. 10, 2004

(86) PCT No.: PCT/JP2004/008494

§ 371 (c)(1),
(2), (4) Date: Dec. 19, 2005

(87) PCT Pub. No.: WO2005/000778

PCT Pub. Date: Jan. 6, 2005

(65) Prior Publication Data

US 2007/0032532 A1 Feb. 8, 2007

(30) Foreign Application Priority Data

Jun. 27, 2003 (JP) ............................. 2003/185475

(51) Int. Cl.
*C07D 211/22* (2006.01)
*C07C 49/303* (2006.01)

(52) U.S. Cl. ...................................... 546/234; 568/332
(58) Field of Classification Search ................. 546/234; 568/332
See application file for complete search history.

(56) References Cited

U.S. PATENT DOCUMENTS 3,322,705 A 5/1967 Kauder et al.

FOREIGN PATENT DOCUMENTS

| JP | 2001-525824 | 12/2001 |
| WO | WO 00/53169 | 9/2000 |
| WO | WO 01/30341 | 3/2001 |
| WO | WO 02/36075 | 5/2002 |

OTHER PUBLICATIONS

STN CAPLUS record for Hassall et al. (J. Chem. Soc., Perkin Transactions 1: Organic and Bio-Organic Chemistry, 1973, vol. 23, p. 2853-61): ID 1974: 108242 CAPLUS.*
Gosman et al. (Tetrahedron Letters, 1996, v. 37, No. 25, p. 4369-4372).*
Kimata et al. (abstract of Memoirs of the Research Institute for Food Science, Kyoto University (1953), No. 6, 3-11; CAPLUS accession No. 1953:73378).*
Sala et al. (Journal of the Chemical Society, Perkin Transactions 1: Organic and Bio-Organic Chemistry (1972-1999), (1981), (3), 855-69).*
Abstract of Muller (Appl Microbiol Biotechnol. 2001 Jul.;56(1-2):9-16.).*
Silverman (The Org. Chem. of Drug Design and Drug Action, Academic Press, Inc.: San Diego, 1992, pp. 4-51).*
Comber, et al., "Depsidone Synthesis, Part 24. The Synthesis of Epiphorellic Acid . . . ", *J. Chem. Soc. Perkin Trans.*, vol. I, No. 3 (1989), pp. 441-448.
Coll, et al., "Stereoselective Photocyclization of Some Phenolic, Highly Congested . . . ", *J. Org. Chem*, vol. 57, No. 23 (1992), pp. 6222-6231.
Sala, et al., Depsidone Synthesis. Part 16. Benzophenone-Grisa-3',5'-diene-2', . . . , *J. Chem. Soc. Perkin Trans.* I, No. 3 (1981), pp. 855-869.
Igarashi, et al. "Biosynthesis of hibarimicins: III. Structures of new hibarimicin-related metabolites produced by blocked mutants," Journal of Antibiotics, vol. 55, No. 1 (2002) 61-70.

(Continued)

*Primary Examiner*—Rebecca L Anderson
*Assistant Examiner*—Robert Havlin
(74) *Attorney, Agent, or Firm*—Fitzpatrick, Cella, Harper & Scinto

(57) ABSTRACT

The present invention provides Hsp90 family protein inhibitors comprising, as an active ingredient, a benzoyl compound represented by general formula (I):

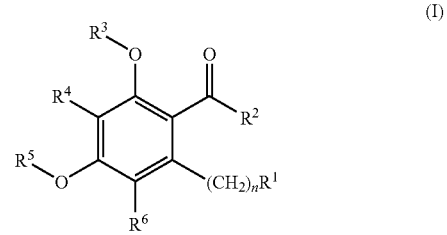

(wherein n represents an integer of 0 to 10; $R^1$ represents substituted or unsubstituted lower alkoxy, substituted or unsubstituted lower alkoxycarbonyl, $CONR^7R^8$ or the like; $R^2$ represents substituted or unsubstituted aryl, a substituted or unsubstituted aromatic heterocyclic group or the like; $R^3$ and $R^5$, which may be the same or different, each represent a hydrogen atom, substituted or unsubstituted lower alkyl, substituted or unsubstituted lower alkenyl or the like; and $R^4$ and $R^6$, which may be the same or different, each represent a hydrogen atom, halogen, substituted or unsubstituted lower alkyl, substituted or unsubstituted aryl or the like) or a prodrug thereof, or a pharmaceutically acceptable salt of said benzoyl compound or said prodrug.

12 Claims, No Drawings

OTHER PUBLICATIONS

Wohlert, et al., "Production of aromatic minimal polyketides by the daunorubicin polyketide synthase genes reveals the incompatibility of the heterologous DpsY and JadI cyclases", Journal of Natural Products, vol. 64, No. 8 (2001) 1077-80.

Wittek, et al., "Synthesis of beta-hexa-, beta-hepta-, and beta-octaketones", Journal of the American Chemical Society, vol. 95, No. 20 (1973) 6865-7.

Harris, et al., "Synthesis of 1,3,5,7,9-pentacarbonyl compounds", Journal of the American Chemical Society, vol. 93, No. 24 (1971) 6708-9.

Katoh, et al., "Synthetic studies on Sch 202596, an antagonist of the galanin receptor subtype GaIR1: an efficient synthesis of (:±)-geodin, the spirocoumaranone part of Sch 202596", Tetrahedron, vol. 58, No. 7 (2002) 1289-99.

Graybill, et al. "Silyl Triflate-Mediated Ring-Closure and Rearrangement in the Synthesis of Potential Bisfuran-Containing Intermediates of Aflatoxin Biosynthesis", Journal of the American Chemical Society, vol. 121. No. 34 (1999) 7729-46.

Rao, et al., "Synthesis of optically active O,O,O-trimethylkorupensamines A and B", Heterocycles, vol. 43, No. 1 (1996) 1-6.

Holton, et al., "A new regiospecific synthesis of aryl ketones from palladocycles", Tetrahedron Letters, vol. 22, No. 4 (1981) 267-70.

Broadhurst, et al., "Tetracycline studies. Part 5. New syntheses of anthracenes and anthraquinones through benzophenone carbanions", Journal of the Chemical Society: Perkin Transactions.1: Organic and Rio-Organic Chemistry, vol. 22 (1972-1999) (1977) 2502-12.

Registry RN 16298-77-4 Registry (1984) CN Phthalic acid, 4,4'-diester with 2-(3-chloropropyl)-2',4,4',6- trihydroxybenzophenone.

\* cited by examiner

HSP90 FAMILY PROTEIN INHIBITORS

TECHNICAL FIELD

The present invention relates to heat shock protein 90 (Hsp90) family protein inhibitors comprising, as an active ingredient, a benzoyl compound or a prodrug thereof, or a pharmaceutically acceptable salt of said benzoyl compound or said prodrug.

BACKGROUND ART

Among benzoyl compounds, those which are known as compounds having benzophenone in the structure include: Compound A having anti-tumor activity (WO01/81288); Compound B referred to as HMP-M4 (J. Antibiotics, 2002, Vol. 55, p. 61-70); Compound C (J. Am. Chem. Soc., 1971, Vol. 93, p. 6708-6709); Compound D having eosinophilic leukocyte function inhibiting activity (Japanese Published Unexamined Patent Application No. 92082/1996; Bioorg. & Med. Chem. Lett., 1999, Vol. 9, p. 1945-1948); Compound E (Tetrahedron Lett., 2002, Vol. 43, p. 291-293); and Compound F (J. Chem. Soc., Perkin Trans. 1, 1989, p. 441-448). Further, compounds having benzophenone in the structure and methods for synthesis of the compounds are known [e.g. Japanese Published Unexamined Patent Application No. 39968/2001; U.S. Pat. No. 6,125,007; J. Chem. Soc., Perkin Trans. 1, 1977, p. 2502-2512; J. Chem. Soc., Perkin Trans. 1, 1974, p. 1417-1421; J. Chem. Soc. (C), 1971, p. 3899-3902; Tetrahedron Lett., 1981, Vol. 22, p. 267-270].

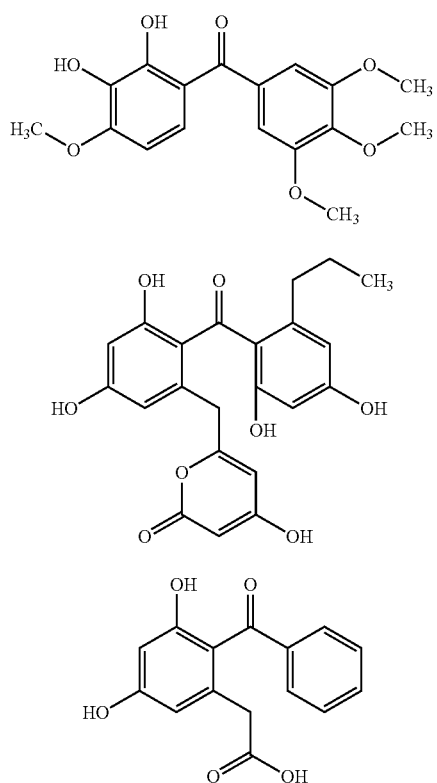

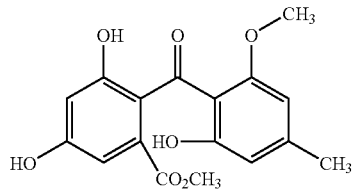

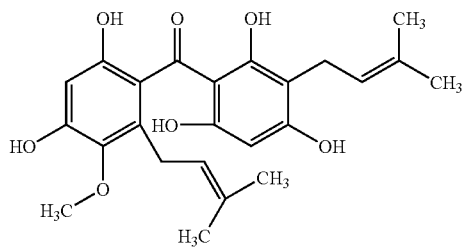

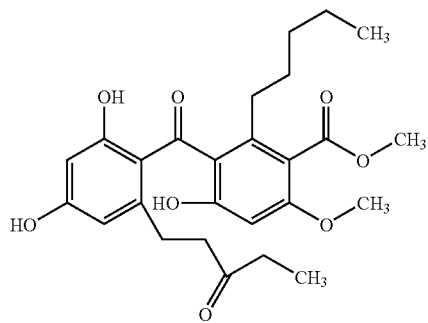

Benzoquinone ansamycin antibiotics such as Geldanamycin and Herbimycin, and Radicicol are known as compounds which bind to heat shock protein 90 (Hsp90) family proteins (Cell Stress' & Chaperones, 1998, Vol., 3, p. 100-108; J. Med. Chem., 1999, Vol., 42, p. 260-266). These compounds are all reported to bind to Hsp90 family proteins and inhibit the functions of Hsp90 family proteins, thereby exhibiting pharmacological activities such as anti-tumor activity. Therefore, compounds binding to Hsp90 family proteins are considered to be useful as therapeutic agents for diseases associated with Hsp90 family proteins or proteins to which Hsp90 family proteins bind (Hsp90 client proteins).

Examples of known Hsp90 family proteins include Hsp90α protein, Hsp90β protein, grp94 and hsp75/TRAP1 (Pharmacology & Therapeutics, 1998, Vol., 79, p. 129-168; Molecular Endocrinology, 1999, Vol., 13, p. 1435-1448; etc.).

DISCLOSURE OF THE INVENTION

An object of the present invention is to provide Hsp90 family protein inhibitors comprising, as an active ingredient, for example, a benzoyl compound or a prodrug thereof, or a pharmaceutically acceptable salt of said benzoyl compound or said prodrug, and the like.

The present invention relates to the following (1) to (31).

(1) A heat shock protein 90 (Hsp90) family protein inhibitor comprising, as an active ingredient, a benzoyl compound represented by general formula (I):

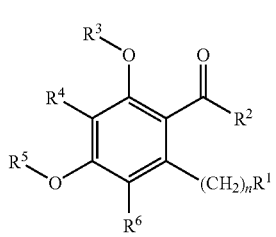

(I)

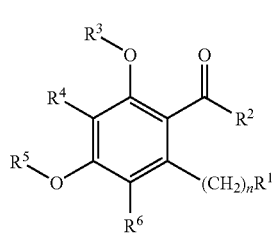

(I)

[wherein n represents an integer of 0 to 10;

R¹ represents a hydrogen atom, hydroxy, cyano, carboxy, nitro, halogen, substituted or unsubstituted lower alkyl, substituted or unsubstituted lower alkenyl, substituted or unsubstituted lower alkynyl, substituted or unsubstituted lower alkoxy, substituted or unsubstituted cycloalkyl, substituted or unsubstituted lower alkoxycarbonyl, substituted or unsubstituted lower alkanoyloxy, substituted or unsubstituted heterocyclic alkyl, substituted or unsubstituted aryl, substituted or unsubstituted arylsulfonyl, a substituted or unsubstituted heterocyclic group, $CONR^7R^8$ (wherein $R^7$ and $R^8$, which may be the same or different, each represent a hydrogen atom, substituted or unsubstituted lower alkyl, substituted or unsubstituted cycloalkyl, substituted or unsubstituted lower alkanoyl, substituted or unsubstituted aryl, a substituted or unsubstituted heterocyclic group, substituted or unsubstituted aralkyl, substituted or unsubstituted heterocyclic alkyl, or substituted or unsubstituted aroyl, or $R^7$ and $R^8$ form a substituted or unsubstituted heterocyclic group together with the adjacent nitrogen atom) or $NR^9R^{10}$ (wherein $R^9$ and $R^{10}$ have the same meanings as the above $R^7$ and $R^8$, respectively);

R² represents substituted or unsubstituted lower alkyl, substituted or unsubstituted lower alkenyl, substituted or unsubstituted lower alkynyl, substituted or unsubstituted cycloalkyl, substituted or unsubstituted aryl, or a substituted or unsubstituted heterocyclic group;

R³ and R⁵, which may be the same or different, each represent a hydrogen atom, substituted or unsubstituted lower alkyl, substituted or unsubstituted lower alkenyl, substituted or unsubstituted lower alkanoyl, substituted or unsubstituted cycloalkyl, substituted or unsubstituted aralkyl, or substituted or unsubstituted aroyl; and R⁴ and R⁶, which may be the same or different, each represent a hydrogen atom, hydroxy, halogen, cyano, nitro, substituted or unsubstituted lower alkyl, substituted or unsubstituted lower alkenyl, substituted or unsubstituted lower alkynyl, substituted or unsubstituted lower alkoxy, substituted or unsubstituted cycloalkyl, amino, lower alkylamino, di-lower alkylamino, carboxy, substituted or unsubstituted lower alkoxycarbonyl, substituted or unsubstituted lower alkanoyl, substituted or unsubstituted aryloxy, substituted or unsubstituted aryl, a substituted or unsubstituted heterocyclic group, substituted or unsubstituted aralkyl, or substituted or unsubstituted heterocyclic alkyl] or a prodrug thereof, or a pharmaceutically acceptable salt of said benzoyl compound or said prodrug.

(2) An Hsp90 family protein inhibitor comprising, as an active ingredient, a benzoyl compound represented by general formula (I):

(wherein n, R¹, R², R³, R⁴, R⁵ and R⁶ each have the same meanings as defined above) or a pharmaceutically acceptable salt thereof.

(3) The Hsp90 family protein inhibitor according to the above: (1) or (2), wherein R¹ is a hydrogen atom, hydroxy, cyano, carboxy, nitro, halogen, substituted or unsubstituted lower alkyl, substituted or unsubstituted lower alkynyl, substituted or unsubstituted lower alkoxy, substituted or unsubstituted cycloalkyl, substituted or unsubstituted lower alkoxycarbonyl, substituted or unsubstituted lower alkanoyloxy, substituted or unsubstituted heterocyclic alkyl, substituted or unsubstituted aryl, substituted or unsubstituted arylsulfonyl, $CONR^7R^8$ (wherein $R^7$ and $R^8$ each have the same meanings as defined above) or $NR^9R^{10}$ (wherein $R^9$ and $R^{10}$ each have the same meanings as defined above).

(4) The Hsp90 family protein inhibitor according to the above (1) or (2), wherein R¹ is substituted or unsubstituted lower alkyl, substituted or unsubstituted lower alkynyl, substituted or unsubstituted lower alkoxy, substituted or unsubstituted cycloalkyl, substituted or unsubstituted lower alkoxycarbonyl, substituted or unsubstituted heterocyclic alkyl, substituted or unsubstituted aryl, $CONR^7R^8$ (wherein $R^7$ and $R^8$ each have the same meanings as defined above) or $NR^9R^{10}$ (wherein $R^9$ and $R^{10}$ each have the same meanings as defined above).

(5) The Hsp90 family protein inhibitor according to the above (1) or (2), wherein R¹ is $CONR^7R^8$ (wherein $R^7$ and $R^8$ each have the same meanings as defined above).

(6) The Hsp90 family protein inhibitor according to any one of the above (1) to (5), wherein R² is substituted or unsubstituted aryl or a substituted or unsubstituted aromatic heterocyclic group.

(7) The Hsp90 family protein inhibitor according to any one of the above (1) to (6), wherein R⁴ is a hydrogen atom, hydroxy or halogen.

(8) The Hsp90 family protein inhibitor according to any one of the above (1) to (7), wherein R³ and R⁵, which may be the same or different, each are a hydrogen atom, substituted or unsubstituted lower alkyl, substituted or unsubstituted lower alkenyl, substituted or unsubstituted lower alkanoyl, or substituted or unsubstituted aroyl.

(9) The Hsp90 family protein inhibitor according to any one of the above (1) to (6), wherein R³, R⁴ and R⁵ each are a hydrogen atom.

(10) The Hsp90 family protein inhibitor according to any one of the above (1) to (9), wherein R⁶ is a hydrogen atom, lower alkyl, halogen or aryl.

(11) A benzoyl compound represented by general formula (IA):

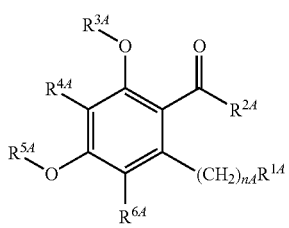

(IA)

[wherein
nA represents an integer of 1 to 5;
$R^{1A}$ represents substituted or unsubstituted lower alkyl, substituted or unsubstituted lower alkoxy, substituted or unsubstituted cycloalkyl, substituted or unsubstituted lower alkoxycarbonyl, substituted or unsubstituted heterocyclic alkyl, substituted or unsubstituted aryl, $CONR^7R^8$ (wherein $R^7$ and $R^8$ each have the same meanings as defined above) or $NR^9R^{10}$ (wherein $R^9$ and $R^{10}$ each have the same meanings as defined above);
$R^{2A}$ represents substituted or unsubstituted aryl or a substituted or unsubstituted aromatic heterocyclic group;
$R^{3A}$ and $R^{5A}$, which may be the same or different, each represent a hydrogen atom, substituted or unsubstituted lower alkyl, substituted or unsubstituted lower alkenyl, substituted or unsubstituted lower alkanoyl, substituted or unsubstituted cycloalkyl, substituted or unsubstituted aralkyl, or substituted or unsubstituted aroyl;
$R^{4A}$ represents a hydrogen atom, hydroxy or halogen; and
$R^{6A}$ represents a hydrogen atom, halogen, cyano, nitro, substituted or unsubstituted lower alkyl, substituted or unsubstituted lower alkenyl, substituted or unsubstituted lower alkynyl, substituted or unsubstituted lower alkoxy, substituted or unsubstituted, cycloalkyl, amino, lower alkylamino, di-lower alkylamino, carboxy, substituted or unsubstituted lower alkoxycarbonyl, substituted or unsubstituted lower alkanoyl, substituted or unsubstituted aryloxy, substituted or unsubstituted aryl, a substituted or unsubstituted heterocyclic group, substituted or unsubstituted aralkyl, or substituted or unsubstituted heterocyclic alkyl; provided that:
(i) when $R^{3A}$ and $R^{5A}$ each are methyl, $R^{4A}$ and $R^{6A}$ each are a hydrogen atom, and
—$(CH_2)_{nA}R^{1A}$ is
(a) methoxycarbonylmethyl,
$R^{2A}$ is not a group selected from the group consisting of 2,4,6-trimethoxy-5-methoxycarbonyl-3-nitrophenyl, 3-cyano-2,4,6-trimethoxyphenyl, 5-cyano-2-ethoxy-4,6-dimethoxy-3-nitrophenyl, 2,6-dimethoxyphenyl, 2-chloro-6-methoxyphenyl and 2-chloro-4,6-dimethoxy-5-methoxycarbonyl-3-nitrophenyl,
(b) ethoxycarbonylmethyl;
$R^{2A}$ is not 2,4,6-trimethoxy-3-methoxycarbonyl-phenyl, and
(c) N,N-dimethylaminomethyl,
$R^{2A}$ is not phenyl;
(ii) when $R^{3A}$, $R^{4A}$, $R^{5A}$ and $R^{6A}$ each are a hydrogen atom, and —$(CH_2)_{nA}R^{1A}$ is
(a) 2-(acetoxymethyl)heptyl, 3-oxopentyl or pentyl,
$R^{2A}$ is not 6-hydroxy-4-methoxy-3-methoxycarbonyl-2-pentylphenyl, (b) 3-oxopentyl,
$R^{2A}$ is not a group selected from the group consisting of 3-benzyloxycarbonyl-6-hydroxy-4-methoxy-2-pentylphenyl and 3-carboxy-6-hydroxy-4-methoxy-2-pentylphenyl, and
(c) n-propyl,
$R^{2A}$ is not 2,4-dihydroxy-6-[(4-hydroxy-2-oxopyran-6-yl)methyl]phenyl;
(iii) when $R^{3A}$ and $R^{4A}$ each are a hydrogen atom, $R^{5A}$ is methyl, $R^{6A}$ is methoxycarbonyl, and —$(CH_2)_{nA}R^{1A}$ is pentyl;
$R^{2A}$ is not a group selected from the group consisting of 6-[2-(acetoxymethyl)heptyl]-2,4-dihydroxyphenyl, 2,4-dihydroxy-6-pentylphenyl and 2,4-dihydroxy-6-(3-oxopentyl)phenyl;
(iv) when $R^{3A}$ and $R^{5A}$ each are benzyl, $R^{4A}$ and $R^{6A}$ each are a hydrogen atom, and —$(CH_2)_{nA}R^{1A}$ is 3-oxopentyl,
$R^{2A}$ is not a group selected from the group consisting of 6-benzyloxy-4-methoxy-3-methoxycarbonyl-2-pentylphenyl and 6-benzyloxy-3-benzyloxycarbonyl-4-methoxy-2-pentylphenyl;
(v) when $R^{3A}$ is benzyl, $R^{4A}$ is a hydrogen atom, $R^{5A}$ is methyl, —$(CH_2)_{nA}R^{1A}$ is pentyl, and $R^{6A}$ is methoxycarbonyl or benzyloxycarbonyl,
$R^{2A}$ is not 2,4-bis(benzyloxy)-6-(3-oxopentyl)phenyl;
(vi) when $R^{3A}$ and $R^{4A}$ each, are a hydrogen atom, $R^{5A}$ is methyl, —$(CH_2)_{nA}R^{1A}$ is pentyl, and $R^{6A}$ is carboxy or benzyloxycarbonyl,
$R^{2A}$ is not 2,4-dihydroxy-6-(3-oxopentyl)phenyl; and
(vii) when $R^{3A}$, $R^{4A}$ and $R^{6A}$ each are a hydrogen atom, $R^{5A}$ is n-propyl, and —$(CH_2)_{nA}R^{1A}$ is 5-(1,1-dimethylpropyl)-4-(2-hydrobenzotriazol-2-yl)-2-hydroxyphenylmethyl,
$R^{2A}$ is not phenyl]
or a pharmaceutically acceptable salt thereof.

(12) The benzoyl compound according to the above (11), wherein $R^{2A}$ is a substituted or unsubstituted aromatic heterocyclic group, substituted aryl having 1 to 3 substituents, or aryl, or a pharmaceutically acceptable salt thereof.

(13) The benzoyl compound according to the above (11) or (12), wherein $R^{3A}$ and $R^{5A}$, which may be the same or different, each are a hydrogen atom, substituted or unsubstituted lower alkyl, substituted or unsubstituted lower alkanoyl, substituted or unsubstituted aroyl, or substituted or unsubstituted lower alkenyl, or a pharmaceutically acceptable salt thereof.

(14) The benzoyl compound according to the above (11) or (12), wherein $R^{3A}$, $R^{4A}$ and $R^{5A}$ each are a hydrogen atom, or a pharmaceutically acceptable salt thereof.

(15) The benzoyl compound according to any one of the above (11) to (14), wherein $R^{1A}$ is $CONR^7R^8$ (wherein $R^7$ and $R^8$ each have the same meanings as defined above), or a pharmaceutically acceptable salt thereof.

(16) The benzoyl compound according to any one of the above (11) to (15), wherein $R^{6A}$ is a hydrogen atom, lower alkyl, halogen or aryl, or a pharmaceutically acceptable salt thereof.

(17) A pharmaceutical composition comprising, as an active ingredient, the benzoyl compound according to any one of the above (11) to (16) or a prodrug thereof, or a pharmaceutically acceptable salt of said benzoyl compound or said prodrug.

(18) A pharmaceutical composition comprising, as an active ingredient, the benzoyl compound according to any one of the above (11) to (16) or a pharmaceutically acceptable salt thereof.

(19) An Hsp90 family protein inhibitor comprising, as an active ingredient, the benzoyl compound according to any one of the above (11) to (16) or a prodrug thereof, or a pharmaceutically acceptable salt of said benzoyl compound or said prodrug.

(20) An Hsp90 family protein inhibitor comprising, as an active ingredient, the benzoyl compound according to any one of the above (11) to (16) or a pharmaceutically acceptable salt thereof.

(21) A therapeutic agent for a disease associated with an Hsp90 family protein or a protein to which an Hsp90 family protein binds (Hsp90 client protein) comprising, as an active ingredient, the benzoyl compound according to any one of the above (11) to (16) or a prodrug thereof, or a pharmaceutically acceptable salt of said benzoyl compound or said prodrug.

(22) A therapeutic agent for diseases associated with an Hsp90 family protein or a protein to which an Hsp90 family protein binds (Hsp90 client protein) comprising, as an active ingredient, the benzoyl compound according to any one of the above (11) to (16) or a pharmaceutically acceptable salt thereof.

(23) An anti-tumor agent comprising, as an active ingredient, the benzoyl compound according to any one of the above (11) to (16) or a prodrug thereof, or a pharmaceutically acceptable salt of said benzoyl compound or said prodrug.

(24) An anti-tumor agent comprising, as an active ingredient, the benzoyl compound according to any one of the above (11) to (16) or a pharmaceutically acceptable salt thereof.

(25) A method of inhibiting a heat shock protein 90 (Hsp90) family protein, which comprises administering an effective amount of a benzoyl compound represented by general formula (I):

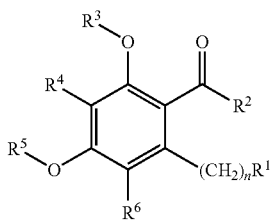

(wherein n, $R^1$, $R^2$, $R^3$, $R^4$, $R^5$ and $R^6$ each have the same meanings as defined above) or a prodrug thereof, or a pharmaceutically acceptable salt of said benzoyl compound or said prodrug.

(26) A method of treating a disease associated with an Hsp90 family protein or a protein to which an Hsp90 family protein binds (Hsp90 client protein), which comprises administering an effective amount of the benzoyl compound according to any one of the above (11) to (16) or a prodrug thereof, or a pharmaceutically acceptable salt of said benzoyl compound or said prodrug.

(27) A method of treating malignant tumors, which comprises administering an effective amount of the benzoyl compound according to any one of the above (11) to (16) or a prodrug thereof, or a pharmaceutically acceptable salt of said benzoyl compound or said prodrug.

(28) Use of a benzoyl compound represented by general formula (I):

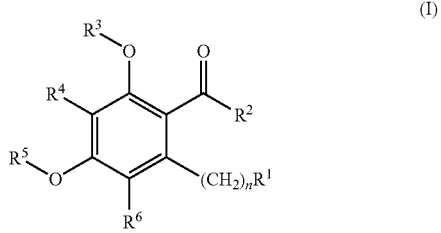

(wherein n, $R^1$, $R^2$, $R^3$, $R^4$, $R^5$ and $R^6$ each have the same meanings as defined above) or a prodrug thereof, or a pharmaceutically acceptable salt of said benzoyl compound or said prodrug for the manufacture of a heat shock protein 90 (Hsp90) family protein inhibitor.

(29) Use of the benzoyl compound according to any one of the above (11) to (16) or a prodrug thereof, or a pharmaceutically acceptable salt of said benzoyl compound or said prodrug for the manufacture of an Hsp90 family protein inhibitor.

(30) Use of the benzoyl compound according to any one of the above (11) to (16) or a prodrug thereof, or a pharmaceutically acceptable salt of said benzoyl compound or said prodrug for the manufacture of a therapeutic agent for diseases associated with an Hsp90 family protein or a protein to which an Hsp90 family protein binds (Hsp90 client protein).

(31) Use of the benzoyl compound according to any one of the above (11) to (16) or a prodrug thereof, or a pharmaceutically acceptable salt of said benzoyl compound or said prodrug for the manufacture of an anti-tumor agent.

In the definitions of the groups in general formula (I) or (IA):

Examples of the lower alkyl moiety of the lower alkyl, lower alkoxy, lower alkoxycarbonyl, lower alkylamino and di-lower alkylamino include straight-chain or branched alkyl groups having 1 to 8 carbon atoms, such as methyl, ethyl, propyl, isopropyl, butyl, sec-butyl, tert-butyl, pentyl, isopentyl, neopentyl, hexyl, heptyl and octyl. The two lower alkyl moieties of the di-lower alkylamino may be the same or different.

Examples of the lower alkenyl include straight-chain or branched alkenyl groups having 2 to 8 carbon atoms, such as vinyl, allyl, 1-propenyl, methacryl, crotyl, 1-butenyl, 3-butenyl, 2-pentenyl, 4-pentenyl, 2-hexenyl, 5-hexenyl, 2-heptenyl and 2-octenyl.

Examples of the lower alkynyl include straight-chain or branched alkynyl groups having 2 to 8 carbon atoms, such as ethynyl, propynyl, butynyl, pentynyl, hexynyl, heptynyl and octynyl.

Examples of the lower alkanoyl moiety of the lower alkanoyl and lower alkanoyloxy include straight-chain or branched alkanoyl groups having 1 to 7 carbon atoms, such as formyl, acetyl, propionyl, butyryl, isobutyryl, valeryl, isovaleryl, pivaloyl, hexanoyl and heptanoyl.

Examples of the cycloalkyl include cycloalkyl groups having 3 to 8 carbon atoms, such as cyclopropyl, cyclobutyl, cyclopentyl, cyclohexyl, cycloheptyl and cyclooctyl.

Examples of the aryl moiety of the aryl, arylsulfonyl, aryloxy and aroyl include monocyclic, bicyclic or tricyclic aryl groups having 6 to 14 carbon atoms, such as phenyl, indenyl, naphthyl and anthryl.

Examples of the aralkyl include aralkyl groups having 7 to 15 carbon atoms, such as benzyl, phenethyl, benzhydryl and naphthylmethyl.

Examples of the aromatic, heterocyclic group include 5- or 6-membered monocyclic aromatic heterocyclic groups containing at least one atom selected from a nitrogen atom, an oxygen atom and a sulfur atom, and bicyclic or tricyclic condensed-ring aromatic heterocyclic groups containing at least one atom selected from a nitrogen atom, an oxygen atom and a sulfur atom in which 3- to 8-membered rings are condensed, such as pyridyl, pyrazinyl, pyrimidinyl, pyridazinyl, quinolinyl, isoquinolinyl, phthalazinyl, quinazolinyl, quinoxalinyl, naphthyridinyl, cinnolinyl, pyrrolyl, pyrazolyl, imidazolyl, triazolyl, tetrazolyl, thienyl, furyl, thiazolyl, oxazolyl, indolyl, indazolyl, benzimidazolyl, benzotriazolyl, benzothiazolyl, benzoxazolyl, purinyl and benzodioxolanyl.

Examples of the heterocyclic group moiety of the heterocyclic group and heterocyclic alkyl include groups described in the above definition of the aromatic heterocyclic group and also alicyclic heterocyclic groups. Examples of the alicyclic heterocyclic group include 5- or 6-membered monocyclic alicyclic heterocyclic groups containing at least one atom selected from a nitrogen atom, an oxygen atom and a sulfur atom, and bicyclic or tricyclic condensed-ring alicyclic heterocyclic groups containing at least one atom selected from a nitrogen atom, an oxygen atom and a sulfur atom in which 3- to 8-membered rings are condensed, such as pyrrolidinyl, piperidino, piperazinyl, morpholino, morpholinyl, thiomorpholino, thiomorpholinyl, homopiperidino, homopiperazinyl, tetrahydropyridinyl, tetrahydroquinolinyl, tetrahydroisoquinolinyl, tetrahydrofuranyl, tetrahydropyranyl, dihydrobenzofuranyl, oxopiperazinyl and 2-oxopyrrolidinyl.

Examples of the heterocyclic group formed together with the adjacent nitrogen atom include 5- or 6-membered monocyclic heterocyclic groups containing at least one nitrogen atom (the monocyclic heterocyclic groups may also contain another nitrogen atom, an oxygen atom or a sulfur atom), and bicyclic or tricyclic condensed-ring heterocyclic groups containing at least one nitrogen atom in which 3- to 8-membered rings are condensed (the condensed-ring heterocyclic groups may also contain another nitrogen atom, an oxygen atom or a sulfur atom), such as pyrrolidinyl, piperidino, piperazinyl, morpholino, thiomorpholino, homopiperidino, homopiperazinyl, tetrahydropyridinyl, tetrahydroquinolinyl, tetrahydroisoquinolinyl, oxopiperazinyl and 2-oxopyrrolidinyl.

The alkylene moiety of the heterocyclic alkyl has the same meaning as a group produced by removing one hydrogen atom from the above-described lower alkyl.

The halogen means fluorine, chlorine, bromine and iodine atoms.

Examples of the substituents (A) in the substituted lower alkyl, the substituted lower alkoxy, the substituted lower alkoxycarbonyl, the substituted lower alkenyl and the substituted lower alkynyl include 1 to 3 substituents which are the same or different, such as hydroxy, oxo, cyano, nitro, carboxy, amino, halogen, substituted or unsubstituted lower alkoxy, cycloalkyl, lower alkanoyl, lower alkoxycarbonyl, lower alkylamino and di-lower alkylamino. The position(s) to be substituted by the substituent(s) is/are not particularly limited. The halogen, the lower alkoxy, the cycloalkyl, the lower alkanoyl, the lower alkoxycarbonyl, the lower alkylamino and the di-lower alkylamino described as examples of substituents (A) each have the same meanings as defined above. Examples of the substituents in the substituted lower alkoxy described as an example of substituent (A) include 1 to 3 substituents which are the same or different, such as hydroxy and halogen, and the halogen has the same meaning as defined above.

Examples of substituents (B) in the substituted lower alkanoyl, the substituted lower alkanoyloxy, the substituted cycloalkyl, the substituted aryl, the substituted arylsulfonyl, the substituted aryloxy, the substituted aralkyl, the substituted aroyl, the substituted heterocyclic alkyl, the substituted heterocyclic group, the substituted aromatic heterocyclic group and the substituted heterocyclic group formed together with the adjacent nitrogen atom include 1 to 3 substituents which are the same or different, such as hydroxy, halogen, nitro, cyano, amino, carboxy, carbamoyl, substituted or unsubstituted lower alkyl, substituted or unsubstituted lower alkoxy, aralkyloxy, lower alkylsulfonyl, lower alkylsulfanyl, cycloalkyl, lower alkoxycarbonyl, lower alkylamino, di-lower alkylamino, lower alkanoyl, a heterocyclic group, substituted or unsubstituted aryl, substituted or unsubstituted heterocyclic alkyloxy, and substituted or unsubstituted heterocyclic carbonylalkyloxy. The position(s) to be substituted by substituent(s) is/are not particularly limited. The halogen, the lower alkyl, the lower alkoxy, the cycloalkyl, the lower alkoxycarbonyl, the lower alkylamino, the di-lower alkylamino, the lower alkanoyl, the heterocyclic group and the aryl described as examples of substituents (B) each have the same meanings as defined above; the lower alkyl moiety of the lower alkylsulfonyl and lower alkylsulfanyl has the same meaning as the above-described lower alkyl; the aralkyl moiety of the aralkyloxy has the same meaning as the above-described aralkyl; and the heterocyclic group moiety and the alkylene of the heterocyclic alkyloxy and heterocyclic carbonylalkyloxy, respectively, have the same meanings as the above-described heterocyclic group and the group produced by removing a hydrogen atom from the above-described lower alkyl. Examples of the substituents in the substituted lower alkyl, the substituted lower alkoxy and the substituted aryl described as examples of substituents (B) include 1 to 3 substituents which are the same or different, such as hydroxy, halogen, lower alkoxy, cyano, lower alkylamino and di-lower alkylamino. Herein, the halogen, the lower alkoxy, the lower alkylamino and the di-lower alkylamino each have the same meanings as defined above. Examples of the substituents in the substituted heterocyclic alkyloxy and the substituted heterocyclic carbonylalkyloxy described as examples of substituents (B) include 1 to 3 substituents which are the same or different, such as hydroxy, halogen, lower alkyl, lower alkoxy and a heterocyclic group. Herein, the halogen, the lower alkyl, the lower alkoxy and the heterocyclic group each have the same meanings as defined above.

Hereinafter, the compounds represented by general formula (I) are referred to as Compounds (I), and the same applies to compounds of other formula numbers.

The prodrugs of Compounds (I) include compounds which are converted in vivo, for example, by various mechanisms such as hydrolysis in blood to form Compounds (I) of the present invention, and the like. Such compounds can be specified by techniques well known in the art (e.g. J. Med. Chem., 1997, Vol. 40, p. 2011-2016; Drug Dev. Res., 1995, Vol. 34, p. 220-230; Advances in Drug Res., 1984, Vol. 13, p. 224-331; Bundgaard, Design of Prodrugs, 1985, Elsevier Press and the like).

Specifically, when Compound (I) has carboxy in its structure, examples of prodrugs of Compound (I) include compounds in which the hydrogen atom of said carboxy is substituted by a group selected from lower alkyl, lower alkanoyloxyalkyl [e.g. lower alkanoyloxymethyl, 1-(lower alkanoyloxy)ethyl and 1-methyl-1-(lower alkanoyloxy)

ethyl], lower alkoxycarbonyloxyalkyl [e.g. lower alkoxycarbonyloxymethyl, 1-(lower alkoxycarbonyloxy)ethyl, and 1-methyl-1-(lower alkoxycarbonyloxy)ethyl], N-(lower alkoxycarbonyl)aminoalkyl {e.g. N-(lower alkoxycarbonyl) aminomethyl and 1-[N-(lower alkoxycarbonyl)amino] ethyl}, 3-phthalidyl, 4-crotonolactonyl, γ-butyrolacton-4-yl, di-lower alkylaminoalkyl, carbamoylalkyl, di-lower alkylcarbamoylalkyl, piperiditoalkyl, pyrrolidinoalkyl, morpholinoalkyl and the like.

Also, when Compound (I) has alcoholic hydroxy in its structure, examples of prodrugs of Compound (I) include compounds in which the hydrogen atom of said hydroxy is substituted by a group selected from lower alkanoyloxyalkyl, 1-(lower alkanoyloxy)ethyl, 1-methyl-1-(lower alkanoyloxy) ethyl, lower alkoxycarbonyloxyalkyl, N-lower alkoxycarbonylaminoalkyl, succinoyl, lower alkanoyl, α-amino lower alkanoyl and the like.

Also, when Compound (I) has amino in its structure, examples of prodrugs of Compound (I) include compounds in which one or two hydrogen atoms of said amino are substituted by a group selected from lower alkylcarbonyl, lower alkoxycarbonyl, lower alkylcarbamoyl, di-lower alkylcarbamoyl and the like.

The lower alkyl moiety of the above-described lower alkyl, lower alkoxycarbonyloxyalkyl, lower alkoxycarbonyloxymethyl, 1-(lower alkoxycarbonyloxy)ethyl, 1-methyl-1-(lower alkoxycarbonyloxy)ethyl, N-(lower alkoxycarbonyl)aminoalkyl, N-(lower alkoxycarbonyl)aminomethyl, 1-[N-(lower alkoxycarbonyl)amino]ethyl, di-lower alkylaminoalkyl, di-lower alkylcarbamoylalkyl, lower alkoxycarbonyloxymethyl, N-lower alkoxycarbonylaminomethyl, lower alkylcarbonyl, lower alkoxycarbonyl, lower alkylcarbamoyl and di-lower alkylcarbamoyl has the same meaning as the above-described lower alkyl. The two lower alkyl moieties of the di-lower alkylaminoalkyl, di-lower alkylcarbamoylalkyl and di-lower alkylcarbamoyl may be the same or different.

Also, the lower alkanoyl moiety of the above-described lower alkanoyloxyalkyl, lower alkanoyloxymethyl, 1-(lower alkanoyloxy)ethyl, 1-methyl-1-(lower alkanoyloxy)ethyl, lower alkanoyl and α-amino lower alkanoyl has the same meaning as the above-described lower alkanoyl.

Also, the alkylene moiety of the above-described lower alkanoyloxyalkyl, lower alkoxycarbonyloxyalkyl, N-(lower alkoxycarbonyl)aminoalkyl, di-lower alkylaminoalkyl, carbamoylalkyl, di-lower alkylcarbamoylalkyl, piperidinoalkyl, pyrrolidinoalkyl and morpholinoalkyl has the same meaning as the group produced by removing a hydrogen atom from the above-described lower alkyl.

These prodrugs of Compounds (I) can be prepared from Compounds (I) according to, for example, the methods described in T. W. Greene, Protective Groups in organic Synthesis, third edition, John Wiley & Sons Inc. (1999), or methods similar thereto.

The pharmaceutically acceptable salts of Compounds (I) or prodrugs thereof include pharmaceutically acceptable acid addition salts, metal salts, ammonium salts, organic amine addition salts and amino acid addition salts.

Examples of the pharmaceutically acceptable acid addition salts of Compounds (I) or prodrugs thereof include inorganic acid addition salts such as hydrochloride, sulfate, nitrate and phosphate, and organic acid addition salts such as acetate, maleate, fumarate and citrate. Examples of the pharmaceutically acceptable metal salts include alkali metal salts such as sodium salt and potassium salt, alkaline earth metal salts such as magnesium salt and calcium salt, aluminum salt, and zinc salt. Examples of the pharmaceutically acceptable ammonium salts include ammonium and tetramethylammonium. Examples of the pharmaceutically acceptable organic amine addition salts include an addition salt of morpholine or piperidine. Examples of the pharmaceutically acceptable amino acid addition salts include an addition salt of glycine, phenylalanine, lysine, aspartic acid or glutamic acid.

The term "inhibition of Hsp90 family protein" refers to inhibition of the binding of Hsp90 family protein to a protein to which Hsp90 family protein binds (Hsp90 client protein).

Examples of Hsp90 family proteins include Hsp90α protein, Hsp90β protein, grp94 and hsp75/TRAP1.

The proteins to which Hsp90 family proteins bind include any proteins to which Hsp90 family proteins bind, for example, EGFR, Erb-B2, Bcr-Abl, src, raf-1, AKT, Flt-3, PLK, Wee1, FAK, cMET, hTERT, HIF1-α, mutant p53, estrogen receptors and androgen receptors (Expert Opinion on Biological Therapy, 2002, Vol. 2, p. 3-24).

The processes for preparing Compounds (I) are described below.

In the processes shown below, when the defined groups undergo changes under the reaction conditions or are not suitable to carry out the processes, production can be easily performed by applying means generally used in synthetic organic chemistry, such as protection of functional groups, removal of protecting groups and the like [e.g. T. W. Greene, Protective Groups in Organic Synthesis, third edition, John Wiley & Sons Inc. (1999)] If necessary, the order of reaction steps such as introduction of a substituent may be changed.

Compounds (I) can be obtained, for example, according to Production Processes 1 to 4 shown below.

Production Process 1:

Compound (I) can be produced, for example, according to the following step.

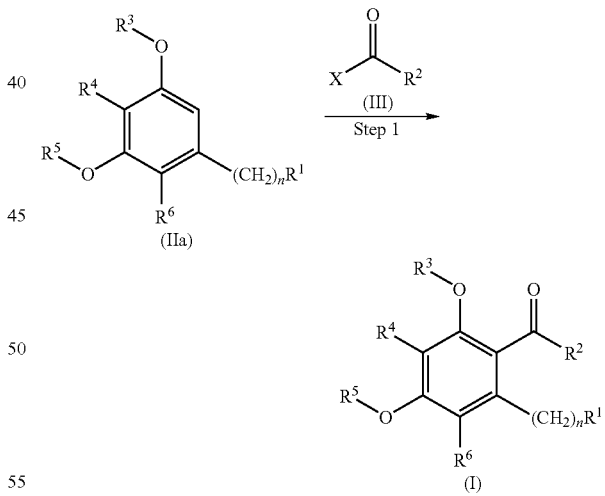

(wherein $R^1$ to $R^6$ and n each have the same meanings as defined above; and X represents hydroxy or halogen, and said halogen has the same meaning as defined above)

(Step 1)

Compound (I) can be obtained by reacting Compound (IIa) with 1 to 10 equivalents of Compound (III) in an inert solvent in the presence of an acid.

Examples of the acid include organic acids such as acetic acid and trifluoroacetic acid, and Lewis acids such as aluminum trichloride and titanium tetrachloride. The acid is preferably used in an amount of 1 to 50 equivalents based on Compound (IIa).

Examples of the inert solvent include dichloromethane and chloroform, but acetic acid, trifluoroacetic acid or the like may also be used as the solvent.

The reaction is generally carried out at a temperature between −50° C. and the boiling point of the solvent used for 5 minutes to 24 hours. The reaction can be accelerated by adding 1 to 10 equivalents of acetic anhydride, trifluoroacetic anhydride or the like.

Compound (IIa), which is a raw material, can be obtained according to a known method [e.g. R. C. Larock, Comprehensive Organic Transformations, second edition, John Wiley & Sons Inc. (1999)] or methods similar thereto.

Compound (III), which is a raw material, can be obtained as a commercially available product or according to a known method [e.g., R. C. Larock, Comprehensive Organic Transformations, second edition, John Wiley & Sons Inc. (1999)] or methods similar thereto.

It is also possible to prepare Compound (IIa-ii), i.e. Compound (IIa) in which $R^6$ is $R^{6a}$ (wherein $R^{6a}$ represents substituted or unsubstituted lower alkanoyl, substituted or unsubstituted lower alkenyl, substituted or unsubstituted lower alkynyl, substituted or unsubstituted aryl, or a substituted or unsubstituted aromatic heterocyclic group in the definition of $R^6$), from Compound (IIa-i), i.e. Compound (IIa) in which $R^6$ is a hydrogen atom, according to a method similar to Production Process 6 described below.

It is also possible to obtain Compound (IIa-iv), i.e. Compound (IIa) in which $R^6$ is ethyl, by preparing Compound (IIa-iii), i.e. Compound (IIa) in which $R^6$ is acetyl, from Compound (IIa-i), i.e. Compound (IIa) in which $R^6$ is a hydrogen atom, according to a method similar to the above Production Process 1, and then treating the resulting Compound (IIa-iii) with triethylsilane or the like in trifluoroacetic acid or the like.

Production Process 2:

Compound (I) can also be produced, for example, according to the following steps.

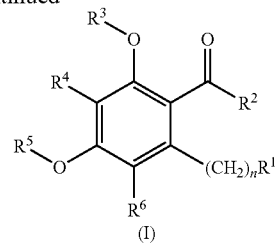

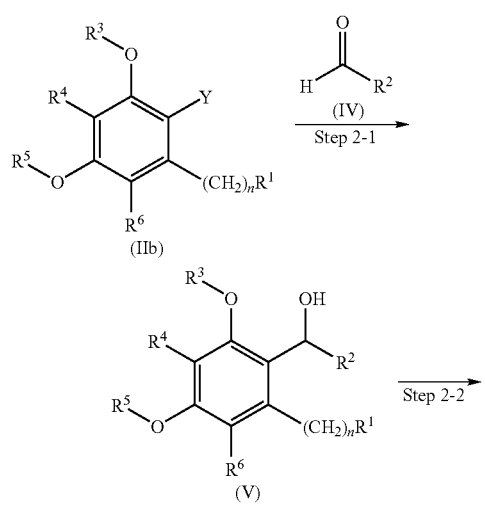

-continued

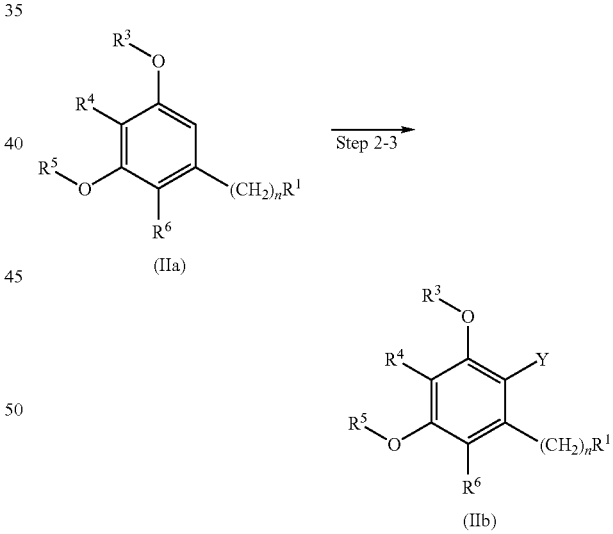

(wherein $R^1$ to $R^6$ and n each have the same meanings as defined above; and Y represents halogen, and said halogen has the same meaning as defined above)

(Step 2-1)

Compound (V) can be obtained by treating Compound (IIb) with 1 to 5 equivalents of a strong base such as n-butyllithium in an inert solvent and then reacting the resulting compound with Compound (IV).

Examples of the inert solvent include diethyl ether and tetrahydrofuran.

The reaction is generally carried out at a temperature between −78° C. and 30° C. for 5 minutes to 24 hours.

Compound (IIb), which is a raw material, can be obtained as a commercially available product or according to a known method [e.g. R. C. Larock, Comprehensive Organic Transformations, second edition, John Wiley & Sons Inc. (1999)] or methods similar thereto. Compound (IIb) can also be produced, for example, according to the following step.

(wherein $R^1$, $R^3$ to $R^6$, n and Y each have the same meanings as defined above)

Compound (IIb) can be obtained by treating Compound (IIa) with 1 to 2 equivalents of a corresponding halogenating agent such as N-bromosuccinimide, N-chlorosuccinimide, chlorine, bromine or iodine in an inert solvent.

Examples of the inert solvent include dichloromethane, chloroform and N,N-dimethylformamide.

The reaction is generally carried out at a temperature between 0° C. and 50° C. for 5 minutes to 24 hours.

(Step 2-2)

Compound (I) can be obtained by treating Compound (V) with 1 to 10 equivalents of an oxidizing agent in an inert solvent. Examples of the oxidizing agent, include chromic acid, manganese dioxide, pyridinium dichromate (PDC) and 1-hydroxy-1,2-benziodoxol-3(1H)-one 1-oxide (IBX). This reaction may also be carried out in the presence of molecular sieves.

Examples of the inert solvent include "dichloromethane, chloroform, acetone, ethyl acetate and dimethyl sulfoxide.

The reaction is generally carried out at a temperature between 0° C. and the boiling point of the solvent used for 5 minutes to 24 hours.

Production Process 3:

Compound (Ia), i.e. Compound (I) in which $R^1$ is $CONR^7R^8$, can also be produced according to the following process.

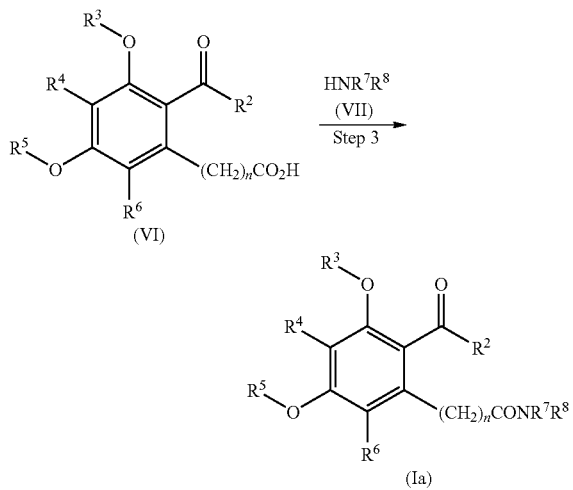

(wherein $R^2$ to $R^8$ and n each have the same meanings as defined above)

(Step 3)

Compound (Ia) can be obtained by condensation reaction of Compound (VI) and Compound (VII).

For example, Compound (Ia) can be obtained by reacting Compound (VI) with Compound (VII) in a solvent in the presence of an activator such as 1-hydroxybenzotriazole or N-hydroxysuccinimide and a condensing agent. If necessary, 1 to 20 equivalents of a base may be added thereto when the reaction is carried out. In general, the condensing agent, the activator and Compound (VII) are used in an amount of 1 to 20 equivalents based on Compound (VI), and the reaction is carried out at a temperature between −20 C. and the boiling point of the solvent used for 1 minute to 24 hours.

Examples of the solvent include halogenated hydrocarbons such as dichloromethane and chloroform; esters such as methyl acetate, ethyl acetate and isobutyl acetate; ethers such as ether, tetrahydrofuran and 1,4-dioxane; aromatic hydrocarbons such as benzene and toluene, acetonitrile; N,N-dimethylformamide; N-methylpiperidone; and mixtures thereof.

Examples of the condensing agent include dicyclohexylcarbodiimide, 1-(3-dimethylaminopropyl)-3-ethylcarbodiimide hydrochloride, polymer-bound 1-(3-dimethylaminopropyl)-3-ethylcarbodiimide and triphenylphosphine oxide trifluoromethanesulfonic anhydride.

Examples of the base include alkylamines such as triethylamine, diisopropyl ethylamine and N-methylmorpholine; pyridines such as pyridine, lutidine, collidine and 4-dimethylaminopyridine; alkali metal carbonates such as potassium carbonate and sodium hydrogencarbonate; and alkali metal hydroxides such as potassium hydroxide, sodium hydroxide and lithium hydroxide.

Prior to use in the reaction, Compound (VI) may be treated with the activator, or the carboxyl group of Compound (VI) may be converted to a highly reactive group such as chlorocarbonyl, bromocarbonyl, p-nitrophenoxycarbonyl, pentafluorophenoxycarbonyl or pentafluorothiophenoxycarbonyl according to an ordinary method.

Compound (VI), which is a raw material, can be obtained according to Production Process 1, Production Process 2, a known method (e.g. J. Am. Chem. Soc., 1971, Vol. 93, p. 6708-6709) or methods similar thereto. Compound (VII), which is a raw material, can be obtained as a commercially available product, or according to a known method [e.g. R. C. Larock, Comprehensive Organic Transformations, second edition, John Wiley & Sons Inc. (1999)] or methods similar thereto.

Production Process 4:

Compound (Ic), i.e. Compound (I) in which $R^3$ and $R^5$ each are a hydrogen atom, can also be produced from Compound (Ib), i.e. Compound (I) in which $R^3$ is $R^{3a}$ (wherein $R^{3a}$ has the same meaning as the above-described $R^3$ except a hydrogen atom is excluded) and $R^5$ is $R^{5a}$ (wherein $R^{5a}$ has the same meaning as the above-described $R^5$ except a hydrogen atom is excluded), According to the following step.

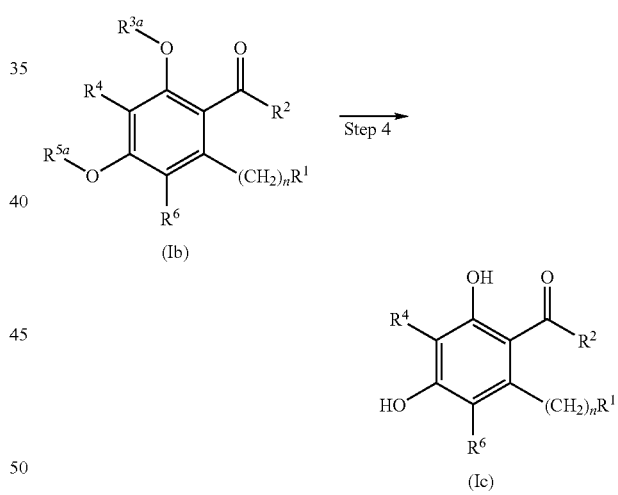

(wherein $R^1$, $R^2$, $R^{3a}$, $R^4$, $R^{5a}$, $R^6$ and n each have the same meanings as defined above)

(Step 4)

Compound (Ic) can be obtained by treating Compound (Ib) with a Lewis acid such as boron tribromide, boron trichloride, boron trifluoride, aluminum trichloride, titanium tetrachloride or a complex thereof in an inert solvent such as dichloromethane. In general, the Lewis acid is used in an amount of 1 to 20 equivalents based on Compound (Ib), and the reaction is carried out at a temperature between −78° C. and the boiling point of the solvent used for 1 minute to 24 hours.

When the starting compound is Compound (Ib-i), i.e. Compound (Ib) in which $R^{3a}$ and $R^{5a}$ each are allyl, Compound (Ic) can also be obtained by treating Compound (Ib-i) with a nucleophilic reagent, for example, a combination of a palladium complex such as bis(triphenylphosphine)palladium (II) dichloride and a formate such as ammonium formate, a typical metal hydride such as tributyltin hydride, a secondary amine such as morpholine, or an active methylene compound such as dimedone, in an inert solvent.

Examples of the inert solvent include tetrahydrofuran, acetic acid and 1,4-dioxane.

These reactions are generally carried out at a temperature between room temperature and the boiling point of the solvent used for 1 minute to 24 hours.

Compound (Ic) can also be obtained by treating Compound (Ib-i) with palladium (II) acetate in the presence or absence of a ligand such as triphenylphosphine, or with a palladium complex such as tetrakis triphenylphosphine palladium (0), selenium dioxide or the like, in an organic acid such as acetic acid or formic acid or in a mixed solvent of an organic acid and tetrahydrofuran.

These reactions are generally carried out at a temperature between room temperature and the boiling point of the solvent used for 1 minute to 24 hours.

When the starting compound is Compound (Ib-ii), i.e. Compound (Ib) in which $R^{3a}$ and $R^{5a}$ each are methoxymethyl, Compound (Ic) can also be obtained by treating Compound (Ib-ii) with an acid such as hydrochloric acid or acetic acid in a solvent.

Examples of the solvent include protic solvents such as water, methanol and isopropyl alcohol, and mixed solvents of a protic solvent and an inert solvent such as 1,4-dioxane.

These reactions are generally carried out at a temperature between 0° C. and the boiling point of the solvent used for 5 minutes to 24 hours.

When $R^{3a}$ and $R^{5a}$ in Compound (Ib) are different from each other, the desired Compound (Ic) can be obtained by appropriately combining the above processes. Compound (Id), i.e. Compound (I) in which either $R^3$ or $R^5$ is a hydrogen atom, can be obtained from Compound (Ib) according to the above processes by adjusting the amount of the reagents used, the reaction temperature, and the like.

Compound (Ib), which is a raw material, can be obtained according to Production Process 1, Production Process 2, a known method [e.g. R. C. Larock, Comprehensive Organic Transformations, second edition, John Wiley & Sons Inc. (1999)] or a method similar thereto.

Production Process 5:

Compound (IIa-v), i.e. Compound (IIa) used as a starting compound in Production Process 1 or 2 in which $R^1$ is substituted or unsubstituted lower alkoxy, can also be produced according to the following process.

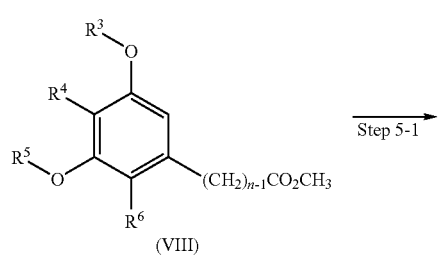

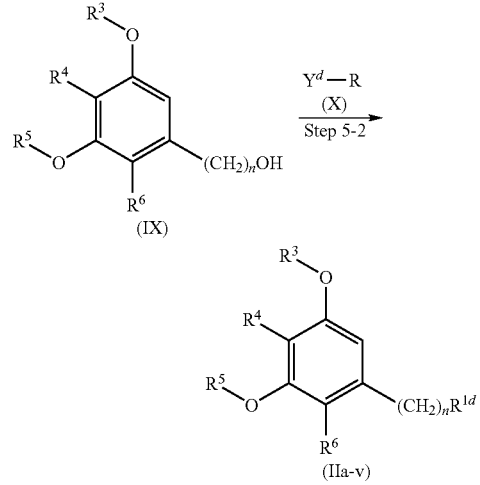

(wherein $R^3$ to $R^6$ and n each have the same meanings as defined above; $Y^d$ has the same meaning as the above-described Y; $R^{1d}$ represents substituted or unsubstituted lower alkyl; and $R^{1d}$ represents substituted or unsubstituted lower alkoxy, wherein the lower alkyl and the lower alkoxy each have the same meanings as defined above, and the substituents in the substituted lower alkyl and substituted lower alkoxy have the same meanings as the above-described substituent in the substituted lower alkyl)

(Step 5-1)

Compound (IX) can be obtained by treating Compound (VIII) with 1 to 5 equivalents of a reducing agent such as isobutyl aluminum hydride or lithium aluminum hydride in an inert solvent.

Examples of the inert solvent include tetrahydrofuran, toluene and dichloromethane.

The reaction is generally carried out at a temperature between −78° C. and the boiling point of the solvent used for 5 minutes to 24 hours.

The starting Compound (VIII) can be obtained according to Production Process 1, Production Process 2, a known method [e.g. R. C. Larock, Comprehensive Organic Transformations, second edition, John Wiley & Sons Inc. (1999)] or a method similar thereto.

(Step 5-2)

Compound (IIA-V) can be obtained by treating Compound (IX) with to 5 equivalents of sodium hydride or the like in an inert solvent and then reacting the resulting compound with 1 to 5 equivalents of Compound (X).

Examples of the inert solvent include tetrahydrofuran, dichloromethane and N,N-dimethylformamide.

The reaction is generally carried out at a temperature between 0° C. and the boiling point of the solvent used for 5 minutes to 24 hours.

Production Process 6:

Compound (If), i.e. Compound (I) in which $R^6$ is halogen, or Compound (Ig), i.e. Compound (I) in which $R^6$ is $R^{6a}$ (wherein $R^{6a}$ has the same meaning as defined above), can also be produced according to the following process.

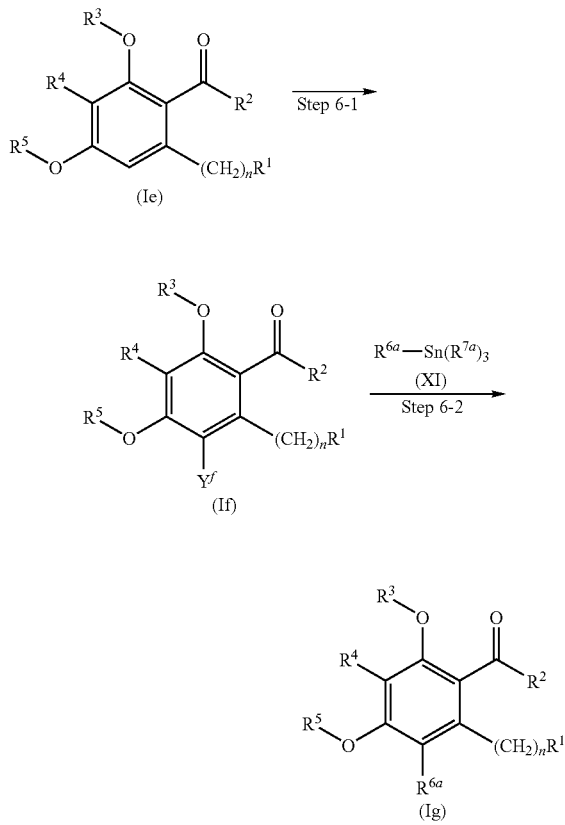

(wherein $R^1$ to $R^5$, $R^{6a}$ and n each have the same meanings as defined above; $Y^f$ has the same meaning as the above-described Y; and $R^{7a}$ represents lower alkyl, wherein the lower alkyl has the same meaning as defined above)

(Step 6-1)

Compound (If) can be obtained by treating Compound (Ie) with 1 to 2 equivalents of a corresponding halogenating agent such as N-bromosuccinimide, N-chlorosuccinimide, chlorine, bromine or iodine in an inert solvent.

Examples of the inert solvent include dichloromethane, chloroform and N,N-dimethylformamide.

The reaction is generally carried out at a temperature between 0° C. and 50° C. for 5 minutes to 24 hours.

Compound (Ie), which is a raw material, can be obtained according to Production Processes 1 to 4, a known method [e.g. R. C. Larock, Comprehensive Organic Transformations, second edition, John Wiley & Sons Inc. (1999)] or methods similar thereto.

(Step 6-2)

Compound (Ig) can be obtained by reacting Compound (If) with 1 to 5 equivalents of Compound (XI) in an inert solvent in the presence of 0.01 to 1 equivalent of bis(tri-o-tolylphosphine)palladium (II) dichloride, bis(triphenylphosphine)palladium (II) dichloride or the like and then, if necessary, treating the product with an acid such as hydrochloric acid.

Examples of the inert solvent include 1,2-dimethoxymethane, tetrahydrofuran, dichloromethane, chloroform, toluene and mixtures thereof.

The reaction is generally carried out at a temperature between 50° C. and the boiling point of the solvent used for 5 minutes to 24 hours.

Compound (XI), which is a raw material, can be obtained as a commercially available product or according to a known method [e.g. R. C. Larock, Comprehensive Organic Transformations, second edition, John Wiley & Sons Inc. (1999)] or methods similar thereto.

In addition to the above-described production processes, Compounds (I) can also be obtained according to the methods described in WO01/81288; Japanese Published Unexamined Patent Application No. 92082/1996; Japanese Published Unexamined Patent Application No. 39968/2001; U.S. Pat. No. 6,125,007; J. Antibiotics, 2002, Vol. 55, p. 61-70; J. Am. Chem. Soc., 1971, Vol. 93, p. 6708-6709; Bioorg. & Med. Chem. Lett., 1999, Vol. 9, p. 1945-1948; Tetrahedron Lett., 2002, Vol. 43, p. 291-293; J. Chem. Soc., Perkin Trans. 1, 1989, p. 441-448; J. Chem. Soc., Perkin Trans. 1, 1977, p. 2502-2512; J. Chem. Soc. (C), 1971, p. 3899-3902; J. Chem. Soc., Perkin Trans. 1, 1974, p. 1417-1421; Tetrahedron Lett., 1981, Vol. 22, p. 267-270, etc., or methods similar thereto.

Further, the transformation of the functional groups in Compounds (I), the starting compounds and the intermediates and the transformation of the functional groups contained in the substituents can be carried out according to a known method [e.g. R. C. Larock, Comprehensive Organic Transformations, second edition, John Wiley & Sons Inc. (1999)] or methods similar thereto.

By appropriately combining the above-described processes and the like, Compounds (I) having desired functional groups at desired positions can be obtained.

The intermediates and the desired compounds in the above-described production processes can be isolated and purified by appropriately combining separation and purification methods conventionally used in synthetic organic chemistry, for example, filtration, extraction, washing, drying, concentration, recrystallization, and various kinds of chromatography. The intermediates can also be subjected to the subsequent reactions without purification.

For some of Compounds (I), there may exist stereoisomers such as geometrical isomers and optical isomers, and all possible isomers including them and mixtures thereof can be used for the Hsp90 family protein inhibitors of the present invention.

When it is desired to obtain a salt of Compound (I), in the case where Compound (I) is produced in the form of the salt, it can be purified as such, but where it is produced in the free state, it can be converted into a salt by dissolving or suspending it in an appropriate solvent and then adding an acid or a base thereto.

Further, Compounds (I) and pharmaceutically acceptable salts thereof may exist in the form of adducts with water or various solvents, and these adducts can also be used for the Hsp90 family protein inhibitors of the present invention.

Examples of Compounds (I) obtained by the present invention are shown in Table 1 and Table 2.

In the tables, Ph represents phenyl, and the numbers preceding the groups in $R^{2a}$, $R^{2b}$ and $R^{2c}$ refer to the substituted positions.

TABLE 1

(I-I)

[Structure: benzophenone core with R³O, R⁴, R⁵O, R⁶ on left ring; (CH₂)ₙR¹ at position ortho to carbonyl; right ring with R²ᵃ (pos 2), R²ᵇ (pos 3), R²ᶜ (pos 4)]

| Compd. | R¹ | n | R²ᵃ | R²ᵇ | R²ᶜ | R³ | R⁴ | R⁵ | R⁶ |
|---|---|---|---|---|---|---|---|---|---|
| 1 | OCH₃ | 2 | H | H | H | H | H | H | H |
| 2 | OCH₃ | 2 | H | H | H | H | H | H | Br |
| 3 | OCH₃ | 2 | H | H | H | H | H | H | Ph |
| 4 | OCH₃ | 2 | H | H | H | H | H | H | COCH₃ |
| 5 | CO₂CH₃ | 1 | H | H | H | H | H | H | CH₂CH₃ |
| 6 | CO₂CH₃ | 1 | 3-OCH₃ | H | H | H | H | H | CH₂CH₃ |
| 7 | OCH₃ | 2 | H | H | H | H | H | H | CH₂CH₃ |
| 8 | CO₂CH₃ | 1 | 4-OCH₃ | H | H | H | H | H | CH₂CH₃ |
| 9 | OCH₃ | 2 | 4-OCH₃ | H | H | H | H | H | CH₂CH₃ |
| 10 | CON(CH₃)CH₂CH₂OCH₃ | 1 | 4-OCH₃ | H | H | H | H | H | CH₂CH₃ |
| 11 | OCH₃ | 2 | 4-NO₂ | H | H | H | H | H | CH₂CH₃ |
| 12 | OCH₂CH₂OCH₃ | 2 | 4-OCH₃ | H | H | H | H | H | CH₂CH₃ |
| 13 | CON(CH₂CH₂OH)₂ | 1 | 4-OCH₃ | H | H | H | H | H | CH₂CH₃ |
| 14 | CON(CH₃)CH₂CH₂OH | 1 | 4-OCH₃ | H | H | H | H | H | CH₂CH₃ |
| 15 | CO₂CH₃ | 1 | 4-OCH₃ | H | H | H | H | H | I |
| 16 | N-methyl-N-(pyridin-3-ylmethyl)acetamide group | 1 | 4-OCH₃ | H | H | H | H | H | CH₂CH₃ |
| 17 | 4-(2-cyanophenyl)piperazin-1-yl acetyl group | 1 | 4-OCH₃ | H | H | H | H | H | CH₂CH₃ |
| 18 | CO₂CH₃ | 1 | 4-OCH₃ | H | H | H | H | CH₂CH=CH₂ | H |
| 19 | CO₂CH₃ | 1 | 4-OCH₃ | H | H | H | H | H | H |
| 20 | CO₂CH₃ | 1 | 4-OH | H | H | H | H | H | H |
| 21 | 3-hydroxypiperidin-1-yl acetyl group | 1 | 4-OCH₃ | H | H | H | H | H | CH₂CH₃ |
| 22 | 3-(hydroxymethyl)piperidin-1-yl acetyl group | 1 | 4-OCH₃ | H | H | H | H | H | CH₂CH₃ |
| 23 | 3-carbamoylpiperidin-1-yl acetyl group | 1 | 4-OCH₃ | H | H | H | H | H | CH₂CH₃ |

TABLE 1-continued

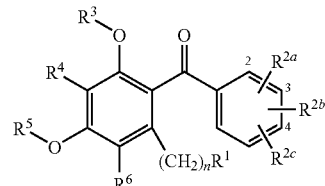

(I-I)

| Compd. | R¹ | n | R²ᵃ | R²ᵇ | R²ᶜ | R³ | R⁴ | R⁵ | R⁶ |
|---|---|---|---|---|---|---|---|---|---|
| 24 | 1-acetylpiperidine-4-carboxamide | 1 | 4-OCH₃ | H | H | H | H | H | CH₂CH₃ |
| 25 | 1-acetyl-3-hydroxypyrrolidine | 1 | 4-OCH₃ | H | H | H | H | H | CH₂CH₃ |
| 26 | CON(CH₃)CH₂CH(OH)CH₂OH | 1 | 4-OCH₃ | H | H | H | H | H | CH₂CH₃ |
| 27 | CO₂CH₃ | 1 | 4-OCH₃ | H | H | CH₃ | H | H | H |
| 28 | N-(pyridin-3-ylmethyl)acetamide | 1 | 4-OCH₃ | H | H | H | H | H | CH₂CH₃ |
| 29 | CO₂CH₃ | 1 | 3-OCH₃ | 4-OCH₃ | H | H | H | H | CH₂CH₃ |
| 30 | 1-acetyl-4-phenylpiperazine | 1 | 4-OCH₃ | H | H | H | H | H | CH₂CH₃ |
| 31 | 1-acetyl-4-hydroxy-4-phenylpiperidine | 1 | 4-OCH₃ | H | H | H | H | H | CH₂CH₃ |
| 32 | 1-acetyl-4-(pyrimidin-2-yl)piperazine | 1 | 4-OCH₃ | H | H | H | H | H | CH₂CH₃ |
| 33 | CON(CH₂CH₂OH)CH₂CH₂OCH₃ | 1 | 4-OCH₃ | H | H | H | H | H | CH₂CH₃ |
| 34 | OCH₂CH(OH)CH₂OH | 2 | 2-F | 4-OCH₃ | H | H | H | H | CH₂CH₃ |

TABLE 1-continued (I-I)

[Structure: R³O, R⁴, R⁵O, R⁶ substituted benzoyl group connected to phenyl ring bearing R²ᵃ, R²ᵇ, R²ᶜ with (CH₂)ₙR¹ substituent]

| Compd. | R¹ | n | R²ᵃ | R²ᵇ | R²ᶜ | R³ | R⁴ | R⁵ | R⁶ |
|---|---|---|---|---|---|---|---|---|---|
| 35 | [1-acetyl-4-(3-methoxyphenyl)piperazine] | 1 | 4-OCH₃ | H | H | H | H | H | CH₂CH₃ |
| 36 | [1-acetyl-4-acetylpiperazine] | 1 | 4-OCH₃ | H | H | H | H | H | CH₂CH₃ |
| 37 | [1-acetyl-4-methylpiperazine] | 1 | 4-OCH₃ | H | H | H | H | H | CH₂CH₃ |
| 38 | [2-acetyl-6,7-dimethoxy-1,2,3,4-tetrahydroisoquinoline] | 1 | 4-OCH₃ | H | H | H | H | H | CH₂CH₃ |
| 39 | [N-methyl-N-(2-furylmethyl)acetamide] | 1 | 4-OCH₃ | H | H | H | H | H | CH₂CH₃ |
| 40 | [1-acetyl-4-(2-hydroxyethyl)piperazine] | 1 | 4-OCH₃ | H | H | H | H | H | CH₂CH₃ |
| 41 | [1-acetyl-4-phenylpiperazine] | 1 | 3-OCH₃ | 4-OCH₃ | H | H | H | H | CH₂CH₃ |
| 42 | CON(CH₃)₂ | 1 | 4-OCH₃ | H | H | H | H | H | CH₂CH₃ |

TABLE 1-continued (I-I)

[Structure: benzophenone with R³O, R⁴, R⁵O, R⁶, (CH₂)ₙR¹ on one ring and R²ᵃ, R²ᵇ, R²ᶜ on the other ring at positions 2, 3, 4]

| Compd. | R¹ | n | R²ᵃ | R²ᵇ | R²ᶜ | R³ | R⁴ | R⁵ | R⁶ |
|---|---|---|---|---|---|---|---|---|---|
| 43 | [1-acetyl-4-(3-hydroxyphenyl)piperazine] | 1 | 4-OCH₃ | H | H | H | H | H | CH₂CH₃ |
| 44 | [1-acetylmorpholine] | 1 | 4-OCH₃ | H | H | H | H | H | CH₂CH₃ |
| 45 | [N-(3-(2-oxopyrrolidin-1-yl)propyl)acetamide] | 1 | 4-OCH₃ | H | H | H | H | H | CH₂CH₃ |
| 46 | OCH₂CH(OH)CH₂OH | 2 | 4-OCH₃ | H | H | H | H | H | CH₂CH₃ |
| 47 | CONHCH(CH₂OH)₂ | 1 | 4-OCH₃ | H | H | H | H | H | CH₂CH₃ |
| 48 | CONHCCH₃(CH₂OH)₂ | 1 | 4-OCH₃ | H | H | H | H | H | CH₂CH₃ |
| 49 | CON(CH₂CH₂OH)₂ | 1 | 3-OCH₃ | 4-OCH₃ | H | H | H | H | CH₂CH₃ |
| 50 | CON(CH₂CH₂OH)₂ | 1 | 4-F | H | H | H | H | H | CH₂CH₃ |
| 51 | OCH₂CH(OH)CH₂OH | 2 | 3-OCH₃ | 4-OCH₃ | H | H | H | H | CH₂CH₃ |
| 52 | OCH₂CH(OH)CH₂OH | 2 | 3-F | 4-OCH₃ | H | H | H | H | CH₂CH₃ |
| 53 | OCH₂CH(OH)CH₂OH | 2 | 3-OCH₃ | 4-OCH₃ | 5-OCH₃ | H | H | H | CH₂CH₃ |
| 54 | [2-acetyl-6,7-dimethoxy-1,2,3,4-tetrahydroisoquinoline] | 1 | 4-F | H | H | H | H | H | CH₂CH₃ |
| 55 | [1-acetyl-4-phenylpiperazine] | 1 | 4-OH | H | H | H | H | H | CH₂CH₃ |
| 56 | CON(CH₂CH₂OH)CH₂CH₂OCH₃ | 1 | 3-OCH₃ | 4-OCH₃ | H | H | H | H | CH₂CH₃ |
| 57 | OCH₂CH(OH)CH₂OH | 2 | 3-Cl | 4-F | H | H | H | H | CH₂CH₃ |
| 58 | OCH₂CH(OH)CH₂OH | 2 | 3-(3-hydroxyphenyl) | 4-OCH₃ | H | H | H | H | CH₂CH₃ |

TABLE 1-continued

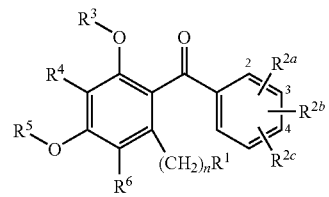

(I-I)

| Compd. | R¹ | n | R²ᵃ | R²ᵇ | R²ᶜ | R³ | R⁴ | R⁵ | R⁶ |
|---|---|---|---|---|---|---|---|---|---|
| 59 | OCH₂CH(OH)CH₂OH | 2 | 3-[3-methylphenyl with OCH₃] | 4-OCH₃ | H | H | H | H | CH₂CH₃ |
| 60 | OCH₂CH₂OH | 2 | 4-OCH₃ | H | H | H | H | H | CH₂CH₃ |
| 61 | [1-acetyl-4-(hydroxymethyl)piperidine] | 1 | 4-OCH₃ | H | H | H | H | H | CH₂CH₃ |
| 62 | OCH₂CH₂OH | 2 | H | H | H | H | H | H | CH₂CH₃ |
| 63 | OCH₂CH₂OH | 2 | 3-OH | 4-OCH₃ | H | H | H | H | CH₂CH₃ |
| 64 | [4-acetyl-1-(3-chlorophenyl)piperazin-2-one] | 1 | 4-OCH₃ | H | H | H | H | H | CH₂CH₃ |
| 65 | OCH₂CH₂OH | 2 | 4-OCHF₂ | H | H | H | H | H | CH₂CH₃ |
| 66 | CON(CH₂CH₂OH)CH₂CH₂OCH₃ | 1 | 4-F | H | H | H | H | H | CH₂CH₃ |
| 67 | [1-acetyl-4-(methylsulfonyl)piperidine] | 1 | 4-OCH₃ | H | H | H | H | H | CH₂CH₃ |
| 68 | [4-acetyl-1-phenylpiperazin-2-one] | 1 | 4-OCH₃ | H | H | H | H | H | CH₂CH₃ |
| 69 | [N-acetyl-N-(2-hydroxyethyl)-furfurylamine] | 1 | 4-OCH₃ | H | H | H | H | H | CH₂CH₃ |

TABLE 1-continued

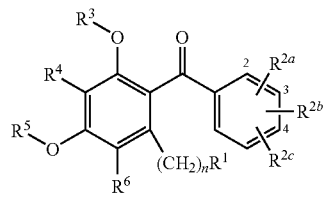

(I-I)

| Compd. | R¹ | n | R²ᵃ | R²ᵇ | R²ᶜ | R³ | R⁴ | R⁵ | R⁶ |
|---|---|---|---|---|---|---|---|---|---|
| 75 | ![piperazinone-benzonitrile] | 1 | H | H | H | H | H | H | $CH_2CH_3$ |
| 76 | $CON(CH_2CH_2OH)_2$ | 1 | H | H | H | H | H | H | $CH_2CH_3$ |
| 77 | $CON(CH_2CH_2OH)CH_2CH_2OCH_3$ | 1 | H | H | H | H | H | H | $CH_2CH_3$ |
| 78 | ![acetylpiperidinyl-methanol] | 1 | H | H | H | H | H | H | $CH_2CH_3$ |
| 79 | $CON(CH_2CH_2OH)CH_2CH_2OCH_3$ | 1 | 3-OH | H | H | H | H | H | $CH_2CH_3$ |
| 80 | $CON(CH_2CH_2OH)_2$ | 1 | 4-OH | H | H | H | H | H | $CH_2CH_3$ |
| 81 | $CON(CH_2CH_2OH)CH_2CH_2OCH_3$ | 1 | 4-OH | H | H | H | H | H | $CH_2CH_3$ |
| 82 | ![acetylpiperazinone-phenyl] | 1 | 4-F | H | H | H | H | H | $CH_2CH_3$ |
| 83 | $CON(CH_2CH_2OH)_2$ | 1 | 3-OH | 4-$OCH_3$ | H | H | H | H | $CH_2CH_3$ |
| 84 | $CON(CH_2CH_2OH)CH_2CH_2OCH_3$ | 1 | 3-OH | 4-$OCH_3$ | H | H | H | H | $CH_2CH_3$ |
| 85 | $CON(CH_2CH_2OH)_2$ | 1 | 3-F | 4-$OCH_3$ | H | H | H | H | $CH_2CH_3$ |
| 86 | $CON(CH_2CH_2OH)CH_2CH_2OCH_3$ | 1 | 3-F | 4-$OCH_3$ | H | H | H | H | $CH_2CH_3$ |
| 87 | $CON(CH_2CH_2OH)_2$ | 1 | 4-$OCF_3$ | H | H | H | H | H | $CH_2CH_3$ |
| 88 | $CON(CH_2CH_2OH)CH_2CH_2OCH_3$ | 1 | 4-$OCF_3$ | H | H | H | H | H | $CH_2CH_3$ |
| 89 | $CON(CH_2CH_2OCH_3)_2$ | 1 | 3-OH | 4-$OCH_3$ | H | H | H | H | $CH_2CH_3$ |
| 90 | $CON(CH_2CH_2OH)_2$ | 1 | 4-$OCHF_2$ | H | H | H | H | H | $CH_2CH_3$ |
| 91 | $CON(CH_2CH_2OH)CH_2CH_2OCH_3$ | 1 | 4-$OCHF_2$ | H | H | H | H | H | $CH_2CH_3$ |
| 92 | $CON(CH_2CH_2OH)_2$ | 1 | 3-OH | 4-$CH_3$ | H | H | H | H | $CH_2CH_3$ |
| 93 | $CON(CH_2CH_2OH)CH_2CH_2OCH_3$ | 1 | 3-OH | 4-$CH_3$ | H | H | H | H | $CH_2CH_3$ |
| 94 | $CON(CH_2CH_2OH)CH_2CH_2CH_2OH$ | 1 | 4-$OCF_3$ | H | H | H | H | H | $CH_2CH_3$ |
| 95 | $CON(CH_2CH_2OH)CH_2CH_2OCH_3$ | 1 | 4-$SCH_3$ | H | H | H | H | H | $CH_2CH_3$ |
| 96 | $CON(CH_2CH_2OH)_2$ | 1 | 4-$SO_2CH_3$ | H | H | H | H | H | $CH_2CH_3$ |
| 97 | $CON(CH_2CH_2OH)CH_2CH_2OCH_3$ | 1 | 4-$SO_2CH_3$ | H | H | H | H | H | $CH_2CH_3$ |
| 98 | ![acetylpyrrolidinyl-methanol] | 1 | 4-$OCH_3$ | H | H | H | H | H | $CH_2CH_3$ |
| 99 | $CON(CH_2CH_2OH)CH_2CH_2CH_2OH$ | 1 | 3-$OCH_3$ | 4-$OCH_3$ | H | H | H | H | $CH_2CH_3$ |

TABLE 1-continued (I-I)

[Structure: benzophenone with R³O-, R⁴-, R⁵O-, R⁶- on one ring (with (CH₂)ₙR¹ at position 2), and R²ᵃ (pos 2), R²ᵇ (pos 3/4), R²ᶜ (pos 4) on the other ring]

| Compd. | R¹ | n | R²ᵃ | R²ᵇ | R²ᶜ | R³ | R⁴ | R⁵ | R⁶ |
|---|---|---|---|---|---|---|---|---|---|
| 100 | [N-acetyl-N-(2-hydroxyethyl)-furfurylamine group: CH₃C(O)N(CH₂CH₂OH)(CH₂-furan-2-yl)] | 1 | 3-OCH₃ | 4-OCH₃ | H | H | H | H | CH₂CH₃ |
| 101 | CON(CH₂CH₂OH)CH₂CH₂CH₂OH | 1 | 4-OCH₃ | H | H | H | H | H | CH₂CH₃ |
| 102 | CON(CH₂CH₂OH)CH₂CH₂OCH₃ | 1 | 3-OCH₂CH₂—OH | 4-OCH₃ | H | H | H | H | CH₂CH₃ |
| 103 | CON(CH₂CH₂OH)CH₂CH₂OCH₃ | 1 | 3-OCH₂CH₂—OCH₃ | 4-OCH₃ | H | H | H | H | CH₂CH₃ |
| 104 | CON(CH₂CH₂OH)CH₂CH₂OCH₃ | 1 | 3-[OCH₂CH₂-morpholino] | 4-OCH₃ | H | H | H | H | CH₂CH₃ |
| 105 | CON(CH₂CH₂OH)CH₂CH₂OCH₃ | 1 | 3-OCH₃ | 4-OH | H | H | H | H | CH₂CH₃ |
| 106 | CON(CH₂CH₂OCH₃)₂ | 1 | 3-OCH₃ | 4-OH | H | H | H | H | CH₂CH₃ |
| 107 | CON(CH₂CH₂OCH₃)₂ | 1 | 4-SO₂CH₃ | H | H | H | H | H | CH₂CH₃ |
| 108 | CON(CH₂CH₂OH)CH₂CH₂OCH₃ | 1 | 3-OCH₃ | 4-OCH₂—CH₂OH | H | H | H | H | CH₂CH₃ |
| 109 | CON(CH₂CH₂OH)CH₂CH₂OCH₃ | 1 | 3-OCH₃ | 4-OCH₂—CH₂OCH₃ | H | H | H | H | CH₂CH₃ |
| 110 | CON(CH₂CH₂OH)CH₂CH₂OCH₃ | 1 | 3-OCH₃ | 4-[OCH₂CH₂-morpholino] | H | H | H | H | CH₂CH₃ |
| 111 | [N-acetyl-N-(2-morpholinoethyl)-(2-hydroxyethyl)amine group: CH₃C(O)N(CH₂CH₂-morpholino)(CH₂CH₂OH)] | 1 | 4-OCH₃ | H | H | H | H | H | CH₂CH₃ |
| 112 | CON(CH₂CH₂OCH₃)CH₂CH₂N(CH₃)₂ | 1 | 3-OCH₃ | 4-OCH₃ | H | H | H | H | CH₂CH₃ |
| 113 | CON(CH₂CH₂OCH₃)CH₂CH₂N(CH₃)₂ | 1 | 4-OCH₃ | H | H | H | H | H | CH₂CH₃ |
| 114 | CON(CH₂CH₂OH)CH₂CH₂N—(CH₂CH₃)₂ | 1 | 3-OCH₃ | 4-OCH₃ | H | H | H | H | CH₂CH₃ |

TABLE 1-continued

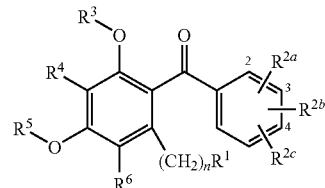

(I-I)

| Compd. | R¹ | n | R²ᵃ | R²ᵇ | R²ᶜ | R³ | R⁴ | R⁵ | R⁶ |
|---|---|---|---|---|---|---|---|---|---|
| 115 | ![structure: acetyl-N(CH2CH2-morpholine)(CH2CH2OCH3)] | 1 | 3-OCH₃ | 4-OCH₃ | H | H | H | H | CH₂CH₃ |
| 116 | ![structure: acetyl-N(CH2CH2-morpholine)(CH2CH2OCH3)] | 1 | 4-OCH₃ | H | H | H | H | H | CH₂CH₃ |
| 117 | CON(CH₂CH₂CH₂OH)CH₂CH₂—OCH₃ | 1 | 4-OCH₃ | H | H | H | H | H | CH₂CH₃ |
| 118 | CON(CH₂CH₂OH)CH₂CH₂—OCH₃ | 1 | 4-OCH₃ | H | H | H | H | H | CH₂CH₃ |
| 119 | CON(CH₂CH₂CH₂OH)CH₂CH₂—OCH₃ | 1 | 3-OCH₃ | 4-OCH₃ | H | H | H | H | CH₂CH₃ |
| 120 | CON(CH₂CH₂OH)CH₂CH₂—OCH₃ | 1 | 3-OCH₃ | 4-OCH₃ | H | H | H | H | CH₂CH₃ |
| 121 | CON(CH₂CH₂OH)₂ | 1 | 4-OCH₂CH₃ | H | H | H | H | H | CH₂CH₃ |
| 122 | CON(CH₂CH₂OH)CH₂CH₂OCH₃ | 1 | 4-OCH₂CH₃ | H | H | H | H | H | CH₂CH₃ |
| 123 | CON(CH₂CH₂OH)₂ | 1 | 4-OCH(CH₃)₂ | H | H | H | H | H | CH₂CH₃ |
| 124 | CON(CH₂CH₂OH)CH₂CH₂OCH₃ | 1 | 4-OCH(CH₃)₂ | H | H | H | H | H | CH₂CH₃ |
| 125 | CON(CH₂CH₂OCH₃)₂ | 1 | 3-OCH₃ | 4-OCH₂CH₂-(N-morpholine) | H | H | H | H | CH₂CH₃ |
| 126 | CON(CH₂CH₂OCH₃)₂ | 1 | 3-OCH₃ | 4-OCH₂—CH₂OH | H | H | H | H | CH₂CH₃ |
| 127 | CON(CH₂CH₂OCH₃)CH₂CH₂—CH₂N(CH₃)₂ | 1 | 3-OCH₃ | 4-OCH₃ | H | H | H | H | CH₂CH₃ |
| 128 | CON(CH₂CH₂OCH₃)CH₂CH₂—CH₂N(CH₃)₂ | 1 | 4-OCH₃ | H | H | H | H | H | CH₂CH₃ |
| 129 | CON(CH₂CH₂OCH₃)CH₂CH₂—N(CH₂CH₃)₂ | 1 | 3-OCH₃ | 4-OCH₃ | H | H | H | H | CH₂CH₃ |
| 130 | CON(CH₂CH₂OCH₃)CH₂CH₂—N(CH₂CH₃)₂ | 1 | 4-OCH₃ | H | H | H | H | H | CH₂CH₃ |
| 131 | ![structure: acetyl-piperidine-morpholine] | 1 | 3-OCH₃ | 4-OCH₃ | H | H | H | H | CH₂CH₃ |

TABLE 1-continued (I-I)

| Compd. | R¹ | n | $R^{2a}$ | $R^{2b}$ | $R^{2c}$ | $R^3$ | $R^4$ | $R^5$ | $R^6$ |
|---|---|---|---|---|---|---|---|---|---|
| 132 | (1-acetylpiperidin-4-yl)morpholine | 1 | 4-OCH$_3$ | H | H | H | H | H | CH$_2$CH$_3$ |
| 133 | N-acetyl-N-(2-methoxyethyl)-2-morpholinoethylamine | 1 | 4-OCH$_2$CH$_3$ | H | H | H | H | H | CH$_2$CH$_3$ |
| 134 | N-acetyl-N-(2-methoxyethyl)-2-morpholinoethylamine | 1 | 4-OCH(CH$_3$)$_2$ | H | H | H | H | H | CH$_2$CH$_3$ |
| 135 | CON(CH$_2$CH$_2$OH)CH$_2$CH$_2$OCH$_3$ | 1 | 4-OCH$_3$ | H | H | H | H | H | Br |
| 136 | CON(CH$_2$CH$_2$OH)CH$_2$CH$_2$OCH$_3$ | 1 | 4-OCH$_3$ | H | H | H | H | H | COCH$_3$ |
| 137 | CON(CH$_2$CH$_2$OH)$_2$ | 1 | 3-OCH$_2$—CH$_2$OCH$_3$ | 4-OCH$_2$—CH$_2$OCH$_3$ | H | H | H | H | CH$_2$CH$_3$ |
| 138 | CON(CH$_2$CH$_2$OH)CH$_2$CH$_2$OCH$_3$ | 1 | 3-OCH$_2$—CH$_2$OCH$_3$ | 4-OCH$_2$—CH$_2$OCH$_3$ | H | H | H | H | CH$_2$CH$_3$ |
| 139 | CON(CH$_2$CH$_2$OCH$_3$)$_2$ | 1 | 3-OCH$_3$ | 4-(2-morpholinoethoxymethyl).HCl | H | H | H | H | CH$_2$CH$_3$ |
| 140 | CON(CH$_2$CH$_2$CH$_2$OCH$_3$)—CH$_2$CH$_2$N(CH$_3$)$_2$ | 1 | 4-OCH$_3$ | H | H | H | H | H | CH$_2$CH$_3$ |
| 141 | CON(CH$_2$CH$_2$CH$_2$OCH$_3$)CH$_2$—CH$_2$N(CH$_3$)$_2$ | 1 | 3-OCH$_3$ | 4-OCH$_3$ | H | H | H | H | CH$_2$CH$_3$ |
| 142 | CON(CH$_2$CH$_2$OCH$_3$)CH$_2$CH$_2$—N(CH$_3$)$_2$.HCl | 1 | 4-OCH$_3$ | H | H | H | H | H | CH$_2$CH$_3$ |
| 143 | CON(CH$_2$CH$_2$OH)$_2$ | 1 | 4-CF$_3$ | H | H | H | H | H | CH$_2$CH$_3$ |
| 144 | CON(CH$_2$CH$_2$OH)CH$_2$CH$_2$OCH$_3$ | 1 | 4-CF$_3$ | H | H | H | H | H | CH$_2$CH$_3$ |
| 145 | CON(CH$_2$CH$_2$OH)$_2$ | 1 | 3-F | 4-F | H | H | H | H | CH$_2$CH$_3$ |
| 146 | CON(CH$_2$CH$_2$OH)CH$_2$CH$_2$OCH$_3$ | 1 | 3-F | 4-F | H | H | H | H | CH$_2$CH$_3$ |

TABLE 1-continued
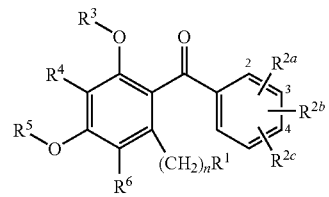
(I-I)
| Compd. | R¹ | n | R²ᵃ | R²ᵇ | R²ᶜ | R³ | R⁴ | R⁵ | R⁶ |
|---|---|---|---|---|---|---|---|---|---|
| 147 | CON(CH₂CH₂OCH₃)₂ | 1 | 3-OCH₃ | 4- (2-methoxyethyl)piperidinyl | H | H | H | H | CH₂CH₃ |
| 148 | CON(CH₂CH₂OCH₃)₂ | 1 | 3-OCH₃ | 4- [1-(2-methoxyethyl)piperidin-4-yl]morpholinyl | H | H | H | H | CH₂CH₃ |
| 149 | CON(CH₂CH₂OCH₃)₂ | 1 | 3-OCH₃ | 4- [3-methoxypropyl]morpholinyl | H | H | H | H | CH₂CH₃ |
| 150 | CON(CH₂CH₂OCH₃)₂ | 1 | 3-OCH₃ | 4- methoxyacetyl-(4-methylpiperazinyl) | H | H | H | H | CH₂CH₃ |

TABLE 2

(I-II)

Structure: Benzene ring with R³O- at position, R⁴, R⁵O-, R⁶ substituents, C(=O)R² and (CH₂)ₙR¹ groups.

| Compd. | R¹ | n | R² | R³ | R⁴ | R⁵ | R⁶ |
|---|---|---|---|---|---|---|---|
| 70 | OCH₂CH(OH)CH₂OH | 2 | 4-pyridyl | H | H | H | CH₂CH₃ |
| 71 | OCH₂CH₂OH | 2 | 3-thienyl | H | H | H | CH₂CH₃ |
| 72 | OCH₂CH₂OH | 2 | 2-thienyl | H | H | H | CH₂CH₃ |
| 73 | OCH₂CH₂OH | 2 | 3-furyl | H | H | H | CH₂CH₃ |
| 74 | CON(CH₂CH₂OH)₂ | 1 | 3-thienyl | H | H | H | CH₂CH₃ |
| 151 | CON(CH₂CH₂OH)CH₂CH₂OCH₃ | 1 | 3-thienyl | H | H | H | CH₂CH₃ |
| 152 | CON(CH₂CH₂OH)₂ | 1 | 3-furyl | H | H | H | CH₂CH₃ |
| 153 | CON(CH₂CH₂OH)CH₂CH₂OCH₃ | 1 | 3-furyl | H | H | H | CH₂CH₃ |
| 154 | 4-acetyl-3-oxopiperazin-1-yl attached to 2-cyanophenyl | 1 | 3-thienyl | H | H | H | CH₂CH₃ |
| 155 | 1-acetyl-4-(hydroxymethyl)piperidin-4-yl group | 1 | 3-thienyl | H | H | H | CH₂CH₃ |
| 156 | CON(CH₂CH₂OCH₃)₂ | 1 | 3-furyl | H | H | H | CH₂CH₃ |
| 157 | CON(CH₂CH₂OH)₂ | 1 | 1,3-benzodioxol-5-yl | H | H | H | CH₂CH₃ |
| 158 | CON(CH₂CH₂OH)CH₂CH₂OCH₃ | 1 | 1,3-benzodioxol-5-yl | H | H | H | CH₂CH₃ |

The pharmacological activity of Compounds (I) is illustrated below referring to a test example.

TEST EXAMPLE 1

Hsp90 Protein Binding Assay
(1) Human N-terminal recombinant Hsp90 protein (region of amino acids 9 to 236) prepared according to the method described in "Cell"; 1997, Vol. 89, p. 239-250 was diluted to 1 μg/mL with Tris-buffered saline (TBS, pH 7.5) and added to each well of a 96-well ELISA assay plate (Greiner) in an amount of 70 μL/well. The plate was incubated overnight at 4° C. to obtain the solid phase coated with the Hsp90 protien.
(2) The supernatant was removed, and Tris-buffered saline containing 1% bovine serum albumin (BSA) was added in an amount of 350 μL/well for blocking.
(3) After the blocking solution was removed, each resulting solid phase was washed by the addition of Tris-buffered saline containing 0.05% Tween 20 (TBST) in an amount of 500 μL/well. This washing procedure was repeated three times.
(4) A test compound having the highest concentration of 0.1 mmol/L was diluted with TBST to prepare eight √10-fold serial dilutions in separate vials. Each of these test compound solutions was added, in an amount of 10 μL/well, to the assay plate containing TBST (90 μL/well) previously added thereto, and the plate was allowed to stand at 24° C. for 1 hour. In this assay, a positive control using dimethyl sulfoxide (final volume: 0.1 μL/well) and a negative control using Radicicol (final concentration: 0.29 μmol/L) were subjected to the same procedure as the test compound, and these controls' were on the same plate which was placed the test compound thereon.
(5) Biotinylated Radicicol represented by formula (G) was added to give a final concentration of 0.1 μmol/L, and the plate was incubated at 24° C. for further 1 hour for competitive binding reaction to measure the binding activity of the test compound to the immobilized Hsp90 protein.

proteins or proteins to which Hsp90 family proteins bind (Hsp90 client proteins) (e.g. anti-tumor agents).

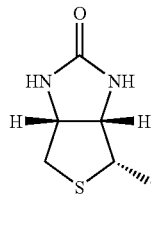 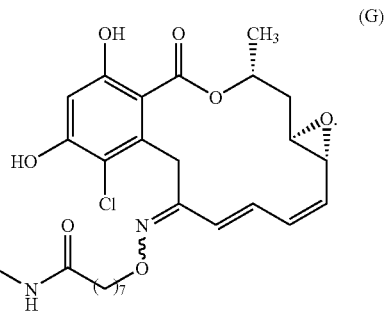

(6) After the reaction mixture of (5) was removed, each resulting solid phase was washed by the addition of TBST in an amount of 500 μL/well. This washing procedure was repeated three times.
(7) Europium-labeled streptoavidin (Wallac Oy) was diluted to a final concentration of 0.1 μg/mL with Assay Buffer (Wallac Oy) and added to the wells of the plate in an amount of 100 μL/well. The plate was incubated at room temperature for 1 hour to carry out biotin-avidin binding reaction.
(8) After the reaction mixture of (7) was removed, each resulting solid phase was washed by the addition of TBST in an amount of 500 μL/well. This washing procedure was repeated four times more.
(9) Enhancement solution (Wallac Oy) was added thereto in an amount of 100 μL/well and color developing reaction was carried out at room temperature for 5 minutes, followed by measurement of time-resolved fluorescence (excitation wavelength: 340 nm, measurement wavelength: 615 nm) using Multilabel Counter (ARVO 1420, Wallac Oy).

The binding rate in each well treated the test compound was calculated from the time-resolved fluorescence measured for each well based on the time-resolved fluorescence measured with the positive control taken as 100% binding rate and that with the negative control taken as 0% binding rate.

In the above method, it was revealed that Compounds 1, 2, 4 to 14, 17, 21 to 25, 30 to 46, 50 to 68, 70 and 72 to 158 inhibited the binding of biotinylated Radicicol to the Hsp90 protein by more than 30% at concentrations below 10 μmol/L and thus have Hsp90 protein-binding activity.

As described above, benzoquinone ansamycin antibiotics such as Geldanamycin and Herbimycin, and Radicicol are known as compounds which bind to Hsp90 family proteins (Cell Stress & Chaperones, 1998, Vol., 3, p. 100-108; J. Med. Chem., 1999, Vol., 42, p. 260-266) and these compounds are all reported to bind to Hsp90 family proteins and inhibit the functions of Hsp90 family proteins, thereby exhibiting pharmacological activities such as anti-tumor activity. Further, it is reported that a Geldanamycin derivative (17-AAG; Invest. New Drugs, 1999, No. 17, p. 361-373) and Radicicol derivatives (Cancer Research, 1999, No. 59, p. 2931-2938; Blood, 2000, No. 96, p. 2284-2291; Cancer Chemotherapy and Pharmacology, 2001, No. 48, p. 435-445; WO96/33989; WO98/18780; WO99/55689; WO02/16369) show anti-tumor effect.

Therefore, Compounds (I) are considered to be useful as therapeutic agents for diseases associated with Hsp90 family proteins or proteins to which Hsp90 family proteins bind (Hsp90 client proteins) (e.g. anti-tumor agents).

Although Compounds (I), prodrugs thereof, or pharmaceutically acceptable salts of Compounds (I) or said prodrugs can be administered as such, it is generally preferred to offer them in the form of various pharmaceutical preparations. Such pharmaceutical preparations are to be used in animals and humans.

The pharmaceutical preparations of the present invention can comprise Compound (I) or a prodrug thereof, or a pharmaceutical salt of Compound (I) or said prodrug as the active ingredient alone or in combination with any other active ingredients for the therapy. These pharmaceutical preparations may be produced by any methods well known in the technical field of pharmaceutics by mixing the active ingredient with one or more pharmaceutically acceptable carriers.

It is desirable to select a route of administration that is most effective for the therapy, examples thereof being oral administration and intravenous and other parenteral administrations.

Examples of the dosage form include tablets and injections.

Preparations suitable for oral administration such as tablets can be produced using, for example, excipients (e.g., lactose and mannitol), disintegrators (e.g., starch), lubricants (e.g., magnesium stearate), binders (e.g., hydroxypropyl cellulose), surfactants (e.g., fatty acid esters) and plasticizers (e.g., glycerin).

Preparations suitable for parenteral administration preferably comprise a sterilized aqueous preparation containing an active compound which is isotonic to the recipient's blood. In the case of an injection, for example, a solution for injection is prepared using a carrier comprising a saline solution, a glucose solution, or a mixture of a saline solution and a glucose solution.

The parenteral preparations may also comprise one or more auxiliary components selected from the excipients, disintegrators, lubricants, binders, surfactants and plasticizers described in the above description of oral preparations and diluents, antiseptics, flavors, etc.

The dose and the administration schedule of Compound (I) or a prodrug thereof, or a pharmaceutical salt of Compound (I) or said prodrug will vary depending upon the administration route, the age and body weight of a patient, and the nature and degree of severeness of the symptom to be treated. In general, in the case of oral administration, the active ingredient is administered in a dose of 0.01 mg to 1 g, preferably-0.05 to 50 mg, per adult once to several times per day. In the case of parenteral administration such as intravenous administration, the active ingredient is administered in a dose of 0.001 to 500 mg, preferably 0.01 to 100 mg, per adult once to several times per day. However, the dose and the administration schedule may vary depending upon various conditions as given above.

Certain embodiments of the present invention are illustrated in the following examples and reference examples.

BEST MODES FOR CARRYING OUT THE INVENTION

EXAMPLE 1

Synthesis of 2,4-dihydroxy-6-(2-methoxyethyl) phenyl=phenyl=ketone (Compound 1)

(Step 1)

Methyl 3,5-dihydroxyphenylacetate (40 g, 0.22 mol) was dissolved in dichloromethane (0.40 L). After the solution was cooled to 4° C., diisopropylethylamine (0.15 L, 0.86 mol) and chloromethyl methyl ether (67 mL, 0.88 mol) were added thereto, followed by stirring at room temperature for 24 hours. To the reaction mixture was added water (0.50 L), and the mixture was extracted with chloroform (0.30 L×2). The organic layer was dried over anhydrous sodium sulfate and then concentrated under reduced pressure. The resulting residue was purified by silica gel column chromatography (ethyl acetate/hexane=4/1-1/1) to obtain methyl 3,5-bis(methoxymethoxy)phenylacetate (43 g, 72%) as a colorless oil.

$^1$H-NMR (CDCl$_3$, 270 MHz) δ (ppm): 6.66-6.62 (m, 3H), 5.14 (s, 4H), 3.69 (s, 3H), 3.56 (s, 2H), 3.47 (s, 6H) APCI-MS (m/z); 269 [M−H]$^−$ (Step 2)

A solution of lithium aluminum hydride (1.0 g, 26 mmol) in tetrahydrofuran (50 mL) was cooled to 4° C., and a solution of methyl 3,5-bis(methoxymethoxy)phenylacetate (5.3 g, 20 mmol) obtained in Example 1, Step 1 in tetrahydrofuran (50 mL) was added dropwise thereto, followed by stirring at 4° C. for 30 minutes. To the reaction mixture was added anhydrous sodium sulfate decahydrate to stop the reaction, and the mixture was stirred at room temperature for 12 hours. The resulting suspension was filtered under reduced pressure, and the filtrate was concentrated under reduced pressure. The resulting residue was purified by silica gel column chromatography (ethyl acetate/hexane=1/9-1/1) to obtain 2-[3,5-bis(methoxymethoxy)phenyl]ethanol (4.6 g, 98%). $^1$H-NMR (CDCl$_3$, 270 MHz) δ (ppm): 6.62 (t, J=2.2 Hz, 1H), 6.58 (d, J=2.2 Hz, 2H), 5.14 (s, 4H), 3.85 (q, J=6.4 Hz, 2H), 3.48 (s, 6H), 2.81 (t, J=6.4 Hz, 2H), 1.42 (t, J=6.4 Hz, 1H)

(Step 3)

2-[3,5-Bis(methoxymethoxy)phenyl]ethanol (4.6 g, 19 mmol) obtained in Example 1, Step 2 was dissolved in N,N-dimethylformamide (40 mL), and a 60% sodium hydride dispersion in mineral oil (0.30 g, 7.5 mmol) was added thereto at 4° C. in an atmosphere of nitrogen, followed by stirring at 4° C. for 1 hour. Methyl iodide (3.6 mL, 58 mmol) was added dropwise to the reaction mixture, followed by stirring at 4° C. for 3 hours. To the reaction mixture were added a saturated aqueous solution of ammonium chloride (30 mL) and water (0.2 L), and the mixture was extracted with ethyl acetate (0.20 L). The organic layer was dried over anhydrous sodium sulfate and then concentrated under reduced pressure. The resulting residue was purified by silica gel column chromatography (ethyl acetate/hexane=1/9-1/2) to obtain a quantitative yield of 1,3-bis(methoxymethoxy)-5-(2-methoxyethyl) benzene. $^1$H-NMR (CDCl$_3$, 270 MHz) δ (ppm): 6.61-6.59 (m, 3H), 5.14 (s, 4H), 3.59 (t, J=7.1 Hz, 2H), 3.48 (s, 6H), 3.36 (s, 3H), 2.83 (t, J=7.1 Hz, 2H)

FAB-MS (m/z); 225 [M−OCH$_3$]$^+$ (Step 4)

1,3-Bis(methoxymethoxy)-5-(2-methoxyethyl)benzene (5.00 g, 19.5 mmol) obtained in Example 1, Step 3 was dissolved in N,N-dimethylformamide (40 mL). After the solution was cooled to 4° C., N-bromosuccinimide (3.47 g, 19.5 mmol) was added thereto, followed by stirring for 1 hour. To the reaction mixture was added water (0.10 L), and the mixture was extracted with a mixed solvent of hexane and ethyl acetate (hexane/ethyl acetate=1/1, 0.30 L). The organic layer was dried over anhydrous sodium sulfate and then concentrated under reduced pressure. The resulting residue was purified by silica gel column chromatography (ethyl acetate/hexane=1/9-1/2) to obtain 3,5-bis(methoxymethoxy)-2-bromo-1-(2-methoxyethyl)benzene (5.7 g, 87%).

$^1$H-NMR (CDCl$_3$, 270 MHz) δ (ppm): 6.75 (d, J=2.7 Hz, 1H), 6.68 (d, J=2.7 Hz, 1H), 5.22 (s, 2H), 5.14 (s, 2H), 3.61 (t, J=7.1 Hz, 2H), 3.52 (s, 3H), 3.47 (s, 3H), 3.37 (s, 3H), 3.03 (t, J=7.1 Hz, 2H)

FAB-MS (m/z) 335, 337 [M+H]$^+$ (Step 5)

3,5-Bis(methoxymethoxy)-2-bromo-1-(2-methoxyethyl)-benzene (5.3 g, 16 mmol) obtained in Example 1, Step 4 was dissolved in tetrahydrofuran (0.10 L). After the solution was cooled to −78° C., a 1.6 mol/L solution of n-butyllithium in hexane (30 mL, 48 mmol) was added thereto, followed by stirring for 5 minutes. Benzaldehyde (6.4 mL, 62 mmol) was added to the reaction mixture, followed by stirring for 1 hour. To the reaction mixture was added a saturated aqueous solution of ammonium chloride (30 mL), and the mixture was extracted with ethyl acetate (0.30 L). The organic layer was dried over anhydrous sodium sulfate and then concentrated under reduced pressure. The resulting residue was purified by silica gel column chromatography (ethyl acetate/hexane=1/9-1/2) to obtain [2,4-bis(methoxymethoxy)-6-(2-methoxyethyl)phenyl]phenylmethanol (3.0 g, 53%). Then, [2,4-bis(methoxymethoxy)-6-(2-methoxyethyl)phenyl]phenylmethanol (3.0 g, 8.4 mmol) was dissolved in dichloromethane (50 mL), and Molecular Sieves 4 Å (7.9 g) and pyridinium dichromate (7.9 g, 21 mmol) were added thereto, followed by stirring at room temperature for 5 hours. The reaction mixture was filtered, and the filtrate was concentrated under reduced pressure. The resulting residue was purified by silica gel column chromatography (ethyl acetate/hexane=1/9-1/2) to obtain 2,4-bis(methoxymethoxy)-6-(2-methoxyethyl)phenyl=phenyl=ketone (2.9 g, 96%).

$^1$H-NMR (CDCl$_3$, 270 MHz) δ (ppm): 7.85-7.39 (m, 5H), 6.74 (d, J=2.1 Hz, 1H), 6.69 (d, J=2.1 Hz, 1H), 5.20 (s, 2H), 4.97 (s, 2H), 3.51 (s, 3H), 3.48 (t, J=7.1 Hz, 2H), 3.20 (s, 3H), 3.19 (s, 3H), 2.71 (t, J=7.1 Hz, 2H) APCI-MS (m/z); 359 [M−H]$^−$ (Step 6)

2,4-Bis(methoxymethoxy)-6-(2-methoxyethyl) phenyl=phenyl=ketone (0.14 g, 0.38 mmol) obtained in Example 1, Step 5 was dissolved in methanol (3.0 mL), and a 4 mol/L solution of hydrogen chloride in 1,4-dioxane (3.0 mL) was added thereto, followed by stirring at room temperature for 1 hour. The reaction mixture was concentrated under reduced pressure, and the resulting residue was purified by preparative thin layer chromatography (methanol/chloroform=1/9) to obtain a quantitative yield of Compound 1.

¹H-NMR (CDCl₃, 270 MHz) δ (ppm): 9.91 (s, 1H), 7.66-7.42 (m, 5H), 6.36 (s, 2H), 5.60 (brs, 1H), 3.29 (t, J=6.8 Hz, 2H), 3.15 ('s, 3H), 2.51 (t, J=6.8 Hz, 2H)
APCI-MS (m/z); 271 [M−H]⁻

EXAMPLE 2

Synthesis of 5-bromo-2,4-dihydroxy-6-(2-methoxyethyl)phenyl=phenyl=ketone (Compound 2)

(Step 1)
2,4-Bis(methoxymethoxy)-6 (2-methoxyethyl)phenyl=phenyl=ketone (0.11 g, 0.24 mmol) obtained in Example 1, Step 5 was dissolved in N,N-dimethylformamide (2.0 mL), and N-bromosuccinimide (47 mg, 0.26 mmol) was added thereto, followed by stirring at room temperature for 3 hours. To the reaction mixture was added water (50 mL), and the mixture was extracted with a mixed solvent of hexane and ethyl acetate (hexane/ethyl acetate=1/1, 50 mL). The organic layer was dried over anhydrous sodium sulfate and then concentrated under reduced pressure. The resulting residue was purified by preparative thin layer chromatography (ethyl acetate/hexane=1/2) to obtain 4,6-bis(methoxymethoxy)-3-bromo-2-(2-methoxyethyl)phenyl=phenyl=ketone (0.11 g, 96%).
¹H-NMR (CDCl₃, 270 MHz) δ (ppm): 7.84-7.41 (m, 5H), 6.94 (s, 1H), 5.28 (s, 2H), 4.98 (s, 2H), 3.56 (s, 3H), 3.48 (t, J=7.4 Hz, 2H), 3.22 (s, 3H), 3.19 (s, 3H), 2.94 (t, J=7.4 Hz, 2H)
FAB-MS (m/z); 407, 409 [M−OCH₃]⁺

(Step 2)
In a manner similar to that in Example 1, Step 6, Compound 2 (71 mg, 85%) was obtained from 4,6-bis(methoxymethoxy)-3-bromo-2-(2-methoxyethyl)phenyl=phenyl=ketone (0.11 g, 0.24 mmol) obtained in Example 2, Step 1, using methanol (3.0 mL) and a 4 mol/L solution of hydrogen chloride in 1,4-dioxane (3.0 mL).
¹H-NMR (CDCl₃, 300 MHz) δ (ppm): 8.26 (s, 1H), 7.72-7.40 (m, 5H), 6.61 (s, 1H), 6.05 (s, 1H), 3.31 (t, J=7.1 Hz, 2H), 3.14 (s, 3H), 2.88 (t, J=7.1 Hz, 2H)
APCI-MS (m/z); 349, 351 [M−H]⁻

EXAMPLE 3

Synthesis of 2,4-dihydroxy-6-(2-methoxyethyl)-5-phenylphenyl=phenyl=ketone (Compound 3)

(Step 1)
Methyl 3,5-bis(methoxymethoxy)phenylacetate (43 g, 0.16 mol) obtained in Example 1, Step 1 was dissolved in N,N-dimethylformamide (0.68 L). After the solution was cooled to 4° C., N-bromosuccinimide (28 g, 0.16 mol) was added thereto, followed by stirring for 3 hours, while the temperature of the reaction mixture was raised to room temperature. To the reaction mixture was added water (0.50 L), and the mixture was extracted with a mixed solvent of hexane and ethyl acetate (hexane/ethyl acetate=1/2, 0.40 L×4). The organic layer was washed with a saturated aqueous solution of sodium chloride (50 mL) and dried over anhydrous sodium sulfate, followed by concentration under reduced pressure. The resulting residue was purified by silica gel column chromatography (ethyl acetate/hexane=1/4-1/2) to obtain a quantitative yield of methyl 3,5-bis(methoxymethoxy)-2-bromophenyl-acetate.
¹H-NMR (CDCl₃, 270 MHz) δ (ppm): 6.81 (d, J=2.6 Hz, 1H), 6.69 (d, J=2.6 Hz, 1H), 5.22 (s, 2H), 5.14 (s, 2H), 3.78 (s, 2H), 3.71 (s, 3H), 3.51 (s, 3H), 3.47 (s, 3H),
APCI-MS (m/z); 349, 351 [M+H]⁺

(Step 2)
Methyl 3,5-bis(methoxymethoxy)-2-bromophenylacetate (15.0 g, 43.0 mmol) obtained in Example 3, Step 1 was dissolved in a mixed solvent of 1,2-dimethoxymethane (0.15 L) and water (6.0 mL). To the solution were added phenylboric acid (7.3 g, 60 mmol), bis(tri-o-tolylphosphine)palladium (II) dichloride (0.68 g, 0.86 mmol) and cesium carbonate (42 g, 0.13 mol) in an atmosphere of argon, followed by stirring for 16.5 hours under heating and reflux. After cooling to room temperature, the reaction mixture was filtered under reduced pressure, and the filtrate was concentrated under reduced pressure. To the resulting residue was added water (0.50 L), followed by extraction with ethyl acetate (0.40 L×2). The organic layer was dried over anhydrous sodium sulfate and then concentrated under reduced pressure. The resulting residue was purified by silica gel column chromatography (ethyl acetate/hexane=1/4-1/3) to obtain a quantitative yield of methyl 3,5-bis(methoxymethoxy)-2-phenylphenylacetate.
¹H-NMR (270 MHz, CDCl₃) δ (ppm): 7.38-7.17 (m, 5H), 6.83 (d, J=2.3 Hz, 1H), 6.72 (d, J=2.3 Hz, 1H), 5.19 (s, 2H), 5.00 (s, 2H), 3.57 (s, 3H), 3.54 (s, 3H), 3.51 (s, 2H), 3.28 (s, 3H)
APCI-MS (m/z); 347 [M+H]⁺

(Step 3)
In a manner similar to that in Example 1, Step 2, 2-[3,5-bis(methoxymethoxy)-2-phenylphenyl]ethanol (0.37 g, 81%) was obtained from methyl 3,5-bis(methoxymethoxy)-2-phenylphenylacetate (0.50 g, 1.4 mmol) obtained in Example 3, Step 2, using lithium aluminum hydride (0.10 g, 2.6 mmol) and tetrahydrofuran (10 mL).
¹H-NMR (CDCl₃, 270 MHz) δ (ppm): 7.18-7.40 (m, 5H), 6.78 (d, J=2.4 Hz, 1H), 6.71 (d, J=2.4 Hz, 1H), 5.20 (s, 2H), 4.99 (s, 2H), 3.61 (t, J=7.2 Hz, 2H), 3.52 (s, 3H), 3.28 (s, 3H), 2.67 (t, J=7.2 Hz, 2H),
FAB-MS (m/z) 319 [M+H]⁺

(Step 4)
2-[3,5-Bis(methoxymethoxy)-2-phenylphenyl]ethanol (1.2 g, 3.7 mmol) obtained in Example 3, Step 3 was dissolved in N,N-dimethylformamide (15 mL), and a 60% sodium hydride dispersion in mineral oil (0.30 g, 7.5 mmol) was added thereto in an atmosphere of nitrogen, followed by stirring at 4° C. for 4 minutes. After methyl iodide (0.70 mL, 11 mmol) was added dropwise to the reaction mixture, the mixture was stirred at 4° C. for 1 hour, followed by further stirring for 48 hours, while the temperature of the mixture was raised to room temperature. To the reaction mixture was added water (10 mL) and a saturated aqueous solution of ammonium chloride (20 mL), and the mixture was extracted with ethyl acetate (0.10 L). The organic layer was washed with water (0.10 L) and dried over anhydrous sodium sulfate, followed by concentration under reduced pressure. The resulting residue was purified by silica gel column chromatography (ethyl acetate/hexane=1/9-1/2) to obtain 3,5-bis(methoxymethoxy)-1-(2-methoxyethyl)-2-phenylbenzene (1.1 g, 91%).
¹H-NMR (CDCl₃, 270 MHz) δ (ppm): 7.18-7.41 (m, 5H), 6.76 (d, J=2.5 Hz, 1H), 6.71 (d, J=2.5 Hz, 1H), 5.19 (s, 2H), 4.98 (s, 2H), 3.51 (s, 3H), 3.38 (t, J=7.3 Hz, 2H), 3.27 (s, 3H), 3.19 (s, 3H), 2.66 (t, J=7.3 Hz, 2H)
FAB-MS (m/z); 333 [M+H]⁺

(Step 5)

In a manner similar to that in Example 1, Step 4, 1,5-bis(methoxymethoxy)-2-bromo-3-(2-methoxyethyl)-4-phenylbenzene (1.3 g, 96%) was obtained from 3,5-bis(methoxymethoxy)-1-(2-methoxyethyl)-2-phenylbenzene (1.1 g, 3.3 mmol) obtained in Example 3, Step 4, using N-bromosuccinimide (0.59 g, 3.3 mmol) and N,N-dimethylformamide (20 mL).

$^1$H-NMR (CDCl$_3$, 270 MHz) δ (ppm): 7.40-7.34 (m, 3H), 7.19-7.15 (m, 2H), 6.94 (s, 1H), 5.27 (s, 2H), 4.97 (s, 2H), 3.56 (s, 3H), 3.38 (dd, J=7.6, 8.6 Hz, 2H), 3.26 (s, 3H), 3.16 (s, 3H), 2.66 (dd, J=7.6, 8.6 Hz, 2H)

FAB-MS (m/z); 411, 413 [M−H]$^-$ (Step 6)

In a manner similar to that in Example 1, Step 5, [4,6-bis(methoxymethoxy)-2-(2-methoxyethyl)-3-phenylphenyl]-phenylmethanol (0.12 g, 51%) was obtained from 1,5-bis(methoxymethoxy)-2-bromo-3-(2-methoxyethyl)-4-phenylbenzene (0.22 g, 0.54 mmol) obtained in Example 3, Step 5, using a 1.6 mol/L solution of n-butyllithium in hexane (1.0 mL, 1.6 mmol), benzaldehyde (0.22 mL, 2.2 mmol) and tetrahydrofuran (9.0 mL). Further, 4,6-bis(methoxymethoxy)-2-(2-methoxyethyl)-3-phenylphenyl=phenyl=ketone (56.0 mg, 68%) was obtained from [4,6-bis(methoxymethoxy)-2-(2-methoxyethyl)-3-phenylphenyl]-phenylmethanol (82 mg, 0.19 mmol), using Molecular Sieves 4 Å (0.20 g), pyridinium dichromate (0.20 g, 0.53 mmol) and dichloromethane (2.0 mL).

$^1$H-NMR (CDCl$_3$, 270 MHz) δ (ppm) 7.92-7.89 (m, 2H), 7.76-7.23 (m, 8H), 6.93 (s, 1H), 5.04 (s, 2H), 5.02 (s, 2H), 3.30 (s, 3H), 3.25 (s, 3H), 3.17 (t, J=7.4 Hz, 2H), 2.88 (s, 3H), 2.59 (t, J=7.4 Hz, 2H)

APCI-MS (m/z); 437 [M+H]$^+$ (Step 7)

In a manner similar to that in Example 1, Step 6, Compound 3 (27 mg, 63%) was obtained from 4,6-bis(methoxymethoxy)-2-(2-methoxyethyl)-3-phenylphenyl=phenyl=ketone (54 mg, 0.12 mmol) obtained in Example 3, Step 6, using a 4 mol/L solution of hydrogen chloride in 1,4-dioxane (3.0 mL) and methanol (3.0 mL).

$^1$H-NMR (CDCl$_3$, 270 MHz) δ (ppm): 8.92 (s, 1H), 7.75-7.72 (m, 2H), 7.55-7.26 (m, 8H), 6.56 (s, 1H), 5.03 (s, 1H), 3.05 (t, J=7.3 Hz, 2H), 2.93 (s, 3H), 2.47 (t, J=7.3 Hz, 2H)

FAB-MS (m/z); 349 [M+H]$^+$

EXAMPLE 4

Synthesis of 5-acetyl-2,4-dihydroxy-6-(2-methoxyethyl)phenyl=phenyl=ketone (Compound 4)

(Step 1)

2,4-Bis(methoxymethoxy)-6-(2-methoxyethyl)phenyl=phenyl=ketone (1.4 g, 3.8 mmol) obtained in Example 1, Step 5 was dissolved in chloroform (30 ml). After the solution was cooled to 4° C., iodine (0.97 g, 3.8 mmol) and [bis(trifluoroacetoxy)iodo]benzene (1.6 g, 3.8 mmol) were added thereto, followed by stirring for 4 hours while the temperature of the reaction mixture was raised to room temperature. To the reaction mixture were added a saturated aqueous solution of sodium thiosulfate (50 ml) and a saturated aqueous solution of sodium hydrogencarbonate (50 mL) to stop the reaction, followed by liquid separation. The organic layer was dried over anhydrous sodium sulfate and then concentrated under reduced pressure. The resulting residue was purified by silica gel column chromatography (ethyl acetate/hexane=1/4-1/2) to obtain 4,6-bis(methoxymethoxy)-3-iodo-2-(2-methoxyethyl)phenyl=phenyl=ketone (1.6 g, 87%).

$^1$H-NMR (CDCl$_3$, 270 MHz) δ (ppm): 7.84-7.40 (m, 5H), 6.87 (s, 1H), 5.28 (s, 2H), 4.98 (s, 2H), 3.55 (s, 3H), 3.47 (t, J=7.5 Hz, 2H), 3.21 (s, 3H), 3.20 (s, 3H), 2.95 (t, J=7.5 Hz, 2H)

APCI-MS (m/z); 487 [M+H]$^+$ (Step 2)

4,6-Bis(methoxymethoxy)-3-iodo-2-(2-methoxyethyl)phenyl=phenyl=ketone (0.14 g, 0.28 mmol) obtained in Example 4, Step 1 was dissolved in toluene (5.0 mL) in an atmosphere of argon. To the solution were added tributyl(1-ethoxyvinyl)tin (0.13 mL, 0.39 mmol) and bis(triphenylphosphine)palladium (II) dichloride (20 mg, 0.029 mmol), followed by stirring at 110° C. for 10 hours. After the reaction mixture was cooled to room temperature, a 10% aqueous solution of ammonium fluoride (20 mL) was added thereto, and the mixture was stirred at room temperature for 2 hours and then filtered. The filtrate was extracted with ethyl acetate (0.10 L), and 3 mol/L hydrochloric acid (10 mL) was added to the extract, followed by stirring at room temperature for 4 hours. After liquid separation, the organic layer was washed with a saturated aqueous solution of sodium hydrogencarbonate (10' mL), dried over anhydrous sodium sulfate, and then concentrated under reduced pressure. The resulting residue was purified by silica gel column chromatography (ethyl acetate/hexane=1/9-1/3) to obtain 3-acetyl-4,6-bis(methoxymethoxy)-2-(2-methoxyethyl)phenyl=phenyl=ketone (83 mg, 74%).

$^1$H-NMR (CDCl$_3$, 270 MHz) δ (ppm): 7.85-7.40 (m, 5H), 6.89 (s, 1H), 5.23 (s, 2H), 5.00 (s, 2H), 3.51 (s, 3H), 3.39 (t, J=6.9 Hz, 2H), 3.22 (s, 3H), 3.12 (s, 3H), 2.70 (t, J=6.9 Hz, 2H), 2.55 (s, 3H)

APCI-MS (m/z); 403 [M+H]$^+$ (Step 3)

In a manner similar to that in Example 1, Step 6, Compound 4 (45 mg, 80%) was obtained from 3-acetyl-4,6-bis(methoxymethoxy)-2-(2-methoxyethyl)phenyl=phenyl=ketone (72 mg, 0.18 mmol) obtained in Example 4, Step 2, using methanol (2.0 mL) and a 4 mol/L solution of hydrogen chloride in 1,4-dioxane (2.0 mL).

$^1$H-NMR (CDCl$_3$, 270 MHz). δ (ppm): 11.74 (brs, 1H), 8.52 (brs, 1H), 7.79-7.43 (m, 5H), 6.40 (s, 1H), 3.27 (t, J=6.8 Hz, 2H), 3.12 (s, 3H), 2.95 (t, J=6.8 Hz, 2H), 2.64 (s, 3H)

APCI-MS (m/z); 313 [M−H]$^-$

EXAMPLE 5

Synthesis of methyl 2-benzoyl-6-ethyl-3,5-dihydroxy-phenylacetate (Compound 5)

(Step 1)

Methyl 3,5-dihydroxyphenylacetate (30 g, 0.17 mol) was dissolved in acetone (0.50 L), and potassium carbonate (91 g, 0.66 mol) and allyl bromide (0.11 L, 1.3 mol) were added thereto at room temperature. The mixture was stirred for 8 hours under heating and reflux, and then stirred at room temperature for 10 hours. The reaction mixture was concentrated under reduced pressure, and water was added to the resulting residue, followed by extraction with ethyl acetate. The organic layer was washed with a saturated aqueous solution of sodium chloride, dried over anhydrous sodium sulfate, and then concentrated under reduced pressure. The resulting residue was purified by silica gel column chromatography (ethyl acetate/hexane=1/15-1/3) to obtain methyl 3,5-diallyloxyphenylacetate (40 g, 93%).

$^1$H-NMR (CDCl$_3$, 300 MHz) δ (ppm): 6.45 (d, J=2.2 Hz, 2H), 6.41 (t, J=2.2 Hz, 1H), 6.04 (ddt, J=1.0.6, 17.2, 5.1 Hz, 2H), 5.40 (dq, J=17.2, 1.5 Hz, 2H), 5.27 (dq, J=10.6, 1.5 Hz, 2H), 4.49 (dt, J=5.1, 1.5 Hz, 4H), 3.54 (s, 2H), 3.68 (s, 3H)

APCI-MS (m/z); 263 [M+H]$^+$ (Step 2)

Methyl 3,5-diallyloxyphenylacetate (40 g, 0.14 mol) obtained in Example 5, Step 1 was dissolved in trifluoroacetic acid (0.15 L). After the solution was cooled to 4° C., acetic acid (9.5 mL, 0.17 mol) and trifluoroacetic anhydride (40 mL, 0.28 mol) were added thereto, followed by stirring at 4° C. for 3.5 hours. The reaction mixture was gradually added to a saturated aqueous solution of sodium hydrogencarbonate for neutralization, followed by extraction with ethyl acetate. The organic layer was washed with a saturated aqueous solution of sodium chloride, dried over anhydrous sodium sulfate, and then concentrated under reduced pressure. The resulting residue was purified by silica gel column chromatography (ethyl acetate/hexane=1/20-1/6) to obtain methyl 2-acetyl-3,5-diallyloxyphenylacetate (30 g, 65%). $^1$H-NMR (CDCl$_3$, 300 MHz) δ (ppm): 6.43 (d, J=2.2 Hz, 1H), 6.37 (d, J=2.2 Hz, 1H), 6.07-5.98 (m, 2H), 5.44-5.27 (m, 4H), 4.57-4.52 (m, 4H), 3.69 (s, 2H), 3.68 (s, 3H), 2.53 (s, 3H)

ESI-MS (m/z); 305 [M+H]$^+$ (Step 3)

Methyl 2-acetyl-3,5-diallyloxyphenylacetate (1.1 g, 3.7 mmol) obtained in Example 5, Step 2 was dissolved in trifluoroacetic acid (5.0 mL), and triethylsilane (1.2 mL, 7.5 mmol) was added thereto, followed by stirring at room temperature for 1 hour. The reaction mixture was gradually added to a saturated aqueous solution of sodium hydrogencarbonate for neutralization, followed by extraction with ethyl acetate. The organic layer was dried over anhydrous sodium sulfate and then concentrated under reduced pressure. The resulting residue was purified by silica gel column chromatography (hexane-ethyl acetate/hexane=1/4) to obtain methyl 3,5-diallyloxy-2-ethylphenylacetate (0.66 g, 62%).

$^1$H-NMR (CDCl$_3$, 270 MHz) δ (ppm): 6.40 (d, J=2.4 Hz, 1H), 6.39 (d, J=2.4 Hz, 1H), 6.12-5.97 (m, 2H), 5.45-5.24 (m, 4H), 4.51-4.48 (m, 4H), 3.68 (s, 3H), 3.62 (s, 2H), 2.63 (q, J=7.5 Hz, 2H), 1.07 (t, J=7.5 Hz, 3H)

APCI-MS (m/z); 289 [M−H]$^-$ (Step 4)

Methyl 3,5-diallyloxy-2-ethylphenylacetate (0.31 g, 1.3 mmol) obtained in Example 5, Step 3 was dissolved in trifluoroacetic acid (2.0 mL). After the solution was cooled to 4° C., benzoic acid (0.40 g, 3.3 mmol) and trifluoroacetic anhydride (1.0 mL) were added thereto, followed by stirring for 18 hours, while the temperature of the reaction mixture was raised to room temperature. The reaction mixture was gradually added to a saturated aqueous solution of sodium hydrogencarbonate for neutralization, followed by extraction with ethyl acetate. The organic layer was dried over anhydrous sodium sulfate and then concentrated under reduced pressure. The resulting residue was purified by silica gel column chromatography (ethyl acetate/hexane=1/9-1/4) to obtain methyl 3,5-diallyloxy-2-benzoyl-6-ethylphenylacetate (0.29 g, 55%).

$^1$H-NMR (CDCl$_3$, 270 MHz) δ (ppm): 7.83-7.36 (m, 5H), 6.43 (s, 1H), 6.07 (ddt, J=10.5, 17.3, 4.9 Hz, 1H), 5.61 (ddt, J=10.5, 17.3, 4.9 Hz, 1H), 5.45 (dq, J=17.3, 1.6 Hz, 1H), 5.30 (dq, J=10.5, 1.6 Hz, 1H), 5.03-4.92 (m, 2H), 4.58 (dt, J=4.9, 1.6 Hz, 2H), 4.33 (dt, J=4.9, 1.6, Hz, 2H), 3.68 (s, 2H), 3.43 (s, 3H), 2.67 (q, J=7.4 Hz, 2H), 1.10 (t, J=7.4 Hz, 3H)

APCI-MS (m/z); 395 [M+H]$^+$ (Step 5)

Methyl 3,5-diallyloxy-2-benzoyl-6-ethylphenylacetate (0.29 g, 0.72 mmol) obtained in Example 5, Step 4 was dissolved in acetic acid (5.0 mL) in an atmosphere of argon. To the solution were added triphenylphosphine (74 mg, 0.28 mmol) and palladium (II) acetate (16 mg, 0.071 mmol), followed by stirring at 80° C. for 5 hours. To the reaction mixture were further added triphenylphosphine (0.15 g, 0.57 mmol) and palladium (II) acetate (32 mg, 0.14 mmol), followed by stirring at 100° C. for 13 hours. The reaction mixture was cooled to room temperature and then concentrated under reduced pressure. The resulting residue was purified by silica gel column chromatography (ethyl acetate/hexane=1/9-3/1) to obtain Compound 5 (0.23 g, 60%).

$^1$H-NMR (CDCl$_3$, 270 MHz) δ (ppm): 7.66-7.39 (m, 5H), 6.36 (s, 1H), 3.50 (s, 3H), 3.45 (s, 2H), 2.57 (q, J=7.4 Hz, 2H), 1.09 (t, J=7.4 Hz, 3H)

APCI-MS (m/z); 315 [M+H]$^+$

EXAMPLE 6

Synthesis of methyl 2-ethyl-3,5-dihydroxy-6-(3-methoxy-benzoyl)phenylacetate (Compound 6)

(Step 1)

In a manner similar to that in Example 5, Step 4, methyl 3,5-diallyloxy-2-ethyl-6-(3-methoxybenzoyl)phenylacetate was quantitatively obtained from methyl 3,5-diallyloxy-2-ethylphenylacetate (0.33 g, 1.1 mmol) obtained in Example 5, Step 3, using 3-methoxybenzoic acid (0.52 g, 3.4 mmol), trifluoroacetic acid (3.0 mL) and trifluoroacetic anhydride (0.80 mL).

$^1$H-NMR (CDCl$_3$, 270 MHz) δ (ppm): 7.44-7.25 (m, 3H), 7.06 (dt, J=7.8, 2.2 Hz, 1H), 6.43 (s, 1H), 6.07 (ddt, J=10.6, 17.4, 5.0 Hz, 1H), 5.64 (ddt, J=10.6, 17.4, 5.1 Hz, 1H), 5.45 (dq, J=17.4, 1.7 Hz, 1H), 5.31 (dq, J=10.6, 1.7 Hz, 1H), 5.05-4.97 (m, 2H), 4.57 (dt, J=5.0, 1.7 Hz, 2H), 4.35 (dt, J=5.0, 1.7 Hz, 2H), 3.84 (s, 3H), 3.67 (s, 2H), 3.46 (s, 3H), 2.66 (q, J=7.5 Hz, 2H), 1.10 (t, J=7.5 Hz, 3H)

APCI-MS (m/z); 425 [M+H]$^+$ (Step 2)

In a manner similar to that in Example 5, Step 5, Compound 6 (0.21 g, 51%) was obtained from methyl 3,5-diallyloxy-2-ethyl-6-(3-methoxybenzoyl)phenylacetate (0.51 g, 1.2 mmol) obtained in Example 6, Step 1, using acetic acid (7.0 mL), triphenylphosphine (0.25 g, 0.97 mmol) and palladium (II) acetate (55 mg, 0.25 mmol).

$^1$H-NMR (CDCl$_3$, 270 MHz) δ (ppm): 9.13 (s, 1H), 7.36-7.06 (m, 4H), 6.37 (s, 1H), 5.69 (s, 1H), 3.83 (s, 3H), 3.51 (s, 3H), 3.46 (s, 2H), 2.56 (q, J=7.5 Hz, 2H), 1.08 (t, J=7.5 Hz, 3H)

APCI-MS (m/z); 343 [M−H]$^-$

EXAMPLE 7

Synthesis of 5-ethyl-2,4-dihydroxy-6-(2-methoxy-ethyl)phenyl=phenyl=ketone (Compound 7)

(Step 1)

Methyl 2-acetyl-3,5-diallyloxyphenylacetate (22 g, 72 mmol) obtained in Example 5, Step 2 was dissolved in 1,4-dioxane (0.20 L). To the solution were added ammonium formate (18 g, 0.29 mol) and bis(triphenylphosphine)palladium (II) dichloride (2.5 g, 3.6 mmol), followed by stirring for 8 hours under heating and reflux. After cooling to room temperature, the reaction mixture was made acidic by addition of 3 mol/L hydrochloric acid (0.20 L) and then concentrated under reduced pressure. The resulting residue was extracted with a mixed solvent of ethyl acetate and methanol (ethyl acetate/methanol=4/1, 0.20 L×4). The organic layer was dried over anhydrous sodium sulfate and concentrated under reduced pressure. The resulting residue was purified by silica gel column chromatography (ethyl acetate/hexane=1/2) to obtain methyl 2-acetyl-3,5-dihydroxyphenylacetate (6.2 g, 39%).

$^1$H-NMR (CDCl$_3$, 270 MHz) δ (ppm): 6.26 (d, J=2.2 Hz, 1H), 6.17 (d, J=2.2 Hz, 1H), 3.65 (s, 5H), 2.50 (s, 3H) ESI-MS (m/z); 223 [M−H]$^-$ (Step 2)

In a manner similar to that in Example 5, Step 3, methyl 2-ethyl-3,5-dihydroxyphenylacetate (3.6 g, 72%) was obtained as colorless crystals from methyl 2-acetyl-3,5-dihydroxyphenylacetate (5.4 g, 24 mmol) obtained in Example 7, Step 1, using triethylsilane (10 mL, 63 mmol) and trifluoroacetic acid (25 mL).

$^1$H-NMR (CDCl$_3$, 270 MHz) δ (ppm): 6.31 (d, J=2.5 Hz, 1H), 6.24 (d, J=2.5 Hz, 1H), 3.70 (s, 3H), 3.58 (s, 2H), 2.59 (q, J=7.5 Hz, 2H), 1.10 (t, J=7.5 Hz, 3H)
APCI-MS (m/z); 209 [M−H]$^-$ (Step 3)

In a manner similar to that in Example 1, Step 1, methyl 3,5-bis(methoxymethoxy)-2-ethylphenylacetate (3.9 g, 44%) was obtained from methyl 2-ethyl-3,5-dihydroxyphenylacetate (6.2 g, 30 mmol) obtained in Example 7, Step 2, using chloromethyl methyl ether (9.0 mL, 0.12 mol), diisopropylethylamine (21 mL, 0.12 mol) and dichloromethane (60 mL).

$^1$H-NMR (CDCl$_3$, 270 MHz) δ (ppm): 6.74 (d, J=2.5 Hz, 1H), 6.59 (d, J=2.5 Hz, 1H), 5.18 (s, 2H), 5.13 (s, 2H), 3.69 (s, 3H), 3.62 (s, 2H), 3.48 (s, 3H), 3.48 (s, 3H), 2.59 (q, J=7.3 Hz, 2H), 1.08 (t, J=7.3 Hz, 3H)
APCI-MS (m/z); 299 [M+H]$^+$ (Step 4)

In a manner similar to that in Example 1, Step 2, 2-[3,5-bis(methoxymethoxy)-2-ethylphenyl]ethanol (3.5 g, 99%) was obtained from methyl 3,5-bis(methoxymethoxy)-2-ethylphenylacetate (3.8 g, 13 mmol) obtained in Example 7, Step 3, using lithium aluminum hydride (0.70 g, 18 mmol) and tetrahydrofuran (50 mL).

$^1$H-NMR (CDCl$_3$, 270 MHz) δ (ppm): 6.70 (d, J=2.4 Hz, 1H), 6.56 (d, J=2.4 Hz, 1H), 5.18 (s, 2H), 5.13 (s, 2H), 3.83 (t, J=6.9 Hz, 2H), 3.48 (s, 3H), 3.47 (s, 3H), 2.88 (t, J=6.9 Hz, 2H), 2.64 (q, J=7.4 Hz, 2H), 1.11 (t, J=7.4 Hz, 3H)
APCI-MS (m/z); 271 [M+H]$^+$ (Step 5)

In a manner similar to that in Example 1, Step 3, 3,5-bis(methoxymethoxy)-2-ethyl-1-(2-methoxyethyl)benzene (3.5 g, 96%) was obtained from 2-[3,5-bis(methoxymethoxy)-2-ethylphenyl]ethanol (3.5 g, 13 mmol) obtained in Example 7, Step 4, using a 60% sodium hydride dispersion in mineral oil (1.0 g, 26 mmol), methyl iodide (1.6 mL, 25 mmol) and N,N-dimethylformamide (30 mL).

$^1$H-NMR (CDCl$_3$, 300 MHz) δ (ppm): 6.68 (d, J=2.4 Hz, 1H), 6.55 (d, J=2.4 Hz, 1H), 5.17 (s, 2H), 5.13 (s, 2H), 3.55 (t, J=7.5 Hz, 2H), 3.48 (s, 6H), 3.37 (s, 3H), 2.88 (t, J=7.5 Hz, 2H), 2.64 (q, J=7.4 Hz, 2H), 1.11 (t, J=7.4 Hz, 3H)
APCI-MS (m/z); 285 [M+H]$^+$ (Step 6)

In a manner similar to that in Example 1, Step 4, 1,5-bis(methoxymethoxy)-2-bromo-4-ethyl-3-(2-methoxyethyl)benzene (4.3 g, 95%) was obtained from 3,5-bis(methoxymethoxy)-2-ethyl-1-(2-methoxyethyl)benzene (3.5 g, 12 mmol) obtained in Example 7, Step 5, using N-bromosuccinimide (2.2 g, 12 mmol) and N,N-dimethylformamide (55 mL).

$^1$H-NMR (CDCl$_3$, 300 MHz) δ (ppm): 6.87 (s, 1H), 5.20 (s, 2H), 5.17 (s, 2H), 3.53 (s, 3H), 3.52 (t, J=7.4 Hz, 2H), 3.48 (s, 3H), 3.40 (s, 3H), 3.17 (t, J=7.4 Hz, 2H), 2.71 (q, J=7.5 Hz, 2H), 1.11 (t, J=7.5 Hz, 3H)
FAB-MS (m/z); 363, 365 [M+H]$^+$ (Step 7)

In a manner similar to that in Example 1, Step 5, [4,6-bis(methoxymethoxy)-3-ethyl-2-(2-methoxyethyl)phenyl]phenylmethanol (0.46 g, 95%) was obtained from 1,5-bis(methoxymethoxy)-2-bromo-4-ethyl-3-(2-methoxyethyl)benzene (0.45 g, 1.2 mmol) obtained in Example 7, Step 6, using a 1.6 mol/L solution of n-butyllithium in hexane (3.1 mL, 4.9 mmol), benzaldehyde (0.63 mL, 6.2 mmol) and tetrahydrofuran (10 mL). Further, 4,6-bis(methoxymethoxy)-3-ethyl-2-(2-methoxyethyl)phenyl=phenyl=ketone (0.33 g, 72%) was obtained from [4,6-bis(methoxymethoxy)-3-ethyl-2-(2-methoxyethyl)phenyl]phenylmethanol (0.46 g, 1.2 mmol), using Molecular Sieves 4 Å (0.80 g), pyridinium dichromate (0.89 g, 2.4=mol) and dichloromethane (6.0 mL).

$^1$H-NMR (CDCl$_3$, 270 MHz) δ (ppm): 7.85-7.39 (m, 5H), 6.84 (s, 1H), 5.23 (s, 2H), 5.00 (s, 2H), 3.52 (s, 3H), 3.40 (t, J=7.6 Hz, 2H), 3.20 (s, 3H), 3.18 (s, 3H), 2.75 (t, J=7.6 Hz, 2H), 2.69 (q, J=7.4 Hz, 2H), 1.15 (t, J=7.4 Hz, 3H)
APCI-MS (m/z); 343 [M−CH$_2$OCH$_3$]$^-$ (Step 8)

In a manner similar to that in Example 1, Step 6, Compound 7 (85 mg, 59%) was obtained from 4,6-bis(methoxymethoxy)-3-ethyl-2-(2-methoxyethyl)phenyl=phenyl=ketone (0.19 g, 0.48 mmol) obtained in Example 7, Step 7, using a 4 mol/L solution of hydrogen chloride in 1,4-dioxane (3.0 mL) and methanol (3.0 mL).

$^1$H-NMR (CDCl$_3$, 270 MHz) δ (ppm): 8.54 (s, 1H), 7.70-7.41 (m, 5H), 6.30 (s, 1H), 5.55 (s, 1H), 3.23 (t, J=7.3 Hz, 2H), 3.13 (s, 3H), 2.71 (t, J=7.3 Hz, 2H), 2.63 (q, J=7.5 Hz, 2H), 1.15 (t, J=7.5 Hz, 3H)
APCI-MS (m/z); 299 [M−H]$^-$

EXAMPLE 8

Synthesis of methyl 2-ethyl-3,5-dihydroxy-6-(4-methoxybenzoyl)phenylacetate (Compound 8)

(Step 1)

In a manner similar to that in Example 5, Step 4, methyl 3,5-diallyloxy-2-ethyl-6-(4-methoxybenzoyl)phenylacetate was obtained quantitatively from methyl 3,5-diallyloxy-2-ethylphenylacetate (0.42 g, 1.4 mmol) obtained in Example 5, Step 3, using 4-methoxybenzoic acid (0.66 g, 4.3 mmol), trifluoroacetic acid (3.0 mL) and trifluoroacetic anhydride (0.80 mL).

$^1$H-NMR (CDCl$_3$, 270 MHz) δ (ppm): 7.80 (d, J=9.0 Hz, 2H), 6.88 (d, J=9.0 Hz, 2H), 6.43 (s, 1H), 6.07 (ddt, J=10.6, 17.4, 4.5 Hz, 1H), 5.69 (ddt, J=10.6, 17.4, 5.0 Hz, 1H), 5.46 (dq, J=17.4, 1.7 Hz, 1H), 5.31 (dq, J=10.6, 1.7 Hz, 1H), 5.07-4.99 (m, 2H), 4.57 (dt, J=4.5, 1.7 Hz, 2H), 4.37 (dt, J=5.0, 1.7 Hz, 2H), 3.85 (s, 3H), 3.65 (s, 2H), 3.44 (s, 3H), 2.65 (q, J=7.3 Hz, 2H), 1.09 (t, J=7.3 Hz, 3H)
APCI-MS (m/z); 425 [M+H]$^+$ (Step 2)

In a manner similar to that in Example 5, Step 5, Compound 8 (0.33 g, 64%) was obtained from methyl 3,5-diallyloxy-2-ethyl-6-(4-methoxybenzoyl)phenylacetate (0.63 g, 1.5 mmol) obtained in Example 8, Step 1, using acetic acid (10 mL), triphenylphosphine (0.31 g, 1.2 mmol) and palladium (II) acetate (66 mg, 0.29 mmol).
$^1$H-NMR (CDCl$_3$, 270 MHz) δ (ppm): 8.13 (s, 1H), 7.70 (d, J=8.9 Hz, 2H), 6.90 (d, J=8.9 Hz, 2H), 6.30 (s, 1H), 5.76 (s, 1H), 3.87 (s, 3H), 3.54 (s, 3H), 3.50 (s, 2H), 2.57 (q, J=7.5 Hz, 2H), 1.10 (t, J=7.5 Hz, 3H)
APCI-MS (m/z); 345 [M+H]$^+$

EXAMPLE 9

Synthesis of 5-ethyl-2,4-dihydroxy-6-(2-methoxyethyl)phenyl=4-methoxyphenyl=ketone (Compound 9)

(Step 1)

In a manner similar to that in Example 1, Step 5, [4,6-bis(methoxymethoxy)-3-ethyl-2-(2-methoxyethyl)phenyl](4-methoxyphenyl)methanol (0.22 g, 89%) was obtained from 1,5-bis(methoxymethoxy)-2-bromo-4-ethyl-3-(2'-methoxyethyl)benzene (0.21 g, 0.58 mmol) obtained in Example 7, Step 6, using a 1.6 mol/L solution of n-butyllithium in hexane (1.1 mL, 1.8 mmol), 4-methoxybenzaldehyde (0.21 mL, 1.7 mmol) and tetrahydrofuran (5.0 mL). Further, 4,6-bis(methoxymethoxy)-3-ethyl-2-(2-methoxyethyl)phenyl=4-methoxyphenyl=ketone (0.19 g, 89%) was obtained from [4,6-bis(methoxymethoxy)-3-ethyl-2-(2-methoxyethyl)phenyl]-(4-methoxyphenyl)methanol (0.21 g, 0.49 mmol), using Molecular Sieves 4 Å (0.37 g), pyridinium dichromate (0.37 g, 0.98 mmol) and dichloromethane (8.0 mL).
$^1$H-NMR (CDCl$_3$, 300 MHz) δ (ppm): 7.81 (d, J=9.0 Hz, 2H), 6.90 (d, J=9.0 Hz, 2H), 6.84 (s, 1H), 5.23 (s, 2H), 4.98 (s, 2H), 3.86 (s, 3H), 3.52 (s, 3H), 3.40 (t, J=7.9 Hz, 2H), 3.24 (s, 3H), 3.20 (s, 3H), 2.74 (t, J=7.9 Hz, 2H), 2.68 (q, J=7.3 Hz, 2H), 1.14 (t, J=7.3 Hz, 3H)
APCI-MS (m/z); 419 [M+H]$^+$ (Step 2)

In a manner similar to that in Example 1, Step 6, Compound 9 (45 mg, 32%) was obtained from 4,6-bis(methoxymethoxy)-3-ethyl-2-(2-methoxyethyl)phenyl=4-methoxyphenyl=ketone (0.18 g, 0.42 mmol) obtained in Example 9, Step 1, using a 4 mol/L solution of hydrogen chloride in 1,4-dioxane (2.5 mL) and methanol (2.5 mL).
$^1$H-NMR (CDCl$_3$, 300 MHz) δ (ppm): 7.93 (s, 1H), 7.72 (d, J=8.9 Hz, 2H), 6.92 (d, J=8.9 Hz, 2H), 6.27 (s, 1H), 5.56 (s, 1H), 3.87 (s, 3H), 3.27 (t, J=7.4 Hz, 2H), 3.17 (s, 3H), 2.76 (t, J=7.4 Hz, 2H), 2.64 (q, J=7.3 Hz, 2H), 1.16 (t, J=7.3 Hz, 3H)
APCI-MS (m/z); 331 [M+H]$^+$

Example 10

Synthesis of 2-[2-ethyl-3,5-dihydroxy-6-(4-methoxybenzoyl)phenyl]-N-(2-methoxyethyl)-N-methylacetamide (Compound 10)

(Step 1)

Compound 8 (0.18 g, 0.53 mmol) obtained in Example 8 was dissolved in methanol (1.5 mL), and a 2 mol/L aqueous solution of sodium hydroxide (1.5 mL) was added thereto. The mixture was stirred at room temperature for 6 hours, and then stirred at 50° C. for 1.5 hours. After cooling to room temperature, the reaction mixture was made acidic by addition of 4 mol/L hydrogen chloride (3.0 mL), followed by extraction with chloroform (50 mL×3). The organic layer was dried over anhydrous sodium sulfate and then concentrated under reduced pressure to obtain 2-ethyl-3,5-dihydroxy-6-(4-methoxybenzoyl)phenylacetic acid (0.17 g, 0.52 mmol).
$^1$H-NMR (CD$_3$OD, 270 MHz) δ (ppm): 7.78 (d, J=9.0 Hz, 2H), 6.92 (d, J=9.0 Hz, 2H), 6.33 (s, 1H), 3.84 (s, 3H), 3.50 (s, 2H), 2.59 (q, J=7.4 Hz, 2H), 1.08 (t, J=7.4 Hz, 3H)
APCI-MS (m/z); 329 [M–H]$^-$ (Step 2)

2-Ethyl-3,5-dihydroxy-6-(4-methoxybenzoyl)phenylacetic acid (0.18 g, 0.53 mmol) obtained in Example 10, Step 1 was dissolved in dichloromethane (2.0 mL). To the solution were added 1-hydroxybenzotriazole hydrate (0.11 g, 0.72 mmol), 1-(3-dimethylaminopropyl)-3-ethylcarbodiimide hydrochloride (0.14 g, 0.72 mmol) and 2-methoxy-N-methylethylamine (0.12 mL, 1.1 mmol), followed by stirring at room temperature for 14 hours. To the reaction mixture was added water (10 mL), and the mixture was extracted with chloroform (50 mL×2). The organic layer was dried over anhydrous sodium sulfate and then concentrated under reduced pressure. The resulting residue was purified by preparative thin layer chromatography (methanol/chloroform=1/9) to obtain Compound 10 (28 mg, 13%).
$^1$H-NMR (CDCl$_3$, 270 MHz) δ (ppm): 7.80 (d, J=9.6 Hz, 2H), 6.87 (d, J=9.6 Hz, 2H), 6.13 (s, 1H), 3.84 (s, 3H), 3.49 (s, 2H), 3.46 (s, 3H), 3.32 (s, 2H), 3.27 (s, 2H), 2.89 and 2.86 (s, total 3H), 2.54-2.43 (m, 2H), 1.07-1.03 (m, 3H)
APCI-MS (m/z); 402 [M+H]$^+$

EXAMPLE 11

Synthesis of 5-ethyl-2,4-dihydroxy-6-(2-methoxyethyl)phenyl=4-nitrophenyl=ketone (Compound 11)

(Step 1)

In a manner similar to that in Example 1, Step 5, [4,6-bis(methoxymethoxy)-3-ethyl-2-(2-methoxyethyl)phenyl](4-nitrophenyl)methanol (0.24 g, 41%) was obtained from 1,5-bis(methoxymethoxy)-2-bromo-4-ethyl-3-(2-methoxyethyl)benzene (0.49 g, 1.3 mmol) obtained in Example 7, Step 6, using a 1.6 mol/L solution of n-butyllithium in hexane (2.6 mL, 4.2 mmol), 4-nitrobenzaldehyde (0.61 g, 4.0 mmol) and tetrahydrofuran (10 mL). Further, 4,6-bis (methoxymethoxy)-3-ethyl-2-(2-methoxyethyl)phenyl=4-nitrophenyl=ketone (0.20 g, 87%) was obtained from [4,6-bis(methoxymethoxy)-3-ethyl-2-(2-methoxyethyl)phenyl](4-nitrophenyl)methanol (0.23 g, 0.53 mmol), using Molecular Sieves 4 Å (0.40 g), pyridinium dichromate (0.40 g, 1.1 mmol) and dichloromethane (8.0 mL) $^1$H-NMR (CDCl$_3$, 270 MHz) δ (ppm): 8.27 (d, J=9.0 Hz, 2H), 7.98 (d, J=9.0 Hz, 2H), 6.86 (s, 1H), 5.25 (s, 2H), 4.91 (s, 2H), 3.53 (s, 3H), 3.42 (t, J=7.4 Hz, 2H), 3.20 (s, 3H), 3.13 (s, 3H), 2.81 (t, J=7.4 Hz, 2H), 2.70 (q, J=7.4 Hz, 2H), 1.15 (t, J=7.4 Hz, 3H)
APCI-MS (m/z); 456 [M+H]$^+$ (Step 2)

In a manner similar to that in Example 1, Step 6, Compound 11 (31 mg, 70%) was obtained from 4,6-bis(methoxymethoxy)-3-ethyl-2-(2-methoxyethyl)phenyl=4-nitrophenyl=ketone (55 mg, 0.13 mmol) obtained in Example 11, Step 1, using a 4 mol/L solution of hydrogen chloride in 1,4-dioxane (1.0 mL) and methanol (1.0 mL).

¹H-NMR (CDCl₃, 270 MHz) δ (ppm): 8.70 (s, 1H), 8.27 (d, J=8.4 Hz, 2H), 7.81 (d, J=8.4 Hz, 2H), 6.34 (s, 1H), 5.73 (s, 1H), 3.79-3.65 (m, 2H), 3.24 (t, J=6.9 Hz, 2H), 3.14 (s, 3H), 2.68-2.59 (m, 2H), 1.15 (t, J=7.3 Hz, 3H) FAB-MS (m/z); 346 [M+H]⁺

EXAMPLE 12

Synthesis of 5-ethyl-2,4-dihydroxy-6-[2-(2-methoxyethoxy)ethyl]phenyl=4-methoxyphenyl=ketone (Compound 12)

(Step 1)

Methyl 3,5-diallyloxy-2-ethylphenylacetate (0.84 g, 2.9 mmol) obtained in Example 5, Step 3 was dissolved in dichloromethane (15 mL). After the solution was cooled to −78° C. in an atmosphere of nitrogen, a 1.0 mol/L solution of diisobutylaluminum hydride in toluene (8.4 mL, 8.4 mmol) was added dropwise thereto, followed by stirring at −78° C. for 4 hours. To the reaction mixture was added a saturated aqueous solution of potassium sodium tartrate (50 mL), and the mixture was stirred at room temperature for 3 hours and then extracted with ethyl acetate (0.10 L×2). The organic layer was dried over anhydrous sodium sulfate and concentrated under reduced pressure. The resulting residue was purified by silica gel column chromatography (ethyl acetate/hexane=1/9-1/1) to obtain 2-(3,5-diallyloxy-2-ethylphenyl)ethanol (0.74 g, 97%). ¹H-NMR (CDCl₃, 270 MHz) δ (ppm): 6.37 (brs, 2H), 6.11-5.98 (m, 2H), 5.47-5.35 (m, 2H), 5.30-5.23 (m, 2H), 4.52-4.49 (m, 4H), 3.82 (q, J=6.8 Hz, 2H), 2.88 (t, J=6.8 Hz, 2H), 2.64 (q, J=7.4 Hz, 2H), 1.10 (t, J=7.4 Hz, 3H)

(Step 2)

In a manner similar to that in Example 1, Step 3, 3,5-diallyloxy-2-ethyl-1-[2-(2-methoxyethoxy)ethyl]benzene (0.27 g, 84%) was obtained from 2-(3,5-diallyloxy 2-ethylphenyl)ethanol (3.5 g, 13 mmol) obtained in Example 12, Step 1, using a 60% sodium hydride dispersion in mineral oil (0.12 g, 3.0 mmol), 2-bromoethyl methyl ether (0.28 mL, 3.0 mmol) and N,N-dimethylformamide (2.0 mL). ¹H-NMR (CDCl₃, 270 MHz) δ (ppm): 6.37 (d, J=2.4 Hz, 1H), 6.35 (d, J=2.4 Hz, 1H), 6.12-5.98 (m, 2H), 5.45-5.23 (m, 4H), 4.50-4.48 (m, 4H), 3.66-3.54 (m, 6H), 3.40 (s, 3H), 2.92 (t, J=7.8 Hz, 2H), 2.63 (q, J=7.4 Hz, 2H), 1.09 (t, J=7.4 Hz, 3H)

APCI-MS (m/z); 321 [M+H]⁺

(Step 3)

In a manner similar to that in Example 5, Step 4, 4,6-diallyloxy-3-ethyl-2-[2-(2-methoxyethoxy)ethyl]phenyl=4-methoxyphenyl=ketone (0.14 g, 62%) was obtained from 3,5-diallyloxy-2-ethyl-1-[2-(2-methoxyethoxy)ethyl]benzene (0.16 g, 0.48 mmol) obtained in Example 12, Step 2, using 4-methoxybenzoic acid (0.22 g, 1.5 mmol), trifluoroacetic acid (1.5 mL) and trifluoroacetic anhydride (0.40 mL).

¹H-NMR (CDCl₃, 270 MHz) δ (ppm): 7.77 (d, J=9.0 Hz, 2H), 6.88 (d, J=9.0 Hz, 2H), 6.38 (s, 1H), 6.07 (ddt, J=10.6, 17.2, 5.0 Hz, 1H), 5.73 (ddt, J=10.6, 17.2, 5.0 Hz, 1H), 5.45 (dq, J=17.2, 1.6 Hz, 1H), 5.30 (dq, J=10.6, 1.6 Hz, 1H), 5.10-5.04 (m, 2H), 4.55 (dt, J=5.0, 1.6 Hz, 2H), 4.38 (dt, J=5.0, 1.6 Hz, 2H), 3.86 (s, 3H), 3.53-3.33 (m, 6H), 3.32 (s, 3H), 2.78 (t, J=7.5. Hz, 2H), 2.69 (q, J=7.4 Hz, 2H), 1.13 (t, J=7.4 Hz, 3H)

APCI-MS (m/z); 455 [M+H]⁺

(Step 4)

In a manner similar to that in Example 5, Step 5, Compound 12 (59 mg, 52%) was obtained from 4,6-diallyloxy-3-ethyl-2-[2-(2-methoxyethoxy)ethyl]phenyl=4-methoxyphenyl=ketone (0.14 g, 0.30 mmol) obtained in Example 12, Step 3, using acetic acid (4.0 mL), triphenylphosphine (0.13 g, 0.48 mmol) and palladium (II) acetate (26 mg, 0.12 mmol). ¹H-NMR (CDCl₃, 270 MHz) δ (ppm): 7.94 (s, 1H), 7.70 (d, J=8.7 Hz, 2H), 6.91 (d, J=8.7 Hz, 2H), 6.30 (s, 1H), 5.21 (s, 1H), 3.87 (s, 3H), 3.44-3.31 (m, 6H), 3.32 (s, 3H), 2.79 (t, J=7.6 Hz, 2H), 2.64 (q, J=7.5 Hz, 2H), 1.16 (t, J=7.5 Hz, 3H)

APCI-MS (m/z); 375 [M+H]⁺

EXAMPLE 13

Synthesis of 2-[2-ethyl-3,5-dihydroxy-6-(4-methoxybenzoyl)phenyl]-N,N-bis(2-hydroxyethyl)acetamide (Compound 13)

In a manner similar to that in Example 10, Step 2, Compound 13 (40 mg, 30%) was obtained from 2-ethyl-3,5-dihydroxy-6-(4-methoxybenzoyl)phenylacetic acid (0.10 g, 0.30 mmol) obtained in Example 10, Step 1, using N-hydroxysuccinimide (0.11 g, 0.96 mmol), 1-(3-dimethylaminopropyl)-3-ethylcarbodiimide hydrochloride (0.12 g, 0.61 mmol), diethanolamine (0.087 mL, 0.91 mmol) and N,N-dimethylformamide (1.0 mL).

¹H-NMR (CD₃OD, 270 MHz) δ (ppm): 7.77 (d, J=8.9 Hz, 2H), 6.91 (d, J=8.9 Hz, 2H), 6.31 (s, 1H), 3.84 (s, 3H), 3.69 (s, 2H), 3.60 (t, J=5.40 Hz, 2H), 3.30-3.29 (m, 2H), 3.41 (q, J=5.4 Hz, 4H), 2.54 (q, J=7.6 Hz, 2H), 1.07 (t, J=7.6 Hz, 3H)

APCI-MS (m/z); 418 [M+H]⁺

EXAMPLE 14

Synthesis of 2-[2-ethyl-3,5-dihydroxy-6-(4-methoxybenzoyl)phenyl]-N-(2-hydroxyethyl)-N-methylacetamide (Compound 14)

In a manner similar to that in Example 10, Step 2, Compound 14 (19 mg, 37%) was obtained from 2-ethyl-3,5-dihydroxy-6-(4-methoxybenzoyl)phenylacetic acid (43 mg, 0.13 mmol) obtained in Example 10, Step 1, using 1-hydroxybenzotriazole hydrate (40 mg, 0.26 mmol), 1-(3-dimethylaminopropyl)-3-ethylcarbodiimide hydrochloride (50 mg, 0.26 mmol), 2-(methylamino)ethanol (29 mg, 0.39 mmol) and N,N-dimethylformamide (0.50 mL).

¹H-NMR (CD₃OD, 300 MHz) δ (ppm): 7.78 (d, J=8.8 Hz, 2H), 6.91 (br. d, J=8.8 Hz, 2H), 6.32 and 6.31 (s, total 1H), 3.844 and 3.839 (s, total 3H), 3.67 and 3.60 (s, total 2H), 3.58 (t, 1H), 3.41 (t, 1H), 3.33 (t, 1H), 3.20 (t, 1H), 2.98 and 2.69 (s, total 3H), 2.59-2.52 (m, 2H), 1.10-1.04 (m, 3H)

APCI-MS (m/z); 388 [M+H]⁺

EXAMPLE 15

Synthesis of methyl 3,5-dihydroxy-2-iodo-6-(4-methoxybenzoyl)phenylacetate (Compound 15)

(Step 1)

In a manner similar to that in Example 5, Step 4, methyl 3,5-diallyloxy-2-(4-methoxybenzoyl)phenylacetate (4.4 g, 53%) was obtained from methyl 3,5-diallyloxyphenylacetate (5.2 g, 20 mmol) obtained in Example 5, Step 1, using trifluoroacetic acid (40 mL), 4-methoxybenzoic acid (9.1 g, 3.3 mmol) and trifluoroacetic anhydride (8.0 mL).

APCI-MS (m/z); 397 [M+H]⁺

(Step 2)

In a manner similar to that in Example 4, Step 1, methyl 3,5-diallyloxy-2-iodo-6-(4-methoxybenzoyl)phenylacetate (1.0 g, 69%) was obtained from methyl 3,5-diallyloxy-2-(4-methoxybenzoyl)phenylacetate (1.1 g, 2.9 mmol) obtained in Example 15, Step 1, using iodine (0.73 g, 2.9 mmol), [bis(trifluoroacetoxy)iodo]benzene (1.3 g, 2.9 mmol) and chloroform (30 mL).

APCI-MS (m/z); 523 [M+H]$^+$ (Step 3)

Methyl 3,5-diallyloxy-2-iodo-6-(4-methoxybenzoyl)phenylacetate (80 mg, 0.15 mmol) obtained in Example 15, Step 2 was dissolved in 1,4-dioxane (1.0 mL), and selenium dioxide (36 mg, 0.34 mmol) and acetic acid (0.028 mL; 0.46 mmol) were added thereto, followed by stirring at 75° C. for half a day. The reaction mixture was poured into a saturated aqueous solution of sodium hydrogencarbonate, followed by extraction with chloroform. The organic layer was dried over anhydrous sodium sulfate and then concentrated under reduced pressure. The resulting residue was purified by preparative thin layer chromatography (chloroform/methanol=9/1) to obtain Compound 15 (1.2 mg, 8.2%).

$^1$H-NMR (CDCl$_3$, 270 MHz) δ (ppm): 8.05 (brs, 1H), 7.71 (d, J=8.8 Hz, 2H), 6.92 (d, J=8.8 Hz, 2H), 6.63 (s, 1H), 6.03 (brs, 1H), 3.88 (s, 3H), 3.71 (s, 2H), 3.56 (s, 3H) FAB-MS (m/z); 443 [M+H]$^+$

EXAMPLE 16

Synthesis of 2-[2-ethyl-3,5-dihydroxy-6-(4-methoxybenzoyl)phenyl]-N-methyl-N-(pyridin-3-ylmethyl)acetamide (Compound 16)

In a manner similar to that in Example 10, Step 2, Compound 16 (27 mg, 38%) was obtained from 2-ethyl-3,5-dihydroxy-6-(4-methoxybenzoyl)phenylacetic acid (54 mg, 0.16 mmol) obtained in Example 10, Step 1, using 1-hydroxybenzotriazole hydrate (90 mg, 0.59 mmol), 1-(3-dimethylaminopropyl)-3-ethylcarbodiimide hydrochloride (94 mg, 0.49 mmol), methyl(pyridin-3-ylmethyl)amine (60 mg, 0.49 mmol) and N,N-dimethyl formamide (0.50 mL).

$^1$H-NMR (CD$_3$OD, 300 MHz) δ (ppm): 8.47-8.35 (m, 2H), 7.81-7.75 (m, 2H), 7.55-7.21 (m, 2H), 6.95-6.90 (m, 2H), 6.33 (s, 0.75H), 6.32 (s, 0.25H), 4.60 (s. 0.5H), 4.41 (s, 1.5H), 3.85 (s, 2.25H), 3.84 (s, 0.75H), 3.72 (s, 1.5H), 3.66 (s, 0.5H), 2.92 (s, 2.25H), 2.75 (s, 0.75H), 2.57 (q, J=7.3 Hz, 1.5H), 2.48 (q, J=7.3 Hz, 0.5H), 1.08 (t, J=7.3 Hz, 2.25H), 1.01 (t, J=7.3 Hz, 0.75H)

APCI-MS (m/z); 435 [M+H]$^+$

EXAMPLE 17

Synthesis of 2-(4-{2-[2-ethyl-3,5-dihydroxy-6-(4-methoxybenzoyl)phenyl]acetyl}piperazin-1-yl)benzenecarbonitrile (Compound 17)

In a manner similar to that in Example 10, Step 2, Compound 17 (46 mg, 57%) was obtained from 2-ethyl-3,5-dihydroxy-6-(4-methoxybenzoyl)phenylacetic acid (54 mg, 0.16 mmol) obtained in Example 10, Step 1, using 1-hydroxybenzotriazole hydrate (90 mg, 0.59 mmol), 1-(3-dimethylaminopropyl)-3-ethylcarbodiimide hydrochloride (94 mg, 0.49 mmol), 2-piperazinylbenzenecarbonitrile (95 mg, 0.51 mmol) and N,N-dimethylformamide (0.50 mL).

$^1$H-NMR (CD$_3$OD, 270 MHz) δ (ppm): 7.78 (d, J=9.0 Hz, 2H), 7.63-7.56 (m, 2H), 7.11 (dt, J=1.0, 7.6 Hz, 1H), 7.04 (d, J=8.2 Hz, 1H), 6.91 (d, J=9.0 Hz, 2H), 6.33 (s, 1H), 3.81 (s, 3H), 3.67 (s, 2H), 3.61 (brt, J=4.9 Hz, 2H), 3.50 (brt, J=4.9 Hz, 2H), 2.99 (brt, J=4.9 Hz, 2H), 2.80 (brt, J=4.9 Hz, 2H), 2.58 (q, J=7.5 Hz, 2H), 1.09 (t, J=7.5 Hz, 3H)

FAB-MS (m/z); 501 [M+H]$^+$

EXAMPLE 18

Synthesis of methyl 5-allyloxy-3-hydroxy-2-(4-methoxybenzoyl)phenylacetate (Compound 18)

Methyl 3,5-diallyloxy-2-(4-methoxybenzoyl)phenylacetate (100 mg, 0.25 mmol) obtained in Example 15, Step 1 was dissolved in dichloromethane (10 mL). After the solution was cooled to −78° C., a 1.0 mol/L solution of boron tribromide in hexane (0.50 mL, 0.5 mmol) was added thereto, followed by stirring at −78° C. for 30 minutes. To the reaction mixture were successively added methanol and a saturated aqueous solution of sodium hydrogencarbonate, followed by extraction with chloroform. The organic layer was dried anhydrous over sodium sulfate and then concentrated under reduced pressure. The resulting residue was purified by preparative thin layer chromatography (chloroform/methanol=20/1) to obtain Compound 18 (54 mg, 61%).

$^1$HNMR (CDCl$_3$, 270 MHz) δ (ppm): 9.83 (s, 1H), 7.61 (d, J=8.9 Hz, 2H), 6.91 (d, J=8.9 Hz, 2H), 6.48 (d, J=2.4 Hz, 1H), 6.42 (d, J=2.4 Hz, 1H), 6.04 (m, 1H), 5.43 (dd, J=7.7, 1.7 Hz, 1H), 5.32 (dd, J=7.7, 1.7 Hz, 1H), 4.56 (dt, J=5.3, 1.5 Hz, 2H), 3.87 (s, 3H), 3.53 (s, 3H), 3.37 (s, 2H)

FAB-MS (m/z); 357 [M+H]$^+$

EXAMPLE 19

Synthesis of methyl 3,5-dihydroxy-2-(4-methoxybenzoyl)phenylacetate (Compound 19) and methyl 3,5-dihydroxy-2-(4-hydroxybenzoyl)phenylacetate (Compound 20)

Methyl 3,5-diallyloxy-2-(4-methoxybenzoyl)phenylacetate (100 mg, 0.25 mmol) obtained in Example 15, Step 1 was dissolved in dichloromethane (10 mL), and a 1.0 mol/L solution of boron tribromide in hexane (2.0 mL, 2.0 mmol) was added thereto, followed by stirring at room temperature for 1 hour. To the reaction mixture was added methanol, and after stirring for 10 minutes, the mixture was concentrated under reduced pressure. The resulting residue was purified by preparative thin layer chromatography (chloroform/methanol=9/1) to obtain Compound 19 (9.9 mg, 13%) and Compound 20 (38 mg, 51%).

Compound 19:

H-NMR (CDCl$_3$, 270 MHz) δ (ppm): 9.21 (brs, 1H), 7.65 (d, J=8.6 Hz, 2H), 6.90 (d, J=8.6 Hz, 2H), 6.33 (brs, 2H), 3.86 (s, 3H), 3.53 (s, 3H), 3.37 (s, 2H)

FAB-MS (m/z); 317 [M+H]$^+$

Compound 20:

$^1$H-NMR (DMSO-d$_6$, 270 MHz) δ (ppm): 9.46 (brs, 3H), 7.52 (d, J=8.8 Hz, 2H), 6.77 (d, J=8.8 Hz, 2H), 6.25 (d, J=2.0 Hz, 1H), 6.22 (d, J=2.0 Hz, 1H), 3.35 (s, 3H), 3.31 (s, 2H)

FAB-MS (m/z); 303 [M+H]$^+$

EXAMPLE 20

Synthesis of 2-[2-ethyl-3,5-dihydroxy-6-(4-methoxybenzoyl)phenyl]-1-(3-hydroxypiperidino)ethanone (Compound 21)

In a manner similar to that in Example 10, Step 2, Compound 21 (50 mg, 43%) was obtained from 2-ethyl-3,5-dihydroxy-6-(4-methoxybenzoyl)phenylacetic acid (93 mg, 0.28 mmol) obtained in Example 10, Step 1, using 1-hydroxybenzotriazole hydrate (0.12 g, 0.75 mmol), 1-(3-dimethylaminopropyl)-3-ethylcarbodiimide hydrochloride (0.13 g, 0.68 mmol), 3-hydroxypiperidine (0.12 g, 1.2 mmol) and N,N-dimethylformamide (1.0 mL).

$^1$H-NMR (DMSO-$d_6$, 270 MHz) δ (ppm): 7.63 (d, J=9.0 Hz, 2H), 6.92 (d, J=9.0 Hz, 2H), 6.33 (brs, 1H), 3.79 (s, 3H), 3.70-3.52 (m, 3H), 3.45 (brs, 2H), 3.03 (brt, J=10.4 Hz, 1H), 2.78 (brt, J=9.7 Hz, 1H), 2.36 (q, J=7.5 Hz, 2H), 1.56 (m, 1H), 1.39 (m, 1H), 1.15 (m, 1H), 0.97 (m, 1H), 0.97 (t, J=7.5 Hz, 3H)

APCI-MS (m/z); 414 [M+H]$^+$

EXAMPLE 21

Synthesis of 2-[2-ethyl-3,5-dihydroxy-6-(4-methoxybenzoyl)phenyl]-1-[3-(hydroxymethyl)piperidino]ethanone (Compound 22)

In a manner similar to that in Example 10, Step 2, Compound 22 (46 mg, 57%) was obtained from 2-ethyl-3,5-dihydroxy-6-(4-methoxybenzoyl)phenylacetic acid (99 mg, 0.30 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.68 mmol), 3-(hydroxymethyl)piperidine (0.14 g, 1.2 mmol) and N,N-dimethylformamide (1.0 mL).

$^1$H-NMR (CD$_3$OD, 270 MHz) δ (ppm): 7.77 (d, J=8.9 Hz, 2H), 6.90 (d, J=8.9 Hz, 2H), 6.32 (brs, 1H), 4.14 (m, 0.5H), 4.14-3.68 (m, 2H), 3.84 (s, 3H), 3.62-3.59 (m, 2H), 3.44-3.25 (m, 2H), 2.92 (m, 0.5H), 2.75 (dd, J=10.4, 13.7 Hz, 0.5H), 2.61-2.43 (m, 2.5H), 2.31 (dd, J=9.9, 12.7 Hz, 0.5H), 1.70-1.04 (m, 5H), 1.07 (t, J=7.4 Hz, 3H)

APCI-MS (m/z); 428 [M+H]$^+$

EXAMPLE 22

Synthesis of 1-{2-[2-ethyl-3,5-dihydroxy-6-(4-methoxybenzoyl)phenyl]acetyl}piperidine-3-carboxamide (Compound 23)

In a manner similar to that in Example 10, Step 2, Compound 23 (72 mg, 52%) was obtained from 2-ethyl-3,5-dihydroxy-6-(4-methoxybenzoyl)phenylacetic acid (0.10 g, 0.31 mmol) obtained in Example 10, Step 1, using 1-hydroxybenzotriazole hydrate (0.12 g, 0.75 mmol), 1-(3-dimethylaminopropyl)-3-ethylcarbodiimide hydrochloride (0.13 g, 0.68 mmol), piperidine-3-carboxamide (0.16 g, 1.2 mmol) and N,N-dimethylformamide (1.0 mL).

$^1$H-NMR (CD$_3$OD, 270 MHz) δ (ppm): 7.77 (d, J=8.9 Hz, 2H), 6.95-6.90 (m, 2H), 6.32 and 6.31 (s, total 1H), 4.26 (m, 0.5H), 4.05 (m, 0.5H), 3.84 (s, 3H), 3.89-3.56 (m, 3H), 3.11-2.86 (m, 1H), 2.64-2.24 (m, 4H), 2.04-1.31 (m, 4H), 1.07 (t, J=7.4 Hz, 3H)

APCI-MS (m/z); 441 [M+H]$^+$

EXAMPLE 23

Synthesis of 1-{2-[2-ethyl-3,5-dihydroxy-6-(4-methoxybenzoyl)phenyl]acetyl}piperidine-4-carboxamide (Compound 24)

In a manner similar to that in Example 10, Step 2, Compound 24 (13 mg, 9.7%) was obtained from 2-ethyl-3,5-dihydroxy-6-(4-methoxybenzoyl)phenylacetic acid (0.10 g, 0.31 mmol), obtained in Example 10, Step 1, using 1-hydroxybenzotriazole hydrate (0.12 g, 0.75 mmol), 1-(3-dimethylaminopropyl)-3-ethylcarbodiimide hydrochloride (0.14 g, 0.73 mmol), piperidine-4-carboxamide (0.16 g, 1.2 mmol) and N,N-dimethylformamide (1.0 mL).

$^1$H-NMR (CD$_3$OD, 270 MHz) δ (ppm): 7.77 (d, J=8.9 Hz, 2H), 6.90 (d, J=8.9 Hz, 2H), 6.32 (brs, 1H), 4.22 (m, 1H), 3.84 (s, 3H), 3.61 and 3.59 (s, total 2H), 3.40-3.29 (m, 2H), 3.11-3.00 (m, 2H), 2.80-2.35 (m, 2H), 2.18-1.20 (m, 4H), 1.07 (t, J=7.5 Hz, 3H)

APCI-MS (m/z); 441 [M+H]$^+$

EXAMPLE 24

Synthesis of 2-[2-ethyl-3,5-dihydroxy-6-(4-methoxybenzoyl)phenyl]-1-(3-hydroxypyrrolidin-1-yl)ethanone (Compound 25)

In a manner similar to that in Example 10, Step 2, Compound 25 (17 mg, 15%) was obtained from 2-ethyl-3,5-dihydroxy-6-(4-methoxybenzoyl)phenylacetic acid (98 mg, 0.30 mmol) obtained in Example 10, Step 1, using 1-hydroxybenzotriazole hydrate (0.12 g, 0.75 mmol), 1-(3-dimethylaminopropyl)-3-ethylcarbodiimide hydrochloride (0.13 g, 0.68 mmol), 3-hydroxypyrrolidine (0.13 mL, 1.4 mmol) and N,N-dimethylformamide (1.0 mL).

$^1$H-NMR (DMSO-$d_6$, 270 MHz) δ (ppm): 9.36 (s, 1H), 9.07 (s, 1H), 7.63 (brd, J=9.0 Hz, 2H), 6.94 (d, J=9.0 Hz, 2H), 6.32 (s, 1H), 4.92 and 4.80 (d, J=3.5 Hz, total 1H), 4.18 and 4.05 (m, total 1H), 3.80 (s, 3H), 3.38-3.29 (m, 3H), 3.11-2.97 (m, 3H), 2.40 (q, J=7.5 Hz, 2H), 1.73 (m, 1H), 1.55 (m, 1H), 0.98 (t, J=7.5 Hz, 3H)

APCI-MS (m/z); 400 [M+H]$^+$

EXAMPLE 25

Synthesis of N-(2,3-dihydroxypropyl)-2-[2-ethyl-3,5-dihydroxy-6-(4-methoxybenzoyl)phenyl]-N-methylacetamide (Compound 26)

In a manner similar to that in Example 10, Step 2, Compound 26 (62 mg, 46%) was obtained from 2-ethyl-3,5-dihydroxy-6-(4-methoxybenzoyl)phenylacetic acid (0.11 g, 0.32 mmol) obtained in Example 10, Step 1, using 1-hydroxybenzotriazole hydrate (0.13 g, 0.82 mmol), 1-(3-dimethylaminopropyl)-3-ethylcarbodiimide hydrochloride (0.15 g, 0.76 mmol), 3-methylamino-1,2-propanediol (0.13 mL, 1.3 mmol) and N,N-dimethylformamide (1.0 mL).

$^1$H-NMR (DMSO-$d_6$, 270 MHz) δ (ppm): 9.36 and 9.32 (s, total 1H), 9.07 and 9.03 (s, total 1H), 7.63 (d, J=8.6 Hz, 2H), 6.92 (d, J=8.6 Hz, 2H), 6.32 and 6.30 (s, total 1H), 4.83 (m, 0.5H), 4.62 (m, 0.5H), 4.53 (m, 0.5H), 4.32 (m, 0.5H), 3.79 (s, 3H), 3.60-2.90 (m, 7H), 2.90 and 2.59 (s, total 3H), 2.38-2.35 (m, 2H), 1.01-0.92 (m, 3H)

APCI-MS (m/z); 418 [M+H]$^+$

EXAMPLE 26

Synthesis of methyl 3-hydroxy-5-methoxy-2-(4-methoxybenzoyl)phenylacetate (Compound 27)

(Step 1)

Compound 19 (0.76 g, 2.1 mmol) obtained in Example 19 was dissolved in N,N-dimethylformamide (12 mL), and potassium carbonate (0.66 g, 4.8 mmol) and methyl iodide (0.34 mL, 5.5 mmol) were added thereto at room temperature, followed by stirring at room temperature for 1 hour. To the reaction mixture were added a saturated aqueous solution of ammonium chloride (30 mL) and water (0.20 L), and the mixture was extracted with ethyl acetate (0.20 L). The organic layer was dried over anhydrous sodium sulfate and then concentrated under reduced pressure to obtain methyl 3,5-dimethoxy-2-(4-methoxybenzoyl)phenylacetate. APCI-MS (m/z); 371 [M+H]$^+$ (Step 2)

Triphenylphosphine (0.22 g, 0.84 mmol) and palladium (II) acetate (47 mg, 0.21 mmol) were dissolved in tetrahydrofuran (2.0 mL) in an atmosphere of argon, followed by stirring at room temperature for 10 minutes. To the reaction mixture was added a solution of methyl 3,5-dimethoxy-2-(4-methoxybenzoyl)phenylacetate (0.78 g, 2.1 mmol) obtained in Example 26, Step 1 in formic acid (20 mL), followed by stirring at 80° C. for 5 hours. The reaction mixture was cooled to room temperature and then concentrated. The resulting residue was purified by silica gel column chromatography (ethyl acetate/hexane=1/4-1/1) to obtain Compound 27 (0.39 g, 56%).

$^1$H-NMR (CDCl$_3$, 270 MHz) δ (ppm): 7.77 (d, J=8.9 Hz, 2H), 6.77 (d, J=8.9 Hz, 2H), 6.40 (s, 1H), 6.38 (s, 1H), 5.70 (brs, 1H), 3.85 (s, 3H), 3.61 (s, 2H), 3.49 (s, 6H)

APCI-MS (m/z); 331 [M+H]$^+$

EXAMPLE 27

Synthesis of 2-[2-ethyl-3,5-dihydroxy-6-(4-methoxybenzoyl)phenyl]-N-(pyridin-3-ylmethyl)acetamide (Compound 28)

In a manner similar to that in Example 10, Step 2, Compound 28 (62 mg, 46%) was obtained from 2-ethyl-3,5-dihydroxy-6-(4-methoxybenzoyl)phenylacetic acid (98 mg, 0.29 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.68 mmol), (pyridin-3-ylmethyl)amine (0.12 mL, 1.2 mmol) and N,N-dimethylformamide (1.0 mL).

$^1$H-NMR (CD$_3$OD, 270 MHz) δ (ppm): 8.38-8.36 (m, 2H), 8.06 (t, J=4.8 Hz, 1H), 7.77 (brd, J=9.0 Hz, 2H), 7.60 (brd, J=7.9 Hz, 1H), 7.30 (dd, J=4.8, 7.9 Hz, 1H), 6.91 (t, J=9.0 Hz, 1H), 6.35 (s, 1H), 4.27 (m, 2H), 3.85 (s, 3H), 3.46 (s, 2H), 2.60 (q, J=7.5 Hz, 2H), 1.05 (t, J=7.5 Hz, 3H)

APCI-MS (m/z); 421 [M+H]$^+$

EXAMPLE 28

Synthesis of methyl 2-(3,4-dimethoxybenzoyl)-6-ethyl-3,5-dihydroxyphenylacetate (Compound 29)

(Step 1)

In a manner similar to that in Example 5, Step 4, methyl 3,5-diallyloxy-2-(3,4-dimethoxybenzoyl)-6-ethylphenylacetate (0.87 g, 81%) was obtained from methyl 3,5-diallyloxy-2-ethylphenylacetate (0.69 g, 2.4 mmol) obtained in Example 5, Step 3, using 3,4-dimethoxybenzoic acid (0.95 g, 5.2 mmol), trifluoroacetic acid (3.0 mL) and trifluoroacetic anhydride (0.70 mL).

$^1$H-NMR (CDCl$_3$, 270 MHz) δ (ppm): 7.54 (d, J=2.0 Hz, 1H), 7.31 (dd, J=2.0, 8.4 Hz, 1H), 6.80 (d, J=8.4 Hz, 1H), 6.44 (s, 1H), 6.06 (m, 1H), 5.71 (m, 1H), 5.45 (dq, J=17.3, 1.6 Hz, 1H), 5.30 (dq, J=10.6, 1.6 Hz, 1H), 5.09-5.02 (m, 2H), 4.57 (dt, J=4.9, 1.6 Hz, 2H), 4.38 (dt, J=4.9, 1.6 Hz, 2H), 3.93 (s, 3H), 3.92 (s, 3H), 3.63 (s, 2H), 3.46 (s, 3H), 2.65 (q, J=7.4 Hz, 2H), 1.10 (t, J=7.4 Hz, 3H)

ESI-MS (m/z); 455 [M+H]$^+$ (Step 2)

In a manner similar to that in Example 5, Step 5, Compound 29 (0.30 g, 42%) was obtained from methyl 3,5-diallyloxy-2-(3,4-dimethoxybenzoyl)-6-ethylphenylacetate (0.87 g, 1.9 mmol) obtained in Example 28, Step 1, using acetic acid (15 mL), triphenylphosphine (0.39 g, 1.5 mmol) and palladium (II) acetate (86 mg, 0.38 mmol).

$^1$H-NMR (CDCl$_3$; 270 MHz) δ (ppm): 7.44 (d, J=2.0 Hz, 1H), 7.36 (dd, J=2.0, 8.6 Hz, 1H), 6.95 (d, J=8.6 Hz, 1H), 6.35 (s, 1H), 3.88 (s, 3H), 3.83 (s, 3H), 3.53 (s, 2H), 3.44 (s, 3H), 2.58 (q, J=7.3 Hz, 2H), 1.07 (t, J=7.3 Hz, 3H)

ESI-MS (m/z); 375 [M+H]$^+$

EXAMPLE 29

Synthesis of 2-[2-ethyl-3,5-dihydroxy-6-(4-methoxybenzoylphenyl]-1-(4-phenylpiperazin-1-yl)ethanone (Compound 30)

In a manner similar to that in Example 10, Step 2, Compound 30 (95 mg, 70%) was obtained from 2-ethyl-3,5-dihydroxy-6-(4-methoxybenzoyl)phenylacetic acid (95 mg, 0.29 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.66 mmol), 1-phenylpiperazine (0.18 mL, 1.2 mmol) and N,N-dimethylformamide (1.0 mL).

$^1$H-NMR (DMSO-d$_6$, 270 MHz) δ (ppm): 9.37 (s, 1H), 9.08 (s, 1H), 7.62 (d, J=8.8 Hz, 2H), 7.20 (t, J=8.5 Hz, 2H), 6.88-6.76 (m, 5H), 6.33 (s, 1H), 3.72 (s, 3H), 3.51 (brs, 4H), 3.31 (brs, 2H), 2.93 (brs, 2H), 2.76 (brs, 2H), 2.40 (q, J=7.2 Hz, 2H), 0.99 (t, J=7.2 Hz, 3H)

APCI-MS (m/z); 473 [M−H]$^-$

EXAMPLE 30

Synthesis of 2-[2-ethyl-3,5-dihydroxy-6-(4-methoxybenzoyl)phenyl]-1-(4-hydroxy-4-phenylpiperidino)ethanone (Compound 31)

In a manner similar to that in Example 10, Step 2, Compound 31 (82 mg, 58%) was obtained from 2-ethyl-3,5-dihydroxy-6-(4-methoxybenzoyl)phenylacetic acid (96 mg, 0.29 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.67 mmol), 4-hydroxy-4-phenylpiperidine (0.21 g, 1.2 mmol) and N,N-dimethylformamide (1.0 mL).

$^1$H-NMR (DMSO-d$_6$, 270 MHz) δ (ppm): 9.37 (s, 1H), 9.06 (s, 1H), 7.66 (d, J=8.9 Hz, 2H), 7.33-7.29 (m, 4H), 7.22 (m, 1H), 6.92 (d, J=8.9 Hz, 2H), 6.32 (s, 1H), 5.02 (s, 1H), 4.09-4.01 (m, 2H), 3.76 (s, 3H), 3.59 (d, J=16.5 Hz, 1H), 3.46 (d, J=16.5 Hz, 1H), 3.30 (m, 1H), 2.75 (m, 1H), 2.50-2.35 (m, 2H), 1.60-1.24 (m, 4H), 1.00 (t, J=7.6 Hz, 3H)

APCI-MS (m/z); 488 [M−H]$^-$

EXAMPLE 31

Synthesis of 2-[2-ethyl-3,5-dihydroxy-6-(4-methoxybenzoyl)phenyl]-1-[4-(pyrimidin-2-yl)piperazin-1-yl]ethanone (Compound 32)

In a manner similar to that in Example 10, Step 2, Compound 32 (26 mg, 19%) was obtained from 2-ethyl-3,5-dihydroxy-6-(4-methoxybenzoyl)phenylacetic acid (92 mg, 0.28 mmol) obtained in Example 10, Step 1, using 1-hydroxybenzotriazole hydrate (0.11 g, 0.72 mmol), 1-(3-dimethylaminopropyl)-3-ethylcarbodiimide (0.10 g, 0.64 mmol), 1-(pyrimidin-2-yl)piperazine dihydrochloride (0.27 g, 1.1 mmol) and N,N-dimethylformamide (1.0 mL).

$^1$H-NMR (CD$_3$OD, 270 MHz) δ (ppm): 8.32 (d, J=4.6 Hz, 2H), 7.75 (d, J=9.1 Hz, 2H), 6.87 (d, J=9.1 Hz, 2H), 6.61 (t, J=4.6 Hz, 1H), 6.33 (s, 1H), 3.79 (s, 3H), 3.65 (brs, 4H), 3.50-3.44 (m, 4H), 3.40-3.34 (m, 2H), 2.58 (q, J=7.6 Hz, 2H), 1.09 (t, J=7.6 Hz, 3H)

APCI-MS (m/z); 477 [M+H]$^+$

EXAMPLE 32

Synthesis of 2-[2-ethyl-3,5-dihydroxy-6-(4-methoxybenzoyl)phenyl]-N-(2-hydroxyethyl)-N-(2-methoxyethyl)acetamide (Compound 33)

In a manner similar to that in Example 10, Step 2, Compound 33 (45 mg, 34%) was obtained from 2-ethyl-3,5-dihydroxy-6-(4-methoxybenzoyl)phenylacetic acid (0.10 g, 0.30 mmol) obtained in Example 10, Step 1, using 1-hydroxybenzotriazole hydrate (0.12 g, 0.78 mmol), 1-(3-dimethylaminopropyl)-3-ethylcarbodiimide hydrochloride (0.13 g, 0.68 mmol), 2-(2-methoxyethylamino)ethanol (0.15 g, 1.2 mmol) obtained in Reference Example 1 and N,N-dimethylformamide (1.0 mL).

$^1$H-NMR (CD$_3$OD, 270 MHz) δ (ppm): 7.80 (brd, J=8.9 Hz, 2H), 6.93 (d, J=8.9 Hz, 2H), 6.32 (s, 1H), 3.86 (s, 3H), 3.72 and 3.70 (s, total 2H), 3.61-3.28 (m, 8H), 3.18-3.12 (m, 3H), 2.62-2.50 (m, 2H), 1.08 (t, J=7.3 Hz, 3H) APCI-MS (m/z); 430 [M−H]$^-$

EXAMPLE 33

Synthesis of 6-[2-(2,3-dihydroxypropyloxy)ethyl]-5-ethyl-2,4-dihydroxyphenyl=2-fluoro-4-methoxyphenyl=ketone (Compound 34)

(Step 1)

In a manner similar to that in Example 1, Step 3, 1-(2-allyloxyethyl)-3,5-bis(methoxymethoxy)-2-ethylbenzene (4.2 g, 81%) was obtained as a pale yellow oil from 2-[3,5-bis(methoxymethoxy)-2-ethylphenyl]ethanol (4.5 g, 17 mmol) obtained in Example 7, Step 4, using a 60% sodium hydride dispersion in mineral oil (2.7 g, 68 mmol), allyl bromide (5.8 mL, 67 mmol) and N,N-dimethylformamide (90 mL).

$^1$H-NMR (CDCl$_3$, 300 MHz) δ (ppm): 6.67 (d, J=2.5 Hz, 1H), 6.56 (d, J=2.5 Hz, 1H), 5.93 (ddt, J=17.2, 10.8, 5.9 Hz, 1H), 5.27 (dq, J=17.2, 1.1 Hz, 1H), 5.19 (dq, J=10.8, 1.1 Hz, 1H), 5.17 (s, 2H), 5.12 (s, 2H), 4.00 (dt, J=5.9, 1.1 Hz, 2H), 3.60 (t, J=7.7 Hz, 2H), 3.48 (s, 3H), 3.47 (s, 3H), 2.90 (t, J=7.7 Hz, 2H), 2.63 (q, J=7.3 Hz, 2H), 1.10 (t, J=7.3 Hz, 3H)

(Step 2)

In a manner similar to that in Example 1, Step 4, 3-(2-allyloxyethyl)-1,5-bis(methoxymethoxy)-2-bromo-4-ethylbenzene (5.0 g, 95%) was obtained as a pale yellow oil from 1-(2-allyloxyethyl)-3,5-bis(methoxymethoxy)-2-ethylbenzene (4.2 g, 14 mmol) obtained in Example 33, Step 1, using N-bromosuccinimide (2.7 g, 15 mmol) and N,N-dimethylformamide (60 mL).

$^1$H-NMR (CDCl$_3$, 300 MHz) δ (ppm): 6.87 (s, 1H), 5.93 (ddt, J=17.2, 10.5, 5.8 Hz, 1H), 5.26 (dq, J=17.2, 1.5 Hz, 1H), 5.19 (s, 2H), 5.17 (s, 2H), 5.19-5.17 (m, 1H), 4.02 (dt, J=5.8, 1.5 Hz, 2H), 3.58 (t, J=7.9 Hz, 2H), 3.52 (s, 3H), 3.47 (s, 3H), 3.18 (t, J=7.9 Hz, 2H), 2.68 (q, J=7.3 Hz, 2H), 1.11 (t, J=7.3 Hz, 3H)

(Step 3)

3-(2-Allyloxyethyl)-1,5-bis(methoxymethoxy)-2-bromo-4-ethylbenzene (5.0 g, 13 mmol) obtained in Example 33, Step 2 was dissolved in a mixed solvent of tetrahydrofuran (50 mL) and water (10 mL). To the solution were added 4-methylmorpholine N-oxide (1.9 g, 16 mmol) and a 2.5% solution of osmium tetroxide in 2-methyl-2-propanol (1.0 mL) at room temperature with stirring, and the mixture was stirred overnight. After addition of a saturated aqueous solution of sodium thiosulfate, the reaction mixture was further stirred for 2 hours and then extracted twice with ethyl acetate. The organic layers were combined, washed with a saturated aqueous solution of sodium chloride, dried over anhydrous sodium sulfate and concentrated under reduced pressure to obtain 3-{2-[3,5-bis(methoxymethoxy)-2-bromo-6-ethylphenyl]ethoxy}propane-1,2-diol. The obtained 3-{2-[3,5-bis(methoxymethoxy)-2-bromo-6-ethylphenyl]ethoxy}propane-1,2-diol was dissolved in N,N-dimethylformamide (50 mL), and 2,2-dimethoxypropane (6.4 mL, 52 mmol) and p-toluenesulfonic acid monohydrate (0.12 g, 0.63 mmol) were added thereto at room temperature with stirring, followed by stirring for 30 minutes. After neutralization with a saturated aqueous solution of sodium hydrogencarbonate, the reaction mixture was extracted twice with ethyl acetate. The organic layers were combined, washed with a saturated aqueous solution of sodium chloride, dried over anhydrous sodium sulfate and concentrated under reduced pressure. The resulting residue was purified by silica gel column chromatography (ethyl acetate/hexane=1/9-1/4) to obtain 1,5-bis(methoxymethoxy)-3-{2-[(2,2-dimethyl-1,3-dioxolan-4-yl)methoxy]ethyl}-2-bromo-4-ethylbenzene (5.6 g, 93%) as a colorless oil.

$^1$H-NMR (CDCl$_3$, 300 MHz) δ (ppm): 6.87 (s, 1H), 5.19 (s, 2H), 5.16 (s, 2H), 4.28 (m, 1H), 4.06 (dd, J=8.2, 6.4 Hz, 1H), 3.73 (dd, J=8.2, 6.4 Hz, 1H), 3.65-3.46 (m, 4H), 3.52 (s, 3H), 3.47 (s, 3H), 3.17 (t, J=7.9 Hz, 2H), 2.68 (q, J=7.4 Hz, 2H), 1.43 (s, 3H), 1.37 (s, 3H), 1.11 (t, J=7.4 Hz, 3H)

ESI-MS (m/z); 480, 482 [M+NH$_3$]$^+$ (Step 4)

In a manner similar to that in Example 1, Step 5, (4,6-bis(methoxymethoxy)-2-{2-[(2,2-dimethyl-1,3-dioxolan-4-yl)methoxy]ethyl}-3-ethylphenyl)(2-fluoro-4-methoxyphenyl)

methanol was obtained from 1,5-bis(methoxymethoxy)-3-{2-[(2,2-dimethyl-1,3-dioxolan-4-yl)methoxy]ethyl}-2-bromo-4-ethylbenzene (0.39 g, 0.84 mmol) obtained in Example 33, Step 3, using a 1.5 mol/L solution of n-butyl-lithium in tetrahydrofuran (1.0 mL, 1.5 mmol), 2-fluoro-4-methoxybenzaldehyde (0.13 g, 0.84 mmol) and tetrahydrofuran (10 mL). Further, 4,6-bis(methoxymethoxy)-2-{2-[(2,2-dimethyl-1,3-dioxolan-4-yl)methoxy]ethyl}-3-ethylphenyl=2-fluoro-4-methoxyphenyl=ketone (0.21 g, 46%) was obtained from (4,6-bis(methoxymethoxy)-2-{2-[(2,2-dimethyl-1,3-dioxolan-4-yl)methoxy]ethyl}-3-ethylphenyl) (2-fluoro-4-methoxyphenyl)methanol, using pyridinium dichromate (0.16 g, 0.43 mmol) and dichloromethane (10 mL) $^1$H-NMR (CDCl$_3$, 300 MHz) δ (ppm): 7.72 (t, J=8.8 Hz, 1H), 6.81 (s, 1H), 6.70 (dd, J=8.8, 2.3 Hz, 1H), 6.57 (dd, J=13, 2.3 Hz, 1H), 5.21 (s, 2H), 4.97 (s, 2H), 4.14 (m, 1H), 3.97 (dd, J=8.3, 6.4 Hz, 1H), 3.84 (s, 3H), 3.62 (dd, J=8.3, 6.4 Hz, 1H), 3.60-3.53 (m, 2H), 3.50 (s, 3H), 3.42 (dd, J=9.9, 5.8 Hz, 1H), 3.35 (dd, J=9.9, 5.8 Hz, 1H), 3.25 (s, 3H), 2.81 (dd, J=9.9, 6.8 Hz, 2H), 2.66 (q, J=7.4 Hz, 2H), 1.38 (s, 3H), 1.33 (s, 3H), 1.13 (t, J=7.4 Hz, 3H)

(Step 5)

In a manner similar to that in Example 1, Step 6, Compound 34 (54 mg, 60%) was obtained from 4,6-bis(methoxymethoxy)-2-{2-[(2,2-dimethyl-1,3-dioxolan-4-yl)methoxy]ethyl}-3-ethylphenyl=2-fluoro-4-methoxyphenyl=ketone (0.12 g, 0.23 mmol) obtained in Example 33, Step 4, using methanol (2.0 mL) and a 4 mol/L solution of hydrogen chloride in 1,4-dioxane (2.0 mL).

$^1$H-NMR (CD$_3$OD, 300 MHz) δ (ppm): 7.52 (t, J=8.8 Hz, 1H), 6.68 (dd, J=8.8, 2.5 Hz, 1H), 6.62 (dd, J=13, 2.5 Hz, 1H), 6.17 (s, 1H), 3.76 (s, 3H), 3.57 (m, 1H), 3.45-3.20 (m, 6H), 2.70 (t, J=8.2 Hz, 2H), 2.54 (q, J=7.4 Hz, 2H), 1.03 (t, J=7.4 Hz, 3H)

APCI-MS (m/z); 407 [M−H]$^−$

EXAMPLE 34

Synthesis of 2-[2-ethyl-3,5-dihydroxy-6-(4-methoxybenzoyl)phenyl]-1-[4-(3-methoxyphenyl)piperazin-1-yl]ethanone (Compound 35)

In a manner similar to that in Example 10, Step 2, Compound 35 (0.11 g, 74%) was obtained from 2-ethyl-3,5-dihydroxy-6-(4-methoxybenzoyl)phenylacetic acid (93 mg, 0.28 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.68 mmol), 1-(3-methoxyphenyl)piperazine (0.22 g, 1.1 mmol) and N,N-dimethylformamide (1.0 mL).

$^1$H-NMR (CD$_3$OD, 270 MHz) δ (ppm): 7.75 (d, J=8.9 Hz, 2H), 7.13 (t, J=8.3 Hz, 1H), 6.84 (d, J=8.9 Hz, 2H), 6.50-6.41 (m, 3H), 6.33 (s, 1H), 3.76 (s, 3H), 3.75 (s, 3H), 3.65 (s, 2H), 3.57-3.52 (m, 2H), 3.45-3.41 (m, 2H), 2.96-2.92 (m, 2H), 2.76-2.72 (m, 2H), 2.58 (q, J=7.6 Hz, 2H), 1.09 (t, J=7.6 Hz, 3H)

APCI-MS (m/z); 505 [M+H]$^+$

EXAMPLE 35

Synthesis of 1-acetyl-4-{2-[2-ethyl-3,5-dihydroxy-6-(4-methoxybenzoyl)phenyl]acetyl}piperazine (Compound 36)

In a manner similar to that in Example 10, Step 2, Compound 36 (77 mg, 65%) was obtained from 2-ethyl-3,5-dihydroxy-6-(4-methoxybenzoyl)phenylacetic acid (89 mg, 0.27 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.12 g, 0.63 mmol), 1-acetylpiperazine (0.14 g, 1.1 mmol) and N,N-dimethylformamide (1.0 mL).

$^1$H-NMR (DMSO-d$_6$, 80° C., 300 MHz) δ (ppm): 9.39 (brs, 1H), 9.09 (brs, 1H), 7.65 (d, J=8.9 Hz, 2H), 6.92 (d, J=8.9 Hz, 2H), 6.35 (s, 1H), 3.81 (s, 3H), 3.50 (s, 2H), 3.25-3.07 (m, 8H), 2.50-2.41 (m, 2H), 1.96 (s, 3H), 1.01 (t, J=7.2 Hz, 3H)

APCI-MS (m/z); 439 [M−H]$^−$

EXAMPLE 36

Synthesis of 2-[2-ethyl-3,5-dihydroxy-6-(4-methoxybenzoyl)phenyl]-1-(4-methylpiperazin-1-yl)ethanone (Compound 37)

In a manner similar to that in Example 10, Step 2, Compound 37 (58 mg, 49%) was obtained from 2-ethyl-3,5-dihydroxy-6-(4-methoxybenzoyl)phenylacetic acid (95 mg, 0.29 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.68 mmol), 1-methylpiperazine (0.13 mL, 1.2 mmol) and N,N-dimethylformamide (1.0 mL).

$^1$H-NMR (DMSO-d$_6$, 300 MHz) δ (ppm): 9.35 (s, 1H), 9.06 (s, 1H), 7.63 (d, J=8.8 Hz, 2H), 6.93 (d, J=8.8 Hz, 2H), 6.32 (s, 1H), 3.80 (s, 3H), 3.44 (s, 2H), 3.31 (brs, 2H), 3.16 (brs, 2H), 2.38 (q, J=7.2 Hz, 2H), 2.06 (brs, 5H), 1.92 (brs, 2H), 0.97 (t, J=7.2 Hz, 3H)

APCI-MS (m/z); 413 [M+H]$^+$

EXAMPLE 37

Synthesis of 2-[2-ethyl-3,5-dihydroxy-6-(4-methoxybenzoyl)phenyl]-1-(6,7-dimethoxy-1,2,3,4-tetrahydroisoquinolin-2-yl)ethanone (Compound 38)

In a manner similar to that in Example 10, Step 2, Compound 38 (61 mg, 41%) was obtained from 2-ethyl-3,5-dihydroxy-6-(4-methoxybenzoyl)phenylacetic acid (98 mg, 0.30 mmol) obtained in Example 10, Step 1, using 1-hydroxybenzotriazole hydrate (0.12 g, 0.75 mmol), 1-(3-dimethylaminopropyl)-3-ethylcarbodiimide (0.11 g, 0.69 mmol), 6,7-dimethoxy-1,2,3,4-tetrahydroisoquinoline hydrochloride (0.28 g, 1.2 mmol) and N,N-dimethylformamide (1.0 mL).

$^1$H-NMR (DMSO-d$_6$, 80° C., 300 MHz) δ (ppm): 9.09 (brs, 1H), 8.81 (brs, 1H), 7.60 (d, J=8.7 Hz, 2H), 6.83 (brd, J=8.7 Hz, 2H), 6.67 (s, 2H), 6.35 (s, 1H), 4.31 (brs, 1H), 3.76 (s, 3H), 3.73 (s, 3H), 3.71 (s, 3H), 3.55 (s, 2H), 3.46 (brs, 2H), 3.07 (s, 1H), 2.54-2.40 (m, 4H), 0.99 (t, J=7.2 Hz, 3H)

APCI-MS (m/z); 504 [M−H]$^−$

EXAMPLE 38

Synthesis of 2-[2-ethyl-3,5-dihydroxy-6-(4-methoxybenzoyl)phenyl]-N-(furan-2-ylmethyl)-N-methylacetamide (Compound 39)

In a manner similar to that in Example 10, Step 2, Compound 39 (86 mg, 70%) was obtained from 2-ethyl-3,5-dihydroxy-6-(4-methoxybenzoyl)phenylacetic acid (96 mg, 0.29 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.67 mmol), N-methylfurfurylamine (0.13 mL, 1.2 mmol) and N,N-dimethylformamide (1.0 mL), ¹H-NMR (DMSO-d₆, 80° C., 300 MHz) δ (ppm): 9.09 (s, 1H), 8.81 (s, 1H), 7.66 (d, J=9.0 Hz, 2H), 7.47 (bs, 1H), 6.92 (d, J=9.0 Hz, 2H), 6.34 (s, 1H), 6.32 (bs, 1H), 6.10 (brs, 1H), 4.33 (brs, 2H), 3.81 (s, 3H), 3.56 (brs, 2H), 2.80 (brs, 3H), 2.39 (q, J=7.2 Hz, 2H), 0.99 (t, J=7.2 Hz, 3H)

APCI-MS (m/z); 422 [M−H]⁻

EXAMPLE 39

Synthesis of 2-[2-ethyl-3,5-dihydroxy-6-(4-methoxybenzoyl)phenyl]-1-[4-(2-hydroxyethyl)piperazin-1-yl]ethanone (Compound 40)

In a manner similar to that in Example 10, Step 2, Compound 40 (39 mg, 32%) was obtained from 2-ethyl-3,5-dihydroxy-6-(4-methoxybenzoyl)phenylacetic acid (93 mg, 0.28 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.65 mmol), 1-(2-hydroxyethyl)piperazine (0.14 mL, 1.1 mmol) and N,N-dimethylformamide (1.0 mL).

¹H-NMR (CD₃OD, 270 MHz) δ (ppm): 7.76 (d, J=8.9 Hz, 2H), 6.93 (d, J=8.9 Hz, 2H), 6.32 (s, 1H), 3.85 (s, 3H), 3.70 (t, J=5.4 Hz, 2H), 3.65 (s, 2H), 3.54 (brs, 2H), 3.42, (brs, 2H), 2.71-2.46 (m, 8H), 1.08 (t, J=7.6 Hz, 3H) APCI-MS (m/z); 441 [M−H]⁻

EXAMPLE 40

Synthesis of 2-[2-(3,4-dimethoxybenzoyl)-6-ethyl-3,5-dihydroxyphenyl]-1-(4-phenylpiperazin-1-yl)ethanone (Compound 41)

(Step 1)

In a manner similar to that in Example 10, Step 1, 2-(3,4-dimethoxybenzoyl)-6-ethyl-3,5-dihydroxyphenylacetic acid was quantitatively obtained from Compound 29 (0.34 g, 0.89 mmol) obtained in Example 28, using a 2 mol/L aqueous solution of sodium hydroxide (10 mL) and acetonitrile (10 mL).

¹H-NMR (CD₃OD, 270 MHz) δ (ppm): 7.46 (d, J=2.0 Hz, 1H), 7.40 (dd, J=2.0, 8.4 Hz, 1H), 6.94 (d, J=8.4 Hz, 1H), 6.34 (s, 1H), 3.87 (s, 3H), 3.82 (s, 3H), 3.50 (m, 2H), 2.59 (q, J=7.3 Hz, 2H), 1.09 (t, J=7.3 Hz, 3H)

FAB-MS (m/z); 361 [M+H]⁺

(Step 2)

In a manner similar to that in Example 10, Step 2, Compound 41 (49 mg, 34%) was obtained from 2-(3,4-dimethoxybenzoyl-6-ethyl-3,5-dihydroxyphenylacetic acid) phenylacetic acid (0.10 g, 0.29 mmol) obtained in Example 40, Step 1, using 1-hydroxybenzotriazole hydrate (0.11 g, 0.71 mmol), 1-(3-dimethylaminopropyl)-3-ethylcarbodiimide hydrochloride (0.13 g, 0.66 mmol), 1-phenylpiperazine (0.13 mL, 0.86 mmol) and N,N-dimethylformamide (1.0 mL).

¹H-NMR (DMSO-d₆, 270 MHz) δ (ppm): 9.35 (s, 1H), 9.05 (s, 1H), 7.24-7.17 (m, 4H), 6.90-6.76 (m, 4H), 6.33 (s, 1H), 3.70 (s, 3H), 3.63 (s, 3H), 3.51-3.28 (m, 6H), 2.92-2.84 (m, 2H), 2.75-2.67 (m, 2H), 2.40 (q, J=7.3 Hz, 2H), 0.99 (t, J=7.3 Hz, 3H)

ESI-MS (m/z); 505 [M+H]⁺

EXAMPLE 41

Synthesis of 2-[2-ethyl-3,5-dihydroxy-6-(4-methoxybenzoyl)phenyl]-N,N-dimethylacetamide (Compound 42)

In a manner similar to that in Example 10, Step 2, Compound 42 (69 mg, 69%) was obtained from 2-ethyl-3,5-dihydroxy-6-(4-methoxybenzoyl)phenylacetic acid (92 mg, 0.28 mmol) obtained in Example 10, Step 1, using 1-hydroxybenzotriazole dimethylamine salt (0.22 g, 1.1 mmol), 1-(3-dimethylaminopropyl)-3-ethylcarbodiimide hydrochloride (0.12 g, 0.65 mmol) and N,N-dimethylformamide (1.0 mL).

¹H-NMR (CD₃OD, 270 MHz) δ (ppm): 7.76 (d, J=9.0 Hz, 2H), 6.92 (d, J=9.0 Hz, 2H), 6.31 (s, 1H), 3.84 (s, 3H), 3.58 (s, 2H), 2.89 (s, 3H), 2.64 (s, 3H), 2.59 (q, J=7.3. Hz, 2H), 1.07 (t, J=7.3 Hz, 3H)

APCI-MS (m/z); 356 [M−H]⁻

EXAMPLE 42

Synthesis of 2-[2-(3,4-dimethoxybenzoyl)-6-ethyl-3,5-dihydroxyphenyl]-1-[4-(3-hydroxyphenyl)piperazin-1-yl]ethanone (Compound 43)

In a manner similar to that in Example 10, Step 2, Compound 43 (86 mg, 65%) was obtained from 2-ethyl-3,5-dihydroxy-6-(4-methoxybenzoyl)phenylacetic acid (89 mg, 0.27 mmol) obtained in Example 10, Step 1, using 1-hydroxybenzotriazole hydrate (95 mg, 0.62 mmol), 1-(3-dimethylaminopropyl)-3-ethylcarbodiimide hydrochloride (0.12 g, 0.63 mmol), 1-(3-hydroxyphenyl)piperazine (0.19 mg, 1.1 mmol) and N,N-dimethylformamide (1.0 mL).

¹H-NMR (CD₃OD, 300 MHz) δ (ppm): 7.75 (d, J=9.0 Hz, 2H), 7.03 (t, J=8.3 Hz, 1H), 6.84 (d, J=9.0 Hz, 2H), 6.40-6.30 (m, 4H), 3.74 (s, 3H), 3.65 (s, 2H), 3.54-3.51 (m, 2H), 3.44-3.41 (m, 2H), 2.93-2.89 (m, 2H), 2.73-2.70 (m, 2H), 2.59 (q, J=7.3 Hz, 2H), 1.08 (t, J=7.3 Hz, 3H)

APCI-MS (m/z); 489 [M−H]⁻

EXAMPLE 43

Synthesis of 2-[2-ethyl-3,5-dihydroxy-6-(4-methoxybenzoyl)phenyl]-1-morpholinoethanone (Compound 44)

In a manner similar to that in Example 10, Step 2, Compound 44 (68 mg, 63%) was obtained from 2-ethyl-3,5-dihydroxy-6-(4-methoxybenzoyl)phenylacetic acid (90 mg, 0.27 mmol) obtained in Example 10, Step 1, using 1-hydroxybenzotriazole hydrate (0.10 g, 0.68 mmol), 1-(3-dimethylaminopropyl)-3-ethylcarbodiimide hydrochloride (0.12 g, 0.63 mmol), morpholine (0.095 mL, 1.1 mmol) and N,N-dimethylformamide (1.0 mL).

¹H-NMR (CD₃OD, 300 MHz) δ (ppm): 7.76 (d, J=8.9 Hz, 2H), 6.93 (d, J=8.9 Hz, 2H), 6.32 (s, 1H), 3.85 (s, 3H), 3.60 (s, 2H), 3.50-3.29 (m, 8H), 2.56 (q, J=7.5 Hz, 2H), 1.08 (t, J=7.5 Hz, 3H)

APCI-MS (m/z); 398 [M−H]⁻

EXAMPLE 44

Synthesis of 2-[2-ethyl-3,5-dihydroxy-6-(4-methoxybenzoyl)phenyl]-N-[3-(2-oxopyrrolidinyl)propyl]acetamide (Compound 45)

In a manner similar to that in Example 10, Step 2, Compound 45 (75 mg, 59%) was obtained from 2-ethyl-3,5-dihydroxy-6-(4-methoxybenzoyl)phenylacetic acid (93 mg, 0.28 mmol) obtained in Example 10, Step 1, using 1-hydroxybenzotriazole hydrate (0.11 g, 0.69 mmol), 1-(3-dimethylaminopropyl)-3-ethylcarbodiimide hydrochloride (0.12 g, 0.65 mmol), 1-(3-aminopropyl)-2-pyrrolidinone (0.16 mL, 1.1 mmol) and N,N-dimethylformamide (1.0 mL). $^1$H-NMR (CD$_3$OD, 270 MHz) δ (ppm): 7.79 (d, J=9.1 Hz, 2H), 6.94 (d, J=9.1 Hz, 2H), 6.34 (s, 1H), 3.85 (s, 3H), 3.38-3.34 (m, 4H), 3.16 (t, J=7.0 Hz, 2H), 3.01 (t, J=7.0 Hz, 2H), 2.60 (q, J=7.3 Hz, 2H), 2.33 (t, J=8.1 Hz, 2H), 2.05-1.97 (m, 2H), 1.60-1.50 (m, 2H), 1.07 (t, J=7.3 Hz, 3H)

APCI-MS (m/z); 453 [M−H]$^−$

EXAMPLE 45

Synthesis of 6-[2-(2,3-dihydroxypropyloxy)ethyl]-5-ethyl-2,4-dihydroxyphenyl=4-methoxyphenyl=ketone (Compound 46)

(Step 1)

In a manner similar to that in Example 1, Step 5, (4,6-bis(methoxymethoxy)-2-{2-[(2,2-dimethyl-1,3-dioxolan-4-yl)methoxy]ethyl}-3-ethylphenyl) (4-methoxyphenyl)methanol was obtained from 1,5-bis(methoxymethoxy)-3-{2-[(2,2-dimethyl-1,3-dioxolan-4-yl)methoxy]ethyl}-2-bromo-4-ethylbenzene (0.51 g, 1.1 mmol) obtained in Example 33, Step 3, using a 1.5 mol/L solution of n-butyllithium in tetrahydrofuran (1.5 mL, 2.3 mmol), 4-methoxybenzaldehyde (0.27 mL, 2.2 mmol) and tetrahydrofuran (10 mL). Further, 4,6-bis(methoxymethoxy)-2-{2-[(2,2-dimethyl-1,3-dioxolan-4-yl)methoxy]ethyl}-3-ethylphenyl=4-methoxyphenyl=ketone (0.29 g, 61%) was obtained as a colorless oil from (4,6-bis (methoxymethoxy)-2-{2-[(2,2-dimethyl-1,3-dioxolan-4-yl)-methoxy]ethyl}-3-ethylphenyl) (4-methoxyphenyl)methanol, using pyridinium dichromate (0.83 g, 2.2 mmol) and dichloromethane (10 mL).

$^1$H-NMR (CDCl$_3$, 300 MHz) δ (ppm): 7.79 (d, J=7.1 Hz, 2H), 6.90 (d, J=7.1 Hz, 2H), 6.83 (s, 1H), 5.22 (s, 2H), 4.97 (s, 2H), 4.13 (m, 1H), 3.96 (dd, J=8.2, 6.4 Hz, 1H), 3.85 (s, 3H), 3.60 (dd, J=8.2, 6.4 Hz, 1H), 3.51 (s, 3H), 3.52-3.47 (m, 2H), 3.39 (dd, J=9.9, 5.8 Hz, 2H), 3.28 (dd, J=9.9, 5.8 Hz, 2H), 3.25 (s, 3H), 2.74 (t, J=8.2 Hz, 1H), 2.67 (q, J=7.3 Hz, 1H), 1.37 (s, 3H), 1.32 (s, 3H), 1.13 (t, J=7.3 Hz, 3H)

(Step 2)

In a manner similar to that in Example 1, Step 6, Compound 46 (70 mg, 30%) was obtained as a colorless solid from 4,6-bis(methoxymethoxy)-2-{2-[(2,2-dimethyl-1,3-dioxolan-4-yl)methoxy]ethyl}-3-ethylphenyl=4-methoxyphenyl=ketone (0.29 g, 0.56 mmol) obtained in Example 45, Step 1, using a 4 mol/L solution of hydrogen chloride in 1,4-dioxane (1.5 mL) and methanol (1.5 mL).

$^1$H-NMR (CD$_3$OD, 300 MHz) δ (ppm): 7.76 (d, J=8.9 Hz, 2H), 6.95 (d, J=8.9 Hz, 2H), 6.28 (s, 1H), 3.85 (s, 3H), 3.62 (m, 1H), 3.46-3.28 (m, 6H), 2.69 (t, J=8.44 Hz, 2H), 2.63 (q, J=7.3 HZ, 2H), 1.12 (t, J=7.3 Hz, 3H)

APCI-MS (m/z); 389 [M−H]$^−$

EXAMPLE 46

Synthesis of 2-[2-ethyl-3,5-dihydroxy-6-(4-methoxybenzoyl)phenyl]-N-[2-hydroxy-1-(hydroxymethyl)ethyl]acetamide (Compound 47)

In a manner similar to that in Example 10, Step 2, Compound 47 (63 mg, 54%) was obtained from 2-ethyl-3,5-dihydroxy-6-(4-methoxybenzoyl)phenylacetic acid (96 mg, 0.29 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.67 mmol), 2-aminopropane-1,3-diol (0.10 g, 1.2 mmol) and N,N-dimethylformamide (1.0 mL).

$^1$H-NMR (CD$_3$OD, 300 MHz) δ (ppm): 7.78 (d, J=9.0 Hz, 2H), 6.94 (d, J=9.0 Hz, 2H), 6.34 (s, 1H), 3.85 (s, 3H), 3.76 (m, 1H), 3.54-3.41 (m, 6H), 2.63 (q, J=7.3 Hz, 2H), 1.08 (t, J=7.3 Hz, 3H)

APCI-MS (m/z); 402 [M−H]$^−$

EXAMPLE 47

Synthesis of 2-[2-ethyl-3,5-dihydroxy-6-(4-methoxybenzoyl)phenyl]-N-[1-hydroxy-2-(hydroxymethyl)propan-2-yl]acetamide (Compound 48)

In a manner similar to that in Example 10, Step 2, Compound 48 (32 mg, 26%) was obtained from 2-ethyl-3,5-dihydroxy-6-(4-methoxybenzoyl)phenylacetic acid (96 mg, 0.29 mmol) obtained in Example 10, Step 1, using 1-hydroxybenzotriazole hydrate (0.11 g, 0.72 mmol), 1-(3-dimethylaminopropyl)-3-ethylcarbodiimide hydrochloride (0.13 g, 0.67 mmol), 2-amino-2-methylpropane-1,3-diol (0.12 g, 1.2 mmol) and N,N-dimethylformamide (1.0 mL). $^1$H-NMR (CD$_3$OD, 270 MHz) δ (ppm): 7.79 (d, J=9.1 Hz, 2H), 6.94 (d, J=9.1 Hz, 2H), 6.34 (s, 1H), 3.85 (s, 3H), 3.51 (d, J=11.2 Hz, 2H), 3.46 (d, J=11.2 Hz, 2H), 3.39 (s, 2H), 2.44 (q, J=7.4 Hz, 2H), 1.11-1.06 (m, 6H)

APCI-MS (m/z); 416 [M−H]$^−$

EXAMPLE 48

Synthesis of 2-[2-(3,4-dimethoxybenzoyl)-6-ethyl-3,5-dihydroxyphenyl)-N,N-bis(2-hydroxyethyl)acetamide (Compound 49)

In a manner similar to that in Example 10, Step 2, Compound 49 (63 mg, 44%) was obtained from 2-(3,4-dimethoxybenzoyl)-6-ethyl-3,5-dihydroxyphenylacetic acid (0.11 g, 0.32 mmol) obtained in Example 40, Step 1, using 1-hydroxybenzotriazole hydrate (0.12 g, 0.80 mmol), 1-(3-dimethylaminopropyl)-3-ethylcarbodiimide hydrochloride (0.14 g, 0.73 mmol), diethanolamine (0.12 mL, 1.3 mmol) and N,N-dimethylformamide (1.0 mL).

$^1$H-NMR (CD$_3$OD, 270 MHz) δ (ppm): 7.46 (d, J=2.0 Hz, 1H), 7.41 (dd, J=2.0, 8.3 Hz, 1H), 6.94 (d, J=8.3 Hz, 1H), 6.32 (s, 1H), 3.88 (s, 3H), 3.84 (s, 3H), 3.69 (s, 2H), 3.59 (t, J=5.4 Hz, 2H), 3.43 (d, J=5.4 Hz, 2H), 3.40 (d, J=5.4 Hz, 2H), 3.31-3.28 (m, 2H), 2.55 (q, J=7.4 Hz, 2H), 1.07 (t, J=7.4 Hz, 3H) ES-MS (m/z); 448 [M+H]$^+$

EXAMPLE 49

Synthesis of 2-[2-ethyl-3,5-dihydroxy-6-(4-fluorobenzoyl)phenyl]-N,N-bis(2-hydroxyethyl)acetamide (Compound 50)

(Step 1)

In a manner similar to that in Example 5, Step 4, methyl 3,5-diallyloxy-2-ethyl-6-(4-fluorobenzoyl)phenylacetate (0.64 g, 83%) was obtained from methyl 3,5-diallyloxy-2-ethylphenylacetate (0.52 g, 2.2 mmol) obtained in Example 5, Step 3, using 4-fluorobenzoic acid (0.91 g, 6.5 mmol), trifluoroacetic acid (5.0 mL) and trifluoroacetic anhydride (1.7 mL)

$^1$H-NMR (CDCl$_3$, 300 MHz) δ (ppm): 7.83 (dd, J=5.9, 8.4 Hz, 2H), 7.06 (t, J=8.4 Hz, 2H), 6.42 (s, 1H), 6.07 (m, 1H), 5.62 (m, 1H), 5.45 (brd, J=17.2 Hz, 1H), 5.31 (brd, J=10.6 Hz, 1H), 5.03 (brd, J=10.6 Hz, 1H), 4.98 (brd, J=18.0 Hz, 1H), 4.57 (brd, J=4.8 Hz, 2H), 4.34 (brd, J=4.8 Hz, 2H), 3.69 (s, 2H), 3.45 (s, 3H), 2.66 (q, J=7.4 Hz, 2H), 1.10 (t, J=7.4 Hz, 3H)

APCI-MS (m/z); 413 [M+H]$^+$ (Step 2)

In a manner similar to that in Example 7, Step 1, methyl 2-ethyl-6-(4-fluorobenzoyl)-3,5-dihydroxyphenylacetate (0.30 g, 61%) was obtained from methyl 3,5-diallyloxy-2-ethyl-6-(4-fluorobenzoyl)phenylacetate (0.87 g, 1.9 mmol) obtained in Example 49, Step 1, using ammonium formate (0.38 g, 6.0 mmol), bis(triphenylphosphine)palladium (II) dichloride (53 mg, 0.076 mmol) and 1,4-dioxane (25 mL)

$^1$H-NMR (CD$_3$OD, 300 MHz) δ (ppm): 7.82 (dd, J=5.7, 9.0 Hz, 2H), 7.13 (t, J=9.0 Hz, 1H), 6.33 (s, 1H), 3.59 (s, 2H), 3.44 (s, 3H), 2.59 (q, J=7.5 Hz, 2H), 1.06 (t, J=7.5 Hz, 3H)

APCI-MS (m/z); 331 [M–H]$^-$ (Step 3)

In a manner similar to that in Example 10, Step 1, 2-ethyl-6-(4-fluorobenzoyl)-3,5-dihydroxyphenylacetic acid was quantitatively obtained from methyl 2-ethyl-6-(4-fluorobenzoyl)-3,5-dihydroxyphenylacetate (0.30 g, 0.92 mmol) obtained in Example 49, Step 2, using a 2 mol/L aqueous solution of sodium hydroxide (6.0 mL) and acetonitrile (6.0 mL).

$^1$H-NMR (CD$_3$OD, 270 MHz) δ (ppm): 7.82 (dd, J=5.5, 8.9 Hz, 2H), 7.11 (t, J=8.9 Hz, 2H), 6.33 (s, 1H), 3.59 (s, 2H), 2.61 (q, J=7.5 Hz, 2H), 1.09 (t, J=7.5 Hz, 3H), APCI-MS (m/z); 317 [M–H]$^-$ (Step 4)

In a manner similar to that in Example 10, Step 2, Compound 50 (47 mg, 42%) was obtained from 2-ethyl-6-(4-fluorobenzoyl)-3,5-dihydroxyphenylacetic acid (88 mg, 0.28 mmol) obtained in Example 49, Step 3, using 1-hydroxybenzotriazole hydrate (0.11 g, 0.69 mmol), 1-(3-dimethylaminopropyl)-3-ethylcarbodiimide hydrochloride (0.12 g, 0.64 mmol), diethanolamine (0.12 mg, 1.1 mmol) and N,N-dimethylformamide (1.0 mL).

$^1$H-NMR (CD$_3$OD, 270 MHz) δ (ppm): 7.84 (dd, J=5.6, 8.9 Hz, 2H), 7.10 (t, J=8.9 Hz, 2H), 6.31 (s, 1H), 3.77 (s, 2H), 3.64 (t, J=5.4 Hz, 2H), 3.49-3.29 (m, 6H), 2.55 (q, J=7.3 Hz, 2H), 1.07 (t, J=7.3 Hz, 3H)

ESI-MS (m/z); 406 [M–H]$^-$

EXAMPLE 50

Synthesis of 6-[2-(2,3-dihydroxypropyloxy)ethyl]-5-ethyl-2,4-dihydroxyphenyl=3,4-dimethoxyphenyl=ketone (Compound 51)

(Step 1)

In a manner similar to that in Example 1, Step 5, (4,6-bis(methoxymethoxy)-2-{2-[(2,2-dimethyl-1,3-dioxolan-4-yl)methoxy]ethyl}-3-ethylphenyl)(3,4-dimethoxyphenyl)methanol was obtained from 1,5-bis(methoxymethoxy)-3-{2-[(2,2-dimethyl-1,3-dioxolan-4-yl)methoxy]ethyl}-2-bromo-4-ethylbenzene (0.10 g, 0.22 mmol) obtained in Example 33, Step 3, using a 1.5 mol/L solution of n-butyllithium in tetrahydrofuran (0.3 mL, 0.45 mmol), 3,4-dimethoxybenzaldehyde (55 mg, 0.33 mmol) and tetrahydrofuran (4.0 mL). Further, 4,6-bis(methoxymethoxy)-2-{2-[(2,2-dimethyl-1,3-dioxolan-4-yl)-methoxy]ethyl}-3-ethylphenyl=3,4-dimethoxyphenyl=ketone (45 mg, 38%) was obtained from (4,6-bis(methoxymethoxy)-2-{2-[(2,2-dimethyl-1,3-dioxolan-4-yl)methoxy]ethyl}-3-ethylphenyl)(3,4-dimethoxyphenyl)methanol, using pyridinium dichromate (0.15 g, 0.40 mmol) and dichloromethane (4.0 mL).

$^1$H-NMR (CDCl$_3$, 300 MHz) δ (ppm): 7.61 (d, J=1.8 Hz, 1H), 7.23 (dd, J=8.4, 1.8 Hz, 1H), 6.85 (s, 1H), 6.79 (d, J=8.4 Hz, 1H), 5.23 (s, 2H), 4.98 (s, 2H), 4.15 (m, 1H), 3.97 (dd, J=8.3, 6.4 Hz, 1H), 3.95 (s, 3H), 3.92 (s, 3H), 3.61 (dd, J=8.3, 6.4 Hz, 1H), 3.52 (s, 3H), 3.55-3.47 (m, 2H), 3.41 (dd, J=9.9, 5.9 Hz, 1H), 3.30 (dd, J=9.9, 5.9 Hz, 1H), 3.25 (s, 3H), 2.75 (t, J=8.1 Hz, 2H), 2.68 (q, J=7.3 Hz, 2H), 1.37 (s, 3H), 1.32 (s, 3H), 1.14 (t, J=7.3 Hz, 3H)

(Step 2)

In a manner similar to that in Example 1, Step 6, Compound 51 (25 mg, 75%) was obtained from 4,6-bis(methoxymethoxy)-2-{2-[(2,2-dimethyl-1,3-dioxolan-4-yl)methoxy]ethyl}-3-ethylphenyl=3,4-dimethoxyphenyl=ketone (45 mg, 0.082 mmol) obtained in Example 50, Step 1, using a 4 mol/L solution of hydrogen chloride in 1,4-dioxane (1.0 mL) and methanol (1.0 mL).

$^1$H-NMR (CD$_3$OD, 300 MHz) δ (ppm): 7.48 (d, J=2.0 Hz, 1H), 7.31 (dd, J=8.4, 2.0 Hz, 1H), 6.93 (d, J=8.4 Hz, 1H), 6.28 (s, 1H), 3.86 (s, 3H), 3.82 (s, 3H), 3.63 (m, 1H), 3.50-3.26 (m, 6H), 2.69 (t, J=8.1 Hz, 2H), 2.64 (q, J=7.3 Hz, 2H), 1.11 (t, J=7.3 Hz, 3H)

ESI-MS (m/z); 419 [M–H]$^-$

EXAMPLE 51

Synthesis of 6-[2-(2,3-dihydroxypropyloxy)ethyl]-5-ethyl-2,4-dihydroxyphenyl=3-fluoro-4-methoxyphenyl=ketone (Compound 52)

(Step 1)

In a manner similar to that in Example 1, Step 5, (4,6-bis(methoxymethoxy)-2-{2-[(2,2-dimethyl-1,3-dioxolan-4-yl)methoxy]ethyl}-3-ethylphenyl)(3-fluoro-4-methoxyphenyl)methanol was obtained from 1,5-bis(methoxymethoxy)-3-{2-[(2,2-dimethyl-1,3-dioxolan-4-yl)methoxy]ethyl}-2-bromo-4-ethylbenzene (0.10 g, 0.22 mmol) obtained in Example 33, Step 3, using a 1.5 mol/L solution of n-butyllithium in tetrahydrofuran (0.30 mL, 0.45 mmol), 3-fluoro-4-methoxybenzaldehyde (50 mg, 0.33 mmol) and tetrahydrofuran (4.0 mL). Further, 4,6-bis(methoxymethoxy)-2-{2-[(2,2-dimethyl-1,3-dioxolan-4-yl)-methoxy]ethyl}-3-ethylphenyl=3-fluoro-4-methoxyphenyl=ketone (70 mg, 61%) was obtained from (4,6-bis(methoxymethoxy)-2-{2-[(2,2-dimethyl-1,3-dioxolan-4-yl)methoxy]ethyl}-3-ethylphenyl)(3-fluoro-4-methoxyphenyl)methanol, using pyridinium dichromate (0.15 g, 0.40 mmol) and dichloromethane (4.0 mL).

$^1$H-NMR (CDCl$_3$, 300 MHz) δ (ppm): 7.61-7.57 (m, 2H), 6.95 (t, J=8.25 Hz, 1H), 6.84 (s, 1H), 5.23 (s, 2H), 4.97 (s, 2H), 4.13 (m, 1H), 3.97 (dd, J=8.3, 6.6 Hz, 1H), 3.94 (s, 3H), 3.61 (dd, J=8.3, 6.6 Hz, 1H), 3.51-3.47 (m, 2H), 3.51 (s, 3H), 3.40 (dd, J=9.9, 5.9 Hz, 1H), 3.30 (dd, J=9.9, 5.9 Hz, 1H), 3.25 (s, 3H), 2.73 (dd, J=8.8, 6.8 Hz, 2H), 2.68 (q, J=7.3 Hz, 2H), 1.38 (s, 3H), 1.33 (s, 3H), 1.14 (t, J=7.3 Hz, 3H)

(Step 2)

In a manner similar to that in Example 1, Step 6, Compound 52 (33 mg, 61%) was obtained from 4,6-bis(methoxymethoxy)-2-{2-[(2,2-dimethyl-1,3-dioxolan-4-yl)methoxy]ethyl}-3-fluoro-4-methoxyphenyl=ketone (70 mg, 0.13 mmol) obtained in Example 51, Step 1, using a 4 mol/L solution of hydrogen chloride in 1,4-dioxane (1.5 mL) and methanol (1.5 mL).

$^1$H-NMR (CD$_3$OD, 300 MHz) δ (ppm): 7.52-7.47 (m, 2H), 7.06 (t, J=8.6 Hz, 1H), 6.27 (d, 1H), 3.88 (s, 3H), 3.59 (m, 1H), 3.47-3.27 (m, 6H), 2.67 (t, J=8.4 Hz, 2H), 2.59 (q, J=7.3 Hz, 2H), 1.08 (t, J=7.3 Hz, 3H)

ESI-MS (m/z); 407 [M−H]$^-$

EXAMPLE 52

Synthesis of 6-[2-(2,3-dihydroxypropyloxy)ethyl]-5-ethyl-2,4-dihydroxyphenyl=3,4,5-trimethoxyphenyl=ketone (Compound 53)

(Step 1)

In a manner similar to that in Example 1, Step 5, (4,6-bis(methoxymethoxy)-2-{2-[(2,2-dimethyl-1,3-dioxolan-4-yl)methoxy]ethyl}-3-ethylphenyl)(3,4,5-trimethoxyphenyl)methanol was obtained from 1,5-bis(methoxymethoxy)-3-{2-[(2,2-dimethyl-1,3-dioxolan-4-yl)methoxy]ethyl}-2-bromo-4-ethylbenzene (0.10 g, 0.22 mmol) obtained in Example 33, Step 3, using a 1.5 mol/L solution of n-butyllithium in tetrahydrofuran (0.30 mL, 0.45 mmol), 3,4,5-trimethoxybenzaldehyde (65 mg, 0.33 mmol) and tetrahydrofuran (4.0 mL). Further, 4,6-bis(methoxymethoxy)-2-{2-[(2,2-dimethyl-1,3-dioxolan-4-yl)methoxy]ethyl}-3-ethylphenyl=3,4,5-trimethoxyphenyl=ketone (45 mg, 36%) was obtained from (4,6-bis(methoxymethoxy)-2-{2-[(2,2-dimethyl-1,3-dioxolan-4-yl)methoxy]ethyl}-3-ethylphenyl)(3,4,5-trimethoxyphenyl)methanol, using pyridinium dichromate (0.15 g, 0.40 mmol) and dichloromethane (4.0 mL).

$^1$H-NMR (CDCl$_3$, 300 MHz) δ (ppm): 7.09 (s, 2H), 6.85 (s, 1H), 5.23 (s, 2H), 4.99 (s, 0.2H), 4.16 (m, 1H), 3.98 (dd, J=8.3, 6.4 Hz, 1H), 3.92 (s, 3H), 3.82 (s, 6H), 3.62 (dd, J=8.23, 6.4 Hz, 1H), 3.51 (s, 3H), 3.53-3.47 (m, 2H), 3.43 (dd, J=9.9, 5.9 Hz, 1H), 3.31 (dd, J=9.9, 5.9 Hz, 1H), 3.25 (s, 3H), 2.76 (t, J=7.2 Hz, 2H), 2.69 (q, J=7.3 Hz, 2H), 1.37 (s, 3H), 1.32 (s, 3H), 1.13 (t, J=7.3 Hz, 3H)

(Step 2)

In a manner similar to that in Example 1, Step 6, Compound 53 (25 mg, 71%) was obtained from 4,6-bis(methoxymethoxy)-2-{2-[(2,2-dimethyl-1,3-dioxolan-4-yl)methoxy]ethyl}-3-ethylphenyl=3,4,5-trimethoxyphenyl=ketone (45 mg, 0.080 mmol) obtained in Example 52, Step 1, using a 4 mol/L solution of hydrogen chloride in 1,4-dioxane (1.5 mL) and methanol (1.5 mL).

$^1$H-NMR (CDCl$_3$, 300 MHz) δ (ppm): 7.12 (s, 2H), 6.30 (s, 1H), 3.83 (s, 3H), 3.79 (s, 6H), 3.63 (m, 1H), 3.51-3.28 (m, 6H), 2.72 (t, J=8.2 Hz, 2H), 2.64 (q, J=7.3 Hz, 2H), 1.11 (t, J=7.3 Hz, 3H)

ESI-MS (m/z); 449 [M−H]$^-$

EXAMPLE 53

Synthesis of 2-[2-ethyl-3,5-dihydroxy-6-(4-fluorobenzoyl)phenyl]-1-(6,7-dimethoxy-1,2,3,4-tetrahydroisoquinolin-2-yl)ethanone (Compound 54)

In a manner similar to that in Example 10, Step 2, Compound 54 (75 mg, 46%) was obtained from 2-ethyl-6-(4-fluorobenzoyl)-3,5-dihydroxyphenylacetic acid (0.10 g, 0.33 mmol) obtained in Example 49, Step 3, using 1-hydroxybenzotriazole hydrate (0.13 g, 0.82 mmol), 1-(3-dimethylaminopropyl)-3-ethylcarbodiimide (0.12 g, 0.75 mmol), 6,7-dimethoxy-1,2,3,4-tetrahydroisoquinoline hydrochloride (0.31 g, 1.3 mmol) and N,N-dimethylformamide (1.0 mL).

$^1$H-NMR (DMSO-d$_6$, 80° C., 300 MHz) δ (ppm): 9.19 (s, 1H), 8.94 (s, 1H), 7.69 (dd, J=5.4, 8.7 Hz, 2H), 7.10 (t, J=8.7 Hz, 2H), 6.67 (s, 2H), 6.35 (s, 1H), 4.32 (brs, 2H), 3.73 (s, 3H), 3.71 (s, 3H), 3.62 (s, 2H), 3.49 (brs, 2H), 2.58-2.40 (m, 4H), 0.99 (t, J=7.2 Hz, 3H) ESI-MS (m/z); 494 [M+H]$^+$

EXAMPLE 54

Synthesis of 2-[2-ethyl-3,5-dihydroxy-6-(4-hydroxybenzoyl)phenyl]-1-(4-phenylpiperazin-1-yl)ethanone (Compound 55)

(Step 1)

Methyl 3,5-diallyloxy-2-ethylphenylacetate (1.0 g, 3.3 mmol) obtained in Example 5, Step 3 was dissolved in trifluoroacetic acid (9.0 mL), and 4-hydroxybenzoic acid (1.4 g, 10 mmol) and trifluoroacetic anhydride (1.2 mL) were added thereto, followed by stirring at room temperature for 20 hours. To the mixture were further added 4-hydroxybenzoic acid (0.92 g, 6.6 mmol) and trifluoroacetic anhydride (1.4 mL), followed by stirring for 6 hours. The reaction mixture was added dropwise to a saturated aqueous solution of sodium hydrogencarbonate (0.10 L), and the resulting mixture was extracted with ethyl acetate (50 mL×4). The organic layer was dried over anhydrous sodium sulfate and then concentrated under reduced pressure. The resulting residue was dissolved in a 7 mol/L solution of ammonia in methanol (100 mL), followed by stirring at room temperature for 1 day. After the reaction mixture was concentrated under reduced pressure, 3 mol/L hydrochloric acid (40 mL) was added thereto, followed by extraction with ethyl acetate (50 mL×3). The organic layer was washed with water, dried over anhydrous sodium sulfate, and then concentrated under reduced pressure. The resulting residue was purified by silica gel column chromatography (ethyl acetate/hexane=1/10-1/2) to obtain methyl 3,5-diallyloxy-2-ethyl-6-(4-hydroxybenzoyl)phenylacetate (0.84 g, 57%).

$^1$H-NMR (CD$_3$OD, 270 MHz) δ (ppm): 7.63 (d, J=8.9 Hz, 2H), 6.78 (t, J=8.9 Hz, 2H), 6.61 (s, 1H), 6.11 (m, 1H), 5.71 (m, 1H), 5.50-5.26 (m, 2H), 5.07-4.99 (m, 2H), 4.63 (dt, J=5.0, 1.5 Hz, 2H), 4.42 (dt, J=4.8, 1.5 Hz, 2H), 3.57 (s, 2H), 3.44 (s, 3H), 2.65 (q, J=7.4 Hz, 2H), 1.08 (t, J=7.4 Hz, 3H)

ESI-MS (m/z); 409 [M−H]$^-$ (Step 2)

In a manner similar to that in Example 10, Step 1, 3,5-diallyloxy-2-ethyl-6-(4-hydroxybenzoyl)phenylacetic acid was quantitatively obtained from methyl 3,5-diallyloxy-2- ethyl-6-(4-hydroxybenzoyl)phenylacetate (0.84 g, 2.0 mmol) obtained in Example 54, Step 1, using a 2 mol/L aqueous solution of sodium hydroxide (13 mL) and acetonitrile (13 mL).

$^1$H-NMR (CD$_3$OD, 270 MHz) δ (ppm): 7.65 (d, J=8.9 Hz, 2H), 6.76 (t, J=8.9 Hz, 2H), 6.61 (s, 1H), 6.10 (ddt, J=10.6, 17.2, 4.8 Hz, 1H), 5.71 (ddt, J=10.6, 17.2, 5.0 Hz, 1H), 5.46 (dq, J=17.2, 1.6 Hz, 1H), 5.28 (dq, J=10.6, 1.6 Hz, 1H), 5.06-4.98 (m 2H), 4.62 (dt, J=5.0, 1.6 Hz, 2H), 4.41 (dt, J=4.8, 1.6 Hz, 2H), 3.54 (s, 2H), 2.66 (q, J=7.5 Hz, 2H), 1.10 (t, J=7.5 Hz, 3H) ESI-MS (m/z); 395 [M−H]$^-$ (Step 3)

In a manner similar to that in Example 10, Step 2, 2-[3,5-diallyloxy-2-ethyl-6-(4-hydroxybenzoyl)phenyl]-1-(4-phenylpiperazin-1-yl)ethanone (28 mg, 21%) was obtained from 3,5-diallyloxy-2-ethyl-6-(4-hydroxybenzoyl)phenylacetic acid (0.10 g, 0.25 mmol) obtained in Example 54, Step 2, using 1-hydroxybenzotriazole hydrate (0.10 g, 0.65 mmol), 1-(3-dimethylaminopropyl)-3-ethylcarbodiimide hydrochloride (0.11 g, 0.58 mmol), 1-phenylpiperazine (0.16 g, 1.0 mmol) and N,N-dimethylformamide (1.0 mL). $^1$H-NMR (CD$_3$OD, 300 MHz) δ (ppm): 7.63 (d, J=8.9 Hz, 1H), 7.26-7.20 (m, 2H), 6.91-6.83 (m, 3H), 6.70 (t, J=8.9 Hz, 2H), 6.60 (s, 1H), 6.11 (ddt, J=10.6, 17.2, 4.8 Hz, 1H), 5.72 (ddt, J=10.6, 17.2, 5.0 Hz, 1H), 5.46 (dq, J=17.2, 1.7 Hz, 1H), 5.28 (dq, J=10.6, 1.7 Hz, 1H), 5.07-4.99 (m 2H), 4.63 (dt, J=5.0, 1.7 Hz, 2H), 4.42 (dt, J=4.8, 1.7 Hz, 2H), 3.71 (s, 2H), 3.57 (m, 2H), 3.45 (m, 2H), 3.00 (m, 2H), 2.78 (m, 2H), 2.66 (q, J=7.4 Hz, 2H), 1.11 (t, J=7.4 Hz, 3H)

(Step 4)

In a manner similar to that in Example 7, Step 1, Compound 55 (29 mg, 63%) was obtained from 2-[3,5-diallyloxy-2-ethyl-6-(4-hydroxybenzoyl)phenyl]-1-(4-phenylpiperazin-1-yl)ethanone (54 mg, 0.10 mmol) obtained in Example 54, Step 3, using ammonium formate (25 mg, 0.40 mmol), bis(triphenylphosphine)palladium (II) dichloride (3.5 mg, 0.0049 mmol) and 1,4-dioxane (2.0 mL).

$^1$H-NMR (CD$_3$OD, 270 MHz) δ (ppm): 7.66 (d, J=8.9 Hz, 2H), 7.22 (dd, J=7.2, 8.8 Hz, 2H), 6.92-6.82 (m, 3H), 6.70 (d, J=8.9 Hz, 2H), 6.32 (s, 2H), 3.64 (s, 2H), 3.56-3.53 (m, 2H), 3.46-3.42 (m, 2H), 3.00-2.96 (m, 2H), 2.81-2.77 (m, 2H), 2.58 (q, J=7.6 Hz, 2H), 1.08 (t, J=7.6 Hz, 3H) APCI-MS (m/z); 459 [M−H]$^-$

EXAMPLE 55

Synthesis of 2-[2-(3,4-dimethoxybenzoyl)-6-ethyl-3,5-dihydroxyphenyl]-N-(2-hydroxyethyl)-N-(2-methoxyethyl)acetamide (Compound 56)

In a manner similar to that in Example 10, Step 2, Compound 56 (45 mg, 36%) was obtained from 2-(3,4-dimethoxybenzoyl)-6-ethyl-3,5-dihydroxyphenylacetic acid (97 mg, 0.27 mmol) obtained in Example 40, Step 1, using 1-hydroxybenzotriazole hydrate (0.12 g, 0.81 mmol), 1-(3-dimethylaminopropyl)-3-ethylcarbodiimide hydrochloride (0.10 g, 0.52 mmol), 2-(2-methoxyethylamino)ethanol (0.12 g, 1.0 mmol) obtained in Reference Example 1 and N,N-dimethylformamide (1.5 mL).

$^1$H-NMR (CD$_3$OD, 270 MHz) δ (ppm): 7.47-7.41 (m, 2H), 6.94 (dd, J=1.5, 8.5 Hz, 1H), 6.31 (s, 1H), 3.88 and 3.87 (s, total 3H), 3.84 and 3.83 (s, total 3H), 3.70 and 3.69 (s, total 2H), 3.58-3.11 (m, 8H), 3.22 and 3.14 (s, total 3H), 2.58-2.48 (m, 2H), 1.07 (t, J=7.3 Hz, 3H)

ESI-MS (m/z); 460 [M−H]$^-$

EXAMPLE 56

Synthesis of 6-[2-(2,3-dihydroxypropyloxy)ethyl]-5-ethyl-2,4-dihydroxyphenyl=3-chloro-4-fluorophenyl=ketone (Compound 57)

(Step 1)

In a manner similar to that in Example 1, Step 5, (4,6-bis(methoxymethoxy)-2-{2-[(2,2-dimethyl-1,3-dioxolan-4-yl)methoxy]ethyl}-3-ethylphenyl)(3-chloro-4-fluorophenyl)methanol was obtained from 1,5-bis(methoxymethoxy)-3-{2-[(2,2-dimethyl-1,3-dioxolan-4-yl)methoxy]ethyl}-2-bromo-4-ethylbenzene (0.11 g, 0.23 mmol) obtained in Example 33, Step 3, using a 1.5 mol/L solution of n-butyllithium in tetrahydrofuran (0.30 mL, 0.45 mmol), 3-chloro-4-fluorobenzaldehyde (45 mg, 0.29 mmol) and tetrahydrofuran (4.0 mL). Further, 4,6-bis(methoxymethoxy)-2-{2-[(2,2-dimethyl-1,3-dioxolan-4-yl)methoxy]ethyl}-3-ethylphenyl=3-chloro-4-fluorophenyl=ketone (55 mg, 45%) was obtained from (4,6-bis(methoxymethoxy)-2-{2-[(2,2-dimethyl-1,3-dioxolan-4-yl)methoxy]ethyl}-3-ethylphenyl)(3-chloro-4-fluorophenyl)methanol, using pyridinium dichromate (90 mg, 0.24 mmol) and dichloromethane (4.0 mL).

$^1$H-NMR (CDCl$_3$, 300 MHz) δ (ppm): 7.91 (dd, J=7.3, 2.3 Hz, 1H), 7.71 (ddd, J=8.3, 4.6, 1.9 Hz, 1H), 7.18 (t, J=8.3 Hz, 1H), 6.85 (s, 1H), 5.23 (s, 2H), 4.96 (s, 2H), 4.12 (m, 1H), 3.97 (dd, J=8.3, 6.6 Hz, 1H), 3.61 (dd, J=8.3, 6.6 Hz, 1H), 3.52 (s, 3H), 3.54-3.51 (m, 2H), 3.42 (dd, J=9.9, 5.6 Hz, 1H), 3.32 (dd, J=9.9, 5.6 Hz, 1H), 3.24 (s, 3H), 2.75 (dd, J=8.6, 6.6 Hz, 2H), 2.69 (q, J=7.3 Hz, 2H), 1.38 (s, 3H), 1.33 (s, 3H), 1.14 (t, J=7.3 Hz, 3H)

(Step 2)

In a manner similar to that in Example 1, Step 6, Compound 57 (26 mg, 62%) was obtained from 4,6-bis(methoxymethoxy)-2-{2-[(2,2-dimethyl-1,3-dioxolan-4-yl)methoxy]ethyl}-3-ethylphenyl=3-chloro-4-fluorophenyl=ketone (55 mg, 0.10 mmol) obtained in Example 56, Step 1, using a 4 mol/L solution of hydrogen chloride in 1,4-dioxane (1.0 mL) and methanol (1.0 mL).

$^1$H-NMR (CD$_3$OD, 300 MHz) δ (ppm): 7.83 (dd, J=7.3, 2.0 Hz, 1H), 7.71 (ddd, J=8.8, 4.8, 2.0 Hz, 1H), 7.29 (t, J=8.8 Hz, 1H), 6.83 (s, 1H), 3.62 (m, 1H), 3.54-3.26 (m, 6H), 2.73 (t, J=8.1 Hz, 2H), 2.63 (q, J=7.4 Hz, 2H), 1.11 (t, J=7.4 Hz, 3H)

ESI-MS (m/z); 411, 413 [M−H]$^-$

EXAMPLE 57

Synthesis of 6-[2-(2,3-dihydroxypropyloxy)ethyl]-5-ethyl-2,4-dihydroxyphenyl=3-(3-hydroxyphenyl)-4-methoxyphenyl=ketone (Compound 58)

(Step 1)

In a manner similar to that in Example 1, Step 5, (4,6-bis(methoxymethoxy)-2-{2-[(2,2-dimethyl-1,3-dioxolan-4-yl)methoxy]ethyl}-3-ethylphenyl)(3-bromo-4-methoxyphenyl)methanol was obtained from 1,5-bis(methoxymethoxy)-3-{2-[(2,2-dimethyl-1,3-dioxolan-4-yl)methoxy]ethyl}-2-bromo-4-ethylbenzene (0.31 g, 0.66 mmol) obtained in Example 33, Step 3, using a 1.5 mol/L solution of n-butyllithium in tetrahydrofuran (0.9 mL, 1.4 mmol), 3-bromo-4-methoxybenzaldehyde (0.17 g, 0.79 mmol) and tetrahydrofuran (8.0 mL). Further, 4,6-bis(methoxymethoxy)-2-{2-[(2,2-dimethyl-1,3-dioxolan-4-yl)methoxy]ethyl}-3-ethylphenyl=3-bromo-4-methoxyphenyl=ketone (0.17 g, 42%) was obtained from (4,6-bis(methoxymethoxy)-2-{2-[(2,2-dimethyl-1,3-dioxolan-4-yl)methoxy]-ethyl}-3-ethylphenyl)(3-bromo-4-methoxyphenyl)methanol, using pyridinium dichromate (0.50 g, 1.3 mmol) and dichloromethane (10 mL).

$^1$H-NMR (CDCl$_3$, 300 MHz) δ (ppm): 8.03 (d, J=1.9 Hz, 1H), 7.75 (dd, J=8.6, 1.9 Hz, 1H), 6.89 (d, J=8.6 Hz, 1H), 6.83 (s, 1H), 5.22 (s, 2H), 4.96 (s, 2H), 4.12 (m, 1H), 3.94 (s, 3H), 3.93 (dd, J=8.3, 6.6 Hz, 1H), 3.61 (dd, J=8.3, 6.6 Hz, 1H), 3.51 (s, 3H), 3.52-3.50 (m, 2H), 3.42 (dd, J=9.9, 5.6 Hz, 1H), 3.35 (dd, J=9.9, 5.6 Hz, 1H), 3.24 (s, 3H), 2.75 (dd, J=8.3, 6.0 Hz, 2H), 2.69 (q, J=7.3 Hz, 2H), 1.37 (s, 3H), 1.31 (s, 3H), 1.14 (t, J=7.3 Hz, 3H)

(Step 2)

4,6-Bis(methoxymethoxy)-2-{2-[(2,2-dimethyl-1,3-dioxolan-4-yl)methoxy]ethyl}-3-ethylphenyl=3-bromo-4-methoxyphenyl=ketone (90 mg, 0.15 mmol) obtained in Example 57, Step 1 was dissolved in a mixed solvent of 1,2-dimethoxymethane (2.0 mL) and water (0.20 mL). To the solution were added 3-hydroxyphenylboric acid pinacol ester (40 mg, 0.18 mmol), bis(tri-o-tolylphosphine)palladium (II) dichloride (20 mg, 0.027 mmol) and cesium carbonate (0.15 g, 0.46 mmol) in an atmosphere of argon, followed by stirring for 4 hours under heating and reflux. After cooling to room temperature, the reaction mixture was filtered under reduced pressure and the filtrate was concentrated under reduced pressure. To the resulting residue was added water, and the mixture was extracted twice with ethyl acetate. The organic layer was dried over anhydrous sodium sulfate and then concentrated under reduced pressure. The resulting residue was purified by silica gel column chromatography (ethyl acetate/hexane=1/4-1/2) to obtain 4,6-bis(methoxymethoxy)-2-{2-[(2,2-dimethyl-1,3-dioxolan-4-yl)methoxy]ethyl}-3-ethylphenyl=3-(3-hydroxyphenyl)-4-methoxyphenyl=ketone. Then, 4,6-bis(methoxymethoxy)-2-{2-[(2,2-dimethyl-1,3-dioxolan-4-yl)methoxy]ethyl}-3-ethylphenyl=3-(3-hydroxyphenyl)-4-methoxyphenyl=ketone was dissolved in methanol (1.0 mL), and a 4 mol/L solution of hydrogen chloride in 1,4-dioxane (1.0 mL) was added dropwise thereto, followed by stirring at room temperature for 1 hour. The reaction mixture was concentrated under reduced pressure, and the resulting residue was purified by silica gel column chromatography (methanol/chloroform=1/15-1/9) to obtain Compound 58 (35 mg, 43%).

$^1$H-NMR (CD$_3$OD, 300 MHz) δ (ppm): 7.74 (m, 2H), 7.13 (t, J=8.3 Hz, 1H), 7.02 (d, J=9.2 Hz, 1H), 6.87-6.84 (m, 2H), 6.70 (ddd, J=8.3, 2.4, 0.9 Hz, 1H), 6.23 (s, 1H), 3.81 (s, 3H), 3.61 (m, 1H), 3.47-3.22 (m, 6H), 2.70 (t, J=8.3 Hz, 2H), 2.59 (q, J=7.3 Hz, 2H), 1.08 (t, J=7.3 Hz, 3H)

ESI-MS (m/z); 481 [M−H]$^−$

EXAMPLE 58

Synthesis of 6-[2-(2,3-dihydroxypropyloxy)ethyl]-5-ethyl-2,4-dihydroxyphenyl=4-methoxy-3-(3-methoxyphenyl)phenyl=ketone (Compound 59)

In a manner similar to that in Example 57, Step 2, 4,6-bis(methoxymethoxy)-2-{2-[[(2,2-dimethyl-1,3-dioxolan-4-yl)methoxy]ethyl}-3-ethylphenyl=4-methoxy-3-(3-methoxyphenyl)phenyl=ketone was obtained from 4,6-bis(methoxymethoxy)-2-{2-[(2,2-dimethyl-1,3-dioxolan-4-yl)methoxy]-ethyl}-3-ethylphenyl=3-bromo-4-methoxyphenyl=ketone (80 mg, 0.13 mmol) obtained in Example 57, Step 1, using 3-methoxyphenylboric acid (30 mg, 0.20 mmol), bis(tri-o-tolylphosphine)palladium (II) dichloride (20 mg, 0.027 mmol), cesium carbonate (0.13 g, 0.4 mmol) and a mixed solvent of 1,2-dimethoxymethane (2.0 mL) and water (0.20 mL). Further, Compound 59 (39 mg, 59%) was obtained from 4,6-bis(methoxymethoxy)-2-{2-[(2,2-dimethyl-1,3-dioxolan-4-yl)methoxy]ethyl}-3-ethylphenyl=4-methoxy-3-(3-methoxyphenyl)phenyl=ketone, using a 4 mol/L solution of hydrogen chloride in 1,4-dioxane (1.0 mL) and methanol (1.0 mL). $^1$H-NMR (CD$_3$OD, 300 MHz) δ (ppm): 7.75-7.71 (m, 2H), 7.22 (t, J=8.3 Hz, 1H), 7.03 (d, J=9.4 Hz, 1H), 6.97-6.94 (m, 2H), 6.81 (ddd, J=8.3, 2.6, 0.9 Hz, 1H), 6.27 (s, 1H), 3.80 (s, 3H), 3.73 (s, 3H), 3.59 (m, 1H), 3.47-3.23 (m, 6H), 2.71 (t, J=8.1 Hz, 2H), 2.60 (q, J=7.5 Hz, 2H), 1.08 (t, J=7.5 Hz, 3H)

ESI-MS (m/z); 497 [M+H]$^+$

EXAMPLE 59

Synthesis of 5-ethyl-2,4-dihydroxy-6-[2-(2-hydroxyethoxy)ethyl]phenyl=4-methoxyphenyl=ketone (Compound 60)

(Step 1)

In a manner similar to that in Example 1, Step 3, 2-(tetrahydro-2H-pyran-2-yloxy)-1-[2-(3,5-diallyloxy-2-ethylphenyl)ethoxy]ethane (7.2 g, 57%) was obtained as a colorless oil from 2-(3,5-diallyloxy-2-ethylphenyl)ethanol (8.5 g, 32 mmol) obtained in Example 12, Step 1, using a 60% sodium hydride dispersion in mineral oil (3.9 g, 98 mmol), 2-(2-bromoethoxy)tetrahydro-2H-pyran (9.8 mL, 65 mmol) and N,N-dimethylformamide (0.15 L).

$^1$H-NMR (CDCl$_3$, 300 MHz) δ (ppm): 6.37 (d, J=2.4 Hz, 1H), 6.34 (d, J=2.4 Hz, 1H), 6.11-5.98 (m, 2H), 5.45-5.23 (m, 4H), 4.64 (dd, J=4.0, 3.1 Hz, 1H), 4.48 (m, 4H), 3.89-3.57 (m, 2H), 3.67-3.57 (m, 5H), 3.53-3.47 (m, 1H), 2.90 (t, J=7.9 Hz, 2H), 2.64 (q, J=7.3 Hz, 2H), 1.85-1.51 (m, 6H), 1.09 (t, J=7.3 Hz, 3H)

ESI-Ms (m/z); 408 [M+NH$_4$]+

(Step 2)

2-(Tetrahydro-2H-pyran-2-yloxy)-1-[2-(3,5-diallyloxy-2-ethylphenyl)ethoxy]ethane (3.0 g, 7.6 mmol) obtained in Example 59, Step 1 was dissolved in methanol (30 mL), and a 4 mol/L solution of hydrogen chloride in 1,4-dioxane (20 mL) was added thereto, followed by stirring for 30 minutes. After the reaction mixture was neutralized with a saturated aqueous solution of sodium hydrogencarbonate, water was added thereto, and the mixture was extracted twice with ethyl acetate. The organic layers were combined, washed with a saturated aqueous solution of sodium chloride, dried over anhydrous sodium sulfate and concentrated under reduced pressure. The resulting residue was purified by silica gel column chromatography (ethyl acetate/hexane 1/9-1/1) to obtain 2-[2-(3,5-diallyloxy-2-ethylphenyl)ethoxy]ethanol (1.9 g, 81%) as a colorless oil.

$^1$H-NMR (CDCl$_3$, 300 MHz) δ (ppm): 6.35 (s, 2H), 6.12-5.97 (m, 2H), 5.46-5.22 (m, 4H), 4.50-4.48 (m, 4H), 3.72 (t, J=4.9 Hz, 2H), 3.65 (t, J=7.6 Hz, 2H), 3.57 (t, J=4.9 Hz, 2H), 2.90 (t, J=7.6 Hz, 2H), 2.64 (q, J=7.4 Hz, 2H), 1.95 (brs, 1H), 1.10 (t, J=7.4 Hz, 3H)

ESI-MS (m/z); 307[M+H]$^+$ (Step 3)

2-[2-(3,5-Diallyloxy-2-ethylphenyl)ethoxy]ethanol (0.75 g, 0.25 mmol) obtained in Example 59, Step 2 was dissolved in trifluoroacetic acid (2.0 mL). To the solution were successively added 4-methoxybenzoic acid (0.12 g, 0.76 mmol) and trifluoroacetic anhydride (0.50 mL, 3.5 mmol) under ice-cooling, followed by stirring for 5 hours, while the temperature of the reaction mixture was raised to room temperature. After the reaction mixture was concentrated under reduced pressure, acetonitrile (2.0 mL) and a 2 mol/L aqueous solution of sodium hydroxide (2.0 mL) were added to the resulting residue under ice-cooling, followed by stirring at room temperature for 1 hour. To the reaction mixture was added water, and the mixture was extracted twice with ethyl acetate. The organic layers were combined, washed with a saturated aqueous solution of sodium chloride, dried over anhydrous sodium sulfate and concentrated under reduced pressure. The resulting residue was purified by silica gel column chromatography (ethyl acetate/hexane=1/4-1/1) to obtain 4,6-diallyloxy-3-ethyl-2-[2-(2-hydroxyethoxy)ethyl]phenyl=4-methoxyphenyl=ketone (30 mg, 27%).

$^1$H-NMR (CDCl$_3$, 300 MHz) δ (ppm): 7.77 (dd, J=8.9 Hz, 2H), 6.88 (dd, J=8.9 Hz, 2H), 6.39 (s, 1H), 6.05 (ddt, J=17, 11, 4.9 Hz, 1H), 5.71 (ddt, J=17, 11, 4.9 Hz, 1H), 5.45 (dq, J=17, 1.7 Hz, 1H), 5.30 (dq, J=11, 1.7 Hz, 1H), 5.08 (dq, J=17, 1.7 Hz, 1H), 5.03 (dq, J=11, 1.7 Hz, 1H), 4.55 (dt, J=5.0, 1.7 Hz, 2H), 4.38 (dt, J=5.0, 1.7 Hz, 2H), 3.85 (s, 3H), 3.60 (t, J=4.8 Hz, 2H), 3.52 (t, J=7.9 Hz, 2H), 3.40 (t, J=4.8 Hz, 2H), 2.77 (t, J=7.9 Hz, 2H), 2.69 (t, J=7.4 Hz, 2H), 1.14 (t, J=7.4 Hz, 3H)

(Step 4)

4,6-Diallyloxy-3-ethyl-2-[2-(2-hydroxyethoxy)ethyl]phenyl=4-methoxyphenyl=ketone (30 mg, 0.068 mmol) obtained in Example 59, Step 3 was dissolved in 1,4-dioxane (2.0 mL). To the solution were added ammonium formate (20 mg, 0.32 mmol) and bis(triphenylphosphine)palladium (II) dichloride (5.0 mg, 0.0071 mmol), followed by stirring for 3 hours under heating and reflux. The reaction mixture was concentrated under reduced pressure, and the resulting residue was purified by silica gel column chromatography (methanol/chloroform=1/15-1/9) to obtain Compound 60 (20 mg, 81%).

$^1$H-NMR (CDCl$_3$, 300 MHz) δ (ppm): 7.93 (brs, 1H), 7.73 (d, J=8.9 Hz, 2H), 7.03 (brs, 1H), 6.99 (d, J=8.9 Hz, 2H), 6.29 (s, 1H), 3.86 (s, 3H), 3.63 (t, J=4.0 Hz, 2H), 3.41 (t, J=6.2 Hz, 2H), 3.33 (t, J=4.0 Hz, 2H), 2.76 (t, J=6.2 Hz, 2H), 2.60 (q, J=7.3 Hz, 2H), 1.13 (t, J=7.3 Hz, 3H)

ESI-MS (m/z); 359 [M−H]$^-$

EXAMPLE 60

Synthesis of 2-[2-ethyl-3,5-dihydroxy-6-(4-methoxybenzoyl)phenyl]-1-[4-(hydroxymethyl)piperidino]ethanone (Compound 61)

In a manner similar to that in Example 10, Step 2, Compound 61 (76 mg, 31%) was obtained from 2-ethyl-3,5-dihydroxy-6-(4-methoxybenzoyl)phenylacetic acid (0.19 g, 0.57 mmol) obtained in Example 10, Step 1, using 1-(3-dimethylaminopropyl)-3-ethylcarbodiimide hydrochloride (0.25 g, 1.3 mmol), 4-(hydroxymethyl)piperidine (0.26 g, 2.3 mmol) and N,N-dimethylformamide (2.0 mL).

$^1$H-NMR (DMSO-d$_6$, 300 MHz) δ (ppm): 9.33 (s, 1H), 9.04 (s, 1H), 7.63 (d, J=9.0 Hz, 2H), 6.92 (d, J=9.0 Hz, 2H), 6.31 (s, 1H), 4.41 (t, J=5.4 Hz, 1H), 4.08 (m, 1H), 3.79 (s, 3H), 3.77 (m, 1H), 3.49 (d, J=16.4 Hz, 1H), 3.39 (d, J=16.4 Hz, 1H), 3.30 (m, 1H), 3.09 (t, J=5.4 Hz, 1H), 2.79 (m, 1H), 2.39-2.22 (m, 3H), 1.57-1.40 (m, 3H), 0.97 (t, J=7.2 Hz, 3H), 0.74 (m, 1H), 0.48 (m, 1H)

APCI-MS (m/z); 428 [M−H]$^-$

EXAMPLE 61

Synthesis of 5-ethyl-2,4-dihydroxy-6-[2-(2-hydroxyethoxy)ethyl]phenyl=phenyl=ketone (Compound 62)

(Step 1)

In a manner similar to that in Example 59, Step 3, 4,6-diallyloxy-3-ethyl-2-[2-(2-hydroxyethoxy)ethyl]-phenyl=phenyl=ketone (89 mg, 92%) was obtained as a colorless solid from 2-[2-(3,5-diallyloxy-2-ethylphenyl)ethoxy]ethanol (65 mg, 0.20 mmol) obtained in Example 59, Step 2, using benzoic acid (80 mg, 0.66 mmol), trifluoroacetic anhydride (0.50 mL, 3.5 mmol) and trifluoroacetic acid (2.0 mL), and using a 2 mol/L aqueous solution of sodium hydroxide (2.0 mL) and acetonitrile (2.0 mL).

$^1$H-NMR (CDCl$_3$, 300 MHz) δ (ppm): 7.80 (m, 2H), 7.52 (m, 1H), 7.41 (m, 2H), 6.40 (s, 1H), 6.05 (ddt, J=17, 11, 5.0 Hz, 1H), 5.66 (ddt, J=17, 11, 5.0 Hz, 1H), 5.45 (dq, J=17, 1.7 Hz, 1H), 5.32 (dq, J=11, 1.7 Hz, 1H), 5.05 (dq, J=17, 1.7 Hz, 1H), 5.00 (dq, J=11, 1.7 Hz, 1H), 4.56 (dt, J=5.0, 1.7 Hz, 2H), 4.36 (dt, J=5.0, 1.7 Hz, 2H), 3.62 (t, J=4.8 Hz, 2H), 3.55 (t, J=7.5 Hz, 2H), 3.41 (t, J=4.8 Hz, 2H), 2.78 (t, J=7.5 Hz, 2H), 2.69 (t, J=7.5 Hz, 2H), 1.11 (t, J=7.4 Hz, 3H)

(Step 2)

In a manner similar to that in Example 59, Step 4, Compound 62 (49 mg, 68%) was obtained as a colorless solid from 4,6-diallyloxy-3-ethyl-2-[2-(2-hydroxyethoxy)ethyl]phenyl=phenyl=ketone (89 mg, 0.22 mmol) obtained in Example 61, Step 1, using ammonium formate (70 mg, 1.1 mmol), bis(triphenylphosphine)palladium (II) dichloride (5.0 mg, 0.0071 mmol) and 1,4-dioxane (3.0 mL).

$^1$H-NMR (CD$_3$OD, 300 MHz) δ (ppm): 7.72 (m, 2H), 7.50 (tt, J=7.3, 1.5 Hz, 1H), 7.37 (m, 2H), 6.23 (s, 1H), 3.46 (t, J=5.0 Hz, 2H), 3.39 (t, J=7.9 Hz, 2H), 3.30 (t, J=5.0 Hz, 2H), 2.66 (t, J=7.9 Hz, 2H), 2.57 (q, J=7.4 Hz, 2H), 1.07 (t, J=7.4 HZ, 3H)

ESI-MS (m/z); 329 [M−H]$^-$

EXAMPLE 62

Synthesis of 5-ethyl-2,4-dihydroxy-6-[2-(2-hydroxyethoxy)ethyl]phenyl=3-hydroxy-4-methoxyphenyl=ketone (Compound 63)

(Step 1)

In a manner similar to that in Example 59, Step 3, 4,6-diallyloxy-3-ethyl-2-[2-(2-hydroxyethoxy)ethyl]-phenyl=3-hydroxy-4-methoxyphenyl=ketone (0.120 g, 38%) was obtained from 2-[2-(3,5-diallyloxy-2-ethylphenyl)ethoxy]ethanol (0.21 g, 0.68 mmol) obtained in Example 59, Step 2, using 3-hydroxy-4-methoxybenzoic acid (0.23 g, 1.4 mmol), trifluoroacetic anhydride (1 mL, 7.1 mmol) and trifluoroacetic acid (4.0 mL), and using a 2 mol/L aqueous solution of sodium hydroxide (2.0 mL) and acetonitrile (2.0 mL).

$^1$H-NMR (CDCl$_3$, 300 MHz) δ (ppm): 7.41 (dd, J=8.4, 2.2 Hz, 1H), 7.36 (d, J=2.2 Hz, 1H), 6.85 (d, J=8.4 Hz, 1H), 6.38 (s, 1H), 6.06 (ddt, J=17, 11, 4.8 Hz, 1H), 5.81 (brs, 1H), 5.73 (ddt, J=19, 11, 5.0 Hz, 1H), 5.45 (dq, J=17, 1.7 Hz, 1H), 5.30 (dq, J=11, 1.7 Hz, 1H), 5.13 (dq, J=19, 1.7 Hz, 1H), 5.04 (dq, J=11, 1.7 Hz, 1H), 4.56 (dt, J=4.8, 1.7 Hz, 2H), 4.36 (dt, J=5.0, 1.7 Hz, 2H), 3.93 (s, 3H), 3.61 (m, 2H), 3.52 (t, J=7.7 Hz, 2H), 3.40 (t, J=4.5 Hz, 2H), 2.76 (t, J=7.7 Hz, 2H), 2.68 (t, J=7.4 Hz, 2H), 2.20 (brs, 1H), 1.11 (t, J=7.4 Hz, 3H)

APCI-MS (m/z); 457[M+H]$^+$ (Step 2)

In a manner similar to that in Example 59, Step 4, Compound 63 (29 mg, 70%) was obtained from 4,6-diallyloxy-3-ethyl-2-[2-(2-hydroxyethoxy)ethyl]phenyl=3-hydroxy-4-methoxyphenyl=ketone (50 mg, 0.11 mmol) obtained in Example 62, Step 1, using ammonium formate (45 mg, 0.64 mmol), bis(triphenylphosphine)palladium (II) dichloride (5.0 mg, 0.0071 mmol) and 1,4-dioxane (3.0 mL).

$^1$H-NMR (CD$_3$OD, 300 MHz) δ (ppm): 7.23 (dd, J=8.9, 2.2 Hz, 1H), 7.21 (d, J=2.2 Hz, 1H), 6.88 (d, J=8.9 Hz, 1H), 6.22 (s, 1H), 3.83 (s, 3H), 3.48 (t, J=5.1 Hz, 2H), 3.37 (t, J=7.7 Hz, 2H), 3.30 (t, J=5.1 Hz, 2H), 2.62 (t, J=7.7 Hz, 2H), 2.54 (q, J=7.3 Hz, 2H), 1.05 (t, J=7.3 Hz, 3H)

APCI-MS (m/z); 375 [M−H]$^-$

EXAMPLE 63

Synthesis of 1-(3-chlorophenyl)-4-{2-[2-ethyl-3,5-dihydroxy-6-(4-methoxybenzoyl)phenyl]acetyl}piperazin-2-one (Compound 64)

In a manner similar to that in Example 10, Step 2, Compound 64 (56 mg, 39%) was obtained from 2-ethyl-3,5-dihydroxy-6-(4-methoxybenzoyl)phenylacetic acid (90 mg, 0.27 mmol) obtained in Example 10, Step 1, using 1-(3-dimethylaminopropyl)-3-ethylcarbodiimide (97 mg, 0.62 mmol), 1-(3-chlorophenyl)piperazin-2-one hydrochloride (0.27 g, 1.1 mmol) obtained by a method similar to the method described in Tetrahedron Lett., 1998, Vol. 39, p. 7459-7462 and N,N-dimethylformamide (1.0 mL).

$^1$H-NMR (DMSO-d$_6$, 300 MHz) δ (ppm): 9.44 (s, 1H), 9.14 (s, 1H), 7.63 (d, J=8.8 Hz, 2H), 7.46-7.24 (m, 4H), 6.92 (d, J=8.8 Hz, 2H), 6.34 (s, 1H), 4.16 (brs, 1H), 3.87 (s, 1H), 3.78 (s, 3H), 3.71-3.30 (m, 6H), 2.44 (q, J=7.3 Hz, 2H), 1.00 (t, J=7.3 Hz, 3H)

APCI-MS (m/z); 523 [M+H]$^+$

EXAMPLE 64

Synthesis of 5-ethyl-2,4-dihydroxy-6-[2-(2-hydroxyethoxy)ethyl]phenyl=4-(difluoromethoxy)phenyl=ketone (Compound 65)

(Step 1)

In a manner similar to that in Example 59, Step 3, 4,6-diallyloxy-3-ethyl-2-[2-(2-hydroxyethoxy)ethyl]phenyl=4-(difluoromethoxy)phenyl=ketone (0.78 g, 46%) was obtained from 2-[2-(3,5-diallyloxy-2-ethylphenyl)ethoxy]ethanol (0.11 g, 0.36 mmol) obtained in Example 59, Step 2, using 4-(difluoromethoxy)benzoic acid (0.14 g, 0.72 mmol), trifluoroacetic anhydride (1.0 mL, 7.1 mmol) and trifluoroacetic acid (4.0 mL), and using a 2 mol/L aqueous solution of sodium hydroxide (2.0 mL) and acetonitrile (2.0 mL).

$^1$H-NMR (CDCl$_3$, 300 MHz) δ (ppm): 7.82 (m, 2H), 7.13 (m, 2H), 6.65 (d, J=73 Hz, 1H), 6.39 (s, 1H), 6.06 (ddt, J=17, 11, 4.9 Hz, 1H), 5.68 (ddt, J=17, 11, 4.9 Hz, 1H), 5.42 (dq, J=17, 1.7 Hz, 1H), 5.30 (dq, J=11, 1.7 Hz, 1H), 5.04 (dq, J=17, 1.7 Hz, 1H), 4.98 (dq, J=11.5, 1.7 Hz, 1H), 4.57 (dt, J=4.9, 1.7 Hz, 2H), 4.36 (dt, J=4.9, 1.7 Hz, 2H), 3.57 (t, J=4.6 Hz, 2H), 3.50 (t, J=7.8 Hz, 2H), 3.40 (t, J=4.6 Hz, 2H), 2.78 (t, J=7.8 Hz, 2H), 2.68 (t, J=7.3 Hz, 2H), 2.10 (brs, 1H), 1.11 (t, J=7.3 Hz, 3H)

APCI-MS (m/z); 477[M+H]$^+$ (Step 2)

In a manner similar to that in Example 59, Step 4, Compound 65 (28 mg, 43%) was obtained from 4,6-diallyloxy-3-ethyl-2-[2-(2-hydroxyethoxy)ethyl]phenyl=4-(difluoromethoxy)phenyl=ketone (78 mg, 0.16 mmol) obtained in Example 64, Step 1, using ammonium formate (50 mg, 0.79 mmol), bis(triphenylphosphine)palladium (II) dichloride (3.0 mg, 0.0043 mmol) and 1,4-dioxane (2.0 mL).

$^1$H-NMR (CD$_3$OD, 300 MHz) δ (ppm): 7.80-7.74 (m, 2H), 7.11-7.08 (m, 2H), 6.70 (d, J=73 Hz, 1H), 6.22 (s, 1H), 3.46 (t, J=4.9 Hz, 2H), 3.39 (t, J=8.3 Hz, 2H), 3.30 (t, J=4.9 Hz, 2H), 2.65 (t, J=8.3 Hz, 2H), 2.56 (q, J=7.3 Hz, 2H), 1.05 (t, J=7.3 Hz, 3H)

APCI-MS (m/z); 395 [M−H]$^-$

EXAMPLE 65

Synthesis of 2-[2-ethyl-6-(4-fluorobenzoyl)-3,5-dihydroxyphenyl]-N-(2-hydroxyethyl)-N-(2-methoxyethyl)acetamide (Compound 66)

In a manner similar to that in Example 10, Step 2, Compound 66 (94 mg, 66%) was obtained from 2-ethyl-6-(4-fluorobenzoyl)-3,5-dihydroxyphenylacetic acid (0.11 g, 0.34 mmol) obtained in Example 49, Step 3, using 1-(3-dimethylaminopropyl)-3-ethylcarbodiimide hydrochloride (0.15 g, 0.78 mmol), 2-(2-methoxyethylamino)ethanol (0.16 g, 1.4 mmol) obtained in Reference Example 1 and N,N-dimethylformamide (1.0 mL).

$^1$H-NMR (CD$_3$OD, 270 MHz) δ (ppm): 7.85 (dd, J=5.7, 8.7 Hz, 2H), 7.10 (d, J=8.7 Hz, 2H), 6.30 (s, 1H), 3.77 and 3.76 (s, total 2H), 3.65-3.18 (m, 9.5H), 3.16 (s, 1.5H), 2.56-2.52 (m, 2H), 1.07 (t, J=7.4 Hz, 3H)

APCI-MS (m/z); 420 [M+H]$^+$

EXAMPLE 66

Synthesis of 2-(2-ethyl-3,5-dihydroxy-6-(4-methoxybenzoyl)phenyl]-1-[4-(methylsulfonyl)piperidino]ethanone (Compound 67)

In a manner similar to that in Example 10, Step 2, Compound 67 (41 mg, 26%) was obtained from 2-ethyl-3,5-dihydroxy-6-(4-methoxybenzoyl)phenylacetic acid (0.11 g, 0.33 mmol) obtained in Example 10, Step 1, using 1-(3-dimethylaminopropyl)-3-ethylcarbodiimide (0.12 g, 0.77 mmol), 4-(methylsulfonyl)piperidine hydrochloride (0.26 g, 1.3 mmol) obtained in Reference Example 12 and N,N-dimethylformamide (1.0 mL).

$^1$H-NMR (CD$_3$OD, 300 MHz) δ (ppm): 7.76 (d, J=9.0 Hz, 2H), 6.91 (d, J=9.0 Hz, 2H), 6.32 (s, 1H), 4.36 (m, 1H), 4.06 (m, 1H), 3.84 (s, 3H), 3.49 (d, J=16.9 Hz, 1H), 3.39 (d, J=16.9 Hz, 1H), 3.19 (m, 1H), 2.99 (m, 1H), 2.88 (s, 3H), 2.61-2.42 (m, 3H), 1.99 (m, 2H), 1.56 (m, 1H), 1.24 (m, 1H), 1.07 (t, J=7.3 Hz, 3H)

APCI-MS (m/z); 476 [M+H]$^+$

EXAMPLE 67

Synthesis of 4-{2-[2-ethyl-3,5-dihydroxy-6-(4-methoxybenzoyl)phenyl]acetyl}-1-phenylpiperazin-2-one (Compound 68)

In a manner similar to that in Example 10, Step 2, Compound 68 (87 mg, 57%) was obtained from 2-ethyl-3,5-dihydroxy-6-(4-methoxybenzoyl)phenylacetic acid (0.10 g, 0.31 mmol) obtained in Example 10, Step 1, using 1-(3-dimethylaminopropyl)-3-ethylcarbodiimide (0.11 g, 0.71 mmol), 1-phenylpiperazin-2-one hydrochloride (0.27 g, 1.2 mmol) and N,N-dimethylformamide (1.0 mL).

¹H-NMR (CD₃OD, 270 MHz) δ (ppm): 7.77 (d, J=9.1 Hz, 2H), 7.46-7.25 (m, 5H), 6.92 (t, J=9.1 Hz, 2H), 6.34 (s, 1H), 4.23 (s, 1H), 3.99 (s, 1H), 3.82 (s, 3H), 3.80 (m, 1H), 3.69-3.65 (m, 4H), 3.49 (m, 1H), 2.65-2.56 (m, 2H), 1.10 (t, J=7.3 Hz, 3H)

APCI-MS (m/z); 489 [M+H]⁺

EXAMPLE 68

Synthesis of 2-[2-ethyl-3,5-dihydroxy-6-(4-methoxybenzoyl)phenyl]-N-(furan-2-ylmethyl)-N-(2-hydroxyethyl)acetamide (Compound 69)

In a manner similar to that in Example 10, Step 2, Compound 69 (90 mg, 31%) was obtained from 2-ethyl-3,5-dihydroxy-6-(4-methoxybenzoyl)phenylacetic acid (0.21 g, 0.63 mmol) obtained in Example 10, Step 1, using 1-(3-dimethylaminopropyl)-3-ethylcarbodiimide hydrochloride (0.28 g, 1.5 mmol), 2-(furfurylamino)ethanol (0.19 g, 1.3 mmol), triethylamine (0.36 mL, 2.6 mmol) and N,N-dimethylformamide (4.0 mL).

¹H-NMR (CD₃OD, 270 MHz) δ (ppm): 7.80-7.76 (m, 2H), 7.42 (m, 0.5H), 7.28 (m, 0.5H), 6.90 (d, J=9.1 Hz, 2H), 6.35 (m, 0.5H), 6.32 (s, 1H), 6.21 (m, 1H), 5.93 (m, 0.5H), 4.52 and 4.40 (s, total 2H), 3.85 and 3.84 (s, total 3H), 3.78 and 3.74 (s, total 2H), 3.52 (m, 1H), 3.39-3.29 (m, 3H), 2.54-2.44 (m, 2H), 1.06 and 1.05 (t, J=7.3 Hz, total 3H)

APCI-MS (m/z); 454 [M+H]⁺

EXAMPLE 69

Synthesis of 6-[2-(2,3-dihydroxypropyloxy)ethyl]-5-ethyl-2,4-dihydroxyphenyl=4-pyridyl=ketone (Compound 70)

(Step 1)

1,5-Bis(methoxymethoxy)-3-{2-[(2,2-dimethyl-1,3-dioxolan-4-yl)methoxy]ethyl}-2-bromo-4-ethylbenzene (1.1 g, 2.3 mmol) obtained in Example 33, Step 3 was dissolved in tetrahydrofuran (20 mL). After the solution was cooled to −78° C., a 1.6 mol/L solution of n-butyllithium in hexane (4.5 mL, 7.2 mmol) was added dropwise thereto, followed by stirring for 30 minutes. To the reaction mixture was added dropwise 4-pyridinecarboxaldehyde (0.50 g, 4.7 mmol), followed by stirring for 2 hours, while the temperature of the reaction mixture was raised from −78° C. to room temperature. A saturated aqueous solution of ammonium chloride was added to the reaction mixture, and the mixture was extracted twice with ethyl acetate. The organic layers were combined, washed with a saturated aqueous solution of sodium chloride, dried over anhydrous sodium sulfate and concentrated under reduced pressure. The resulting residue was dissolved in acetonitrile (40 mL), and IBX (3.00 g, 11 mmol) was added, thereto, followed by stirring for 1 hour under heating and reflux. After IBX (1.0 g, 3.6 mmol) was further added, the reaction mixture was refluxed under heating and then cooled to room temperature. The reaction mixture was filtered, and the filtrate was concentrated under reduced pressure. The resulting residue was purified by silica gel column chromatography (chloroform-methanol/chloroform=1/1) to obtain 4,6-bis(methoxymethoxy)-2-{2-[(2,2-dimethyl-1,3-dioxolan-4-yl)methoxy]ethyl}-3-ethylphenyl=4-pyridyl=ketone (0.83 g, 74%).

¹H-NMR (CDCl₃, 300 MHz) δ (ppm): 8.76 (d, J=6.1 Hz, 2H), 7.60 (2H, d, J=6.1 Hz, 2H), 6.85 (s, 1H), 5.2.4 (s, 2H), 4.91 (s, 2H), 4.11 (m, 1H), 3.95 (dd, J=6.4, 8.3 Hz, 1H), 3.53 (s, 3H), 3.62-3.50 (m, 3H), 3.41 (dd, J=5.3, 9.9 Hz, 1H), 3.30 (dd, J=5.3, 9.9 Hz, 1H), 3.18 (s, 3H), 2.79 (m, 2H), 2.69 (q, J=7.4 Hz, 2H), 1.37 (s, 3H), 1.32 (s, 3H), 1.14 (t, J=7.4 Hz, 3H)

(Step 2)

In a manner similar to that in Example 1, Step 6, Compound 70 (0.39 g, 64%) was obtained from 4,6-bis(methoxymethoxy)-2-{2-[(2,2-dimethyl-1,3-dioxolan-4-yl)methoxy]ethyl}-3-ethylphenyl=4-pyridyl=ketone (0.83 g, 1.7 mmol) obtained in Example 69, Step 1, using a 4 mol/L solution of hydrogen chloride in 1,4-dioxane (10 mL) and methanol (10 mL).

¹H-NMR (CD₃OD, 270 MHz) δ (ppm): 8.66 (d, J=6.1 Hz, 2H), 7.65 (2H, d, J=6.3 Hz, 2H), 6.28 (s, 1H), 3.62-3.27 (m, 7H), 2.81 (t, J=7.6 Hz, 2H), 2.65 (q, J=7.3 Hz, 2H), 1.12 (t, J=7.3 Hz, 3H)

APCI-MS (m/z); 362 [M+H]⁺

EXAMPLE 70

Synthesis of 5-ethyl-2,4-dihydroxy-6-[2-(2-hydroxyethoxy)ethyl]phenyl=3-thienyl=ketone (Compound 71)

(Step 1)

In a manner similar to that in Example 59, Step 3, 4,6-diallyloxy-3-ethyl-2-[2-(2-hydroxyethoxy)ethyl]phenyl=3-thienyl=ketone (60 mg, 38%) was obtained from 2-[2-(3,5-diallyloxy-2-ethylphenyl)ethoxy]ethanol (0.16 g, 0.38 mmol) obtained in Example 59, Step 2, using trifluoroacetic acid (4.0 mL), 3-thiophenecarboxylic acid (90 mg, 0.70 mmol) and trifluoroacetic anhydride (1.0 mL, 7.1 mmol), and using acetonitrile (2.0 mL) and a 2 mol/L aqueous solution of sodium hydroxide (2.0 mL).

¹H-NMR (CDCl₃, 300 MHz) δ (ppm): 7.77 (dd, J=2.9, 1.1 Hz, 1H), 7.48 (dd, J=5.0, 1.1 Hz, 1H), 7.72 (dd, J=5.0, 2.9 Hz, 1H), 6.39 (s, 1H), 6.04 (ddt, J=17, 11, 5.0 Hz, 1H), 5.75 (ddt, J=16, 11, 5.0 Hz, 1H), 5.43 (dq, J=17, 1.7 Hz, 1H), 5.30 (dq, J=11, 1.7 Hz, 1H), 5.09 (dq, J=16, 1.5 Hz, 1H), 5.05 (dq, J=11, 1.5 Hz, 1H), 4.55 (dt, J=5.0, 1.7 Hz, 2H), 4.40 (dt, J=5.0, 1.5 Hz, 2H), 3.61 (t, J=4.8 Hz, 2H), 3.51 (t, J=7.7 Hz, 2H), 3.42 (t, J=4.8 Hz, 2H), 2.81 (t, J=7.7 Hz, 2H), 2.67 (t, J=7.4 Hz, 2H), 2.11 (brs, 1H), 1.11 (t, J=7.4 Hz, 3H)

(Step 2)

In a manner similar to that in Example 59, Step 4, Compound 71 (39 mg, 80%) was obtained from 4,6-diallyloxy-3-ethyl-2-[2-(2-hydroxyethoxy)ethyl]phenyl=3-thienyl=ketone (60 mg, 0.14 mmol) obtained in Example 70, Step 1, using ammonium formate (0.10 g, 1.6 mmol), bis(triphenylphosphine)palladium (II) dichloride (5.0 mg, 0.0071 mmol) and 1,4-dioxane (2.0 mL).

¹H-NMR (CD₃OD, 300 MHz) δ (ppm): 7.84 (dd, J=2.9, 1.2 Hz, 1H), 7.40 (dd, J=5.1, 1.2 Hz, 1H), 7.36 (dd, J=5.1, 2.9 Hz, 1H), 6.26 (s, 1H), 3.51 (t, J=5.1 Hz, 2H), 3.42 (t, J=7.5 Hz, 2H), 3.34 (t, J=5.1 Hz, 2H), 2.70 (t, J=7.5 Hz, 2H), 2.58 (q, J=7.3 Hz, 2H), 1.07 (t, J=7.3 Hz, 3H)

APCI-MS (m/z); 335 [M−H]⁻

EXAMPLE 71

Synthesis of 5-ethyl-2,4-dihydroxy-6-[2-(2-hydroxyethoxy)ethyl]phenyl=2-thienyl=ketone (Compound 72)

(Step 1)

In a manner similar to that in Example 59, Step 3, 4,6-diallyloxy-3-ethyl-2-[2-(2-hydroxyethoxy)ethyl]phenyl=2-thienyl=ketone (80 mg, 51%) was obtained from 2-[2-(3,5-diallyloxy-2-ethylphenyl)ethoxy]ethanol (0.12 g, 0.38 mmol) obtained in Example 59, Step 2, using trifluoroacetic acid (4.0 mL), 2-thiophenecarboxylic acid (0.90 g, 0.70 mmol) and trifluoroacetic anhydride (1.0 mL, 7.1 mmol), and using acetonitrile (2.0 mL) and a 2 mol/L aqueous solution of sodium hydroxide (2.0 mL).

¹H-NMR (CDCl₃, 300 MHz) δ (ppm): 7.64 (dd, J=4.8, 1.1 Hz, 1H), 7.40 (dd, J=3.7, 1.1 Hz, 1H), 7.06 (dd, J=4.8, 3.7 Hz, 1H), 6.40 (s, 1H), 6.04 (ddt, J=18, 11, 5.0 Hz, 1H), 5.76 (ddt, J=17, 11, 5.0 Hz, 1H), 5.45 (dq, J=18, 1.7 Hz, 1H), 5.30 (dq, J=11, 1.7 Hz, 1H), 5.11 (dq, J=17, 1.7 Hz, 1H), 5.02 (dq, J=11, 1.7 Hz, 1H), 4.56 (dt, J=5.0, 1.7 Hz, 2H), 4.41 (dt, J=5.0, 1.7 Hz, 2H), 3.62 (t, J=4.6 Hz, 2H), 3.55 (t, J=7.9 Hz, 2H), 3.44 (t, J=4.6 Hz, 2H), 2.87 (t, J=7.9 Hz, 2H), 2.67 (t, J=7.7 Hz, 2H), 1.11 (t, J=7.7 Hz, 3H)

(Step 2)

In a manner similar to that in Example 59, Step 4, Compound 72 (54 mg, 83%) was obtained from 4,6-diallyloxy-3-ethyl-2-[2-(2-hydroxyethoxy)ethyl]phenyl=2-thienyl=ketone (80 mg, 0.19 mmol) obtained in Example 71, Step 1, using ammonium formate (0.10 g, 1.6 mmol), bis(triphenylphosphine)palladium (II) dichloride (5.0 mg, 0.0071 mmol) and 1,4-dioxane (2.0 mL).

¹H-NMR (CD₃OD, 300 MHz) δ (ppm): 7.72 (dd, J=4.9, 1.1 Hz, 1H), 7.35 (dd, J=3.9, 1.1 Hz, 1H), 7.02 (dd, J=4.9, 3.9 Hz, 1H), 6.22 (s, 1H), 3.47 (t, J=5.1 Hz, 2H), 3.42 (t, J=7.5 Hz, 2H), 3.32 (t, J=5.1 Hz, 2H), 2.68 (t, J=7.5 Hz, 2H), 2.53 (q, J=7.3 Hz, 2H), 1.00 (t, J=7.3 Hz, 3H)

APCI-MS (m/z); 335 [M−H]⁻

EXAMPLE 72

Synthesis of 5-ethyl-2,4-dihydroxy-6-[2-(2-hydroxyethoxy)ethyl]phenyl=3-furyl=ketone (Compound 73)

(Step 1)

In a manner similar to that in Example 59, Step 3, 4,6-diallyloxy-3-ethyl-2-[2-(2-hydroxyethoxy)ethyl]phenyl=3-furyl-ketone (35 mg, 23%) was obtained from -2-[2-(3,5-diallyloxy-2-ethylphenyl)ethoxy]ethanol (0.11 g, 0.37 mmol) obtained in Example 59, Step 2, using trifluoroacetic acid (4.0 mL), 3-furancarboxylic acid (90 mg, 0.80 mmol) and trifluoroacetic anhydride (1.0 mL, 0.71 mmol), and using acetonitrile, (2.0 mL) and a 2 mol/L aqueous solution of sodium hydroxide (2.0 mL).

¹H-NMR (CDCl₃, 300 MHz) δ (ppm): 7.66 (dd, J=1.3, 0.66 Hz, 1H), 7.42 (dd, J=2.0, 1.3 Hz, 1H), 6.79 (dd, J=2.0, 0.66 Hz, 1H), 6.38 (s, 1H), 6.06 (ddt, J=17, 11, 5.0 Hz, 1H), 5.80 (ddt, J=17, 11, 5.0 Hz, 1H), 5.43 (dq, J=17, 1.7 Hz, 1H), 5.30 (dq, J=0.11, 1.7 Hz, 1H), 5.17 (dq, J=17, 1.7 Hz, 1H), 5.12 (dq, J=11, 1.7 Hz, 1H), 4.55 (dt, J=5.0, 1.7 Hz, 2H), 4.42 (dt, J=5.0, 1.7 Hz, 2H), 3.63 (t, J=5.0 Hz, 2H), 3.56 (t, J=7.6 Hz, 2H), 3.45 (t, J=5.0 Hz, 2H), 2.82 (t, J=7.6 Hz, 2H), 2.67 (q, J=7.3 Hz, 2H), 2.23 (brs, 1H), 1.11 (t, J=7.3 Hz, 3H)

(Step 2)

In a manner similar to that in Example 59, Step 4, Compound 73 (10 mg, 38%) was obtained from 4,6-diallyloxy-3-ethyl-2-[2-(2-hydroxyethoxy)ethyl]phenyl=3-furyl=ketone (35 mg, 0.088 mmol) obtained in Example 72, Step 1, using ammonium formate (30 mg, 0.48 mmol), bis(triphenylphosphine)palladium (II) dichloride (2.0 mg, 0.0028 mmol) and 1,4-dioxane (2.0 mL).

¹H-NMR (CD₃OD, 300. MHz) δ (ppm): 7.79 (dd, J=1.3, 0.73 Hz, 1H), 7.56 (dd, J=2.0, 1.3 Hz, 1H), 6.76 (dd, J=2.0, 0.73 Hz, 1H), 6.28 (s, 1H), 3.57 (t, J=4.9 Hz, 2H), 3.49 (t, J=8.1 Hz, 2H), 3.41 (t, J=4.9 Hz, 2H), 2.76 (t, J=8.1 Hz, 2H), 2.61 (q, J=7.3 Hz, 2H), 1.11 (t, J=7.3 Hz, 3H)

APCI-MS (m/z); 319 [M−H]⁻

EXAMPLE 73

Synthesis of 2-[2-ethyl-3,5-dihydroxy-6-(3-thienylcarbonyl)phenyl]-N,N-bis(2-hydroxyethyl)acetamide (Compound 74)

(Step 1)

In a manner similar to that in Example 5, Step 4, methyl 3,5-diallyloxy-2-ethyl-6-(3-thienylcarbonyl)phenylacetate (3.8 g, 70%) was obtained from methyl 3,5-diallyloxy-2-ethylphenylacetate (3.9 g, 13 mmol) obtained in Example 5, Step 3, using 3-thiophenecarboxylic acid (1.8 g, 1.4 mmol), trifluoroacetic anhydride (6.0 mL) and trifluoroacetic acid (20 mL).

¹H-NMR (CDCl₃, 270 MHz) δ (ppm): 7.82 (dd, J=1.2, 2.8 Hz, 1H), 7.49 (dd, J=1.2, 5.1 Hz, 1H), 7.25 (dd, J=2.8, 5.1 Hz, 1H), 6.43 (s, 1H), 6.07 (m, 1H), 5.72 (m, 1H), 5.44 (dq, J=17.2 Hz, 1.6 Hz, 1H), 5.30 (dq, J=10.6, 1.6 Hz, 1H), 5.10-5.02 (m, 2H), 4.57 (dt, J=4.8, 1.6 Hz, 2H), 4.40 (dt, J=4.8, 1.6 Hz, 2H), 3.66 (s, 2H), 3.48 (s, 3H), 2.64 (q, J=7.4 Hz, 2H), 1.09 (t, J=7.4 Hz, 3H)

APCI-MS (m/z); 401 [M+H]⁺

(Step 2)

In a manner similar to that in Example 7, Step 1, methyl 2-ethyl-3,5-dihydroxy-6-(3-thienylcarbonyl)phenylacetate (1.81 g, 71%) was obtained from methyl 3,5-diallyloxy-2-ethyl-6-(3-thienylcarbonyl)phenylacetate (3.2 g, 8.0 mmol) obtained in Example 73, Step 1, using ammonium formate (2.0 g, 32 mmol), bis(triphenylphosphine)palladium (II) dichloride (56 mg, 0.080 mmol) and 1,4-dioxane (30 mL).

¹H-NMR (CD₃OD, 300 MHz) δ (ppm): 7.79 (dd, J=1.2, 2.9 Hz, 1H), 7.43 (dd, J=1.2, 5.1 Hz, 1H), 7.34 (dd, J=2.9, 5.1 Hz, 1H), 6.32 (s, 1H), 3.57 (s, 2H), 3.55 (s, 3H), 2.56 (q, J=7.5 Hz, 2H), 1.10 (t, J=7.5 Hz, 3H)

APCI-MS (m/z) 319 [M−H]⁻

(Step 3)

In a manner similar to that in Example 10, Step 1, 2-ethyl-3,5-dihydroxy-6-(3-thienylcarbonyl)phenylacetic acid (0.49 g, 92%) was obtained from methyl 2-ethyl-3,5-dihydroxy-6-(3-thienylcarbonyl)phenylacetate (0.56 g, 1.7 mmol) obtained in Example 73, Step 2, using a 2 mol/L aqueous solution of sodium hydroxide (4.0 mL) and acetonitrile (4.0 mL).

¹H-NMR (CD₃OD, 300 MHz) δ (ppm): 7.92 (dd, J=1.3, 2.9 Hz, 1H), 7.46 (dd, J=1.3, 5.1 Hz, 1H), 7.38 (dd, J=2.9, 5.1 Hz, 1H), 6.34 (s, 1H), 3.53 (s, 2H), 2.58 (q, J=7.3 Hz, 2H), 1.08 (t, J=7.3 Hz, 3H)

APCI-MS (m/z); 307 [M+H]⁺

(Step 4)

In a manner similar to that in Example 10, Step 2, Compound 74 (36 mg, 9.2%) was obtained from 2-ethyl-3,5-dihydroxy-6-(3-thienylcarbonyl)phenylacetic acid (304 mg, 1.00 mmol) obtained in Example 73, Step 3, using 1-(3-dimethylaminopropyl)-3-ethylcarbodiimide hydrochloride (0.44 g, 2.3 mmol), diethanolamine (0.42 g, 4.0 mmol) and N,N-dimethylformamide (2.0 mL).

¹H-NMR (CD₃OD, 270 MHz) δ (ppm): 7.93 (dd, J=1.4, 3.0 Hz, 1H), 7.45 (dd, J=1.4, 5.1 Hz, 1H), 7.36 (dd, J=3.0, 5.1

Hz, 1H), 6.32 (s, 1H), 3.71 (s, 2H), 3.62 (t, J=5.4 Hz, 2H), 3.45 (t, J=5.4 Hz, 4H), 3.35-3.29 (m, 2H), 2.54 (q, J=7.4 Hz, 2H), 1.07 (t, J=7.4 Hz, 3H)

ESI-MS (m/z); 394 [M+H]$^+$

EXAMPLE 74

Synthesis of 4-{2-[2-benzoyl-6-ethyl-3,5-dihydroxyphenyl]-acetyl}-1-(2-cyanophenyl)piperazin-2-one (Compound 75)

(Step 1)

In a manner similar to that in Example 10, Step 1, 2-benzoyl-6-ethyl-3,5-dihydroxyphenylacetic acid (2.4 g, 96%) was obtained from Compound 5 (2.6 g, 8.4 mmol) obtained in Example 5, using a 2 mol/L aqueous solution of sodium hydroxide (20 mL) and acetonitrile (20 mL).

$^1$H-NMR (CD$_3$OD, 270 MHz) δ (ppm): 7.80-7.37 (m, 5H), 6.33 (s, 1H), 3.55 (s, 2H), 2.61 (q, J=7.4 Hz, 2H), 1.09 (t, J=7.4 Hz, 3H)

APCI-MS (m/z); 301 [M+H]$^+$ (Step 2) 2-Benzoyl-6-ethyl-3,5-dihydroxyphenylacetic acid (0.11 g, 0.36 mmol) obtained in Example 74, Step 1 was dissolved in N,N-dimethylformamide (1.0 mL), and 1-(2-cyanophenyl)piperazin-2-one hydrochloride (0.34 g, 1.4 mmol) obtained by a method similar to the method described in Tetrahedron Lett., 1998, Vol. 39, p. 7459-7462 and 1-(3-dimethylaminopropyl)-3-ethylcarbodiimide hydrochloride (0.13 g, 0.82 mmol) were added thereto, followed by stirring at room temperature for 2 hours. The reaction mixture was concentrated under reduced pressure, and 1 mol/L hydrochloric acid was added to the resulting residue. The resulting mixture was extracted with ethyl acetate. The organic layer was washed with water, dried over anhydrous sodium sulfate, and then concentrated under reduced pressure. The resulting residue was crystallized from ethanol to obtain Compound 75 (0.14 g, 81%).

Melting Point: 259-261° C.

$^1$H-NMR (CD$_3$OD, 270 MHz) δ (ppm): 7.84-7.75 (m, 4H), 7.57-7.39 (m, 5H), 6.34 (s, 1H), 4.30 (s, 1H), 4.05 (s, 1H), 3.55-3.88 (m, 6H), 2.62 (q, J=7.3 Hz, 2H), 1.11 (t, J=7.3 Hz, 3H)

APCI-MS (m/z): 484 [M+H]$^+$

Elemental Analysis: (C$_{28}$H$_{25}$N$_3$O$_5$·0.2H$_2$O)

Found (%): C, 69.03; H, 5.31; N, 8.63.

Calcd. (%): C, 69.04; H, 5.26; N, 8.63.

EXAMPLE 75

Synthesis of 2-[2-benzoyl-6-ethyl-3,5-dihydroxyphenyl]-N,N-bis(2-hydroxyethyl)acetamide (Compound 76)

In a manner similar to that in Example 74, Step 2, Compound 76 (37 mg, 26%) was obtained from 2-benzoyl-6-ethyl-3,5-dihydroxypheylacetic acid (0.11 g, 0.36 mmol) obtained in Example 74, Step 1, using 1-(3-dimethylaminopropyl)-3-ethylcarbodiimide hydrochloride (0.16 g, 0.83 mmol), diethanolamine (0.15 g, 1.4 mmol) and N,N-dimethylformamide (1.0 mL). In this case, crystallization was carried out with ethyl acetate.

Melting Point: 190-194° C.

$^1$H-NMR (CD$_3$OD, 270 MHz) δ (ppm): 7.78 (brd, J=7.3 Hz, 2H), 7.49 (m, 1H), 7.39 (brt, J=7.3 Hz, 2H), 6.31 (s, 1H), 3.73 (s, 2H), 3.61 (t, J=5.4 Hz, 2H), 3.42 (q, J=5.4 Hz, 4H), 3.31-3.29 (m, 2H), 2.56 (q, J=7.4 Hz, 2H), 1.08 (t, J=7.4 Hz, 3H)

APCI-MS (m/z); 388 [M+H]$^+$

EXAMPLE 76

Synthesis of 2-[2-benzoyl-6-ethyl-3,5-dihydroxyphenyl]-N-(2-hydroxyethyl)-N-(2-methoxyethyl)acetamide (Compound 77)

In a manner similar to that in Example 74, Step 2, Compound 77 (92 mg, 59%) was obtained from 2-benzoyl-6-ethyl-3,5-dihydroxyphenylacetic acid (0.12 g, 0.39 mmol) obtained in Example 74, Step 1, using 1-(3-dimethylaminopropyl)-3-ethylcarbodiimide hydrochloride (0.17 g, 0.89 mmol), 2-(2-methoxyethylamino)ethanol (0.18 g, 1.5 mmol) obtained in Reference Example 1 and N,N-dimethylformamide (1.0 mL). In this case, crystallization was carried out with ethyl acetate. Melting Point: 183-185° C.

$^1$H-NMR (CD$_3$OD, 270 MHz) δ (ppm): 7.79 (brd, J=7.6 Hz, 2H), 7.52 (m, 1H), 7.39 (brt, J=7.6 Hz, 2H), 6.31 (s, 1H), 3.75 and 3.73 (s, total 2H), 3.63-3.15 (m, 11H), 2.57-2.52 (m, 2H), 1.07 (t, J=7.4 Hz, 3H)

APCI-MS (m/z); 402 [M+H]$^+$

Elemental Analysis: (C$_{22}$H$_{27}$NO$_6$)

Found (%): C, 65.96; H, 6.85; N, 3.39.

Calcd. (%): C, 65.82; H, 6.78; N, 3.49.

EXAMPLE 77

Synthesis of 2-[2-benzoyl-6-ethyl-3,5-dihydroxyphenyl]-1-[4-(hydroxymethyl)piperidino]ethanone (Compound 78)

In a manner similar to that in Example 74, Step 2, Compound 78 (88 mg, 60%) was obtained from 2-benzoyl-6-ethyl-3,5-dihydroxyphenylacetic acid (0.11 g, 0.37 mmol) obtained in Example 74, Step 1, using 1-(3-dimethylaminopropyl)-3-ethylcarbodiimide hydrochloride (0.16 g, 0.84 mol), 4-piperidineethanol (0.17 g, 1.5 mmol), 1-hydroxybenzotriazole hydrate (0.14 g, 0.91 mmol) and N,N-dimethylformamide (1.0 mL). In this case, crystallization was carried out with ethyl acetate.

Melting Point: 239-242° C.

$^1$H-NMR (CD$_3$OD, 300 MHz) δ (ppm): 7.37-7.79 (m, 5H), 6.31 (s, 1H), 4.24 (m, 1H), 3.89 (m, 1H), 3.70 (d, J=16.5 Hz, 1H), 3.58 (d, J=16.5 Hz, 1H), 3.11-3.26 (m, 2H), 2.90 (m, 1H), 2.61-2.50 (m, 2H), 2.36 (m, 1H), 1.70-1.50 (m, 3H), 1.08 (t, J=7.3 Hz, 3H), 0.99 (m, 1H), 0.63 (m, 1H)

APCI-MS (m/z); 398 [M+H]$^+$

Elemental Analysis: (C$_{23}$H$_{27}$NO$_5$·0.2H$_2$O)

Found (%): C, 68.82; H, 6.70; N, 3.76.

Calcd. (%): C, 68.88; H, 6.89; N, 3.49.

EXAMPLE 78

Synthesis of 2-[2-ethyl-3,5-dihydroxy-6-(3-hydroxybenzoyl)phenyl]-N-(2-hydroxyethyl)-N-(2-methoxyethyl)acetamide (Compound 79)

(Step 1)

In a manner similar to that in Example 5, Step 4, methyl 3,5-diallyloxy-2-ethyl-6-(3-hydroxybenzoyl)phenylacetate (1.5 g, 70%) was obtained from methyl 3,5-diallyloxy-2-ethylphenylacetate (1.5 g, 5.2 mmol) obtained in Example 5, Step 3, using 4-hydroxybenzoic acid (1.7 g, 10 mmol), trifluoroacetic anhydride (2.0 mL, 14 mmol) and trifluoroacetic acid (8 mL), and using a 7 mol/L solution of ammonia in methanol (10 mL).

$^1$H-NMR (CDCl$_3$, 300 MHz). δ (ppm): 7.36-7.23 (m, 3H), 7.00 (ddd, J=7.2, 2.6, 1.1 Hz, 1H), 6.24 (s, 1H), 6.06 (m, 1H), 5.56 (m, 1H), 5.48 (m, 1H), 5.29 (m, 1H), 5.05-4.97 (m, 2H), 4.57 (m, 2H), 4.35 (m, 2H), 3.66 (s, 2H), 3.46 (s, 3H), 2.65 (q, J=7.5 Hz, 2H), 1.08 (t, J=7.5 Hz, 3H) APCI-MS (m/z); 409 [M−H]$^-$ (Step 2)

In a manner similar to that in Example 10, Step 1, 3,5-diallyloxy-2-ethyl-6-(3-hydroxybenzoyl)phenylacetic acid (1.2 g, 83%) was obtained from methyl 3,5-diallyloxy-2-ethyl-6-(3-hydroxybenzoyl)phenylacetate (1.5 g, 3.7 mmol) obtained in Example 78, Step 1, using a 2 mol/L aqueous solution of sodium hydroxide (10 mL) and acetonitrile (20 mL).

$^1$H-NMR (CDCl$_3$, 300 MHz) δ (ppm): 7.26-7.18 (m, 3H), 7.00 (ddd, J=7.2, 2.6, 1.1 Hz, 1H), 6.40 (s, 1H), 6.04 (m, 1H), 5.56 (m, 1H), 5.40 (m, 1H), 5.28 (m, 1H), 5.05-4.92 (m, 2H), 4.57 (m, 2H), 4.35 (m, 2H), 3.56 (s, 3H), 2.67 (q, J=7.2 Hz, 2H), 1.08 (t, J=7.2 Hz, 3H)

APCI-MS (m/z); 397 [M+H]$^+$ (Step 3)

In a manner similar to that in Example 10, Step 2, 2-[2-ethyl-3,5-diallyloxy-6-(3-hydroxybenzoyl)phenyl]-N-(2-hydroxyethyl)-N-(2-methoxyethyl)acetamide (430 mg, 74%) was obtained from 3,5-diallyloxy-2-ethyl-6-(3-hydroxybenzoyl)phenylacetic acid (470 mg, 1.2 mmol) obtained in Example 78, Step 2, using 1-hydroxybenzotriazole hydrate (220 mg, 1.4 mmol), 1-(3-dimethylaminopropyl)-3-ethylcarbodiimide hydrochloride (270 mg, 1.4 mmol), 2-(2-methoxyethylamino)ethanol (170 mg, 1.4 mmol) obtained in Reference Example 1 and N,N-dimethylformamide (10 mL). $^1$H-NMR (DMSO-d$_6$, 300 MHz) δ (ppm): 9.58 (s, 1H), 7.20 (t, J=7.9 Hz, 1H), 7.11-7.09 (m, 2H), 6.92 (m, 1H), 6.63 (s, 1H), 6.10 (m, 1H), 5.62 (m, 1H), 5.45 (m, 1H), 5.29 (m, 1H), 4.99-4.90 (m, 2H), 4.74 (t, J=5.0 Hz, 0.5H), 4.64 (m, 2H), 4.49 (t, J=5.0 Hz, 0.5H), 4.40 (m, 2H), 3.60 (d, J=8.7 Hz, 2H), 3.41 (m, 2H), 3.34-3.04 (m, 9H), 2.55 (m, 2H), 1.11 (t, J=7.3 Hz, 3H)

APCI-MS (m/z); 498 [M+H]$^+$ (Step 4)

In a manner similar to that in Example 7, Step 1, Compound 79 (25 mg, 23%) was obtained from 2-[2-ethyl-3,5-diallyloxy-6-(3-hydroxybenzoyl)phenyl]-N-(2-hydroxyethyl)-N-(2-methoxyethyl)acetamide (130 mg, 0.26 mmol) obtained in Example 78, Step 3, using ammonium formate (90 mg, 1.4 mmol), bis (triphenylphosphine)palladium (II) dichloride (5.0 mg, 0.0071 mmol) and 1,4-dioxane (5.0 mL).

$^1$H-NMR (CD$_3$OD, 300 MHz) δ (ppm): 7.31-7.21 (m, 3H), 7.0 (m, 1H), 6.33 (s, 1H), 3.72 (d, J=8.7 Hz, 2H), 3.62-3.20 (m, 11H), 2.58 (m, 2H), 1.11 (t, J=7.3 Hz, 3H)

APCI-MS (m/z); 416 [M−H]$^-$

EXAMPLE 79

Synthesis of 2-[2-ethyl-3,5-dihydroxy-6-(4-hydroxybenzoyl)phenyl]-N,N-bis(2-hydroxyethyl)acetamide (Compound 80)

(Step 1)

In a manner similar to that in Example 5, Step 4, methyl 3,5-diallyloxy-2-ethyl-6-(4-hydroxybenzoyl-phenylacetate (1.3 g, 65%) was obtained from methyl 3,5-diallyloxy-2-ethylphenylacetate (1.5 g, 5.2 mmol) obtained in Example 5, Step 3, using 4-hydroxybenzoic acid (1.7 g, 10 mmol), trifluoroacetic anhydride (2.0 mL, 14 mmol) and trifluoroacetic acid (10 mL), and using a 7 mol/L solution of ammonia in methanol (10 mL).

$^1$H-NMR (CDCl$_3$, 300 MHz) δ (ppm): 7.76-7.72 (m, 2H), 6.80-6.76 (m, 2H), 6.43 (s, 1H), 6.08 (m, 1H), 5.57 (m, 1H), 5.44 (m, 1H), 5.31 (m, 1H), 5.05-4.98 (m, 2H), 4.56 (m, 2H), 4.36 (m, 2H), 3.65 (s, 2H), 3.45 (s, 3H), 2.63 (q, J=7.5 Hz, 2H), 1.09 (t, J=7.5 Hz, 3H)

APCI-MS (m/z); 411 [M+H]$^+$ (Step 2)

In a manner similar to that in Example 7, Step 1, methyl 2-ethyl-3,5-dihydroxy-6-(4-hydroxybenzoyl)phenylacetate (1.1 g, 94%) was obtained from methyl 3,5-diallyloxy-2-ethyl-6-(4-hydroxybenzoyl)phenylacetate (1.3 g, 3.2 mmol) obtained in Example 79, Step 1, using ammonium formate (1.0 g, 15 mmol), bis(triphenylphosphine)palladium (II) dichloride (0.12 g, 0.17 mmol) and 1,4-dioxane (20 mL).

$^1$H-NMR (CDCl$_3$, 300 MHz) δ (ppm): 7.64-7.61 (m, 2H), 6.78-6.75 (m, 2H), 6.25 (s, 1H), 3.52 (s, 2H), 3.50 (s, 3H), 2.63 (q, J=7.5 Hz, 2H), 1.09 (t, J=7.5 Hz, 3H)

APCI-MS (m/z); 329 [M−H]$^-$ (Step 3)

In a manner similar to that in Example 10, Step 1, 2-ethyl-3,5-dihydroxy-6-(4-hydroxybenzoyl)phenylacetic acid (0.93 g, 89%) was obtained from methyl 2-ethyl-3,5-dihydroxy-6-(4-hydroxybenzoyl)phenylacetate (1.1 g, 3.3 mmol) obtained in Example 79, Step 2, using a 2 mol/L aqueous solution of sodium hydroxide (10 mL) and tetrahydrofuran (20 mL).

$^1$H-NMR (DMSO-d$_6$, 300 MHz) δ (ppm): 12.0 (brs, 1H), 10.2 (s, 1H), 9.40 (s, 1H), 9.11 (s, 1H), 7.57-7.53 (m, 2H), 6.78-6.73 (m, 2H), 6.34 (s, 1H), 3.33 (s, 2H), 2.44 (q, J=7.5 Hz, 2H), 0.99 (t, J=7.5 Hz, 3H)

APCI-MS (m/z); 315 [M−H]$^-$ (Step 4)

In a manner similar to that in Example 10, Step 2, Compound 80 (30 mg, 10%) was obtained from 2-ethyl-3,5-dihydroxy-6-(4-hydroxybenzoyl)phenylacetic acid (130 mg, 0.41 mmol) obtained in Example 79, Step 3, using 1-hydroxybenzotriazole hydrate (120 mg, 0.78 mmol), 1-(3-dimethylaminopropyl)-3-ethylcarbodiimide hydrochloride (150 mg, 0.79 mmol), diethanolamine (210 mg, 2.0 mmol) and N,N-dimethylformamide (4 mL).

$^1$H-NMR (CD$_3$OD, 300 MHz) δ (ppm): 7.66-7.64 (m, 2H), 6.74-6.70 (m, 2H), 6.27 (s, 1H), 3.64 (brs, 2H), 3.55 (t, J=5.9 Hz, 2H), 3.41-3.36 (m, 4H), 3.30 (s, 2H), 2.50 (q, J=7.3 Hz, 2H), 1.02 (t, J=7.3 Hz, 3H)

APCI-MS (m/z); 404 [M+H]$^+$

EXAMPLE 80

Synthesis of 2-[2-ethyl-3,5-dihydroxy-6-(4-hydroxybenzoyl)phenyl]-N-(2-hydroxyethyl)-N-(2-methoxyethyl)acetamide (Compound 81)

In a manner similar to that in Example 10, Step 2, Compound 81 (30 mg, 10%) was obtained from 2-ethyl-3,5-dihydroxy-6-(4-hydroxybenzoyl)phenylacetic acid (130 mg, 0.41 mmol) obtained in Example 79, Step 3, using 1-hydroxybenzotriazole hydrate (120 mg, 0.78 mmol), 1-(3-dimethylaminopropyl)-3-ethylcarbodiimide hydrochloride (150 mg, 0.79 mmol), 2-(2-methoxyethylamino)ethanol (250 mg, 2.1 mmol) obtained in Reference Example 1 and N,N-dimethylformamide (4 mL).

$^1$H-NMR (CD$_3$OD, 300 MHz) δ (ppm): 7.73-7.70 (m, 2H), 6.79-6.75 (m, 2H), 6.32 (s, 1H), 3.69 (d, J=5.3 Hz, 2H), 3.59 (t, J=5.7 Hz, 1H), 3.50 (t, J=4.8 Hz, 1H), 3.45-3.40 (m, 4H), 3.35-3.28 (m, 2.5H), 3.18-3.13 (m, 2.5H), 2.55 (m, 2H), 1.08 (t, J=7.3 Hz, 3H)

APCI-MS (m/z); 418 [M+H]$^+$

EXAMPLE 81

Synthesis of 4-{2-[2-ethyl-6-(4-fluorobenzoyl)-3,5-dihydroxyphenyl]acetyl}-1-phenylpiperazin-2-one (Compound 82)

In a manner similar to that in Example 74, Step 2, Compound 82 (110 mg, 72%) was obtained from 2-ethyl-6-(4-fluorobenzoyl)-3,5-dihydroxyphenylacetic acid (0.11 g, 0.33 mmol) obtained in Example 49, Step 3, using 1-(3-dimethylaminopropyl)-3-ethylcarbodiimide (0.12 g, 0.76 mmol), 1-phenylpiperazin-2-one hydrochloride (0.28 g, 1.3 mmol) and N,N-dimethylformamide (1.0 mL).

Melting Point: 170-172° C.

$^1$H-NMR (CD$_3$OD, 270 MHz) δ (ppm): 7.83 (dd, J=5.6, 9.0 Hz, 2H), 7.46-7.26 (m, 5H), 7.11 (t, J=8.6 Hz, 2H), 6.33 (s, 1H), 4.30-3.54 (m, 8H), 2.62 (q, J=7.5 Hz, 2H), 1.11 (t, J=7.5 Hz, 3H)

APCI-MS (m/z); 477 [M+H]$^+$

Elemental Analysis: (C$_{27}$H$_{25}$FN$_2$O$_5$)

Found (%): C, 67.98; H, 5.38; N, 5.75.

Calcd. (%): C, 68.06; H, 5.29; N, 5.88.

EXAMPLE 82

Synthesis of 2-[2-ethyl-3,5-dihydroxy-6-(3-hydroxy-4-methoxybenzoyl)phenyl]-N,N-bis(2-hydroxyethyl)acetamide (Compound 83)

(Step 1)

In a manner similar to that in Example 5, Step 4, methyl 3,5-diallyloxy-2-ethyl-6-(3-hydroxy-4-methoxybenzoyl)phenylacetate (1.1 g, 48%) was obtained from methyl 3,5-diallyloxy-2-ethylphenylacetate (1.5 g, 5.2 mmol) obtained in Example 5, Step 3, using 3-hydroxy-4-methoxybenzoic acid (1.7 g, 10 mmol), trifluoroacetic anhydride (2.0 mL, 14 mmol) and trifluoroacetic acid (15 mL), and using a 7 mol/L solution of ammonia in methanol (20 mL) and methanol (20 mL).

$^1$H-NMR (CDCl$_3$, 300 MHz) δ (ppm): 7.42-7.38 (m, 2H), 6.83 (d, J=9.2 Hz, 1H), 6.43 (s, 1H), 6.07 (m, 1H), 5.72 (m, 1H), 5.54 (s, 1H), 5.45 (m, 1H), 5.29° (m, 1H), 5.08-5.03 (m, 2H), 4.58 (m, 2H), 4.37 (m, 2H), 3.93 (s, 3H), 3.61 (s, 2H), 3.47 (s, 3H), 2.64 (q, J=7.7 Hz, 2H), 1.09 (t, J=7.7 Hz, 3H)

(Step 2)

In a manner similar to that in Example 10, Step 1, 3,5-diallyloxy-2-ethyl-6-(3-hydroxy-4-methoxybenzoyl)phenylacetic acid (430 mg, 80%) was obtained from methyl 3,5-diallyloxy-2-ethyl-6-(3-hydroxy-4-methoxybenzoyl)phenylacetate (230 mg, 0.52 mmol) obtained in Example 82, Step 1, using a 2 mol/L aqueous solution of sodium hydroxide (10 mL) and tetrahydrofuran (0.10 mL).

$^1$H-NMR (CD$_3$OD, 300 MHz) δ (ppm): 7.33 (d, J=1.8 Hz, 1H), 7.10 (dd, J=8.5, 1.8 Hz, 1H), 6.93 (d, J=8.5 Hz, 1H), 6.67 (s, 1H), 6.10 (m, 1H), 5.68 (m, 1H), 5.45 (m, 1H), 5.29 (m, 1H), 5.03-4.96 (m, 2H), 4.65 (m, 2H), 4.44 (m, 2H), 3.80 (s, 3H), 3.38 (s, 2H), 2.53 (q, J=7.0 Hz, 2H), 1.03 (t, J=7.0 Hz, 3H)

APCI-MS (m/z); 427 [M+H]$^+$ (Step 3)

In a manner similar to that in Example 10, Step 2, 2-[2-ethyl-3,5-diallyloxy-6-(3-hydroxy-4-methoxybenzoyl)phenyl]-N,N-bis(2-hydroxyethyl)acetamide (85 mg, 35%) was obtained from 3,5-diallyloxy-2-ethyl-6-(3-hydroxy-4-methoxybenzoyl)phenylacetic acid (200 mg, 0.47 mmol) obtained in Example 82, Step 2, using 1-hydroxybenzotriazole hydrate (150 mg, 0.98 mmol), 1-(3-dimethylaminopropyl)-3-ethylcarbodiimide hydrochloride (180 mg, 0.94 mmol), diethanolamine (150 mg, 1.4 mmol) and N,N-dimethylformamide (4 mL).

$^1$H-NMR (CD$_3$OD, 300 MHz) δ (ppm): 7.27-7.23 (m, 2H), 6.89 (d, J=9.0 Hz, 1H), 6.56 (s, 1H), 6.07 (m, 1H), 5.66 (m, 1H), 5.47 (m, 1H), 5.27 (m, 1H), 5.03-4.96 (m, 2H), 4.60 (m, 2H), 4.38 (m, 2H), 3.87 (s, 3H), 3.70 (s, 2H), 3.58 (t, J=6.0 Hz, 2H), 3.45-3.39 (m, 4H), 3.30 (t, J=6.2 Hz, 2H), 2.60 (q, J=7.3 Hz, 2H), 1.03 (t, J=7.3 Hz, 3H)

APCI-MS (m/z); 514 [M+H]$^+$ (Step 4)

In a manner similar to that in Example 7, Step 1, Compound 83 (47 mg, 66%) was obtained from 2-[2-ethyl-3,5-diallyloxy-6-(3-hydroxy-4-methoxybenzoyl)phenyl]-N,N-bis(2-hydroxyethyl)acetamide (85 mg, 0.17 mmol) obtained in Example 82, Step 3, using ammonium formate (50 mg, 0.79 mmol), bis(triphenylphosphine)palladium (II) dichloride (10 mg, 0.14 mmol) and 1,4-dioxane (3 mL).

$^1$H-NMR (CD$_3$OD, 300 MHz) δ (ppm): 7.32-7.29 (m, 2H), 6.90 (d, J=8.6 Hz, 1H), 6.31 (s, 1H), 3.89 (s, 3H), 3.65 (s, 2H), 3.58 (t, J=5.8 Hz, 2H), 3.46-3.39 (m, 4H), 3.32-3.30 (m, 2H), 2.52 (q, J=7.1 Hz, 2H), 1.06 (t, J=7.1 Hz, 3H)

APCI-MS (m/z); 434 [M+H]$^+$

EXAMPLE 83

Synthesis of 2-[2-ethyl-3,5-dihydroxy-6-(3-hydroxy-4-methoxybenzoyl)phenyl]-N-(2-hydroxyethyl)-N-(2-methoxyethyl)acetamide (Compound 84)

(Step 1)

In a manner similar to that in Example 10, Step 2, 2-[3,5-diallyloxy-2-ethyl-6-(3-hydroxy-4-methoxybenzoyl)phenyl]-N-(2-hydroxyethyl)-N-(2-methoxyethyl)acetamide (110 mg, 44%) was obtained from 3,5-diallyloxy-2-ethyl-6-(3-hydroxy-4-methoxybenzoyl)phenylacetic acid (200 mg, 0.47 mmol) obtained in Example 82, Step 2, using 1-hydroxybenzotriazole hydrate (150 mg, 0.98 mmol), 1-(3-dimethylaminopropyl)-3-ethylcarbodiimide hydrochloride (180 mg, 0.94 mmol), 2-(2-methoxyethylamino)ethanol (170 mg, 1.4 mmol) obtained in Reference Example 1 and N,N-dimethylformamide (4 mL).

$^1$H-NMR (CD$_3$OD, 300 MHz) δ (ppm): 7.32-7.30 (m, 2H), 6.92 (dd, J=9.0, 2.8 Hz, 1H), 6.60 (s, 1H), 6.13 (m, 1H), 5.72 (m, 1H), 5.50 (m, 1H), 5.29 (m, 1H), 5.08-5.00 (m, 2H), 4.62 (m, 2H), 4.42 (m, 2H), 3.90 (s, 3H), 3.74 (d, J=7.5 Hz, 2H), 3.61 (t, J=5.7 Hz, 1H), 3.52 (m, 1H), 3.45-3.40 (m, 3H), 3.35-3.30 (m, 3.5H), 3.20-3.16 (m, 2.5H), 2.62 (m, 2H), 1.11 (t, J=7.3 Hz, 3H)

APCI-MS (m/z); 528 [M+H]$^+$ (Step 2)

In a manner similar to that in Example 7, Step 1, Compound 84 (34 mg, 36%) was obtained from 2-[3,5-diallyloxy- 2-ethyl-6-(3-hydroxy-4-methoxybenzoyl)phenyl]-N-(2-hydroxyethyl)-N-(2-methoxyethyl)acetamide (110 mg, 0.21 mmol) obtained in Example 83, Step 1, using ammonium formate (67 mg, 1.1 mmol), bis(triphenylphosphine)palladium (II) dichloride (10 mg, 0.14 mmol) and 1,4-dioxane (3 mL).

$^1$H-NMR (CD$_3$OD, 270 MHz) δ (ppm): 7.34-7.28 (m, 2H), 6.90 (m, 1H), 6.30 (s, 1H), 3.90 (s, 3H), 3.68 (d, J=7.7 Hz, 2H), 3.59 (t, J=5.7 Hz, 2H), 3.49-3.40 (m, 4H), 3.35-3.28 (m, 2.5H), 3.17-3.13 (m, 2.5H), 2.55 (m, 2H), 1.08 (t, J=7.3 Hz, 3H)

APCI-MS (m/z); 448 [M+H]$^+$

EXAMPLE 84

Synthesis of 2-[2-ethyl-6-(3-fluoro-4-methoxybenzoyl)-3,5-dihydroxyphenyl]-N,N-bis(2-hydroxyethyl)acetamide (Compound 85)

(Step 1)

In a manner similar to that in Example 5, Step 4, methyl 3,5-diallyloxy-2-ethyl-6-(3-fluoro-4-methoxybenzoyl)phenylacetate (1.3 g, 84%) was obtained from methyl 3,5-diallyloxy-2-ethylphenylacetate (1.0 g, 3.5 mmol) obtained in Example 5, Step 3, using 3-fluoro-4-methoxybenzoic acid (0.90 g, 5.3 mmol), trifluoroacetic anhydride (0.8 mL, 5.7 mmol) and trifluoroacetic acid (10 mL).

$^1$H-NMR (CDCl$_3$, 300 MHz) δ (ppm): 7.61-7.54 (m, 2H), 6.92 (t, J=8.5 Hz, 1H), 6.43 (s, 1H), 6.09 (m, 1H), 5.71 (m, 1H), 5.47 (m, 1H), 5.30 (m, 1H), 5.07-4.99 (m, 2H), 4.57 (m, 2H), 4.37 (m, 2H), 3.93 (s, 3H), 3.64 (s, 2H), 3.47 (s, 3H), 2.65 (q, J=7.3 Hz, 2H), 1.09 (t, J=7.3 Hz, 3H)

APCI-MS (m/z); 443 [M+H]$^+$ (Step 2)

In a manner similar to that in Example 7, Step 1, methyl 2-ethyl-6-(3-fluoro-4-methoxybenzoyl)-3,5-dihydroxyphenylacetate (1.0 g, 95%) was obtained from methyl 3,5-diallyloxy-2-ethyl-6-(3-fluoro-4-methoxybenzoyl)phenylacetate (1.3 g, 2.9 mmol) obtained in Example 84, Step 1, using ammonium formate (1.0 g, 16 mmol), bis(triphenylphosphine)palladium (II) dichloride (0.10 g, 0.14 mmol) and 1,4-dioxane (20 mL).

$^1$H-NMR (CD$_3$OD, 270 MHz) δ (ppm): 7.57-7.46 (m, 2H), 7.09 (t, J=8.5 Hz, 1H), 6.34 (s, 1H), 3.91 (s, 3H), 3.56 (s, 2H), 3.44 (s, 3H), 2.58 (q, J=7.5 Hz, 2H), 1.09 (t, J=7.5 Hz, 3H)

APCI-MS (m/z); 363 [M+H]$^+$ (Step 3)

In a manner similar to that in Example 10, Step 1, 2-ethyl-6-(3-fluoro-4-methoxybenzoyl)-3,5-dihydroxyphenylacetic acid was obtained from methyl 2-ethyl-6-(3-fluoro-4-methoxybenzoyl)-3,5-dihydroxyphenylacetate (1.2 g, 3.5 mmol) obtained in Example 84, Step 2, using a 2 mol/L aqueous solution of sodium hydroxide (10 mL) and tetrahydrofuran (10 mL).

$^1$H-NMR (DMSO-d$_6$, 300 MHz) δ (ppm): 12.1 (brs, 1H), 9.54 (s, 1H), 9.26 (s, 1H), 7.57-7.44 (m, 2H), 7.22 (t, J=8.5 Hz, 1H), 6.39 (s, 1H), 3.91 (s, 3H), 3.42 (s, 2H), 2.50 (q, J=7.5 Hz, 2H), 1.01 (t, J=7.5 Hz, 3H)

APCI-MS (m/z); 349 [M+H]$^+$ (Step 4)

In a manner similar to that in Example 10, Step 2, Compound 85 (47 mg, 25%) was obtained from 2-ethyl-6-(3-fluoro-4-methoxybenzoyl)-3,5-dihydroxyphenylacetic acid (150 mg, 0.43 mmol) obtained in Example 84, Step 3, using 1-hydroxybenzotriazole hydrate (130 mg, 0.85 mmol), 1-(3-dimethylaminopropyl)-3-ethylcarbodiimide hydrochloride (160 mg, 0.84 mmol), diethanolamine (230 mg, 2.2 mmol) and N,N-dimethylformamide (4 mL).

$^1$H-NMR (CD$_3$OD, 270 MHz) δ (ppm): 7.58 (ddd, J=8.7, 2.1, 1.1 Hz, 1H), 7.53 (dd, J=12.0, 1.5 Hz, 1H), 7.07 (t, J=8.3 Hz, 1H), 6.31 (s, 1H), 3.91 (s, 3H), 3.72 (s, 2H), 3.63 (t, J=5.8 Hz, 2H), 3.48-3.40 (m, 4H), 3.3.7 (m, 2H), 2.54 (q, J=7.4 Hz, 2H), 1.07 (t, J=7.4 Hz, 3H)

APCI-MS (m/z); 436 [M+H]$^+$

EXAMPLE 85

Synthesis of 2-[2-ethyl-6-(3-fluoro-4-methoxybenzoyl)-3,5-dihydroxyphenyl]-N-(2-hydroxyethyl)-N-(2-methoxyethyl)acetamide (Compound 86)

In a manner similar to that in Example 10, Step 2, Compound 86 (53 mg, 27%) was obtained from 2-ethyl-6-(3-fluoro-4-methoxybenzoyl)-3,5-dihydroxyphenylacetic acid (260 mg, 0.43 mmol) obtained in Example 84, Step 3, using 1-hydroxybenzotriazole hydrate (130 mg, 0.85 mmol), 1-(3-dimethylaminopropyl)-3-ethylcarbodiimide hydrochloride (160 mg, 0.84 mmol), 2-(2-methoxyethylamino)ethanol (260 mg, 2.2 mmol) obtained in Reference Example 1 and N,N-dimethylformamide (4 mL).

$^1$H-NMR (CD$_3$OD, 270 MHz) δ (ppm): 7.83 (m, 1H), 7.80 (dd, J=12, 2.0 Hz, 1H), 7.32 (m, 1H), 6.54 (s, 1H), 4.15 (s, 3H), 3.96 (d, J=4.0 Hz, 2H), 3.85 (t, J=5.7 Hz, 1H), 3.78-3.50 (m, 7.5H), 3.42-3.38 (m, 2.5H), 2.55 (m, 2H), 1.08 (t, J=7.3 Hz, 3H)

APCI-MS (m/z); 450 [M+H]$^+$

EXAMPLE 86

Synthesis of 2-{2-ethyl-3,5-dihydroxy-6-(4-(trifluoromethoxy)benzoyl]phenyl}-N,N-bis(2-hydroxyethyl)acetamide, (Compound 87)

(Step 1)

In a manner similar to that in Example 5, Step 4, methyl 3,5-diallyloxy-2-ethyl-6-[4-(trifluoromethoxy)benzoyl]phenylacetate (1.4 g, 87%) was obtained from methyl 3,5-diallyloxy-2-ethylphenylacetate (0.97 g, 3.3 mmol) obtained in Example 5, Step 3, using 4-(trifluoromethoxy)benzoic acid (1.0 g, 5.0 mmol), trifluoroacetic anhydride (0.7 mL, 5.0 mmol) and trifluoroacetic acid (10 mL).

$^1$H-NMR (CDCl$_3$, 300 MHz) δ (ppm): 7.86-7.83 (m, 2H), 7.23-7.20 (m, 2H), 6.42 (s, 1H), 6.06 (m, 1H), 5.60 (m, 1H), 5.44 (m, 1H), 5.30 (m, 1H), 5.02-4.89 (m, 2H), 4.58 (m, 2H), 4.33 (m, 2H), 3.71 (s, 2H), 3.45 (s, 3H), 2.65 (q, J=7.3 Hz, 2H), 1.10 (t, J=7.3 Hz, 3H)

APCI-MS (m/z); 479 [M+H]$^+$ (Step 2)

In a manner similar to that in Example 7, Step 1, methyl 2-ethyl-3,5-dihydroxy-6-[4-(trifluoromethoxy)benzoyl]phenylacetate (1.1 g, 95%) was obtained from methyl 3,5-diallyloxy-2-ethyl-6-[4-(trifluoromethoxy)benzoyl]phenylacetate, (1.4 g, 2.9 mmol) obtained in Example 86, Step 1, using ammonium formate (0.91 g, 14 mmol), bis(triphenylphosphine)palladium (II) dichloride (0.10 g, 0.14 mmol) and 1,4-dioxane (20 mL).

$^1$H-NMR (CD$_3$OD, 300 MHz) δ (ppm): 7.88-7.87 (m, 2H), 7.32-7.29 (m, 2H), 6.33 (s, 1H), 3.63 (s, 2H), 3.44 (s, 3H), 2.59 (q, J=7.5 Hz, 2H), 1.06 (t, J=7.5 Hz, 3H)

APCI-MS (m/z); 399 [M+H]$^+$ (Step 3)

In a manner similar to that in Example 10, Step 1, 2-ethyl-3,5-dihydroxy-6-[4-(trifluoromethoxy)benzoyl]-phenylacetic acid (0.88 g, 75%) was obtained from methyl 2-ethyl-3,5-dihydroxy-6-[4-(trifluoromethoxy)benzoyl]-phenylacetate (1.2 g, 3.1 mmol) obtained in Example 86, Step 2, using a 2 mol/L aqueous solution of sodium hydroxide (20 mL) and tetrahydrofuran (15 mL).

$^1$H-NMR (DMSO-$d_6$, 300 MHz) δ (ppm): 9.65 (s, 1H), 9.37 (s, 1H), 7.79-7.76 (m, 2H), 7.42-7.39 (m, 2H), 6.36 (s, 1H), 3.48 (s, 2H), 2.59 (m, 2H), 0.99 (t, J=7.3 Hz, 3H)

APCI-MS (m/z); 383 [M−H]$^−$ (Step 4)

In a manner similar to that in Example 10, Step 2, Compound 87 (25 mg, 15%) was obtained from 2-ethyl-3,5-dihydroxy-6-[4-(trifluoromethoxy)benzoyl]phenylacetic acid (130 mg, 34 mmol) obtained in Example 86, Step 3, using 1-hydroxybenzotriazole hydrate (80 mg, 0.52 mmol), 1-(3-dimethylaminopropyl)-3-ethylcarbodiimide hydrochloride (100 mg, 0.52 mmol), diethanolamine (150 mg, 1.4 mmol) and N,N-dimethylformamide (5 mL).

$^1$H-NMR (CD$_3$OD, 300 MHz) δ (ppm): 7.89-7.86 (m, 2H), 7.28-7.25 (m, 2H), 6.30 (s, 1H), 3.80 (s, 2H), 3.66 (t, J=5.8 Hz, 2H), 3.49 (t, J=5.5 Hz, 2H), 3.42(t, J=5.8 Hz, 2H), 3.33-3.28 (m, 2H), 2.55 (q, J=7.3 Hz, 2H), 1.08 (t, J=7.3 Hz, 3H)

APCI-MS (m/z); 472 [M+H]$^+$

EXAMPLE 87

Synthesis of 2-{2-ethyl-3,5-dihydroxy-6-[4-(trifluoromethoxy)benzoyl]phenyl}-N-(2-hydroxyethyl)-N-(2-methoxyethyl)acetamide (Compound 88)

In a manner similar to that in Example 10, Step 2, Compound 88 (61 mg, 35%) was obtained from 2-ethyl-3,5-dihydroxy-6-[4-(trifluoromethoxy)benzoyl]phenylacetic acid (140 mg, 35 mmol) obtained in Example 86, Step 3, using 1-hydroxybenzotriazole hydrate (80 mg, 0.52 mmol), 1-(3-dimethylaminopropyl)-3-ethylcarbodiimide hydrochloride (100 mg, 0.52 mmol), 2-(2-methoxyethylamino)ethanol (170 mg, 1.4 mmol) obtained in Reference Example 1 and N,N-dimethylformamide (5 mL).

$^1$H-NMR (CD$_3$OD, 300 MHz) δ (ppm): 7.89-7.86 (m, 2H), 7.28-7.26 (m, 2H), 6.30 (s, 1H), 3.81 (d, J=6.1 Hz, 2H), 3.64 (t, J=5.7 Hz, 1H), 3.55 (t, J=5.0 Hz, 1H), 3.48 (t, J=5.7 Hz, 2H), 3.45-3.40 (m, 4.5H), 3.17 (t, J=5.7 Hz, 1H), 3.14 (s, 1.5H), 2.55 (m, 2H), 1.08 (t, J=7.3 Hz, 3H)

APCI-MS (m/z); 486 [M+H]$^+$

EXAMPLE 88

Synthesis of 2-[2-ethyl-3,5-dihydroxy-6-(3-hydroxy-4-methoxybenzoyl)phenyl]-N,N-bis(2-methoxyethyl)acetamide (Compound 89)

(Step 1)

Methyl 2-ethyl-3,5-dihydroxyphenylacetate (2.0 g, 9.7 mmol) obtained in Example 7, Step 2 was suspended in boron trifluoride diethyl etherate (40 mL), and 3-hydroxy-4-methoxybenzoic acid (1.7 g, 11 mmol) was added thereto, followed by stirring at 80° C. for 5 hours. After cooling to room temperature, the reaction mixture was added dropwise to ice-cold water, and the resulting mixture was extracted with ethyl acetate. The organic layer was washed successively with a saturated aqueous solution of sodium hydrogencarbonate and a saturated aqueous solution of sodium chloride, dried over anhydrous sodium sulfate, and then concentrated under reduced pressure. The resulting residue was purified by silica gel column chromatography (ethyl acetate/hexane=1/4-9/1) to obtain methyl 2-ethyl-3,5-dihydroxy-6-(3-hydroxy-4-methoxybenzoyl)phenylacetate (2.2 g, 65%).

$^1$H-NMR (CD$_3$OD, 300 MHz) δ (ppm): 7.30-7.26 (m, 2H); 6.92 (d, J=8.4 Hz, 1H), 6.34 (s, 1H), 3.89 (s, 3H), 3.51 (s, 2H), 3.44 (s, 3H), 2.57 (q, J=7.5 Hz, 2H), 1.06 (t, J=7.5 Hz, 3H)

APCI-MS (m/z); 361 [M+H]$^+$ (Step 2)

In a manner similar to that in Example 10, Step 1, 2-ethyl-3,5-dihydroxy-6-(3-hydroxy-4-methoxybenzoyl)phenylacetic acid was obtained from methyl 2-ethyl-3,5-dihydroxy-6-(3-hydroxy-4-methoxybenzoyl)phenylacetate (2.1 g, 5.8 mmol) obtained in Example 88, Step 1, using a 2 mol/L aqueous solution of sodium hydroxide (25 mL) and tetrahydrofuran (25 mL).

In a manner similar to that in Example 10, Step 2, Compound 89 (860 mg, 32%) was obtained from 2-ethyl-3,5-dihydroxy-6-(3-hydroxy-74-methoxybenzoyl)phenylacetic acid obtained above, using 1-hydroxybenzotriazole hydrate (1.5 g, 9.8 mmol), 1-(3-dimethylaminopropyl)-3-ethylcarbodiimide hydrochloride (1.9 g, 9.9 mmol), bis(2-methoxyethyl)amine (1.2 g, 10 mmol) and N,N-dimethylformamide (13 mL).

$^1$H-NMR (CD$_3$OD, 300 MHz) δ (ppm): 7.34-7.31 (m, 2H), 6.91 (d, J=9.0 Hz, 1H), 6.32 (s, 1H), 3.90 (s, 3H), 3.68 (s, 2H), 3.49-3.39 (m, 4H), 3.36-3.30 (m, 5H), 3.19-3.15 (m, 5H), 2.52 (q, J=7.5 Hz, 2H), 1.08 (t, J=7.5 Hz, 3H)

APCI-MS (m/z); 462 [M+H]$^+$

EXAMPLE 89

Synthesis of 2-{2-[4-(difluoromethoxy)benzoyl]-6-ethyl-3,5-dihydroxyphenyl}-N,N-bis(2-hydroxyethyl)acetamide (Compound 90)

(Step 1)

In a manner similar to that in Example 5, Step 4, methyl 3,5-diallyloxy-2-[4-(difluoromethoxy)benzoyl]-6-ethylphenylacetate (0.69 g, 83%) was obtained from methyl 3,5-diallyloxy-2-ethylphenylacetate (0.54 g, 1.9 mmol) obtained in Example 5, Step 3, using 4-(difluoromethoxy)benzoic acid (0.71 g, 3.8 mmol), trifluoroacetic anhydride (0.55 mL, 3.9 mmol) and trifluoroacetic acid (10 mL).

$^1$H-NMR (CDCl$_3$, 300 MHz) δ (ppm): 7.85-7.81 (m, 2H), 7.12-7.08 (m, 2H), 6.57 (t, J=73 Hz, 1H), 6.42 (s, 1H), 6.07 (m, 1H), 5.60 (m, 1H), 5.48 (m, 1H), 5.40 (m, 1H), 5.04-4.92 (m, 2H), 4.58 (m, 2H), 4.30 (m, 2H), 3.69 (s, 2H), 3.47 (s, 3H), 2.66 (q, J=7.4 Hz, 2H), 1.09 (t, J=7.4 Hz, 3H)

APCI-MS (m/z); 461 [M+H]$^+$ (Step 2)

In a manner similar to that in Example 7, Step 1, methyl 2-[4-(difluoromethoxy)benzoyl]-6-ethyl-3,5-dihydroxyphenylacetate (0.55 g, 96%) was obtained from methyl 3,5-diallyloxy-2-[4-(difluoromethoxy)benzoyl]-6-ethylphenylacetate (0.69 g, 1.5 mmol) obtained in Example 89, Step 1, using ammonium formate (0.50 g, 7.9 mmol), bis(triphenylphosphine)palladium (II) dichloride (0.05 g, 0.071 mmol) and 1,4-dioxane (15 mL).

$^1$H-NMR (CD$_3$OD, 300 MHz) δ (ppm): 7.83-7.79 (m, 2H), 7.16-7.14 (m, 2H), 6.94 (t, J=73 Hz, 1H), 6.33 (s, 1H), 3.59 (s, 2H), 3.43 (s, 3H), 2.58 (q, J=7.5 Hz, 2H), 1.06 (t, J=7.5 Hz, 3H)

APCI-MS (m/z); 379 [M−H]$^−$ (Step 3)

In a manner similar to that in Example 10, Step 1, 2-[4-(difluoromethoxy)benzoyl]-6-ethyl-3,5-dihydroxyphenylacetic acid (0.38 g, 65%) was obtained from methyl 2-[4-(difluoromethoxy)benzoyl]-6-ethyl-3,5-dihydroxyphenylacetate (0.61 g, 1.6 mmol) obtained in Example 89, Step 2, using a 2 mol/L aqueous solution of sodium hydroxide (8 mL) and tetrahydrofuran (8 mL).

$^1$H-NMR (CDOD$_3$, 300 MHz) δ (ppm): 7.85-7.82 (m, 2H), 7.15-7.12 (m, 2H), 6.93 (t, J=73 Hz, 1H), 6.68 (s, 1H), 3.56 (s, 2H), 2.60 (q, J=7.5 Hz, 2H), 1.08 (t, J=7.5 Hz, 3H)

APCI-MS (m/z); 365 [M−H]$^−$ (Step 4)

In a manner similar to that in Example 10, Step 2, Compound 90 (50 mg, 34%) was obtained from 2-[4-(difluoromethoxy)benzoyl]-6-ethyl-3,5-dihydroxyphenylacetic acid (120 mg, 0.33 mmol) obtained in Example 89, Step 3, using 1-hydroxybenzotriazole hydrate (80 mg, 0.52 mmol), 1-(3-dimethylaminopropyl)-3-ethylcarbodiimide hydrochloride (100 mg, 0.52 mmol), diethanolamine (200 mg, 1.9 mmol) and N,N-dimethylformamide (4 mL).

$^1$H-NMR (CD$_3$OD, 300 MHz) δ (ppm): 7.85-7.82 (m, 2H), 7.17-7.10 (m, 2H), 6.80 (t, J=74 Hz, 1H), 6.31 (s, 1H), 3.76 (s, 2H), 3.64 (t, J=5.8 Hz, 2H), 3.52-3.48 (m, 4H), 3.32-3.28 (m, 2H), 2.52 (q, J=7.5 Hz, 2H), 1.08 (t, J=7.5 Hz, 3H)

APCI-MS (m/z); 454 [M+H]$^+$

EXAMPLE 90

Synthesis of 2-{2-[4-(difluoromethoxy)benzoyl]-6-ethyl-3,5-dihydroxyphenyl}-N-(2-hydroxyethyl)-N-(2-methoxyethyl)acetamide (Compound 91)

In a manner similar to that in Example 10, Step 2, Compound 91 (44 mg, 28%) was obtained from 2-[4-(difluoromethoxy)benzoyl]-4-ethyl-3,5-dihydroxyphenylacetic acid (120 mg, 0.33 mmol) obtained in Example 89, Step 3, using 1-hydroxybenzotriazole hydrate (80 mg, 0.52 mmol), 1-(3-dimethylaminopropyl)-3-ethylcarbodiimide hydrochloride (100 mg, 0.52 mmol), 2-(2-methoxyethylamino)ethanol (200 mg, 1.7 mmol) obtained in Reference Example 1 and N,N-dimethylformamide (4 mL).

$^1$H-NMR (CD$_3$OD, 300 MHz) δ (ppm): 7.85-7.82 (m, 2H), 7.13-7.11 (m, 2H), 6.93 (t, J=73 Hz, 0.5H), 6.92 (t, J=73 Hz, 0.5H), 6.30 (s, 1H), 3.71 (d, J=3.7 Hz, 2H), 3.59 (t, J=5.7 Hz, 1H), 3.50 (m, 1H), 3.45-3.35 (m, 4H), 3.32-3.28 (m, 2.5H), 3.18-3.13 (m, 2.5H), 2.55 (m, 2H), 1.08 (t, J=7.3 Hz, 3H)

APCI-MS (m/z); 468 [M+H]$^+$

EXAMPLE 91

Synthesis of 2-[2-ethyl-3,5-dihydroxy-6-(3-hydroxy-4-methylbenzoyl)phenyl]-N,N-bis(2-hydroxyethyl)acetamide (Compound 92)

(Step 1)

In a manner similar to that in Example 5, Step 4, methyl 3,5-diallyloxy-2-ethyl-6-(3-hydroxy-4-methylbenzoyl)phenylacetate was obtained from methyl 3,5-diallyloxy-2-ethylphenylacetate (0.65 g, 2.2 mmol) obtained in Example 5, Step 3, using 3-hydroxy-4-methylbenzoic acid (0.70 g, 4.6 mmol), trifluoroacetic anhydride (0.65 mL, 4.6 mmol), and trifluoroacetic acid (10 mL), and using a 7 mol/L solution of ammonia in methanol (10 mL) and methanol (10 mL).

In a manner similar to that in Example 10, Step 1, 3,5-diallyloxy-2-ethyl-6-(3-hydroxy-4-methylbenzoyl)phenylacetic acid (0.32 g, 35% in 2 steps) was obtained from methyl 3,5-diallyloxy-2-ethyl-6-(3-hydroxy-4-methylbenzoyl)phenylacetate obtained above, using a 2 mol/L aqueous solution of sodium hydroxide (20 mL) and tetrahydrofuran (10 mL).

$^1$H-NMR (CD$_3$OD, 300 MHz) δ (ppm): 7.40-7.38 (m, 2H), 7.11 (d, J=7.7 Hz, 1H), 6.61 (s, 1H), 6.11 (m, 1H), 5.70 (m, 1H), 5.46 (m, 1H), 5.28 (m, 1H), 5.04-4.98 (m, 2H), 4.62 (m, 2H), 4.40 (m, 2H), 3.54 (s, 2H), 2.64 (q, J=7.3 Hz, 2H), 2.20 (s, 3H), 1.09 (t, J=7.3 Hz, 3H)

APCI-MS (m/z); 411 [M+H]$^+$ (Step 2)

In a manner similar to that in Example 10, Step 2, 2-[3,5-diallyloxy-2-ethyl-6-(3-hydroxy-4-methylbenzoyl)phenyl]-N,N-bis(2-hydroxyethyl)acetamide (62 mg, 34%) was obtained from 3,5-diallyloxy-2-ethyl-6-(3-hydroxy-4-methylbenzoyl)phenylacetic acid (150 mg, 0.37 mmol) obtained in Example 91, Step 1, using 1-hydroxybenzotriazole hydrate (90 mg, 0.59 mmol), 1-(3-dimethylaminopropyl)-3-ethylcarbodiimide hydrochloride (110 mg, 0.55 mmol), diethanolamine (120 mg, 1.1 mmol) and N,N-dimethylformamide (4 mL).

$^1$H-NMR (CD$_3$OD, 300 MHz) δ (ppm): 7.23-7.08 (m, 3H), 6.58 (s, 1H), 6.10 (m, 1H), 5.66 (m, 1H), 5.45 (m, 1H), 5.28 (m, 1H), 5.04-4.96 (m, 2H), 4.61 (m, 2H), 4.38 (m, 2H), 3.72 (s, 2H), 3.61 (t, J=5.5 Hz, 2H), 3.47-3.41 (m, 4H), 3.29 (t, J=5.5 Hz, 2H), 2.61 (q, J=7.5 Hz, 2H), 2.21 (s, 3H), 1.08 (t, J=7.3 Hz, 3H)

APCI-MS (m/z); 498 [M+H]$^+$ (Step 3)

In a manner similar to that in Example 7, Step 1, Compound 92 (30 mg, 58%) was obtained from 2-[3,5-diallyloxy-2-ethyl-6-(3-hydroxy-4-methylbenzoyl)phenyl]-N,N-bis(2-hydroxyethyl)acetamide (62 mg, 0.13 mmol) obtained in Example 91, Step 2, using ammonium formate (100 mg, 1.6 mmol), bis(triphenylphosphine)palladium (II) dichloride (5 mg, 0.0071 mmol) and 1,4-dioxane (2 mL). $^1$H-NMR (CD$_3$OD, 300 MHz) δ (ppm): 7.17-7.12 (m, 2H), 7.05 (d, J=7.7 Hz, 1H), 6.27 (s, 1H), 3.62 (s, 2H), 3.55 (t, J=5.5 Hz, 2H), 3.43-3.34 (m, 4H), 3.29 (m, 2H), 2.50 (q, J=7.3 Hz, 2H), 2.17 (s, 3H), 1.08 (t, J=7.3 Hz, 3H) APCI-MS (m/z); 418 [M+H]$^+$

EXAMPLE 92

Synthesis of 2-[2-ethyl-3,5-dihydroxy-6-(3-hydroxy-4-methylbenzoyl)phenyl]-N-(2-hydroxyethyl)-N-(2-methoxyethyl)acetamide (Compound 93)

(Step 1)

In a manner similar to that in Example 88, Step 1, methyl 2-ethyl-3,5-dihydroxy-6-(3-hydroxy-4-methylbenzoyl)phenylacetate (2.1 g, 60%) was obtained from methyl 2-ethyl-3,5-dihydroxyphenylacetate (2.1 g, 9.9 mmol) obtained in Example 7, Step 2, using 3-hydroxy-4-methylbenzoic acid (1.9 g, 11 mmol) and boron trifluoride diethyl etherate (40 mL).

$^1$H-NMR (CD$_3$OD, 300 MHz) δ (ppm): 7.18-7.09 (m, 3H), 6.34 (s, 1H), 3.51 (s, 2H), 3.43 (s, 3H), 2.57 (q, J=7.3 Hz, 2H), 2.21 (s, 3H), 1.05 (t, J=7.3 Hz, 3H)

APCI-MS (m/z); 345 [M+H]$^+$ (Step 2)

In a manner similar to that in Example 10, Step 1, 2-ethyl-3,5-dihydroxy-6-(3-hydroxy-4-methylbenzoyl)phenylacetic acid was obtained from methyl 2-ethyl-3,5-dihydroxy-6-(3-hydroxy-4-methylbenzoyl)phenylacetate (2.1 g, 6.2 mmol)

obtained in Example 92, Step 1, using a 2 mol/L aqueous solution of sodium hydroxide (30 mL) and tetrahydrofuran (30 mL).

In a manner similar to that in Example 10, Step 2, Compound 93 (770 mg, 28%) was obtained from 2-ethyl-3,5-dihydroxy-6-(3-hydroxy-4-methylbenzoyl)phenylacetic acid obtained above, using 1-hydroxybenzotriazole hydrate (1.5 g, 9.8 mmol), 1-(3-dimethylaminopropyl)-3-ethylcarbodiimide hydrochloride (1.9 g, 9.9 mmol), 2-(2-methoxyethylamino)ethanol (1.2 g, 10 mmol) obtained in Reference Example 1 and N,N-dimethylformamide (13 mL). $^1$H-NMR (CD$_3$OD, 300 MHz) δ (ppm): 7.22-7.18 (m, 2H), 7.10 (d, J=7.8 Hz, 1H), 6.30 (s, 1H), 3.67 (d, J=8.7 Hz, 2H), 3.58 (t, J=5.7 Hz, 1H), 3.47-3.36 (m, 5H), 3.35-3.28 (m, 4H), 3.19-3.13 (m, 3H), 2.55 (m, 2H), 2.21 (s, 1.5H), 2.20 (s, 1.5H), 1.08 (t, J=7.3 Hz, 3H)

APCI-MS (m/z); 432 [M+H]$^+$

EXAMPLE 93

Synthesis of 2-{2-ethyl-3,5-dihydroxy-6-[4-(trifluoromethoxy)benzoyl]phenyl}-N-(2-hydroxyethyl)-N-(3-hydroxypropyl)acetamide (Compound 94)

In a manner similar to that in Example 10, Step 2, Compound 94 (57 mg, 30%) was obtained from 2-ethyl-3,5-dihydroxy-6-[4-(trifluoromethoxy)benzoyl]phenylacetic acid (150 mg, 0.39 mmol) obtained in Example 86, Step 3, using 1-hydroxybenzotriazole hydrate (120 mg, 0.79 mmol), 1-(3-dimethylaminopropyl)-3-ethylcarbodiimide hydrochloride (150 mg, 0.79 mmol), 3-(2-hydroxyethylamino)propanol (200 mg, 1.7 mmol) and N,N-dimethylformamide (4 mL).

$^1$H-NMR (CD$_3$OD, 300 MHz) δ (ppm): 7.89-7.85 (m, 2H), 7.28-7.25 (m, 2H), 6.30 (s, 1H), 3.82 (s, 1H), 3.76 (s, 1H), 3.65 (t, J=5.8 Hz, 1H), 3.54 (t, J=6.0 Hz, 1H), 3.45-3.40 (m, 3H), 3.32-3.24 (m, 3H), 2.55 (q, J=7.5 Hz, 2H), 1.74 (m, 1H), 1.45 (m, 1H), 1.08 (m, 3H)

APCI-MS (m/z); 486 [M+H]$^+$

EXAMPLE 94

Synthesis of 2-[2-ethyl-3,5-dihydroxy-6-(4-methylsulfanylbenzoyl)phenyl]-N-(2-hydroxyethyl)-N-(2-methoxyethyl)acetamide (Compound 95)

(Step 1)

In a manner similar to that in Example 5, Step 4, methyl 3,5-diallyloxy-2-ethyl-6-(3-methylsulfanylbenzoyl)phenylacetate (1.5 g, 98%) was obtained from methyl 3,5-diallyloxy-2-ethylphenylacetate (1.0 g, 3.5 mmol) obtained in Example 5, Step 3, using 3-methylsulfanylbenzoic acid (1.2 g, 6.9 mmol), trifluoroacetic anhydride (0.98 mL, 6.9 mmol) and trifluoroacetic acid (10 mL).

$^1$H-NMR (CDCl$_3$, 300 MHz) δ (ppm): 7.75-7.70 (m, 2H), 7.22-7.18 (m, 2H), 6.43 (s, 1H), 6.05 (m, 1H), 5.64 (m, 1H), 5.45 (m, 1H), 5.30 (m, 1H), 5.06-4.97 (m, 2H), 4.56 (m, 2H), 4.35 (m, 2H), 3.65 (s, 2H), 3.45 (s, 3H), 2.65 (q, J=7.5 Hz, 2H), 2.50 (s, 3H), 1.09 (t, J=7.3 Hz, 3H)

APCI-MS (m/z); 441 [M+H]$^+$ (Step 2)

In a manner similar to that in Example 10, Step 1, 3,5-diallyloxy-2-ethyl-6-(3-methylsulfanybenzoyl)phenylacetic acid was obtained from methyl 3,5-diallyloxy-2-ethyl-6-(3-methylsulfanylbenzoyl)phenylacetate (200 mg, 0.46 mmol) obtained in Example 94, Step 1, using a 2 mol/L aqueous solution of sodium hydroxide (5 mL) and tetrahydrofuran (5 mL).

In a manner similar to that in Example 10, Step 2, 2-[3,5-diallyloxy-2-ethyl-6-(4-methylsulfanylbenzoyl)phenyl]-N-(2-hydroxyethyl)-N-(2-methoxyethyl)acetamide was obtained as a crude product from 3,5-diallyloxy-2-ethyl-6-(3-methylsulfanylbenzoyl)phenylacetic acid obtained above, using 1-hydroxybenzotriazole hydrate (100 mg, 0.66 mmol), 1-(3-dimethylaminopropyl)-3-ethylcarbodiimide hydrochloride (130 mg, 0.68 mmol), 2-(2-methoxyethylamino)ethanol (110 mg, 0.92 mmol) obtained in Reference Example 1 and N,N-dimethylformamide (5 mL).

In a manner similar to that in Example 7, Step 1, Compound 95 (130 mg, 62% in 3 steps) was obtained from 2-[3,5-diallyloxy-2-ethyl-6-(4-methylsulfanylbenzoyl)phenyl]-N-(2-hydroxyethyl)-N-(2-methoxyethyl)acetamide obtained above, using ammonium formate (150 mg, 2.4 mmol), bis(triphenylphosphine)palladium (II) dichloride (20 mg, 0.029 mmol) and 1,4-dioxane (5 mL).

$^1$H-NMR (CD$_3$OD, 300 MHz) δ (ppm): 7.74-7.69 (m, 2H), 7.26-7.21 (m, 2H), 6.31 (s, 1H), 3.74 (d, J=5.0 Hz, 2H), 3.61 (t, J=5.8 Hz, 1H), 3.52 (m, 1H), 3.45-3.39 (m, 3H), 3.35-3.28 (m, 3.5H), 3.15-3.11 (m, 2.5H), 2.55 (m, 2H), 2.51 (s, 1.5H), 2.50 (s, 1.5H), 1.08 (t, J=7.3 Hz, 3H) APCI-MS (m/z); 448 [M+H]$^+$

EXAMPLE 95

Synthesis of 2-[2-ethyl-3,5-dihydroxy-6-(4-methanesulfonylbenzoyl)phenyl]-N,N-bis(2-hydroxyethyl)acetamide (Compound 96)

(Step 1)

Methyl 3,5-diallyloxy-2-ethyl-6-(3-methylsulfanylbenzoyl)phenylacetate (550 mg, 1.3 mmol) obtained in Example 94, Step 1 was dissolved in a mixed solvent of methanol (12 mL) and water (6 mL), and Oxone (trademark; 1.9 g, 3.1 mmol) was slowly added thereto with stirring under ice-cooling. The reaction mixture was stirred at room temperature for 3 hours, and water was added thereto, followed by extraction with ethyl acetate. The organic layer was washed successively with a saturated aqueous solution of sodium thiosulfate and a saturated aqueous solution of sodium chloride, dried over anhydrous sodium sulfate, and then concentrated under reduced pressure. The resulting residue was purified by silica gel column chromatography (ethyl acetate/hexane=1/1) to obtain methyl 3,5-diallyloxy-2-ethyl-6-(3-methanesulfonylbenzoyl)phenylacetate (550 mg, 93%).

$^1$H-NMR (CDCl$_3$, 300 MHz) δ (ppm): 7.93 (s, 4H), 6.43 (s, 1H), 6.05 (m, 1H), 5.54 (m, 1H), 5.45 (m, 1H), 5.29; (m, 1H), 5.01-4.90 (m, 2H), 4.58 (m, 2H), 4.28 (m, 2H), 3.76 (s, 2H), 3.47 (s, 3H), 3.02 (s, 3H), 2.68 (q, J=7.5 Hz, 2H), 1.10 (t, J=7.5 Hz, 3H)

APCI-MS (m/z); 473 [M+H]$^+$ (Step 2)

In a manner similar to that in Example 10, Step 1, 3,5-diallyloxy-2-ethyl-6-(3-methanesulfonylbenzoyl)phenylacetic acid (530 mg, 96%) was obtained from methyl 3,5-diallyloxy-2-ethyl-6-(3-methanesulfonylbenzoyl) phenylacetate (550 mg, 1.2 mmol) obtained in Example 95, Step 1, using a 2 mol/L aqueous solution of sodium hydroxide (6 mL) and tetrahydrofuran (6 mL).

$^1$H-NMR (DMSO-d$_6$, 300 MHz) δ (ppm): 12.1 (brs, 1H), 8.01-7.98 (m, 2H), 7.87-7.84 (m, 2H), 6.71 (s, 1H), 6.10 (m, 1H), 5.54-5.42 (m, 2H), 5.29 (m, 1H), 4.92 (m, 1H), 4.79 (m, 1H), 4.68 (m, 2H), 4.40 (m, 2H), 3.58 (s, 2H), 3.23 (s, 3H), 2.58 (q, J=7.5 Hz, 2H), 1.05 (t, J=7.5 Hz, 3H)

APCI-MS (m/z); 459 [M+H]$^+$ (Step 3)

In a manner similar to that in Example 10, Step 2, 2-[3,5-diallyloxy-2-ethyl-6-(4-methanesulfonylbenzoyl)phenyl]-N,N-bis(2-hydroxyethyl)acetamide was obtained from 3,5-diallyloxy-2-ethyl-6-(3-methanesulfonylbenzoyl)phenylacetic acid (160 mg, 0.35 mmol) obtained in Example 95, Step 2, using 1-hydroxybenzotriazole hydrate (80 mg, 0.52 mmol), 1-(3-dimethylaminopropyl)-3-ethylcarbodiimide hydrochloride (100 mg, 0.52 mmol), diethanolamine (72 mg, 0.69 mmol) and N,N-dimethylformamide (4 mL)

In a manner similar to that in Example 7, Step 1, Compound 96 (67 mg, 41% in 2 steps) was obtained from 2-[3,5-diallyloxy-2-ethyl-6-(4-methanesulfonylbenzoyl)phenyl]-N,N-bis(2-hydroxyethyl)acetamide obtained above, using ammonium formate (110 mg, 1.7 mmol), bis(triphenylphosphine)palladium (II) dichloride (20 mg, 0.029 mmol) and 1,4-dioxane (5 mL).

$^1$H-NMR (CD$_3$OD, 300 MHz) δ (ppm): 7.96 (m, 4H), 6.30 (s, 1H), 3.88 (s, 2H), 3.68 (t, J=5.4 Hz, 2H), 3.52 (t, J=5.4 Hz, 2H), 3.37 (t, J=4.8 Hz, 2H), 3.33-3.30 (m, 2H), 3.14 (s, 3H), 2.57 (q, J=7.2. Hz, 2H), 1.08 (t, J=7.2 Hz, 3H)

APCI-MS (m/z); 466 [M+H]$^+$

EXAMPLE 96

Synthesis of 2-[2-ethyl-3,5-dihydroxy-6-(4-methanesulfonyl-benzoyl)phenyl]-N-(2-hydroxyethyl)-N-(2-methoxyethyl)acetamide (Compound 97)

(Step 1)

In a manner similar to that in Example 10, Step 2, 2-[3,5-diallyloxy-2-ethyl-6-(4-methanesulfonylbenzoyl)phenyl]-N-(2-hydroxyethyl)-N-(2-methoxyethyl)acetamide was obtained from 3,5-diallyloxy-2-ethyl-6-(3-methanesulfonylbenzoyl)phenylacetic acid (160 mg, 0.35 mmol) obtained in Example 95, Step 2, using 1-hydroxybenzotriazole hydrate (80 mg, 0.52 mmol), 1-(3-dimethylaminopropyl)-3-ethylcarbodiimide hydrochloride (100 mg, 0.52 mmol), 2-(2-methoxyethylamino)ethanol (90 mg, 0.67 mmol) obtained in Reference Example 1 and N,N-dimethylformamide (4 mL).

(Step 2)

In a manner similar to that in Example 7, Step 1, Compound 97 (86 mg, 52% in 2 steps) was obtained from 2-[3,5-diallyloxy-2-ethyl-6-(4-methanesulfonylbenzoyl)phenyl]-N-(2-hydroxyethyl)-N-(2-methoxyethyl)acetamide obtained in Example 96, Step 1, using ammonium formate (110 mg, 1.7 mmol), bis(triphenylphosphine)palladium (II) dichloride (20 mg, 0.029 mmol) and 1,4-dioxane (5 ml).

$^1$H-NMR (CD$_3$OD, 300 MHz) δ (ppm): 7.91 (m, 4H), 6.30 (s, 1H), 3.88 (s, 2H), 3.67 (t, J=5.5 Hz, 1H), 3.58 (m, 1H), 3.52-3.51 (m, 2H), 3.38-3.30 (m, 4.5H), 3.18 (t, J=5.3 Hz, 1H), 3.14 (s, 4.5H), 2.55 (m, 2H), 1.08 (t, J=7.3 Hz, 3H)

APCI-MS (m/z); 480 [M+H]$^+$

EXAMPLE 97

Synthesis of 2-{2-[2-ethyl-3,5-dihydroxy-6-(4-methoxybenzoyl)phenyl]acetyl}-1-[2-(hydroxymethyl)pyrrolidin-1-yl]ethanone (Compound 98)

In a manner similar to that in Example 74, Step 2, Compound 98 (14 mg, 7.4%) was obtained from 2-ethyl-3,5-dihydroxy-6-(4-methoxybenzoyl)phenylacetic acid (0.11 g, 0.33 mmol) obtained in Example 10, Step 1, using 1-(3-dimethylaminopropyl)-3-ethylcarbodiimide hydrochloride (0.15 g, 0.76 mmol), (R)-(–)-2-pyrrolidinemethanol (0.13 mL, 1.3 mmol) and N,N-dimethylformamide (1.0 mL). In this case, crystallization was carried out with ethyl acetate.

$^1$H-NMR (CD$_3$OD, 300 MHz) δ (ppm): 7.76 (d, J=8.8 Hz, 2H), 6.92 (d, J=8.8 Hz, 2H), 6.32 (s, 1H), 3.84 (s, 3H), 3.79-3.69 (m, 2H), 3.56 (s, 2H), 3.41-3.17 (m, 3H), 2.60 (q, J=7.3 Hz, 2H), 1.90-1.67 (m, 4H), 1.08 (t, J=7.3 Hz, 3H)

APCI-MS (m/z); 414 [M+H]$^+$

EXAMPLE 98

Synthesis of 2-[2-(3,4-dimethoxybenzoyl)-6-ethyl-3,5-dihydroxyphenyl]-N-(2-hydroxyethyl)-N-(3-hydroxypropyl)acetamide (Compound 99)

In a manner similar to that in Example 74, Step 2, Compound 99 (0.013 g, 17%) was obtained from 2-(3,4-dimethoxybenzoyl)-6-ethyl-3,5-dihydroxyphenylacetic acid (0.059 g, 0.16 mmol) obtained in Example 40, Step 1, using 1-(3-dimethylaminopropyl)-3-ethylcarbodiimide hydrochloride (0.064; g, 0.33 mmol), 3-(2-hydroxyethylamino)propanol (0.040 g, 0.34 mmol) and N,N-dimethylformamide (0.50 mL).

$^1$H-NMR (CD$_3$OD, 270 MHz) δ (ppm): 7.46-7.39 (m, 2H), 6.95-6.91 (m, 1H), 6.32 and 6.31 (s, total 1H), 3.88 and 3.87 (s, total 3H), 3.84 (s, 3H), 3.71 and 3.64 (s, total 2H), 3.61-3.22 (m, 8H), 2.54 (q, J=7.4 Hz, 2H), 1.66 (m, 1H), 1.45 (m, 1H), 1.11-1.04 (m, 3H)

ESI-MS (m/z); 462 [M+H]$^+$

EXAMPLE 99

Synthesis of 2-[2-(3,4-dimethoxybenzoyl)-6-ethyl-3,5-dihydroxyphenyl]-N-(furan-2-ylmethyl)-N-(2-hydroxyethyl)acetamide (Compound 100)

In a manner similar to that in Example 74, Step 2, Compound 100 (17 mg, 17%) was obtained from 2-(3,4-dimethoxybenzoyl)-6-ethyl-3,5-dihydroxyphenylacetic acid (0.073 g, 0.20 mmol) obtained in Example 40, Step 1, using 1-(3-dimethylaminopropyl)-3-ethylcarbodiimide hydrochloride (0.058 g, 0.30 mmol), 2-(furfurylamino)ethanol (0.060 g, 0.43 mmol) obtained in Reference Example 11 and N,N-dimethylformamide (0.50 mL)

$^1$H-NMR (CD$_3$OD, 270 MHz) δ (ppm): 7.36-7.30 (m, 2.5H), 7.18 (m, 0.5H), 6.85-6.81 (m, 1H), 6.25-6.23 (m, 1.5H), 6.11-6.09 (m, 1H), 5.81 (m, 0.5H), 4.43 and 4.31 (s, total 2H), 3.79 and 3.78 (s, total 3H), 3.75 and 3.74 (s, total 3H), 3.64 and 3.61 (s, total 2H), 3.48-3.20 (m, 4H), 2.48-2.35 (m, 2H), 1.03-0.93 (m, 3H)

ESI-MS (m/z); 484 [M+H]$^+$

EXAMPLE 100

Synthesis of 2-[2-ethyl-3,5-dihydroxy-6-(4-methoxybenzoyl)phenyl]-N-(2-hydroxyethyl)-N-(3-hydroxypropyl)acetamide (Compound 101)

In a manner similar to that in Example 74, Step 1, Compound 101 (0.055 g, 33%) was obtained from 2-ethyl-3,5-dihydroxy-6-(4-methoxybenzoyl)phenylacetic acid (0.13 g, 0.40 mmol) obtained in Example 10, Step 1, using 1-(3-dimethylaminopropyl)-3-ethylcarbodiimide hydrochloride (0.12 g, 0.63 mol), 3-(2-hydroxyethylamino)propanol (0.12 g, 1.0 mmol) and N,N-dimethylformamide (1.0 mL).

In this case, crystallization was carried out with ethyl acetate.

Melting Point: 207-210° C.
$^1$H-NMR (CD$_3$OD, 270 MHz) δ (ppm): 7.79-7.76 (t, J=8.9 Hz, 2H), 6.92-6.89 (m, 2H), 6.31 (s, 1H), 3.83 and 3.84 (s, total 3H), 3.71 and 3.65 (s, total 2H), 3.62-3.21 (m, 8H), 2.54 (q, J=7.3 Hz, 2H), 1.67 (m, 1H), 1.43 (m, 1H), 1.10-1.04 (m, 3H)
APCI-MS (m/z); 432 [M+H]$^+$

EXAMPLE 101

Synthesis of 2-{2-ethyl-3,5-dihydroxy-6-[3-(2-hydroxyethoxy)-4-methoxybenzoyl]phenyl}-N-(2-hydroxyethyl)-N-(2-methoxyethyl)acetamide (Compound 102)

(Step 1)
Methyl 3,5-diallyloxy-2-ethyl-6-(3-hydroxy-4-methoxybenzoyl)phenylacetate (330 mg, 0.75 mmol) obtained in Example 82, Step 1 was dissolved in N,N-dimethylformamide (10 mL), and potassium carbonate (550 mg, 4.0 mmol), sodium iodide (100 mg, 0.67 mmol) and 2-(2-bromoethoxy) tetrahydro-2H-pyran (0.6 mL, 4.0 mmol) were added thereto with stirring at room temperature. The reaction mixture was stirred at 80° C. for 3 hours and cooled to room temperature, and water was added thereto, followed by extraction with ethyl acetate. The organic layer was washed with a saturated aqueous solution of sodium chloride, dried over anhydrous sodium sulfate, and then concentrated under reduced pressure. The resulting residue was purified by silica gel column chromatography (ethyl acetate/hexane=1/4-1/1) to obtain methyl 3,5-diallyloxy-2-ethyl-6-[4-methoxy-3-(2-tetrahydro-2H-pyran-2-yloxyethoxy)benzoyl]phenylacetate.

In a manner similar to that in Example 59, Step 2, methyl 3,5-diallyloxy-2-ethyl-6-[3-(2-hydroxyethoxy)-4-methoxybenzoyl]phenylacetate (110 mg, 29%) was obtained from methyl 3,5-diallyloxy-2-ethyl-6-[4-methoxy-3-(2-tetrahydro-2H-pyran-2-yloxyethoxy)benzoyl]phenylacetate obtained above, using a 4 mol/L solution of hydrogen chloride in 1,4-dioxane (5.0 mL) and methanol (5.0 mL). H-NMR (CDCl$_3$, 300 MHz) δ (ppm): 7.54 (d, J=2.0 Hz, 1H), 7.38 (dd, J=8.5, 2.0 Hz, 1H), 6.83 (d, J=8.5 Hz, 1H), 6.43 (s, 1H), 6.05 (m, 1H), 5.70 (m, 1H), 5.45 (m, 1H), 5.30 (m, 1H), 5.07-5.00 (m, 2H), 4.58 (m, 2H), 4.38 (m, 2H), 4.16 (t, J=4.5 Hz, 2H), 3.96 (m, 2H), 3.90 (s, 3H), 3.63 (s, 2H), 3.46 (s, 3H), 2.65 (q, J=7.5 Hz, 2H), 1.09 (t, J=7.5 Hz, 3H)
APCI-MS (m/z); 485 [M+H]$^+$ (Step 2)
In a manner similar to that in Example 10, Step 1, 3,5-diallyloxy-2-ethyl-6-[3-(2-hydroxyethoxy)-4-methoxybenzoyl]phenylacetic acid was obtained from methyl 3,5-diallyloxy-2-ethyl-6-[3-(2-hydroxyethoxy)-4-methoxybenzoyl]phenylacetate (100 mg, 0.21 mmol) obtained in Example 101, Step 1, using a 2 mol/L aqueous solution of sodium hydroxide (5 mL) and tetrahydrofuran (5 mL).

In a manner similar to that in Example 10, Step 2, 2-{3,5-diallyl-2-ethyl-6-[3-(2-hydroxyethoxy)-4-methoxybenzoyl]phenyl}-N-(2-hydroxyethyl)-N-(2-methoxyethyl)acetamide was obtained from 3,5-diallyloxy-2-ethyl-6-[3-(2-hydroxyethoxy)-4-methoxybenzoyl]phenylacetic acid obtained above, using 1-hydroxybenzotriazole hydrate (50 mg, 0.32 mmol), 1-(3-dimethylaminopropyl)-3-ethylcarbodiimide hydrochloride (60 mg, 0.31° mmol), 2-(2-methoxyethylamino)ethanol (50 mg, 0.42 mmol) obtained in Reference Example 1 and N,N-dimethylformamide (5 mL).

In a manner similar to that in Example 7, Step 1, Compound 102 (40 mg, 38% in 3 steps) was obtained from 2-{3,5-diallyloxy-2-ethyl-6-[3-(2-hydroxyethoxy)-4-methoxybenzoyl]phenyl}-N-(2-hydroxyethyl)-N-(2-methoxyethyl) acetamide obtained above, using ammonium formate (100 mg, 1.6 mmol), bis(triphenylphosphine)palladium (II) dichloride (15 mg, 0.021 mmol) and 1,4-dioxane (5 mL).
$^1$H-NMR (CD$_3$OD, 300 MHz) δ (ppm): 7.46-7.42 (m, 2H), 6.97 (m, 1H), 6.31 (s, 1H), 4.06 (m, 2H), 3.89 (s, 3H), 3.86 (m, 2H), 3.69 (d, J=3.7 Hz, 2H), 3.58 (t, J=5.7 Hz, 1H), 3.49 (t, J=4.7 Hz, 1H), 3.43-3.39 (m, 3H), 3.35-3.28 (m, 3.5H), 3.15-3.11 (m, 2.5H), 2.53 (m, 2H), 1.06 (t, J=7.3 Hz, 3H)
APCI-MS (m/z); 492 [M+H]$^+$

EXAMPLE 102

Synthesis of 2-{2-ethyl-3,5-dihydroxy-6-[4-methoxy-3-(2-methoxyethoxy)benzoyl]phenyl}-N-(2-hydroxyethyl)-N-(2-methoxyethyl)acetamide (Compound 103)

(Step 1)
In a manner similar to that in Example 101, Step 1, methyl 3,5-diallyloxy-2-ethyl-6-[4-methoxy-3-(2-methoxyethoxy) benzoyl]phenylacetate (0.24 g, 41%) was obtained from methyl 3,5-diallyloxy-2-ethyl-6-(3-hydroxy-4-methoxybenzoyl)phenylacetate (0.5 g, 1.1 mmol) obtained in Example 82, Step 1, using 2-bromoethyl methyl ether (1.0 mL, 11 mmol), potassium carbonate (1.6 g, 11 mmol), sodium iodide (0.1 g, 0.70 mmol) and N,N-dimethylformamide (15 mL).
$^1$H-NMR (CD$_3$Cl, 300 MHz) δ (ppm): 7.53 (d, J=2.0 Hz, 1H), 7.33 (dd, J=8.4, 2.0 Hz, 1H), 6.80 (d, J=8.5 Hz, 1H), 6.43 (s, 1H), 6.05 (m, 1H), 5.70 (m, 1H), 5.45 (m, 1H), 5.30 (m, 1H), 5.07-5.00 (m, 2H), 4.58 (m, 2H), 4.38 (m, 2H), 4.20 (m, 2H), 3.88 (s, 3H), 3.80 (m, 2H), 3.62 (s, 2H), 3.45 (s, 3H), 3.44 (s, 3H), 2.65 (q, J=7.5 Hz, 2H), 1.09 (t, J=7.5 Hz, 3H)
APCI-MS (m/z); 499 [M+H]$^+$ (Step 2)
In a manner similar to that in Example 10, Step 1, 3,5-diallyloxy-2-ethyl-6-[4-methoxy-3-(2-methoxyethoxy)benzoyl]phenylacetic acid was obtained from methyl 3,5-diallyloxy-2-ethyl-6-[4-methoxy-3-(2-methoxyethoxy)benzoyl] phenylacetate (230 mg, 0.46 mmol) obtained in Example 102, Step 1, using a 2 mol/L aqueous solution of sodium hydroxide (5 mL) and tetrahydrofuran (5 mL).

In a manner similar to that in Example 10, Step 2, 2-{3,5-diallyloxy-2-ethyl-6-[4-methoxy-3-(2-methoxethoxy)benzoyl]phenyl}-N-(2-hydroxyethyl)-N-(2-methoxyethyl)acetamide was obtained from 3,5-diallyloxy-2-ethyl-6-[4-methoxy-3-(2-methoxyethoxy)benzoyl]phenylacetic acid obtained above, using 1-hydroxybenzotriazole hydrate (110 mg, 0.69 mmol), 1-(3-dimethylaminopropyl)-3-ethylcarbodiimide hydrochloride (130 mg, 0.69 mmol), 2-(2-methoxyethylamino)ethanol (110 mg, 0.92 mmol) obtained in Reference Example 1 and N,N-dimethylformamide (4 mL).

In a manner similar to that in Example 7, Step 1, Compound 103 (46 mg, 20% in 3 steps) was obtained from 2-{3, 5-diallyloxy-2-ethyl-6-[4-methoxy-3-(2-methoxyethoxy) benzoyl]phenyl}-N-(2-hydroxyethyl)-N-(2-methoxyethyl) acetamide obtained above, using ammonium formate (150 mg, 2.4 mmol), bis(triphenylphosphine)palladium (II) dichloride (20 mg, 0.029 mmol) and 1,4-dioxane (5 mL).
$^1$H-NMR (CD$_3$OD, 300 MHz) δ (ppm): 7.46-7.42 (m, 2H), 6.95 (m, 1H), 6.31 (s, 1H), 4.13 (m, 2H), 3.88 (s, 1.5H), 3.87

(s, 1.5H), 3.74 (m, 2H), 3.69 (d, J=3.7 Hz, 2H), 3.58 (t, J=5.7 Hz, 1H), 3.49 (t, J=4.7 Hz, 1H), 3.43-3.39 (m, 3H), 3.40 (s, 3H), 3.35-3.28 (m, 3.5H), 3.15-3.11 (m, 2.5H), 2.53 (m, 2H), 1.06 (t, J=7.3 Hz, 3H)

APCI-MS (m/z); 506 [M+H]$^+$

EXAMPLE 103

Synthesis of 2-{2-ethyl-3,5-dihydroxy-6-[4-methoxy-3-(2-morpholinoethoxy)benzoyl]phenyl}-N-(2-hydroxyethyl)-N-(2-methoxyethyl)acetamide (Compound 104)

(Step 1)

In a manner similar to that in Example 101, Step 1, methyl 3,5-diallyloxy-2-ethyl-6-[4-methoxy-3-(2-morpholinoethoxy)benzoyl]phenylacetate (0.36 g, 53%) was obtained from methyl 3,5-diallyloxy-2-ethyl-6-(3-hydroxy-4-methoxybenzoyl)phenylacetate (0.53 g, 1.2 mmol) obtained in Example 82, Step 1, using N-(2-chloroethyl)morpholine (1.7 g, 11 mmol), potassium carbonate (2.5 g, 18 mmol), sodium iodide (0.2 g, 1.3 mmol) and N,N-dimethylformamide (15 mL).

$^1$H-NMR (CDCl$_3$, 300 MHz) δ (ppm): 7.5.4 (d, J=2.0 Hz, 1H), 7.33 (dd, J=8.5, 2.0 Hz, 1H), 6.80 (d, J=8.5 Hz, 1H), 6.44 (s, 1H), 6.05 (m, 1H), 5.70 (m, 1H), 5.48 (m, 1H), 5.30 (m, 1H), 5.07-5.01 (m, 2H), 4.58 (m, 2H), 4.38 (m, 2H), 3.89 (s, 3H), 3.74-3.71 (m, 6H), 3.62 (s, 2H), 3.46 (s, 3H), 2.84 (t, J=6.0 Hz, 2H), 2.65-2.56 (m, 6H), 1.09 (t, J=7.5 Hz, 3H)

APCI-MS (m/z); 554 [M+H]$^+$ (Step 2)

In a manner similar to that in Example 10, Step 1, 3,5-diallyloxy-2-ethyl-6-[4-methoxy-3-(2-morpholinoethoxy)benzoyl]phenylacetic acid was obtained from methyl 3,5-diallyloxy-2-ethyl-6-[4-methoxy-3-(2-morpholinoethoxy)benzoyl]phenylacetate (350 mg, 0.63 mmol) obtained in Example 103, Step 1, using a 2 mol/L aqueous solution of sodium hydroxide (5 mL) and tetrahydrofuran (5 mL).

In a manner similar to that in Example 10, Step 2, 2-{3,5-diallyloxy-2-ethyl-6-[4-methoxy-3-(2-morpholinoethoxy)benzoyl]phenyl}-N-(2-hydroxyethyl)-N-(2-methoxyethyl)acetamide was obtained from 3,5-diallyloxy-2-ethyl-6-[4-methoxy-3-(2-morpholinoethoxy)benzoyl]phenylacetic acid obtained above, using 1-hydroxybenzotriazole hydrate (160 mg, 1.1 mmol), 1-(3-dimethylaminopropyl)-3-ethylcarbodiimide hydrochloride (200 mg, 1.1 mmol), 2-(2-methoxyethylamino)ethanol (150 mg, 1.3 mmol) obtained in Reference Example 1 and N,N-dimethylformamide (10 mL).

In a manner similar to that in Example 7, Step 1, Compound 104 (45 mg, 13% in 3 steps) was obtained from 2-{3,5-diallyloxy-2-ethyl-6-[4-methoxy-3-(2-morpholinoethoxy)benzoyl]phenyl}-N-(2-hydroxyethyl)-N-(2-methoxyethyl)acetamide obtained above, using ammonium formate (200 mg, 3.1 mmol), bis(triphenylphosphine)palladium (II) dichloride (50 mg, 0.071 mmol) and 1,4-dioxane (5 mL).

$^1$H-NMR (CD$_3$OD, 300 MHz) δ (ppm): 7.50 (dd, J=8.4, 1.8 Hz, 1H), 7.46 (d, J=1.8 Hz, 1H), 6.99 (d, J=8.4 Hz, 1H), 6.32 (s, 1H), 4.21 (m, 2H), 3.89 (s, 1.5H), 3.87 (s, 1.5H), 3.74-3.71 (m, 6H), 3.58 (t, J=5.7 Hz, 1H), 3.49 (t, J=4.7 Hz, 1H), 3.43-3.39 (m, 3H), 3.35-3.28 (m, 3.5H), 3.15-3.11 (m, 2.5H), 2.91 (m, 2H), 2.73-2.71 (m, 4H), 2.53 (m, 2H), 1.08 (t, J=7.1 Hz, 3H)

APCI-MS (m/z); 561 [M+H]$^+$

EXAMPLE 104

Synthesis of 2-[2-ethyl-3,5-dihydroxy-6-(4-hydroxy-3-methoxybenzoyl)phenyl]-N-(2-hydroxyethyl)-N-(2-methoxyethyl)acetamide (Compound 105)

(Step 1)

In a manner similar to that in Example 5, Step 4, methyl 3,5-diallyloxy-2-ethyl-6-(4-hydroxy-3-methoxybenzoyl)phenylacetate (2.1 g, 71%) was obtained from methyl 3,5-diallyloxy-2-ethylphenylacetate (2.0 g, 6.7 mmol) obtained in Example 5, Step 3, using 4-hydroxy-3-methoxybenzoic acid (2.3 g, 14 mmol), trifluoroacetic anhydride (2.8 mL, 20 mmol) and trifluoroacetic acid (20 mL), and using a 7 mol/L solution of ammonia in methanol (20 mL) and methanol (50 mL).

$^1$H-NMR (CDCl$_3$, 300 MHz) δ (ppm): 7.57 (d, J=2.0 Hz, 1H), 7.23 (dd, J=8.4, 2.0 Hz, 1H), 6.84 (d, J=8.4 Hz, 1H), 6.44 (s, 1H), 6.08 (m, 1H), 5.70 (m, 1H), 5.45 (m, 1H), 5.31 (m, 1H), 5.10-5.02 (m, 2H), 4.58 (m, 2H), 4.38 (m, 2H), 3.94 (s, 3H), 3.61 (s, 2H), 3.46 (s, 3H), 2.65 (q, J=7.5 Hz, 2H), 1.11 (t, J=7.5 Hz, 3H)

APCI-MS (m/z); 441 [M+H]$^+$ (Step 2)

In a manner similar to that in Example 10, Step 1, 3,5-diallyloxy-2-ethyl-6-(4-hydroxy-3-methoxybenzoyl)phenylacetic acid (0.59 g, 92%) was obtained from methyl 3,5-diallyloxy-2-ethyl-6-(4-hydroxy-3-methoxybenzoyl)phenylacetate (0.67 g, 1.5 mmol) obtained in Example 104, Step 1, using a 2 mol/L aqueous solution of sodium hydroxide (10 mL) and tetrahydrofuran (10 mL).

$^1$H-NMR (CDCl$_3$, 300 MHz) δ (ppm): 7.58 (d, J=2.0 Hz, 1H), 7.26 (dd, J=8.4, 2.0 Hz, 1H), 6.86 (d, J=8.4 Hz, 1H), 6.44 (s, 1H), 6.08 (m, 1H), 5.68 (m, 1H), 5.45 (m, 1H), 5.31 (m, 1H), 5.07-4.98 (m, 2H), 4.58 (m, 2H), 4.38 (m, 2H), 3.95 (s, 3H), 3.58 (s, 2H), 2.75 (q, J=7.5 Hz, 2H), 1.11 (t, J=7.5 Hz, 3H)

APCI-MS (m/z); 427 [M+H]$^+$ (Step 3)

In a manner similar to that in Example 10, Step 2, 2-[3,5-diallyloxy-2-ethyl-6-(4-hydroxy-3-methoxybenzoyl)phenyl]-N-(2-hydroxyethyl)-N-(2-methoxyethyl)acetamide was obtained from 3,5-diallyloxy-2-ethyl-6-(4-hydroxy-3-methoxybenzoyl)phenylacetic acid (450 mg, 1.0 mmol) obtained in Example 104, Step 2, using 1-hydroxybenzotriazole hydrate (240 mg, 1.6 mmol), 1-(3-dimethylaminopropyl)-3-ethylcarbodiimide hydrochloride (300 mg, 1.6 mmol), 2-(2-methoxyethylamino)ethanol (240 mg, 2.0 mmol) obtained in Reference Example 1 and N,N-dimethylformamide (10 mL).

In a manner similar to that in Example 7, Step 1, Compound 105 (93 mg, 20%) was obtained from 2-[3,5-diallyloxy-2-ethyl-6-(4-hydroxy-3-methoxybenzoyl)phenyl]-N-(2-hydroxyethyl)-N-(2-methoxyethyl)acetamide obtained above, using ammonium formate (300 mg, 4.8 mmol), bis(triphenylphosphine)palladium (II) dichloride (50 mg, 0.071 mmol) and 1,4-dioxane (10 mL).

$^1$H-NMR (CD$_3$OD, 300 MHz) δ (ppm): 7.46 (m, 1H), 7.35 (m, 1H), 6.80 (d, J=8.3 Hz, 1H), 6.34 (s, 1H), 3.88 (s, 1.5H), 3.87 (s, 1.5H), 3.69 (d, J=4.2 Hz, 2H), 3.59 (t, J=5.7 Hz, 1H), 3.50 (t, J=4.8 Hz, 1H), 3.46-3.40 (m, 3H), 3.35-3.28 (m, 2.5H), 3.17 (s, 1.5H), 3.15 (t, J=5.7 Hz, 2H), 2.55 (m, 2H), 1.09 (t, J=7.5 Hz, 3H)

APCI-MS (m/z); 448 [M+H]$^+$

EXAMPLE 105

Synthesis of 2-[2-ethyl-3,5-dihydroxy-6-(4-hydroxy-3-methoxybenzoyl)phenyl]-N,N-bis(2-methoxyethyl)acetamide (Compound 106)

In a manner similar to that in Example 10', Step 2, 2-[3,5-diallyloxy-2-ethyl-6-(4-hydroxy-3-methoxybenzoyl)phenyl]-N,N-bis(2-methoxyethyl)acetamide was obtained from 3,5-diallyloxy-2-ethyl-6-(4-hydroxy-3-methoxybenzoyl)phenylacetic acid (450 mg, 1.0 mmol) obtained in Example 104, Step 2, using 1-hydroxybenzotriazole hydrate (240 mg, 1.6 mmol), 1-(3-dimethylaminopropyl)-3-ethylcarbodiimide hydrochloride (300 mg, 1.6 mmol), bis(2-methoxyethyl)amine (270 mg, 2.0 mmol) and N,N-dimethylformamide (10 mL).

In a manner similar to that in Example 7, Step 1, Compound 106 (65 mg, 15%) was obtained from 2-[3,5-diallyloxy-2-ethyl-6-(4-hydroxy-3-methoxybenzoyl)phenyl]-N,N-bis(2-methoxyethyl)acetamide obtained above, using ammonium formate (300 mg, 4.8 mmol), bis(triphenylphosphine)palladium (II) dichloride (50 mg, 0.071 mmol) and 1,4-dioxane (10 mL).

$^1$H-NMR (CD$_3$OD, 300 MHz) δ (ppm): 7.46 (d, J=2.0 Hz, 1H), 7.35 (dd, J=8.3, 2.0 Hz, 1H), 6.78 (d, J=8.3 Hz, 1H), 6.33 (s, 1H), 3.86 (s, 3H), 3.69 (s, 2H), 3.47 (t, J=4.6 Hz, 2H), 3.41 (t, J=4.6 Hz, 2H), 3.34-3.30 (m, 5H), 3.17 (s, 3H), 3.14 (t, J=6.0 Hz, 2H), 2.52 (q, J=7.5 Hz, 2H), 1.08 (t, J=7.5 Hz, 3H)

APCI-MS (m/z); 462 [M+H]$^+$

EXAMPLE 106

Synthesis of 2-[2-ethyl-3,5-dihydroxy-6-(4-methanesulfonylbenzoyl)phenyl]-N,N-bis(2-methoxyethyl)acetamide (Compound 107)

(Step 1) 2-[3,5-Diallyloxy-2-ethyl-6-(4-methanesulfonylbenzoyl)phenyl]-N-(2-hydroxyethyl)-N-(2-methoxyethyl)acetamide (450 mg, 0.76 mmol) obtained in Example 96, Step 1 was dissolved in N,N-dimethylformamide (10 mL), and a 60% sodium hydride dispersion in mineral oil (50 mg, 1.3 mmol) was added thereto in an atmosphere of argon with stirring under ice-cooling. The reaction mixture was stirred at room temperature for 30 minutes, and methyl iodide (0.05 mL, 0.8 mmol) was added dropwise thereto, followed by further stirring for 12 hours. After the reaction mixture was ice-cooled, a saturated aqueous solution of ammonium chloride was added thereto to stop the reaction, followed by extraction with ethyl acetate. The organic layer was washed with a saturated aqueous solution of sodium chloride, dried over anhydrous sodium sulfate, and then concentrated under reduced pressure. The resulting residue was purified by silica gel column chromatography (ethyl acetate/hexane=2/1) to obtain 2-[3,5-diallyloxy-2-ethyl-6-(4-methanesulfonylbenzoyl)phenyl]-N,N-bis(2-methoxyethyl)acetamide (95 mg, 21%).

$^1$H-NMR (CDCl$_3$, 300 MHz) δ (ppm): 8.02-7.92(m, 4H), 6.37 (s, 1H), 6.06 (m, 1H), 5.55-5.40 (m, 2H), 5.30 (m, 1H), 4.96 (m, 1H), 4.86 (m, 1H), 4.57 (m, 2H), 4.25 (m, 2H), 3.93 (s, 2H), 3.57-3.47 (m, 4H), 3.35-3.33 (m, 4H), 3.23 (s, 3H), 3.14 (s, 3H), 3.05 (s, 3H), 2.63 (q, J=7.2 Hz, 2H), 1.10 (t, J=7.2 Hz, 3H)

APCI-MS (m/z); 466 [M+H]$^+$ (Step 2)

In a manner similar to that in Example 7, Step 1, Compound 107 (23 mg, 27%) was obtained from 2-[3,5-diallyloxy-2-ethyl-6-(4-methanesulfonylbenzoyl)phenyl]-N,N-bis(2-methoxyethyl)acetamide (95 mg, 0.17 mmol) obtained in Example 106, Step 1, using ammonium formate (200 mg, 3.2 mmol), bis(triphenylphosphine)palladium (II) dichloride (20 mg, 0.029 mmol) and 1,4-dioxane (3 mL). $^1$H-NMR (CD$_3$OD, 300 MHz) δ (ppm): 7.97 (s, 4H), 6.29 (s, 1H), 3.89 (s, 2H), 3.56-3.50 (m, 4H), 3.34-3.30 (m, 5H), 3.18 (t, J=5.3 Hz, 2H), 3.16 (s, 6H), 2.55 (q, J=7.5 Hz, 2H), 1.07 (t, J=7.5 Hz, 3H)

APCI-MS (m/z); 494 [M+H]$^+$

EXAMPLE 107

Synthesis of 2-{2-ethyl-3,5-dihydroxy-6-[4-(2-hydroxyethoxy)-3-methoxybenzoyl]phenyl}-N-(2-hydroxyethyl)-N-(2-methoxyethyl)acetamide (Compound 108)

(Step 1)

In a manner similar to that in Example 101, Step 1, methyl 3,5-diallyloxy-2-ethyl-6-[3-methoxy-4-[(2-tetrahydro-2H-pyran-2-yloxyethoxy)benzoyl]phenylacetate was obtained from methyl 3,5-diallyloxy-2-ethyl-6-(4-hydroxy-3-methoxybenzoyl)phenylacetate (230 mg, 0.52 mmol) obtained in Example 104, Step 1, using 2-(2-bromoethoxy)tetrahydro-2H-pyran (0.25 mL, 1.7 mmol), potassium carbonate (200 mg, 1.5 mmol), sodium iodide (50 mg, 0.33 mmol) and N,N-dimethylformamide (5 mL).

In a manner similar to that in Example 59, Step 2, methyl 3,5-diallyloxy-2-ethyl-6-[4-(2-hydroxyethoxy)-3-methoxybenzoyl]phenylacetate (220 mg, 87% in 2 steps) was obtained from methyl 3,5-diallyloxy-2-ethyl-6-[3-methoxy-4-(2-tetrahydro-2H-pyran-2-yloxyethoxy)benzoyl]phenylacetate obtained above, using a 4 mol/L solution of hydrogen chloride in 1,4-dioxane (3 mL) and methanol (3 mL).

$^1$H-NMR (CDCl$_3$, 300 MHz) δ (ppm): 7.55 (d, J=2.0 Hz, 1H), 7.28 (dd, J=8.5, 2.0 Hz, 1H), 6.83 (d, J=8.5 Hz, 1H), 6.43 (s, 1H), 6.08 (m, 1H), 5.70 (m, 1H), 5.45 (m, 1H), 5.30 (m, 1H), 5.07-5.00 (m, 2H), 4.58 (m, 2H), 4.38 (m, 2H), 4.15 (m, 2H), 3.99 (m, 2H), 3.90 (s, 3H), 3.63 (s, 2H), 3.46 (s, 3H), 2.65 (q, J=7.5 Hz, 2H), 1.09 (t, J=7.5 Hz, 3H)

APCI-MS (m/z); 485 [M+H]$^+$ (Step 2)

In a manner similar to that in Example 10, Step 1, 3,5-diallyloxy-2-ethyl-6-[4-(2-hydroxyethoxy)-3-methoxybenzoyl]phenylacetic acid was obtained from methyl 3,5-diallyloxy-2-ethyl-6-[4-(2-hydroxyethoxy)-3-methoxybenzoyl]phenylacetate (310 mg, 0.52=mol) obtained in Example 107, Step 1, using a 2 mol/L aqueous solution of sodium hydroxide (5 mL) and tetrahydrofuran (5 mL).

In a manner similar to that in Example 10, Step 2, 2-{3,5-diallyloxy-2-ethyl-6-[4-(2-hydroxyethoxy)-3-methoxybenzoyl]phenyl}-N-(2-hydroxyethyl)-N-(2-methoxyethyl)acetamide was obtained from 3,5-diallyloxy-2-ethyl-6-[4-(2-hydroxyethoxy)-3-methoxybenzoyl]phenylacetic acid obtained above, using 1-hydroxybenzotriazole hydrate (130 mg, 0.85 mmol), 1-(3-dimethylaminopropyl)-3-ethylcarbodiimide hydrochloride (150 mg, 0.79 mmol), 2-(2-methoxyethylamino)ethanol (130 mg, 1.1 mmol) obtained in Reference Example 1 and N,N-dimethylformamide (5 mL).

In a manner similar to that in Example 7, Step 1, Compound 108 (62 mg, 25% in 3 steps) was obtained from 2-{3,5-diallyloxy-2-ethyl-6-[4-(2-hydroxyethoxy)-3-methoxybenzoyl]phenyl}-N-(2-hydroxyethyl)-N-(2-methoxyethyl)acetamide obtained above, using ammonium formate (150 mg, 2.4 mmol), bis(triphenylphosphine)palladium (II) dichloride (20 mg, 0.029 mmol) and 1,4-dioxane (5 mL).

$^1$H-NMR (CD$_3$OD, 300 MHz) δ (ppm): 7.49 (d, J=1.8 Hz, 1H), 7.43 (m, 1H), 6.96 (d, J=8.4 Hz, 1H), 6.33 (s, 1H), 4.13 (m, 2H), 3.89 (m, 2H), 3.88 (s, 1.5H), 3.87 (s, 1.5H), 3.70 (d, J=4.2 Hz, 2H), 3.60 (t, J=5.7 Hz, 1H), 3.50 (t, J=5.5 Hz, 1H), 3.45-3.37 (m, 3H), 3.35-3.28 (m, 3.5H), 3.18-3.13 (m, 2.5H), 2.55 (m, 2H), 1.08 (t, J=7.3 Hz, 3H)

APCI-MS (m/z); 492 [M+H]$^+$

EXAMPLE 108

Synthesis of 2-{2-ethyl-3,5-dihydroxy-6-[3-methoxy-4-(2-methoxyethoxy)benzoyl]phenyl}-N-(2-hydroxyethyl)-N-(2-methoxyethyl)acetamide (Compound 109)

(Step 1)

In a manner similar to that in Example 101, Step 1, methyl 3,5-diallyloxy-2-ethyl-6-[3-methoxy-4-(2-methoxyethoxy)benzoyl]phenylacetate (230 mg, 42%) was obtained from methyl 3,5-diallyloxy-2-ethyl-6-(4-hydroxy-3-methoxybenzoyl)phenylacetate (0.23 g, 0.52 mmol) obtained in Example 104, Step 1, using 2-bromoethyl methyl ether (0.15 mL, 1.6 mmol), potassium carbonate (200 mg, 1.5 mmol), sodium iodide (50 mg, 0.33 mmol) and N,N-dimethylformamide (5 mL).

$^1$H-NMR (CDCl$_3$, 300 MHz) δ (ppm): 7.53 (d, J=2.0 Hz, 1H), 7.28 (dd, J=8.4, 2.0 Hz, 1H), 6.80 (d, J=8.5 Hz, 1H), 6.43 (s, 1H), 6.07 (m, 1H), 5.69 (m, 1H), 5.45 (m, 1H), 5.30 (m, 1H), 5.07-5.01 (m, 2H), 4.58 (m, 2H), 4.38 (m, 2H), 4.20 (t, J=4.7 Hz, 2H), 3.89 (s, 3H), 3.80 (t, J=4.7 Hz, 2H), 3.62 (s, 2H), 3.44 (s, 3H), 3.43 (s, 3H), 2.65 (q, J=7.5 Hz, 2H), 1.09 (t, J=7.5 Hz, 3H)

APCI-MS (m/z); 499 [M+H]$^+$ (Step 2)

In a manner similar to that in Example 10, Step 1, 3,5-diallyloxy-2-ethyl-6-[3-methoxy-4-(2-methoxyethoxy)benzoyl]phenylacetic acid was obtained from methyl 3,5-diallyloxy-2-ethyl-6-[3-methoxy-4-(2-methoxyethoxy)benzoyl]phenylacetate (230 mg, 0.45 mmol) obtained in Example 108, Step 1', using a 2 mol/L aqueous solution of sodium hydroxide (5 mL) and tetrahydrofuran (5 mL).

In a manner similar to that in Example 10, Step 2, 2-{3,5-diallyloxy-2-ethyl-6-[3-methoxy-4-(2-methoxyethoxy)benzoyl]phenyl}-N-(2-hydroxyethyl)-N-(2-methoxyethyl)acetamide was obtained from 3,5-diallyloxy-2-ethyl-6-[3-methoxy-4-(2-methoxyethoxy)benzoyl]phenylacetic acid obtained above, using 1-hydroxybenzotriazole hydrate (130 mg, 0.85 mmol), 1-(3-dimethylaminopropyl)-3-ethylcarbodiimide hydrochloride (150 mg, 0.79 mmol), 2-(2-methoxyethylamino)ethanol (130 mg, 1.1 mmol) obtained in Reference Example 1 and N,N-dimethylformamide (5 mL).

In a manner similar to that in Example 7, Step 1, Compound 109 (96 mg, 43% in 3 steps) was obtained from 2-{3,5-diallyloxy-2-ethyl-6-[3-methoxy-4-(2-methoxyethoxy)benzoyl]phenyl}-N-(2-hydroxyethyl)-N-(2-methoxyethyl)acetamide obtained above, using ammonium formate (150 mg, 2.4 mmol), bis(triphenylphosphine)palladium (II) dichloride (20 mg, 0.029 mmol) and 1,4-dioxane (5 mL).

$^1$H-NMR (CD$_3$OD, 300 MHz) δ (ppm): 7.42 (d, J=1.8 Hz, 1H), 7.35 (m, 1H), 6.90 (d, J=8.4 Hz, 1H), 6.27 (s, 1H), 4.13 (m, 2H), 3.80 (s, 1.5H), 3.79 (s, 1.5H), 3.71 (m, 2H), 3.65 (d, J=4.2 Hz, 2H), 3.56 (m, 1H), 3.45 (m, 1H), 3.38-3.34 (m, 3H), 3.36 (s, 3H), 3.27-3.21 (m, 3.5H), 3.18-3.13 (m, 2.5H), 2.55 (m, 2H), 1.03 (t, J=7.3 Hz, 3H)

APCI-MS (m/z); 506 [M+H]$^+$

EXAMPLE 109

Synthesis of 2-{2-ethyl-3,5-dihydroxy-6-[3-methoxy-4-(2-morpholinoethoxy)benzoyl]phenyl}-N-(2-hydroxyethyl)-N-(2-methoxyethyl)acetamide (Compound 110)

(Step 1)

In a manner similar to that in Example 101, Step 1, methyl 3,5-diallyloxy-2-ethyl-6-{3-methoxy-4-(2-morpholinoethoxy)benzoyl}phenylacetate (300 mg, 97%) was obtained from methyl 3,5-diallyloxy-2-ethyl-6-(4-hydroxy-3-methoxybenzoyl)phenylacetate (250 mg, 0.57 mmol) obtained in Example 104, Step 1, using N-(2-chloroethyl)morpholine hydrochloride (160 mg, 0.86 mmol), potassium carbonate (250 mg, 1.8 mmol), sodium iodide (50 mg, 0.33 mmol) and N,N-dimethylformamide (5 mL).

$^1$H-NMR (CDCl$_3$, 300 MHz) δ (ppm): 7.54 (d, J=2.0 Hz, 1H), 7.30 (dd, J=8.5, 2.0 Hz, 1H), 6.80 (d, J=8.5 Hz, 1H), 6.44 (s, 1H), 6.05 (m, 1H), 5.70 (m, 1H), 5.48 (m, 1H), 5.30 (m, 1H), 5.07-5.01 (m, 2H), 4.58 (m, 2H), 4.38 (m, 2H), 4.21 (t, J=6.0 Hz, 2H), 3.89 (s, 3H), 3.74-3.71 (m, 5H), 3.46 (s, 3H), 2.86 (t, J=6.0 Hz, 2H), 2.65-2.56 (m, 6H), 1.09 (t, J=7.5 Hz, 3H)

APCI-MS (m/z); 554 [M+H]$^+$ (Step 2)

In a manner similar to that in Example 10, Step 1, 3,5-diallyloxy-2-ethyl-6-{3-methoxy-4-(2-morpholinoethoxy)benzoyl]phenylacetic acid was obtained from methyl 3,5-diallyloxy-2-ethyl-6-{3-methoxy-4-(2-morpholinoethoxy)benzoyl}phenylacetate (300 mg, 0.54 mmol) obtained in Example 109, Step 1, using a 2 mol/L aqueous solution of sodium hydroxide (5 mL) and tetrahydrofuran (5 mL).

In a manner similar to that in Example 10, Step 2, 2-{3,5-diallyloxy-2-ethyl-6-[3-methoxy-4-(2-morpholinoethoxy)benzoyl]phenyl}-N-(2-hydroxyethyl)-N-(2-methoxyethyl)acetamide was obtained from 3,5-diallyloxy-2-ethyl-6-{3-methoxy-4-(2-morpholinoethoxy)benzoyl}phenylacetic acid obtained above, using 1-hydroxybenzotriazole hydrate (130 mg, 0.85 mmol), 1-(3-dimethylaminopropyl)-3-ethylcarbodiimide hydrochloride (150 mg, 0.79 mmol), 2-(2-methoxyethylamino)ethanol (130 mg, 1.1 mmol) obtained in Reference Example 1 and N,N-dimethylformamide (5 mL).

In a manner similar to that in Example 7, Step 1, Compound 110 (160 mg, 52% in 3 steps) was obtained from 2-{3,5-diallyloxy-2-ethyl-6-[3-methoxy-4-(2-morpholinoethoxy)benzoyl]phenyl}-N-(2-hydroxyethyl)-N-(2-methoxy-ethyl)acetamide obtained above, using ammonium formate (150 mg, 2.4 mmol), bis(triphenylphosphine)palladium (II) dichloride (20 mg, 0.029 mmol) and 1,4-dioxane (5 mL).

$^1$H-NMR (CD$_3$OD, 300 MHz) δ (ppm): 7.42 (d, J=2.2 Hz, 1H), 7.35 (ddd, J=8.4, 2.2, 1.5 Hz, 1H), 6.90 (dd, J=8.4, 1.5 Hz, 1H), 6.27 (s, 1H), 4.16 (m, 2H), 3.79 (s, 1.5H), 3.78 (s, 1.5H), 3.66-3.63 (m, 6H), 3.57 (t, J=5.7 Hz, 1H), 3.43 (t, J=5.1 Hz, 1H), 3.39-3.33 (m, 3H), 3.35-3.28 (m, 3.5H), 3.12-3.09 (m, 2.5H), 2.79 (m, 2H), 2.58-2.56 (m, 4H), 2.49 (m, 2H), 1.03 (t, J=7.4 Hz, 3H)

APCI-MS (m/z); 561 [M+H]$^+$

EXAMPLE 110

Synthesis of 2-[2-ethyl-3,5-dihydroxy-6-(4-methoxybenzoyl)phenyl]-N-(2-hydroxyethyl)-N-(2-morpholinoethyl)acetamide (Compound 111)

(Step 1)

In a manner similar to that in Example 10, Step 1, 3,5-diallyloxy-2-ethyl-6-(4-methoxybenzoyl)phenylacetic acid (2.2 g, 80%) was obtained from methyl-3,5-diallyloxy-2-ethyl-(4-methoxybenzoyl)phenylacetate (2.8 g, 6.6 mmol) obtained in Example 8, Step 1, using a 2 mol/L aqueous solution of sodium hydroxide (10 mL) and acetonitrile (10 mL).

$^1$H-NMR (CDCl$_3$, 300 MHz) δ (ppm): 7.83 (d, J=9.0 Hz, 2H), 6.91 (d, J=9.0 Hz, 2H), 6.43 (s, 1H), 6.07 (m, 1H), 5.63 (m, 1H), 5.45 (m, 1H), 5.33 (m, 1H), 5.05-4.91 (m, 2H), 4.61-4.58 (m, 2H), 4.37-4.34 (m, 2H), 3.88 (s, 3H), 3.55 (s, 2H), 2.84 (t, J=7.4 Hz, 2H), 1.11 (t, J=7.4 Hz, 3H)

APCI-MS (m/z); 411 [M+H]$^+$ (Step 2)

3,5-Diallyloxy-2-ethyl-6'-(4-methoxybenzoyl)phenylacetic acid (0.22 g, 0.53 mmol) obtained in Example 110, Step 1 was dissolved in N,N-dimethylformamide (2.0 mL). To the solution were added 1-hydroxybenzotriazole hydrate (70 mg, 0.46 mmol), N-methylmorpholine (0.20 mL, 1.8 mmol), 2-(2-morpholinoethylamino)ethanol (0.18 mL, 1.1 mmol) obtained in Reference Example 4 and 1-(3-dimethylaminopropyl)-3-ethylcarbodiimide hydrochloride (0.12 g, 0.63 mmol), followed by stirring at room temperature for 15 hours. The reaction mixture was concentrated under reduced pressure, and the resulting residue was dissolved in ethyl acetate. To the resulting solution was added a saturated aqueous solution of sodium chloride for liquid separation. The organic layer was dried over anhydrous sodium sulfate and then concentrated under reduced pressure. The resulting residue was purified by silica gel column chromatography [amino type chemically bonded silica gel: Chromatorex (trademark) NH, product of Fuji Silysia Chemical Ltd., ethyl acetate-methanol/ethyl acetate=1/19] to obtain a quantitative yield of 2,3,5-diallyloxy-2-ethyl-6-(4-methoxybenzoyl)phenyl]-N-(2-hydroxyethyl)-N-(2-morpholinoethyl)acetamide.

$^1$H-NMR (CD$_3$OD, 270 MHz) δ (ppm): 7.75 (d, J=8.9 Hz, 2H), 6.96-6.90 (m, 2H), 6.60 and 6.59 (s, total 1H), 6.11 (m, 1H), 5.68 (m, 1H), 5.46 (m, 1H), 5.28 (m, 1H), 5.03-4.95 (m, 2H), 4.63-4.61 (m, 2H), 4.42-4.38 (m, 2H), 3.85 (s, 3H), 3.77 and 3.70 (s, total 2H), 3.65-3.57 (m, 5H), 3.48-3.25 (m, 6H), 2.63 (q, J=7.5 Hz, 2H), 2.44-2.39 (m, 2H), 2.32-2.28 (m, 2H), 2.11 (t, J=6.8 Hz, 1H), 1.14-1.06 (m, 3H)

APCI-MS (m/z); 567 [M+H]$^+$ (Step 3)

2-[3,5-Diallyloxy-2-ethyl-6-(4-methoxybenzoyl)phenyl]-N-(2-hydroxyethyl)-N-(2-morpholinoethyl)acetamide (0.31 g, 0.55 mmol) obtained in Example 110, Step 2 was dissolved in 1,4-dioxane (1.5 mL), and ammonium formate (0.14 g, 2.2 mmol) and bis(triphenylphosphine)palladium (II) dichloride (0.012 g, 0.017 mmol) were added thereto, followed by stirring at 100° C. for 1.5 hours in an atmosphere of argon. The reaction mixture was cooled to room temperature and then concentrated under reduced pressure. The resulting residue was purified by C18 silica gel column chromatography (water-water/acetonitrile=1/1) to obtain Compound 111 (0.14 g, 51%). Melting Point: 235-237° C.

$^1$H-NMR (CD$_3$OD, 270 MHz) δ (ppm): 7.78 (d, J=8.9 Hz, 2H), 6.95-6.89 (m, 2H), 6.32 and 6.31 (s, total 1H), 3.84 (s, 3H), 3.71-3.55 (m, 7H), 3.47-3.38 (m, 3H), 3.31-3.25 (m, 3H), 2.55 (q, J=7.6 Hz, 2H), 2.44-2.41 (m, 2H), 2.32-2.29 (m, 2H), 2.11 (t, J=7.0 Hz, 1H), 1.11-1.04 (m, 3H)

APCI-MS (m/z); 487 [M+H]$^+$

Elemental Analysis: (C$_{26}$H$_{34}$N$_2$O$_7$·0.2H$_2$O)

Found (%): C, 63.84; H, 7.07; N, 5.63.

Calcd. (%): C, 63.71; H, 7.07; N, 5.72.

EXAMPLE 111

Synthesis of 2-[2-(3,4-dimethoxybenzoyl)-6-ethyl-3,5-dihydroxyphenyl]-N-(2-dimethylaminoethyl)-N-(2-methoxyethyl)acetamide (Compound 112)

(Step 1)

In a manner similar to that in Example 10, Step 1, 3,5-diallyloxy-2-(3,4-dimethoxybenzoyl)-6-ethylphenylacetic acid (2.7 g, 89%) was obtained from methyl 3,5-diallyloxy-2-(3,4-dimethoxybenzoyl)-6-ethylphenylacetate (3.1 g, 6.8 mmol) obtained in Example 28, Step 1, using a 2 mol/L aqueous solution of sodium hydroxide (10 mL) and acetonitrile (10 mL).

$^1$H-NMR (CDCl$_3$, 300 MHz) δ (ppm): 7.55 (d, J=2.0 Hz, 1H), 7.34 (dd, J=2.0, 8.4 Hz, 1H), 6.83 (d, J=8.4 Hz, 1H), 6.44 (s, 1H), 6.07 (m, 1H), 5.64 (m, 1H), 5.45 (m, 1H), 5.33 (m, 1H), 5.07-4.91 (m, 2H), 4.61-4.58 (m, 2H), 4.38-4.35 (m, 2H), 3.95 (s, 3H), 3.94 (s, 3H), 3.56 (s, 2H), 2.83 (t, J=7.4 Hz, 2H), 1.12 (t, J=7.4 Hz, 3H)

APCI-MS (m/z); 441 [M+H]$^+$ (Step 2)

In a manner similar to that in Example 110, Step 2, 2-[3,5-diallyloxy-2-(3,4-dimethoxybenzoyl)-6-ethylphenyl]-N-(2-dimethylaminoethyl)-N-(2-methoxyethyl)acetamide (0.25 g, 96%) was obtained from 3,5-diallyloxy-2-(3,4-dimethoxybenzoyl)-6-ethylphenylacetic acid (0.20 g, 0.45 mmol) obtained in Example 111, Step 1, using 1-(3-dimethylaminopropyl)-3-ethylcarbodiimide hydrochloride (0.13 g, 0.68 mmol), 1-hydroxybenzotriazole hydrate (0.10 g, 0.68 mmol), N-methylmorpholine (0.20 mL, 1.8 mmol), N-(2-methoxyethyl)-N',N'-dimethylethylenediamine (0.13 g, 0.89 mmol) obtained in Reference Example 8 and N,N-dimethylformamide (2.0 mL).

$^1$H-NMR (CDCl$_3$, 300 MHz) δ (ppm): 7.52 (m, 1H), 7.42 (m, 1H), 6.80 (m, 1H), 6.40 and 6.42 (s, total 1H), 6.07 (m, 1H), 5.68 (m, 1H), 5.4-4 (m, 1H), 5.27 (m, 1H), 5.08-5.01 (m, 2H), 4.57-4.55 (m, 2H), 4.39-4.35 (m, 2H), 3.91 (s, 6H), 3.70 and 3.68 (s, total 2H), 3.39 (brs, 3H), 3.35-3.16 (m, 6H), 2.65-2.58 (m, 2H), 2.22 (s, 3H), 2.09 (s, 3H), 2.33-1.98 (m, 2H), 1.11-1.07 (m, 3H)

APCI-MS (m/z); 569 [M+H]$^+$ (Step 3)

In a manner similar to that in Example 110, Step 3, Compound 112 (70 mg, 33%) was obtained from 2-[3,5-diallyloxy-2-(3,4-dimethoxybenzoyl)-6-ethylphenyl]-N-(2-dimethylaminoethyl)-N-(2-methoxyethyl)acetamide (0.25 g, 0.43 mmol) obtained in Example 111, Step 2, using ammonium formate (0.12 g, 1.9 mmol), bis(triphenylphosphine)palladium (II) dichloride (0.11 g, 0.16 mmol) and 1,4-dioxane (16 mL).

$^1$H-NMR (CD$_3$OD, 300 MHz) δ (ppm): 7.46-7.40 (m, 2H), 6.95 (d, J=8.8 Hz, 1H), 6.32 and 6.31 (s, total 1H), 3.87 (s, 3H), 3.84 and 3.83 (s, total 3H), 3.69 and 3.65 (s, total 2H), 3.42 (brs, 3H), 3.39-3.17 (m, 6H), 2.54 (q, J=7.3 Hz, 2H), 2.11 (s, 3H), 2.33-1.98 (m, 2H), 2.22 (s, 3H), 1.04-1.11 (m, 3H)

APCI-MS (m/z); 489 [M+H]$^+$

EXAMPLE 112

Synthesis of N-(2-dimethylaminoethyl)-2-[2-ethyl-3,5-dihydroxy-6-(4-methoxybenzoyl)phenyl]-N-(2-methoxyethyl)acetamide (Compound 113)

(Step 1)

In a manner similar to that in Example 110, Step 2, 2-[3,5-diallyloxy-2-ethyl-6-(4-methoxybenzoyl)phenyl]-N-(2-dimethylaminoethyl)-N-(2-methoxyethyl)acetamide was quantitatively obtained from 3,5-diallyloxy-2-ethyl-6-(4-methoxybenzoyl)phenylacetic acid (2.1 g, 5.2 mmol) obtained in Example 110, Step 1, using 1-(3-dimethylaminopropyl)-3-ethylcarbodiimide hydrochloride (1.5 g, 7.8 mmol), 1-hydroxybenzotriazole hydrate (1.2 g, 7.8 mmol), N-methylmorpholine (2.0 mL, 18 mmol), N-(2-methoxyethyl)-N',N'-dimethylethylenediamine (1.6 g, 11 mmol) obtained in Reference Example 8 and N,N-dimethylformamide (17 mL).

$^1$H-NMR (CD$_3$OD, 270 MHz) δ (ppm): 7.77-7.72 (m, 2H), 6.94-6.89 (m, 2H), 6.59 and 6.58 (s, total 1H), 6.10 (m, 1H), 5.68 (m, 1H), 5.46 (m, 1H), 5.27 (m, 1H), 5.03-4.95 (m, 2H), 4.63-4.60 (m, 2H), 4.41-4.38 (m, 2H), 3.83 (s, 3H), 3.43 (brs, 3H), 3.75 and 3.70 (s, total 2H), 3.75-3.15 (m, 6H), 2.66-2.56 (m, 2H), 2.33 (m, 1H), 2.21 (s, 3H), 2.09 (s, 3H), 2.01 (m, 1H), 1.11-1.05 (m, 3H)

APCI-MS (m/z); 539 [M+H]$^+$ (Step 2)

In a manner similar to that in Example 110, Step 3, Compound 113 (1.3 g, 54%) was obtained from 2-[3,5-diallyloxy-2-ethyl-6-(4-methoxybenzoyl)phenyl]-N-(2-dimethylaminoethyl)-N-(2-methoxyethyl)acetamide (2.8 g, 5.3 mmol) obtained in Example 112, Step 1, using ammonium formate (1.4 g, 22 mmol), bis(triphenylphosphine)palladium (II) dichloride (0.11 g, 0.16 mmol) and 1,4-dioxane (16 mL).

Melting Point: 204-206° C.

$^1$H-NMR (CD$_3$OD, 270 MHz) δ (ppm): 7.79 (d, J=9.1 Hz, 2H), 6.94-6.90 (m, 2H), 6.32 and 6.31 (s, total 1H), 3.84 (s, 3H), 3.70 and 3.66 (s, total 2H), 3.43 (s, 3H), 3.40-3.18 (m, 6H), 2.54 (q, J=7.3 Hz, 2H), 2.22 (s, 3H), 2.10 (s, 3H), 2.39-2.00 (m, 2H), 1.11-1.04 (m, 3H)

APCI-MS (m/z); 459 [M+H]$^+$

Elemental Analysis: (C$_{25}$H$_{34}$N$_2$O$_6$·0.1H$_2$O)

Found (%): C, 65.21; H, 7.57; N, 5.74.

Calcd. (%): C, 65.23; H, 7.49; N, 6.09

EXAMPLE 113

Synthesis of N-(2-diethylaminoethyl)-2-[2-(3,4-dimethoxybenzoyl)-6-ethyl-3,5-dihydroxyphenyl]-N-(2-hydroxyethyl)acetamide (Compound 114)

(Step 1)

In a manner similar to that in Example 110, Step 2, 2-[3,5-diallyloxy-2-(3,4-dimethoxybenzoyl)-6-ethylphenyl]-N-(2-diethylaminoethyl)-N-(2-hydroxyethyl)acetamide (200 mg, 71%) was obtained from 3,5-diallyloxy-2-(3,4-dimethoxybenzoyl)-6-ethylphenylacetic acid (0.21 g, 0.48 mmol) obtained in Example 111, Step 1, using 1-(3-dimethylaminopropyl)-3-ethylcarbodiimide hydrochloride (0.14 g, 0.73 mmol), 1-hydroxybenzotriazole hydrate (0.11 g, 0.71 mmol), N-methylmorpholine (0.20 mL, 1.8 mmol), N,N-diethyl-N'-(2-hydroxyethyl)ethylenediamine (0.17 g, 1.1 mmol) obtained in Reference Example 6 and N,N-dimethylformamide (2.0 mL).

$^1$H-NMR (CD$_3$OD, 270 MHz) δ (ppm): 7.44-7.32 (m, 2H), 6.94 (d, J=8.4 Hz, 1H), 6.60 and 6.59 (s, total 1H), 6.10 (m, 1H), 5.70 (m, 1H), 5.46 (m, 1H), 5.27 (m, 1H), 5.05-4.97 (m, 2H), 4.64-4.62 (m, 2H), 4.43-4.40 (m, 2H), 3.88-3.70 (m, 8H), 3.70-3.22 (m, 6H), 2.66-2.35 (m, 7H), 2.20 (m, 1H), 1.13-0.90 (m, 9H)

APCI-MS (m/z); 583 [M+H]$^+$ (Step 2)

In a manner similar to that in Example 110, Step 3, Compound 114 (15 mg, 8.6%) was obtained from 2-[3,5-diallyloxy-2-(3,4-dimethoxybenzoyl)-6-ethylphenyl]-N-(2-diethylaminoethyl)-N-(2-hydroxyethyl)acetamide (0.20 g, 0.34 mmol) obtained in Example 113, Step 1, using ammonium formate (86 mg, 1.4 mmol), bis(triphenylphosphine) palladium (II) dichloride (7.2 mg, 0.010 mmol) and 1,4-dioxane (1.5 mL).

$^1$H-NMR (CD$_3$OD, 270 MHz) δ (ppm): 7.44-7.42 (m, 2H), 6.97 (d, J=8.9 Hz, 1H), 6.33 (s, 1H), 3.88 (s, 3H), 3.83 (s, 3H), 3.69 (brs, 2H), 3.65 (t, J=5.1 Hz, 2H), 3.53-3.46 (m, 4H), 3.34-3.29 (m, 2H), 2.99-2.88 (m, 4H), 2.63-2.52 (m, 2H), 1.18-1.01 (m, 9H)

APCI-MS (m/z); 503 [M+H]$^+$

EXAMPLE 114

Synthesis of 2-[2-(3,4-dimethoxybenzoyl)-6-ethyl-3,5-dihydroxyphenyl]-N-(2-methoxyethyl)-N-(2-morpholinoethyl)acetamide (Compound 115)

(Step 1)

In a manner similar to that in Example 110, Step 2, 2-[3,5-diallyloxy-2-(3,4-dimethoxybenzoyl)-6-ethylphenyl]-N-(2-hydroxyethyl)-N-(2-morpholinoethyl)acetamide was quantitatively obtained from 3,5-diallyloxy-2-(3,4-dimethoxybenzoyl)-6-ethylphenylacetic acid (0.23 g, 0.53 mmol) obtained in Example 111, Step 1, using 1-(3-dimethylaminopropyl)-3-ethylcarbodiimide hydrochloride (0.15 g, 0.79 mmol), 1-hydroxybenzotriazole hydrate (0.12 g, 0.79 mmol), N-methylmorpholine (0.20 mL, 1.8 mmol), N-(2-methoxyethyl)-2-morpholinoethylamine (0.20 g, 1.8 mmol) obtained in Reference Example 5 and N,N-dimethylformamide (2.0 mL).

$^1$H-NMR (CD$_3$OD, 270 MHz) δ (ppm): 7.43-7.34 (m, 2H), 6.96-6.92 (m, 1H), 6.59 and 6.58 (s, total 1H), 6.10 (m, 1H), 5.70 (m, 1H), 5.46 (m, 1H), 5.27 (m, 1H), 5.04-4.96 (m, 2H), 4.62-4.60 (m, 2H), 4.42-4.39 (m, 2H), 3.87 (s, 3H), 3.82 and 3.81 (s, total 3H), 3.75 and 3.69 (s, total 2H), 3.44 (brs, 3H), 3.63-3.15 (m, 10H), 2.63-2.58 (m, 2H), 2.42-2.25 (m, 4H), 2.05-1.97 (m, 2H), 1.12-1.05 (m, 3H)

APCI-MS (m/z); 611 [M+H]$^+$ (Step 2)

In a manner similar to that in Example 110, Step 3, Compound 115 (0.22 g, 78%) was obtained from 2-[3,5-diallyloxy-2-(3,4-dimethoxybenzoyl)-6-ethylphenyl]-N-(2-hydroxyethyl)-N-(2-(4-morpholinoethyl)acetamide (0.33 g, 0.55 mmol) obtained in Example 114, Step 1, using ammonium formate (0.14 g, 2.2 mmol), bis(triphenylphosphine) palladium (II) dichloride (12 mg, 0.017 mmol) and 1,4-dioxane (1.5 mL).

Melting Point: 126-129° C.

$^1$H-NMR (CD$_3$OD, 270 MHz) δ (ppm): 7.46-7.39 (m, 2H), 6.96-6.92 (m, 1H), 6.32 and 6.30 (s, total 1H), 3.89 (s, 3H), 3.83 and 3.82 (s, total 3H), 3.70 and 3.64 (s, total 2H), 3.43 (brs, 3H), 3.62-3.15 (m, 10H), 2.57-2.49 (m, 2H), 2.43-1.98 (m, 6H), 1.11-1.03 (m, 3H)

APCI-MS (m/z); 531 [M+H]$^+$
Elemental Analysis: ($C_{28}H_{38}N_2O_8$.2.5$H_2O$)
Found (%): C, 58.29; H, 7.75; N, 5.02.
Calcd. (%): C, 58.42; H, 7.53; N, 4.87

EXAMPLE 115

Synthesis of 2-[2-ethyl-3,5-dihydroxy-6-(4-methoxybenzoyl)phenyl]-N-(2-methoxyethyl)-N-(2-morpholinoethyl)acetamide (Compound 116)

(Step 1)

In a manner similar to that in Example 110, Step 2, 2-[3,5-diallyloxy-2-ethyl-6-(4-methoxybenzoyl)phenyl]-N-(2-methoxyethyl)-N-(2-morpholinoethyl)acetamide was quantitatively obtained from 3,5-diallyloxy-2-ethyl-6-(4-methoxybenzoyl)phenylacetic acid (0.21 g, 0.50 mmol) obtained in Example 110, Step 1, using 1-(3-dimethylaminopropyl)-3-ethylcarbodiimide hydrochloride (0.14 g, 0.77 mmol), 1-hydroxybenzotriazole hydrate (0.12 g, 0.79 mmol), N-methylmorpholine (0.20 mL, 1.8 mmol), N-(2-methoxyethyl)-2-morpholinoethylamine (0.19 g, 1.0 mmol) obtained in Reference Example 5 and N,N-dimethylformamide (2.0 mL).

$^1$H-NMR (CD$_3$OD, 270 MHz) δ (ppm): 7.75 (d, J=8.9 Hz, 2H), 6.94-6.89 (m, 2H), 6.59 and 6.57 (s, total 1H), 6.10 (m, 1H), 5.67 (m, 1H), 5.46 (m, 1H), 5.27 (m, 1H), 5.03-4.94 (m, 2H), 4.63-4.60 (m, 2H), 4.40-4.37 (m, 2H), 3.84 (s, 3H), 3.76 and 3.70 (s, total 2H), 3.64-3.54 (m,4H), 3.45 (brs, 3H), 3.43-3.15 (m, 6H), 2.66-2.56 (m, 2H), 2.43-2.26 (m, 4H), 2.07-2.02 (m, 2H), 1.13-1.05 (m, 3H)

APCI-MS (m/z); 581 [M+H]$^+$ (Step 2)

In a manner similar to that in Example 110, Step 3, Compound 116 (0.20 g, 79%) was obtained from 2-[3,5-diallyloxy-2-ethyl-6-(4-methoxybenzoyl)phenyl]-N-(2-methoxyethyl)-N-(2-morpholinoethyl)acetamide (0.29 g, 0.50 mmol) obtained in Example 115, Step 1, using ammonium formate (0.13 g, 2.0 mmol), bis(triphenylphosphine)palladium (II) dichloride (11 mg, 0.016 mmol) and 1,4-dioxane (1.5 mL).
Melting Point: 216-218° C.

$^1$H-NMR (CD$_3$OD, 270 MHz) δ (ppm): 7.81-7.77 (m, 2H), 6.95-6.90 (m, 2H), 6.32 and 6.31 (s, total 1H), 3.84 (s, 3H), 3.71 and 3.66 (s, total 2H), 3.45 (brs, 3H), 3.64-3.18 (m, 10H), 2.57-2.50 (m, 2H), 2.44-2.02 (m, 6H), 1.12-1.04 (m, 3H)

APCI-MS (m/z); 501 [M+H]$^+$
Elemental Analysis: ($C_{27}H_{36}N_2O_7$)
Found (%): C, 64.70; H, 7.35; N, 5.57.
Calcd. (%): C, 64.78; H, 7.25; N, 5.60

EXAMPLE 116

Synthesis of 2-[2-ethyl-3,5-dihydroxy-6-(4-methoxybenzoyl)phenyl]-N-(3-hydroxypropyl)-N-(2-methoxyethyl)acetamide (Compound 117)

In a manner similar to that in Example 74, Step 2, Compound 117 (0.26 g, 62%) was obtained from 2-ethyl-3,5-dihydroxy-6-(4-methoxybenzoyl)phenylacetic acid (0.31 g, 0.93 mmol) obtained in Example 10, Step 1, using 1-(3-dimethylaminopropyl)-3-ethylcarbodiimide hydrochloride (0.23 g, 1.22 mmol), 3-(2-methoxyethylamino)propanol (0.19 g, 1.4 mmol) obtained in Reference Example 2 and N,N-dimethylformamide (3.0 mL). In this case, crystallization was carried out with a mixed solvent of ethyl acetate and acetonitrile.
Melting Point: 203-206° C.

$^1$H-NMR (CD$_3$OD, 270 MHz) δ (ppm): 7.78 (brd, J=8.9 Hz, 2H), 6.94-6.89 (m, 2H), 6.32 and 6.31 (s, total 1H), 3.84 (s, 3H), 3.71 and 3.67 (s, total 1H), 3.50 (t, J=6.0 Hz, 1H), 3.43-3.12 (m, 10H), 2.58-2.48 (m, 2H), 1.68 (m, 1H), 1.46 (m, 1H), 1.10-1.04 (m, 3H) APCI-MS (m/z); 446 [M+H]$^+$ Elemental Analysis: ($C_{24}H_{31}NO_7$.0.2$H_2O$)
Found (%): C, 64.07; H, 7.19; N, 3.16.
Calcd. (%): C, 64.19; H, 7.05; N, 3.12

EXAMPLE 117

Synthesis of 2-[2-ethyl-3,5-dihydroxy-6-(4-methoxybenzoyl)phenyl]-N-(2-hydroxyethyl)-N-(3-methoxypropyl)acetamide (Compound 118)

In a manner similar to that in Example 74, Step 2, Compound 118-(0.17 g, 42%) was obtained from 2-ethyl-3,5-dihydroxy-6-(4-methoxybenzoyl)phenylacetic acid (0.30 g, 0.92 mmol) obtained in Example 10, Step 1, using 1-(3-dimethylaminopropyl)-3-ethylcarbodiimide hydrochloride (0.23 g, 1.20 mmol), 2-(3-methoxypropylamino)ethanol (0.19 g, 1.4 mmol) obtained in Reference Example 3 and N,N-dimethylformamide (3.0 mL) In this case, crystallization was carried out with a mixed solvent of ethyl acetate and acetonitrile.
Melting Point: 189-192° C.

$^1$H-NMR (CD$_3$OD, 270 MHz) δ (ppm): 7.81-7.76 (m, 2H), 6.94-6.88 (m, 2H), 6.32 and 6.31 (s, total 1H), 3.84 and 3.83 (s, total 3H), 3.71 and 3.62 (s, total 2H), 3.59 (t, J=6.0 Hz, 1H), 3.43-3.18 (m, 10H), 3.12 (t, J=6.0 Hz, 1H), 2.59-2.51 (m, 2H), 1.70 (m, 1H), 1.43 (m, 1H), 1.10-1.04 (m, 3H)

APCI-MS (m/z); 446 [M+H]$^+$
Elemental Analysis: ($C_{24}H_{31}NO_7$)
Found (%): C, 64.52; H, 6.98; N, 3.00.
Calcd. (%): C, 64.70; H, 7.01; N, 3.14

EXAMPLE 118

Synthesis of 2-[2-(3,4-dimethoxybenzoyl)-6-ethyl-3,5-dihydroxyphenyl]-N-(3-hydroxypropyl)-N-(2-methoxyethyl)acetamide (Compound 119)

In a manner similar to that in Example 74, Step 2, Compound 119 (0.23 g, 54%) was obtained from 2-(3,4-dimethoxybenzoyl)-6-ethyl-3,5-dihydroxyphenylacetic acid (0.31 g, 0.87 mmol) obtained in Example 40, Step 1, using 1-(3-dimethylaminopropyl)-3-ethylcarbodiimide hydrochloride (0.23 g, 1.2 mmol), 3-(2-methoxyethylamino)propanol (0.19 g, 1.4 mmol) obtained in Reference Example 2 and N,N-dimethylformamide (3.0 mL). In this case, crystallization was carried out with a mixed solvent of ethyl acetate and methanol.
Melting Point: 184-186° C.

$^1$H-NMR (CD$_3$OD, 270 MHz) δ (ppm): 7.47-7.41 (m, 2H) 6.96-6.92 (m, 1H), 6.33 and 6.32 (s, total 1H), 3.88 (s, 3H), 3.84 (s, 3H), 3.71 and 3.66 (s, total 2H), 3.50 (t, J=5.4 Hz, 1H), 3.43-3.12 (m, 10H), 2.58-2.49 (m, 2H), 1.67 (m, 1H), 1.47 (m, H), 1.11-1.05 (m, 3H)

APCI-MS (m/z); 476 [M+H]$^+$
Elemental Analysis: (C$_{25}$H$_{33}$NO$_8$·0.3H$_2$O)
Found (%): C, 62.52; H, 7.16; N, 2.91.
Calcd. (%): C, 62.44; H, 7.04; N, 2.91

EXAMPLE 119

Synthesis of 2-[2-(3,4-dimethoxybenzoyl)-6-ethyl-3,5-dihydroxyphenyl]-N-(2-hydroxyethyl)-N-(3-methoxypropyl)acetamide (Compound 120)

In a manner similar to that in Example 74, Step 2, Compound 120 (0.15 g, 37%) was obtained from 2-(3,4-dimethoxybenzoyl)-6-ethyl-3,5-dihydroxyphenylacetic acid (0.31 g, 0.87 mmol) obtained in Example 40, Step 1, using 1-(3-dimethylaminopropyl)-3-ethylcarbodiimide hydrochloride (0.23 g, 1.2 mmol), 2-(3-methoxypropylamino)ethanol (0.19 g, 1.4 mmol) obtained in Reference Example 3 and N,N-dimethylformamide (3.0 mL). In this case, crystallization was carried out with a mixed solvent of ethyl acetate and methanol.

Melting Point: 189-182° C.
$^1$H-NMR (CD$_3$OD, 270 MHz) δ (ppm): 7.46-7.38 (m, 2H), 6.95-6.91 (m, 1H), 6.32 and 6.31 (s, total 1H), 3.88 and 3.87 (s, total 3H), 3.84 (s, 3H), 3.71 and 3.61 (s, total 2H), 3.58 (t, J=5.4 Hz, 1H), 3.44-3.19 (m, 10H), 3.10 (t, J=5.4 Hz, 1H), 2.59-2.50 (m, 2H), 1.68 (m, 1H), 1.43 (m, 1H), 1.11-1.04 (m, 3H)
APCI-MS (m/z); 476 [M+H]$^+$
Elemental Analysis: (C$_{25}$H$_{33}$NO$_8$)
Found (%): C, 63.29; H, 7.16; N, 2.94.
Calcd. (%): C, 63.14; H, 6.99; N, 2.95.

EXAMPLE 120

Synthesis of 2-[2-(4-ethoxybenzoyl)-6-ethyl-3,5-dihydroxyphenyl]-N,N-bis(2-hydroxyethyl)acetamide (Compound 121)

(Step 1)
In a manner similar to that in Example 5, Step 4, methyl 3,5-diallyloxy-2-(4-ethoxybenzoyl)-6-ethylphenylacetate (1.1 g, 73%) was obtained from methyl 3,5-diallyloxy-2-ethylphenylacetate (1.0 g, 3.5 mmol) obtained in Example 5, Step 3, using 3-ethoxybenzoic acid (0.86 g, 5.2 mmol), trifluoroacetic anhydride (0.73 mL, 5.2 mmol) and trifluoroacetic acid (20 mL).

$^1$H-NMR (CDCl$_3$, 300 MHz) δ (ppm): 7.80-7.76 (m, 2H), 6.88-6.84 (m, 2H), 6.43 (s, 1H), 6.08 (m, 1H), 5.70 (m, 1H), 5.45 (m, 1H), 5.30 (m, 1H), 5.06-4.99 (m, 2H), 4.57 (m, 2H), 4.38 (m, 2H), 4.09 (q, J=7.0 Hz, 2H), 3.64 (s, 2H), 3.44 (s, 3H), 2.65 (q, J=7.5 Hz, 2H), 1.43 (t, J=7.0 Hz, 3H), 1.09 (t, J=7.5 Hz, 3H)
APCI-MS (m/z); 439 [M+H]$^+$ (Step 2)
In a manner similar to that in Example 10, Step 1, 3,5-diallyloxy-2-(4-ethoxybenzoyl)-6-ethylphenylacetic acid (0.98 g, 92%) was obtained from methyl 3,5-diallyloxy-2-(4-ethoxybenzoyl)-6-ethylphenylacetate (1.1 g, 2.5 mmol) obtained in Example 120, Step 1, using a 2 mol/L aqueous solution of sodium hydroxide (10 mL), acetonitrile (5 mL) and tetrahydrofuran (5 mL).

$^1$H-NMR (CDCl$_3$, 300 MHz) δ (ppm): 7.80 (d, J=8.3 Hz, 2H), 6.88 (d, J=8.3 Hz, 2H), 6.44 (s, 1H), 6.08 (m, 1H), 5.66 (m, 1H), 5.45 (m, 1H), 5.32 (m, 1H), 5.06-4.99 (m, 2H), 4.58 (m, 2H), 4.37 (m, 2H), 4.10 (q, J=7.0 Hz, 2H), 3.57 (s, 2H), 2.77 (q, J=7.5 Hz, 2H), 1.43 (t, J=7.0 Hz, 3H), 1.09 (t, J=1.5 Hz, 3H)
APCI-MS (m/z); 425 [M+H]$^+$ (Step 3)
In a manner similar to that in Example 10, Step 2, 2-[3,5-diallyloxy-2-(4-ethoxybenzoyl)-6-ethylphenyl]-N,N-bis(2-hydroxyethyl)acetamide was obtained from 3,5-diallyloxy-2-(4-ethoxybenzoyl)-6-ethylphenylacetic acid (250 mg, 0.59 mmol) obtained in Example 120, Step 2, using 1-hydroxybenzotriazole hydrate (140 mg, 0.92 mmol), 1-(3-dimethylaminopropyl)-3-ethylcarbodiimide hydrochloride (170 mg, 0.89 mmol), diethanolamine (150 mg, 1.4 mmol) and N,N-dimethylformamide (5 mL).

In a manner similar to that in Example 7, Step 1, Compound 121 (130 mg, 52%) was obtained from 2-[3,5-diallyloxy-2-(4-ethoxybenzoyl)-6-ethylphenyl]-N,N-bis(2-hydroxyethyl)acetamide obtained above, using ammonium formate (200 mg, 3.2 mmol), bis(triphenylphosphine)palladium (II) dichloride (20 mg, 0.029 mmol) and 1,4-dioxane (6 mL).

$^1$H-NMR (CD$_3$OD, 300 MHz) δ (ppm): 7.79-7.74 (m, 2H), 6.92-6.87 (m, 2H), 6.31 (s, 1H), 4.10 (q, J=6.7 Hz, 2H), 3.69 (s, 2H), 3.60 (t, J=5.8 Hz, 2H), 3.44-3.39 (m, 4H), 3.31-3.27 (m, 2H), 2.54 (q, J=7.5 Hz, 2H), 1.39 (t, J=6.7 Hz, 3H), 1.08 (t, J=7.5 Hz, 3H)
APCI-MS (m/z); 432 [M+H]$^+$

EXAMPLE 121

Synthesis of 2-[2-(4-ethoxybenzoyl)-6-ethyl-3,5-dihydroxyphenyl]-N-(2-hydroxyethyl)-N-(2-methoxyethyl)acetamide (Compound 122)

In a manner similar to that in Example 10, Step 2, 2-[3,5-diallyloxy-2-(4-ethoxybenzoyl)-6-ethylphenyl]-N,N-bis(2-methoxyethyl)acetamide was obtained from 3,5-diallyloxy-2-(4-ethoxybenzoyl)-6-ethylphenylacetic acid (250 mg, 0.59 mmol) obtained in Example 120, Step 2, using 1-hydroxybenzotriazole hydrate (140 mg, 0.92 mmol), 1-(3-dimethylaminopropyl)-3-ethylcarbodiimide hydrochloride (170 mg, 0.89 mmol), 2-(2-methoxyethylamino)ethanol (150 mg, 1.3 mmol) obtained in Reference Example 1 and N,N-dimethylformamide (5 mL).

In a manner similar to that in Example 7, Step 1, Compound 122 (140 mg, 56%) was obtained from 2-[3,5-diallyloxy-2-(4-ethoxybenzoyl)-6-ethylphenyl]-N,N-bis(2-methoxyethyl)acetamide obtained above, using ammonium formate (200 mg, 3.2 mmol), bis(triphenylphosphine)palladium (II) dichloride (20 mg, 0.029 mmol) and 1,4-dioxane (6 mL).

$^1$H-NMR (CD$_3$OD, 300 MHz) δ (ppm): 7.80-7.77 (m, 2H), 6.92-6.89 (m, 2H), 6.32 (s, 1H), 4.10 (m, 2H), 3.70 (d, J=5.3 Hz, 2H), 3.60 (t, J=5.7 Hz, 1H), 3.51 (t, J=4.8 Hz, 1H), 3.45-3.39 (m, 3H), 3.35-3.28 (m, 3.5H), 3.18-3.13 (m, 2.5H), 2.55 (m, 2H), 1.40 (m, 3H), 1.08, (t, J=7.3° Hz, 3H)
APCI-MS (m/z); 446 [M+H]$^+$

EXAMPLE 122

Synthesis of 2-[2-ethyl-3,5-dihydroxy-6-(4-isopropoxybenzoyl)phenyl]-N,N-bis(2-hydroxyethyl)acetamide (Compound 123)

(Step 1)
In a manner similar to that in Example 5, Step 4, methyl 3,5-diallyloxy-2-ethyl-6-(4-isopropoxybenzoyl)phenylacetate (0.95 g, 61%) was obtained from methyl 3,5-diallyloxy- 2-ethylphenylacetate (1.0 g, 3.5 mmol) obtained in Example 5, Step 3, using 4-isopropoxybenzoic acid (0.95 g, 5.3 mmol), trifluoroacetic anhydride (0.74 mL, 5.2 mmol) and trifluoroacetic acid (20 mL).

H-NMR (CDCl$_3$, 300 MHz) δ (ppm): 7.80-7.76 (m, 2H), 6.87-6.82 (m, 2H), 6.43 (s, 1H), 6.06 (m, 1H), 5.70 (m, 1H), 5.45 (m, 1H), 5.30 (m, 1H), 5.06-4.99 (m, 2H), 4.63 (m, 1H), 4.57 (m, 2H), 4.38 (m, 2H), 3.64 (s, 2H), 3.45 (s, 3H), 2.65 (q, J=7.5 Hz, 2H), 1.35 (d, J=6.0 Hz, 6H), 1.09 (t, J=7.5 Hz, 3H)

APCI-MS (m/z); 453 [M+H]$^+$ (Step 2)

In a manner similar to that in Example 10, Step 1, 3,5-diallyloxy-2-ethyl-6-(4-isopropoxybenzoyl)phenylacetic acid (0.90 g, 97%) was obtained from methyl 3,5-diallyloxy-2-ethyl-6-(4-isopropoyxbenzoyl)phenylacetate (0.95 g, 2.1 mmol) obtained in Example 122, Step 1, using a 2 mol/L aqueous solution of sodium hydroxide (10 mL), acetonitrile (5 mL) and tetrahydrofuran (5 mL).

$^1$H-NMR (CDCl$_3$, 300 MHz) δ (ppm): 7.82-7.77 (m, 2H), 6.87-6.82 (m, 2H), 6.44 (s, 1H), 6.06 (m, 1H), 5.68 (m, 1H), 5.45 (m, 1H), 5.30 (m, 1H), 5.06-4.99 (m, 2H), 4.65 (m, 1H), 4.57 (m, 2H), 4.38 (m, 2H), 3.57 (s, 2H), 2.77 (q, J=7.5 Hz, 2H), 1.35 (d, J=6.0 Hz, 6H), 1.09 (t, J=7.5 Hz, 3H)

APCI-MS (m/z); 439 [M+H]$^+$ (Step 3)

In a manner similar to that in Example 10, Step 2, 2-[3,5-diallyloxy-2-ethyl-6-(4-isopropoxybenzoyl)phenyl]-N,N-bis(2-hydroxyethyl)acetamide was obtained from 3,5-diallyloxy-2-ethyl-6-(4-isopropoxybenzoyl)phenylacetic acid (300 mg, 0.69 mmol) obtained in Example 122, Step 2, using 1-hydroxybenzotriazole hydrate (160 mg, 1.1 mmol), 1-(3-dimethylaminopropyl)-3-ethylcarbodiimide hydrochloride (200 mg, 1.1 mmol), diethanolamine (150 mg, 1.4 mmol) and N,N-dimethylformamide (5 mL).

In a manner similar to that in Example 7, Step 1, Compound 123 (180 mg, 59%) was obtained from 2-[3,5-diallyloxy-2-ethyl-6-(4-isopropoxybenzoyl)phenyl]-N,N-bis(2-hydroxyethyl)acetamide obtained above, using ammonium formate (200 mg, 3.2 mmol), bis(triphenylphosphine)palladium (II) dichloride (25 mg, 0.036 mmol) and 1,4-dioxane (6 mL).

$^1$H-NMR (CD$_3$OD, 300 MHz) δ (ppm): 7.77-7.74 (m, 2H), 6.89-6.86 (m, 2H), 6.31 (s, 1H), 4.69 (m, 1H), 3.69 (s, 2H), 3.60 (t, J=5.8 Hz, 2H), 3.44-3.39 (m, 4H), 3.31-3.27 (m, 2H), 2.52 (q, J=7.5 Hz, 2H), 1.32 (d, J=6.2 Hz, 6H), 1.08 (t, J=7.5 Hz, 3H)

APCI-MS (m/z); 446 [M+H]$^+$

EXAMPLE 123

Synthesis of 2-[2-ethyl-3,5-dihydroxy-6-(4-isopropoxy-benzoyl)phenyl]-N-(2-hydroxyethyl)-N-(2-methoxyethyl)acetamide (Compound 124)

In a manner similar to that in Example 10, Step 2, 2-[3,5-diallyloxy-2-ethyl-6-(4-isopropoxybenzoyl)phenyl]-N-(2-hydroxyethyl)-N-(2-methoxyethyl)acetamide was obtained from 3,5-diallyloxy-2-ethyl-6-(4-isopropoxybenzoyl)phenylacetic acid (300 mg, 0.69 mmol) obtained in Example 122, Step 2, using 1-hydroxybenzotriazole hydrate (160 mg, 1.0 mmol), 1-(3-dimethylaminopropyl)-3-ethylcarbodiimide hydrochloride (200 mg, 1.0 mmol), 2-(2-methoxyethylamino)ethanol (160 mg, 1.4 mmol) obtained in Reference Example 1 and N,N-dimethylformamide (5 mL).

In a manner similar to that in Example 7, Step 1, Compound 124 (150 mg, 47%) was obtained from 2-[3,5-diallyloxy-2-ethyl-6-(4-isopropoxybenzoyl)phenyl]-N-(2-hydroxyethyl)-N-(2-methoxyethyl)acetamide obtained above, using ammonium formate (220 mg, 3.5 mmol), bis(triphenylphosphine)palladium (II) dichloride (25 mg, 0.036 mmol) and 1,4-dioxane (6 mL).

$^1$H-NMR (CD$_3$OD, 300 MHz) δ (ppm): 7.78-7.75 (m, 2H), 6.90-6.85 (m, 2H), 6.31 (s, 1H), 4.69 (m, 1H), 3.69 (d, J=5.3 Hz, 2H), 3.59 (t, J=5.7 Hz, 1H), 3.50 (t, J=4.8 Hz, 1H), 3.43-3.38 (m, 3H), 3.35-3.28 (m, 3.5H), 3.16-3.13 (m, 2.5H), 2.55 (m, 2H), 1.32 (m, 6H), 1.08 (t, J=7.3 Hz, 3H)

APCI-MS (m/z); 460 [M+H]$^+$

EXAMPLE 124

Synthesis of 2-{2-ethyl-3,5-dihydroxy-6-[3-methoxy-4-(2-morpholinoethoxy)benzoyl]phenyl}-N,N-bis(2-methoxyethyl)acetamide (Compound 125)

(Step 1)

In a manner similar to that in Example 10, Step 1, 3,5-diallyloxy-2-ethyl-6-(4-hydroxy-3-methoxybenzoyl)phenylacetic acid was obtained from methyl 3,5-diallyloxy-2-ethyl-6-(4-hydroxy-3-methoxybenzoyl)phenylacetate (1.0 g, 2.3 mmol) obtained in Example 104, Step 1, using a 2 mol/L aqueous solution of sodium hydroxide (20 mL), tetrahydrofuran (10 mL) and acetonitrile (10 mL).

In a manner similar to that in Example 10, Step 2, 2-[3,5-diallyloxy-2-ethyl-6-(4-hydroxy-3-methoxybenzoyl)phenyl]-N,N-bis(2-methoxyethyl)acetamide (550 mg, 44% in 2 steps) was obtained from 3,5-diallyloxy-2-ethyl-6-(4-hydroxy-3-methoxybenzoyl)phenylacetic acid obtained above, using 1-hydroxybenzotriazole hydrate (750 mg, 4.9 mmol), 1-(3-dimethylaminopropyl)-3-ethylcarbodiimide hydrochloride (900 mg, 4.7 mmol), bis(2-methoxyethyl)amine (1.0 mL, 6.7 mmol) and N,N-dimethylformamide (30 mL).

$^1$H-NMR (CD$_3$OD, 300 MHz) δ (ppm): 7.34 (d, J=1.8 Hz, 1H), 7.21 (dd, J=8.7 Hz, 1.8 Hz, 1H), 6.68 (d, J=8.7 Hz, 1H), 6.51 (s, 1H), 6.02 (m, 1H), 5.65 (m, 1H), 5.45 (m, 1H), 5.29 (m, 1H), 4.99-4.91 (m, 2H), 4.64 (m, 2H), 4.40 (m, 2H), 3.76 (s, 3H), 3.66 (s, 2H), 3.42-3.22 (m, 4H), 3.27-3.22 (m, 5H), 3.07-3.04 (m, 5H), 2.52 (q, J=7.3 Hz, 2H), 1.11 (t, J=7.3 Hz, 3H)

APCI-MS (m/z); 542 [M+H]$^+$ (Step 2)

In a manner similar to that in Example 101, Step 1, 2-{3,5-diallyloxy-2-ethyl-6-[3-methoxy-4-(2-morpholinoethoxy)benzoyl]phenyl}-N,N-bis(2-methoxyethyl)acetamide (180 mg, 98%) was obtained from 2-[3,5-diallyloxy-2-ethyl-6-(4-hydroxy-3-methoxybenzoyl)phenyl]-N,N-bis(2-methoxyethyl)acetamide (150 mg, 0.28 mmol) obtained in Example 124, Step 1, using N-(2-chloroethyl)morpholine hydrochloride (80 mg, 0.43 mmol), potassium carbonate (120 mg, 0.86 mmol), sodium iodide (20 mg, 0.13 mmol) and N,N-dimethylformamide (3.0 mL).

$^1$H-NMR (CD$_3$OD, 300 MHz) δ (ppm): 7.46 (d, J=1.8 Hz, 1H), 7.38 (dd, J=8.7 Hz, 1.8 Hz, 1H), 6.96 (d, J=8.7 Hz, 1H), 6.60 (s, 1H), 6.11 (m, 1H), 5.72 (m, 1H), 5.15 (m, 1H), 5.30 (m, 1H), 4.99-4.91 (m, 2H), 4.63 (m, 2H), 4.44 (m, 2H), 4.21 (t, J=5.7 Hz, 2H), 3.83 (s, 3H), 3.77 (s, 2H), 3.71 (m, 4H), 3.52-3.42 (m, 4H), 3.32 (t, J=6.8 Hz, 2H), 3.33 (s, 3H), 3.17 (t, J=5.4 Hz, 2H), 3.15 (s, 3H), 2.83 (t, J=5.7 Hz, 2H), 2.63-2.57 (m, 6H), 1.11 (t, J=7.3 Hz, 3H)

APCI-MS (m/z); 655 [M+H]$^+$ (Step 3)

In a manner similar to that in Example 7, Step 1, Compound 125 (63 mg, 41%) was obtained from 2-{3,5-diallyloxy-2-ethyl-6-[3-methoxy-4-(2-morpholinoethoxy)benzoyl]phenyl}-N,N-bis(2-methoxyethyl)acetamide (180 mg, 0.27 mmol) obtained in Example 124, Step 2, using ammonium formate (90 mg, 1.4 mmol), bis(triphenylphosphine)palladium (II) dichloride (20 mg, 0.029 mmol) and 1,4-dioxane (3 mL).

$^1$H-NMR (CD$_3$OD, 300 MHz) δ (ppm): 7.47 (d, J=2.2 Hz, 1H), 7.41 (dd, J=8.5, 2.2 Hz, 1H), 6.95 (d, J=8.5 Hz, 1H), 6.31 (s, 1H), 4.21 (t, J=5.5 Hz, 2H), 3.83 (s, 3H), 3.71-3.87 (m, 6H), 3.46-3.40 (m, 4H), 3.35-3.29 (m, 5H), 3.17-3.13 (m, 5H), 2.83 (t, J=5.5 Hz, 2H), 2.63-2.60 (m, 4H), 2.52 (q, J=7.5 Hz, 2H), 1.08 (t, J=7.5 Hz, 3H)

APCI-MS (m/z); 575 [M+H]$^+$

EXAMPLE 125

Synthesis of 2-{2-ethyl-3,5-dihydroxy-6-[4-(2-hydroxyethoxy)-3-methoxybenzoyl]phenyl}-N,N-bis(2-methoxyethyl)acetamide (Compound 126)

(Step 1)

In a manner similar to that in Example 101, Step 1, 2-{3,5-diallyloxy-2-ethyl-6-[3-methoxy-4-(2-tetrahydro-2H-pyran-2-ylethoxy)benzoyl]phenyl}-N,N-bis(2-methoxyethyl)acetamide was obtained from 2-[3,5-diallyloxy-2-ethyl-6-(4-hydroxy-3-methoxybenzoyl)phenyl]-N,N-bis(2-methoxyethyl)acetamide (160 mg, 0.30 mmol) obtained in Example 124, Step 1, using 2-(2-bromoethoxy)tetrahydro-2H-pyran (0.1 mL, 0.66 mmol), potassium carbonate (100 mg, 0.73 mmol), sodium iodide (40 mg, 0.27 mmol) and N,N-dimethylformamide (3 mL).

In a manner similar to that in Example 59, Step 2, 2-{3,5-diallyloxy-2-ethyl-6-[4-(2-hydroxyethoxy)-3-methoxybenzoyl]phenyl}-N,N-bis(2-methoxyethyl)acetamide (130 mg, 74%) was obtained from 2-{3,5-diallyloxy-2-ethyl-6-[3-methoxy-4-(2-tetrahydro-2H-pyran-2-ylethoxy)benzoyl]phenyl}-N,N-bis(2-methoxyethyl)acetamide obtained above, using a 4 mol/L solution of hydrogen chloride in L,4-dioxane (1 mL) and methanol (2 mL).

$^1$H-NMR (CDCl$_3$, 300 MHz) δ (ppm): 7.53 (d, J=2.0 Hz, 1H), 7.40 (dd, J=8.4, 2.0 Hz, 1H), 6.82 (d, J=8.4 Hz, 1H), 6.07 (m, 1H), 5.68 (m, 1H), 5.45 (m, 1H), 5.28 (m, 1H), 5.07-5.00 (m, 2H), 4.55 (m, 2H), 4.35 (m, 2H), 4.13 (m, 2H), 3.96 (t, J=4.5 Hz, 2H), 3.88 (s, 3H), 3.72 (s, 2H), 3.57-3.38 (m, 4H), 3.35-3.28 (m, 5H), 3.20-3.13 (m, 5H), 2.60 (q, J=7.5 Hz, 2H), 1.09 (t, J=7.5 Hz, 3H)

APCI-MS (m/z); 586 [M+H]$^+$ (Step 2)

In a manner similar to that in Example 7, Step 1, Compound 126 (90 mg, 81%) was obtained from 2-{3,5-diallyloxy-2-ethyl-6-[4-(2-hydroxyethoxy)-3-methoxybenzoyl]phenyl}-N,N-bis(2-methoxyethyl)acetamide (130 mg, 0.22 mmol) obtained in Example 125, Step 1, using ammonium formate (100 mg, 1.6 mmol), bis(triphenylphosphine)palladium (II) dichloride (20 mg, 0.029 mmol) and 1,4-dioxane (3 mL).

$^1$H-NMR (DMSO-d$_6$, 300 MHz) δ (ppm): 9.32 (brs, 1H), 9.03 (brs, 1H), 7.33 (d, J=1.8 Hz, 1H), 7.21 (dd, J=8.8, 1.8 Hz, 1H), 6.94 (d, J=8.8 Hz, 1H), 6.31 (s, 1H), 4.88 (t, J=5.5 Hz, 1H), 4.00 (t, J=7.0 Hz, 2H), 3.75 (s, 3H), 3.71 (m, 2H), 3.49 (s, 2H), 3.39-3.28 (m, 4H), 3.22-3.15 (m, 5H), 3.05-3.01 (m, 5H), 2.35 (q, J=7.5 Hz, 2H), 0.97 (t, J=7.5 Hz, 3H)

APCI-MS (m/z); 506 [M+H]$^+$

EXAMPLE 126

Synthesis of 2-[2-(3,4-dimethoxybenzoyl)-6-ethyl-3,5-dihydroxyphenyl]-N-(3-dimethylaminopropyl)-N-(2-methoxyethyl)acetamide (Compound 127)

(Step 1)

In a manner similar to that in Example 110, Step 2, 2-[3,5-diallyloxy-2-(3,4-dimethoxybenzoyl)-6-ethylphenyl]-N-(3-dimethylaminopropyl)-N-(2-methoxyethyl)acetamide was quantitatively obtained from 3,5-diallyloxy-2-(3,4-dimethoxybenzoyl)-6-ethylphenylacetic acid (0.32 g, 0.72 mmol) obtained in Example 111, Step 1, using 1-(3-dimethylaminopropyl)-3-ethylcarbodiimide hydrochloride (0.21 g, 0.79 mmol), 1-hydroxybenzotriazole hydrate (0.17 g, 0.79 mmol), N-methylmorpholine (0.30 mL, 2.7 mmol), N-(2-methoxyethyl)-N',N'-dimethylpropane-1,3-diamine (0.23 g, 1.4 mmol) obtained in Reference Example 9 and N,N-dimethylformamide (3.0 mL).

$^1$H-NMR (CD$_3$OD, 270 MHz) δ (ppm): 7.45-7.40 (m, 2H), 6.93 (m, 1H), 6.60 and 6.5.9 (s, total 1H), 6.1.1 (m, 1H), 5.69 (m, 1H), 5.46 (m, 1H), 5.27 (m, 1H), 5.05-4.97 (m, 2H), 4.63-4.60 (m, 2H), 4.42-4.39 (m, 2H), 3.87-3.69 (m, 8H), 3.44 (brs, 3H), 3.34-3.14 (m, 6H), 2.66-2.56 (m, 2H), 2.21 (s, 3H), 2.10 (s, 3H), 2.27-2.10 (m, 2H), 1.65 (m, 1H), 1.44 (m, 1H), 1.13-1.07 (m, 3H)

APCI-MS (m/z); 583 [M+H]$^+$ (Step 2)

In a manner similar to that in Example 110, Step 3, Compound 127 (0.14 g, 34%) was obtained from 2-[3,5-diallyloxy-2-(3,4-dimethoxybenzoyl)-6-ethylphenyl]-N-(3-dimethylaminopropyl)-N-(2-methoxyethyl)acetamide (0.47 g, 0.81 mmol) obtained in Example 126; Step 1, using ammonium formate (0.21 g, 3.3 mmol), bis(triphenylphosphine) palladium (II) dichloride (18 mg, 0.026 mmol) and 1,4-dioxane (2.5 mL).

Melting Point: 183-186° C.

$^1$H-NMR (CD$_3$OD, 270 MHz) δ (ppm): 7.45-7.40 (m, 2H), 6.96-6.92 (m, 1H), 6.32 and 6.31 (s, total 1H), 3.87-3.69 (m, 8H), 3.43 (brs, 3H), 3.34-3.14 (m, 6H), 2.55-2.48 (m, 2H), 2.21 (s, 3H), 2.12 (s, 3H), 2.27-2.10 (m, 2H), 1.64 (m, 1H), 1.45 (m, 1H), 1.04-1.17 (m, 3H)

APCI-MS (m/z); 503 [M+H]$^+$

Elemental Analysis: (C$_{27}$H$_{38}$N$_2$O$_7$·0.3H$_2$O)

Found (%): C, 63.85; H, 7.75; N, 5.42.

Calcd. (%): C, 63.84; H, 7.66; N, 5.51

EXAMPLE 127

Synthesis of N-(3-dimethylaminopropyl)-2-[2-ethyl-3,5-dihydroxy-6-(4-methoxybenzoyl)phenyl]-N-(2-methoxyethyl)acetamide (Compound 128)

(Step 1)

In a manner similar to that in Example 110, Step 2, 2-[3,5-diallyloxy-2-ethyl-6-(4-methoxybenzoyl)phenyl]-N-(3-dimethylaminopropyl)-N-(2-methoxyethyl)acetamide was quantitatively obtained from 3,5-diallyloxy-2-ethyl-6-(4-methoxybenzoyl)phenylacetic acid (0.32 g, 0.78 mmol) obtained in Example 110, Step 1, using 1-(3-dimethylaminopropyl)-3-ethylcarbodiimide hydrochloride (0.22 g, 1.2 mmol), 1-hydroxybenzotriazole hydrate (0.18 g, 1.2 mmol), N-methylmorpholine (0.30 mL, 2.7 mmol), N-(2-methoxyethyl)-N',N'-dimethylpropane-1,3-diamine (0.25 g, 1.6 mmol) obtained in Reference Example 9 and N,N-dimethylformamide (3.0 mL).

$^1$H-NMR (CD$_3$OD, 270 MHz) δ (ppm): 7.77-7.73 (m, 2H), 6.94-6.88 (m, 2H), 6.60 and 6.58 (s, total 1H), 6.11 (m, 1H), 5.69 (m, 1H), 5.46 (m, 1H), 5.28 (m, 1H), 5.03-4.95 (m, 2H), 4.64-4.60 (m, 2H), 4.42-4.37 (m, 2H), 3.87-3.69 (m, 5H), 3.45 (brs, 3H), 3.36-3.14 (m, 6H), 2.66-2.56 (m, 2H), 2.21 (s, 3H), 2.11 (s, 3H), 2.27-2.09 (m, 2H), 1.66 (m, 1H), 1.44 (m, 1H), 1.13-1.06 (m, 3H)

APCI-MS (m/z); 553 [M+H]$^+$ (Step 2)

In a manner similar to that in Example 110, Step 3, Compound 128 (0.18 g, 45%) was obtained from 2-[3,5-diallyloxy-2-ethyl-6-(4-methoxybenzoyl)phenyl]-N-(3-dimethylaminopropyl)-N-(2-methoxyethyl)acetamide (0.46 g, 0.84 mmol) obtained in Example 127, Step 1, using ammonium formate (0.21 g, 3.4 mmol), bis(triphenylphosphine)palladium (II) dichloride (18 mg, 0.026 mmol) and 1,4-dioxane (2.5 mL).

Melting Point: 160-163° C.

$^1$H-NMR (CD$_3$OD, 270 MHz) δ (ppm): 7.81-7.76 (m, 2H), 6.93-6.89 (m, 2H), 6.32 and 6.31 (s, total 1H), 3.84 and 3.83 (s, total 3H), 3.71 and 3.64(s, total 2H), 3.43 (brs, 3H), 3.34-3.14 (m, 6H), 2.55-2.48 (m, 2H), 2.21 (s, 3H), 2.13 (s, 3H), 2.28-2.10 (m, 2H), 1.65 (m, 1H), 1.45 (m, 1H), 1.11-1.04 (m, 3H)

APCI-MS (m/z); 473 [M+H]$^+$

Elemental Analysis: (C$_{26}$H$_{36}$N$_2$O$_6$·0.3H$_2$O)

Found (%): C, 65.31; H, 7.81; N, 5.76.

Calcd. (%): C, 65.33; H, 7.72; N, 5.86.

EXAMPLE 128

Synthesis of N-(3-diethylaminoethyl)-2-[2-(3,4-dimethoxybenzoyl)-6-ethyl-3,5-dihydroxyphenyl]-N-(2-methoxyethyl)acetamide (Compound 129)

(Step 1)

In a manner similar to that in Example 110, Step 2, 2-[3,5-diallyloxy-2-(3,4-dimethoxybenzoyl)-6-ethylphenyl]-N-(2-diethylaminoethyl)-N-(2-methoxyethyl)acetamide was quantitatively obtained from 3,5-diallyloxy-2-(3,4-dimethoxybenzoyl)-6-ethylphenylacetic acid (0.31 g, 0.71 mmol) obtained in Example 111, Step 1, using 1-(3-dimethylaminopropyl)-3-ethylcarbodiimide hydrochloride (0.20 g, 1.1 mmol), 1-hydroxybenzotriazole hydrate (0.16 g, 1.1 mmol), N-methylmorpholine (0.30 mL, 2.7 mmol), N,N-diethyl-N'-(2-methoxyethyl)ethylenediamine (0.25 g, 1.4 mmol) obtained in Reference Example 7 and N,N-dimethylformamide (3.0 mL).

$^1$H-NMR (CD$_3$OD, 270 MHz) δ (ppm): 7.44-7.34 (m, 2H), 6.94, (m, 1H), 6.60 and 6.59 (s, total 1H), 6.10 (m, 1H), 5.70 (m, 1H), 5.46 (m, 1H), 5.27 (m, 1H), 5.05-4.97 (m, 2H), 4.63-4.61 (m, 2H), 4.42-4.40 (m, 2H), 3.87-3.71 (m, 8H), 3.45 (brs, 3H), 3.15-3.41 (m, 6H), 2.66-2.36 (m, 7H), 2.13 (m, 1H), 1.13-0.90 (m, 9H)

APCI-MS (m/z); 597 [M+H]$^+$ (Step 2)

In a manner similar to that in Example 110, Step 3, Compound 129 (98 mg, 26%) was obtained from 2-[3,5-diallyloxy-2-(3,4-dimethoxybenzoyl)-6-ethylphenyl]-N-(2-diethylaminoethyl)-N-(2-methoxyethyl)acetamide (0.43 g, 0.72 mmol) obtained in Example 128, Step 1, using ammonium formate (0.18 g, 2.9 mmol), bis(triphenylphosphine) palladium (II) dichloride (15 mg, 0.022 mmol) and 1,4-dioxane (2.5 mL).

Melting Point: 106-109° C.

$^1$H-NMR (CD$_3$OD, 270 MHz) δ (ppm): 7.45-7.43 (m, 2H), 6.98 (d, J=8.9 Hz, 1H), 6.34 (s, 1H), 3.89 (s, 3H), 3.83 (s, 3H), 3.69 (s, 2H), 3.61-3.47 (m, 6H), 3.35 (s, 3H), 3.17-3.03 (m, 6H), 2.56 (q, J=7.3 Hz, 2H), 1.22 (t, J=7.3 Hz, 6H), 1.08 (t, J=7.3 Hz, 3H)

APCI-MS (m/z); 517 [M+H]$^+$

Elemental Analysis: (C$_{18}$H$_{18}$O$_5$·0.3H$_2$O)

Found (%): C, 67.43; H, 5.79; N, 0.

Calcd. (%): C, 67.82; H, 5.86; N, 0.

EXAMPLE 129

Synthesis of N-(2-diethylaminoethyl)-2-[2-ethyl-3,5-dihydroxy-6-(4-methoxybenzoyl)phenyl]-N-(2-methoxyethyl)acetamide (Compound 130)

(Step 1)

In a manner similar to that in Example 110, Step 2, N-(2-diethylaminoethyl)-2-[3,5-diallyloxy-2-ethyl-6-(4-methoxybenzoyl)phenyl]-N-(2-methoxyethyl)acetamide was quantitatively obtained from 3,5-diallyloxy-2-ethyl-6-(4-methoxybenzoyl)phenylacetic acid (0.31 g, 0.76 mmol) obtained in Example 110, Step 11 using 1-(3-dimethylaminopropyl)-3-ethylcarbodiimide hydrochloride (0.22 g, 1.1 mmol), 1-hydroxybenzotriazole hydrate (0.17 g, 1.1 mmol), N-methylmorpholine (0.30 mL, 2.7 mmol), N,N-diethyl-N'-(2-methoxyethyl)ethylenediamine (0.26 g, 1.5 mmol) obtained in Reference Example 7 and N,N-dimethylformamide (3.0 mL).

$^1$H-NMR (CD$_3$OD, 270 MHz) δ (ppm): 7.76-7.72 (m, 2H), 6.93-6.88 (m, 2H), 6.58 and 6.57 (s, total 1H), 6.10 (m, 1H), 5.70 (m, 1H), 5.44 (m, 1H), 5.26 (m, 1H), 5.05-4.94 (m, 2H), 4.62-4.60 (m, 2H), 4.39-4.37 (m, 2H), 3.83-3.70 (m, 5H), 3.45 (brs, 3H), 3.44-3.16 (m, 6H), 2.66-2.35 (m, 7H), 2.14 (m, 1H), 1.11-0.90 (m, 9H)

APCI-MS (m/z); 567 [M+H]$^+$ (Step 2)

In a manner similar to that in Example 110, Step 3, Compound 130 (0.20 g, 53%) was obtained from N-(2-diethylaminoethyl)-2-[3,5-diallyloxy-2-ethyl-6-(4-methoxybenzoyl) phenyl]-N-(2-methoxyethyl)acetamide (0.43 g, 0.77 mmol) obtained in Example 129, Step 1, using ammonium formate (0.19 g, 3.1 mmol), bis(triphenylphosphine)palladium (II) dichloride (16 mg, 0.023 mmol) and 1,4-dioxane (2.5 mL).

Melting Point: 205-208° C.

$^1$H-NMR (CD$_3$OD, 270 MHz) δ (ppm): 7.78 (d, J=9.0 Hz, 2H) 6.95 (d, J=9.0 Hz, 2H), 6.33 (m, 1H), 3.8.6 (s, 3H), 3.68 (s, 2H), 3.62-3.43 (m, 6H), 3.35 (s, 3H), 3.18-3.10 (m, 6H), 2.56 (q, J=7.6 Hz, 2H), 1.22 (t, J=7.3 Hz, 6H), 1.08 (t, J=7.6 Hz, 3H)

APCI-MS (m/z); 487 [M+H]$^+$

Elemental Analysis: (C$_{27}$H$_{38}$N$_2$O$_6$·2.0H$_2$O)

Found (%): C, 61.86; H, 7.80; N, 5.12.

Calcd. (%): C, 62.05; H, 8.10; N, 5.36

EXAMPLE 130

Synthesis of 2-[2-(3,4-dimethoxybenzoyl)-6-ethyl-3,5-dihydroxyphenyl]-1-(4-morpholinopiperidino)ethanone (Compound 131)

(Step 1)

In a manner similar to that in Example 110, Step 2, 2-[3,5-diallyloxy-2-(3,4-dimethoxybenzoyl)-6-ethylphenyl]-1-(4-morpholinopiperidino)ethanone (0.30 g, 94%) was obtained from 3,5-diallyloxy-2-(3,4-dimethoxybenzoyl)-6-ethylphenylacetic acid (0.24 g, 0.54 mmol) obtained in Example 111, Step 1, using 1-(3-dimethylaminopropyl)-3-ethylcarbodiimide hydrochloride (0.16 g, 0.81 mmol), 1-hydroxybenzotriazole hydrate (0.13 g, 0.81 mmol), 4-morpholinopiperidine (0.92 g, 5.4 mmol) and N,N-dimethylformamide (3.0 mL).

$^1$H-NMR (CD$_3$OD, 270 MHz) δ (ppm): 7.44 (d, J=1.9 Hz, 1H), 7.33 (dd, J=1.9, 8.6 Hz, 1H), 6.94 (d, J=8.6 Hz, 1H), 6.59 (s, 1H), 6.11 (m, 1H), 5.71 (m, 1H), 5.46 (m, 1H), 5.28 (m, 1H), 5.07-4.99 (m, 2H), 4.64-4.61 (m, 2H), 4.42-4.40 (m, 2H), 4.28 (m, 1H), 3.90 (m, 1H), 3.87 (s, 3H), 3.83 (s, 3H), 3.75-3.57 (m, 6H), 2.92 (m, 1H), 2.73-2.33 (m, 8H), 1.80-1.64 (m, 2H), 1.18 (m, 1H), 1.09 (t, J=7.3 Hz, 3H), 0.88 (m, 1H)

APCI-MS (m/z); 593 [M+H]$^+$ (Step 2)

In a manner similar to that in Example 110, Step 3, Compound 131 (0.18 g, 74%) was obtained from 2-[3,5-diallyloxy-2-(3,4-dimethoxybenzoyl)-6-ethylphenyl]-1-(4-morpholinopiperidino)ethanone (0.29 g, 0.48 mmol) obtained in Example 130, Step 1, using ammonium formate (0.12 g, 1.9 mmol), bis(triphenylphosphine)palladium (II) dichloride (11 mg, 0.016 mmol) and 1,4-dioxane (3.0 mL). Melting Point: 263-266° C.

$^1$H-NMR (CD$_3$OD, 270 MHz) δ (ppm): 7.45 (d, J=1.9 Hz, 1H), 7.38 (dd, J=1.9, 8.6 Hz, 1H), 6.93 (d, J=8.6 Hz, 1H), 6.32 (s, 1H), 4.28 (m, 1H), 3.87 (s, 3H), 3.84 (s, 3H), 3.92-3.84 (m, 1H), 3.66-3.51 (m, 6H), 2.89 (t, J=12.7 Hz, 1H), 2.65-2.32 (m, 8H), 1.78-1.64 (m, 2H), 1.12(m, 1H), 1.07 (t, J=7.3 Hz, 3H), 0.91 (m, 1H)

APCI-MS (m/z); 513 [M+H]$^+$

Elemental Analysis: (C$_{28}$H$_{36}$N$_2$O$_7$.0.1H$_2$O)
Found (%): C, 65.31; H, 7.18; N, 5.38.
Calcd. (%): C, 65.38; H, 7.09; N, 5.45.

EXAMPLE 131

Synthesis of 2-[2-ethyl-3,5-dihydroxy-6-(4-methoxybenzoyl)phenyl]-1-(4-morpholinopiperidino)ethanone (Compound 132)

(Step 1)

In a manner similar to that in Example 110, Step 2, 2-[3,5-diallyloxy-2-ethyl-6-(4-methoxybenzoyl)phenyl]-1-(4-morpholinopiperidino)ethanone (0.14 g, 43%) was obtained from 3,5-diallyloxy-2-ethyl-6-(4-methoxybenzoyl)phenylacetic acid (0.24 g, 0.59 mmol) obtained in Example 110, Step 1, using 1-(3-dimethylaminopropyl)-3-ethylcarbodiimide hydrochloride (0.17 g, 0.89 mmol), 1-hydroxybenzotriazole hydrate (0.14 g, 0.89 mmol), 4-morpholinopiperidine (1.0 g, 5.8 mmol) and N,N-dimethylformamide (3.0 mL).

$^1$H-NMR (CD$_3$OD, 270 MHz) δ (ppm): 7.73 (d, J=8.9 Hz, 2H), 6.92 (d, J=8.9 Hz, 2H), 6.59 (s, 1H), 6.11 (m, 1H), 5.69 (m, 1H), 5.46 (m, 1H), −5.28 (m, 1H), 5.04-4.96 (m, 2H), 4.64-4.61 (m, 2H), 4.41-4.38 (m, 2H), 4.26 (m, 1H), 3.93 (m, 1H), 3.84 (s, 3H), 3.76-3.59 (m, 6H), 2.94 (m, 1H), 2.69-2.33 (m, 8H), 1.82-1.66 (m, 2H), 1.24 (m, 1H), 1.10 (t, J=7.3 Hz, 3H), 0.97 (m, 1H)

APCI-MS (m/z); 563 [M+H]$^+$ (Step 2)

In a manner similar to that in Example 110, Step 3, Compound 132 (82 mg, 66%) was obtained from 2-[3,5-diallyloxy-2-ethyl-6-(4-methoxybenzoyl)phenyl]-1-(4-morpholinopiperidino)ethanone (0.14, 0.26 mmol) obtained in Example 131, Step 1, using ammonium formate (0.065 g, 1.0 mmol), bis(triphenylphosphine)palladium (II) dichloride (5.4 mg, 0.0077 mmol) and 1,4-dioxane (2.0 mL). Melting Point: 242-244° C.

$^1$H-NMR (CD$_3$OD, 270 MHz) δ (ppm): 7.77 (d, J=8.8 Hz, 2H), 6.91 (d, J=8.8 Hz, 2H), 6.31 (s, 1H), 4.27 (m, 1H), 3.92 (m, 1H), 3.84 (s, 3H), 3.70-3.53 (m, 6H), 2.91 (t, J=12.7 Hz, 1H), 2.63-2.32 (m, 8H), 1.82-1.67 (m, 2H), 1.20 (m, 1H), 1.07 (t, J=7.3 Hz, 3H), 0.98 (m, 1H)

APCI-MS (m/z); 483 [M+H]
Elemental Analysis: (C$_{27}$H$_{34}$N$_2$O$_6$.0.4H$_2$O)
Found (%): C, 66.22; H, 7.12; N, 5.63.
Calcd. (%): C, 66.21; H, 7.16; N, 5.72.

EXAMPLE 132

Synthesis of 2-[2-(4-ethoxybenzoyl)-6-ethyl-3,5-dihydroxyphenyl]-N-(2-methoxyethyl)-N-(2-morpholinoethyl)acetamide (Compound 133)

In a manner similar to that in Example 10, Step 2, 2-[3,5-diallyloxy-2-(4-ethoxybenzoyl)-6-ethylphenyl]-N-(2-methoxyethyl)-N-(2-morpholinoethyl)acetamide was obtained from 3,5-diallyloxy-2-(4-ethoxybenzoyl)-6-ethylphenylacetic acid (340 mg, 0.80 mmol) obtained in Example 120, Step 2, using 1-hydroxybenzotriazole hydrate (190 mg, 1.2 mmol), 1-(3-dimethylaminopropyl)-3-ethylcarbodiimide hydrochloride (230 mg, 1.2 mmol), N-methylmorpholine (0.27 mL, 2.6 mmol), N-(2-methoxyethyl)-2-morpholinoethylamine (300 mg, 1.6 mmol) obtained in Reference Example 5 and N,N-dimethylformamide (8 mL).

In a manner similar to that in Example 7, Step 1, Compound 133 (190 mg, 47%) was obtained from 2-[3,5-diallyloxy-2-(4-ethoxybenzoyl)-6-ethylphenyl]-N-(2-methoxyethyl)-N-(2-morpholinoethyl)acetamide obtained above, using ammonium formate (260 mg, 4.1 mmol), bis(triphenylphosphine)palladium (II) dichloride (50 mg, 0.072 mmol) and 1,4-dioxane (8 mL).

$^1$H-NMR (CD$_3$OD, 300 MHz) δ (ppm): 7.78-7.74 (m, 2H), 6.90-6.86 (m, 2H), 6.32 (m, 1H), 4.08 (q, J=6.9 Hz, 2H), 3.67-3.58 (m, 7H), 3.45-3.42 (m, 4H), 3.35-3.27 (m, 4H), 3.18-3.13 (m, 2H), 2.54-2.40 (m, 7H), 2.21 (, 1H), 1.37 (m, 3H), 1.08 (m, 3H)

APCI-MS (m/z); 515 [M+H]$^+$

EXAMPLE 133

Synthesis of 2-[2-ethyl-3,5-dihydroxy-6-(4-isopropoxy-benzoyl)phenyl]-N-(2-methoxyethyl)-N-(2-morpholinoethyl)acetamide (Compound 134)

In a manner similar to that in Example 10, Step 2, 2-[3,5-diallyloxy-2-ethyl-6-(4-isopropoxybenzoyl)phenyl]-N-(2-methoxyethyl)-N-(2-morpholinoethyl)acetamide was obtained from 3,5-diallyloxy-2-ethyl-6-(4-isopropoxybenzoyl)phenylacetic acid (350 mg, 0.80 mmol) obtained in Example 122, Step 2, using 1-hydroxybenzotriazole hydrate (190 mg, 1.2 mmol), 1-(3-dimethylaminopropyl)-3-ethylcarbodiimide hydrochloride (230 mg, 1.2 mmol), N-methylmorpholine (0.27 mL, 2.6 mmol), N-(2-methoxyethyl)-2-morpholinoethylamine (300 mg, 1.6 mmol) obtained in Reference Example 5 and N,N-dimethylformamide (8 mL).

In a manner similar to that in Example 7, Step 1, Compound 134 (230 mg, 55%) was obtained from 2-[3,5-diallyloxy-2-ethyl-6-(4-isopropoxybenzoyl)phenyl]-N-(2-methoxyethyl)-N-(2-morpholinoethyl)acetamide obtained above, using ammonium formate (260 mg, 4.1 mmol), bis(triphenylphosphine)palladium (II) dichloride (50 mg, 0.072 mmol) and 1,4-dioxane (8 mL).

$^1$H-NMR (CD$_3$OD, 300 MHz) δ (ppm): 7.76-7.74 (m, 2H), 6.89-6.84 (m, 2H), 6.30 (m, 1H), 4.68 (m, 1H), 3.70-3.55 (m, 6H), 3.43-3.39 (m, 3H), 3.30-3.24 (m, 4H), 3.19-3.15 (m, 2H), 2.57-2.48 (m, 2H), 2.42-2.27 (m, 5H), 2.04 (m, 1H), 1.37 (m, 6H), 1.08 (m, 3H)

APCI-MS (m/z); 529 [M+H]$^+$

EXAMPLE 134

Synthesis of 2-[2-bromo-3,5-dihydroxy-6-(4-methoxybenzoyl)phenyl]-N-(2-hydroxyethyl)-N-(2-methoxyethyl)acetamide (Compound 135)

(Step 1)

In a manner similar to that in Example 88, Step 1, methyl 3,5-dihydroxy-2-(4-methoxybenzoyl)phenylacetate (2.9 g, 82%) was obtained from methyl 3,5-dihydroxyphenylacetate (2.0 g, 11 mmol), using 4-methoxybenzoic acid (2.0 g, 13 mmol) and boron trifluoride diethyl etherate (40 mL).

$^1$H-NMR (CDCl$_3$, 300 MHz) δ (ppm): 7.69-7.64 (m, 2H), 6.90-6.87 (m, 2H), 6.32 (s, 2H), 3.86 (s, 3H), 3.48 (s, 3H), 3.36 (s, 2H)

APCI-MS (m/z); 315 [M−H]$^-$ (Step 2)

Methyl 3,5-dihydroxy-2-(4-methoxybenzoyl)phenylacetate (2.8 g, 8.9 mmol) obtained in Example 134, Step 1 was dissolved in dichloromethane (50 mL), and diisopropylethylamine (4.5 mL, 26 mmol) and chloromethyl methyl ether (2.0 mL, 26 mmol) were successively added dropwise thereto with stirring under ice-cooling. After the reaction mixture was stirred at room temperature for 2 hours, water was added thereto for liquid separation, and the aqueous layer was extracted with chloroform. The organic layers were combined, washed with a saturated aqueous solution of sodium chloride, dried over anhydrous sodium sulfate, and then concentrated under reduced pressure. The resulting residue was purified by silica gel column chromatography (ethyl acetate/hexane=1/9-1/2) to obtain methyl 3,5-bis(methoxymethoxy)-2-(4-methoxybenzoyl)phenylacetate (3.0 g, 83%).

$^1$H-NMR (CClD$_3$, 300 MHz) δ (ppm): 7.82-7.79 (m, 2H), 6.91-6.88 (m, 2H), 6.80 (d, J=2.1 Hz, 1H), 6.70 (d, J=2.1 Hz, 1H), 5.20 (s, 2H), 4.98 (s, 2H), 3.86 (s, 3H), 3.54 (s, 2H), 3.50 (s, 3H), 3.46 (s, 3H), 3.24 (s, 3H)

APCI-MS (m/z); 405 [M+H]$^+$ (Step 3)

Methyl 3,5-bis(methoxymethoxy)-2-(4-methoxybenzoyl) phenylacetate (490 mg, 1.2 mmol) obtained in Example 134, Step 2 was dissolved in N,N-dimethylformamide (10 mL), and N-bromosuccinimide (220 mg, 1.2 mmol) was added thereto, followed by stirring at room temperature for 3 hours. To the reaction mixture was added water for liquid separation, and the aqueous layer was extracted with ethyl acetate. The organic layers were combined, dried over anhydrous sodium sulfate, and then concentrated under reduced pressure. The resulting residue was purified by silica gel column chromatography (ethyl acetate/hexane=1/4-1/1) to obtain methyl 3,5-bis(methoxymethoxy)-2-bromo-6-(4-methoxybenzoyl) phenylacetate (520 mg, 89%).

$^1$H-NMR (CDCl$_3$, 300 MHz) δ (ppm): 7.82-7.79 (m, 2H), 7.00 (s, 1H), 6.91-6.88 (m, 2H), 5.29 (s, 2H), 4.99 (s, 2H), 3.86 (s, 3H), 3.74 (s, 2H), 3.55 (s, 3H), 3.53 (s, 3H), 3.24 (s, 3H)

APCI-MS (m/z); 483, 485 [M+H]$^+$ (Step 4)

In a manner similar to that in Example 10, Step 1, 3,5-bis (methoxymethoxy)-2-bromo-6-(4-methoxybenzoyl)phenylacetic acid was obtained from methyl 3,5-bis(methoxymethoxy)-2-bromo-6-(4-methoxybenzoyl)phenylacetate (520 mg, 1.1 mmol) obtained in Example 134, Step 3, using a 2 mol/L aqueous solution of sodium hydroxide (5 mL) and acetonitrile (5 mL).

In a manner similar to that in Example 10, Step 2, 2-[3,5-bis(methoxymethoxy)-2-bromo-6-(4-methoxybenzoyl)phenyl]-N-(2-hydroxyethyl)-N-(2-methoxyethyl)acetamide (310 mg, 51% in 2 steps) was obtained from 3,5-bis(methoxymethoxy)-2-bromo-6-(4-methoxybenzoyl)phenylacetic acid obtained above, using 1-hydroxybenzotriazole hydrate (240 mg, 1.6 mmol), 1-(3-dimethylaminopropyl)-3-ethylcarbodiimide hydrochloride (300 mg, 1.6 mmol), 2-(2-methoxyethylamino)ethanol (250 mg, 2.1 mmol) obtained in Reference Example 1 and N,N-dimethylformamide (10 mL).

$^1$H-NMR (CDCl$_3$, 300 MHz) δ (ppm): 7.87-7.84 (m, 2H), 6.99 (s, 0.5H), 6.98 (s, 0.5H), 6.91-6.88 (m, 2H), 5.29 (s, 2H), 4.98 (s, 1H), 4.97 (s, 1H), 3.86-3.81 (m, 7H), 3.76-3.60 (m, 2H), 3.54-3.87 (m, 7H), 3.28-3.21 (m, 6H)

APCI-MS (m/z); 570, 572 [M+H]$^+$ (Step 5)

In a manner similar to that in Example 59, Step 2, Compound 135 (180 mg, 47%) was obtained from 2-[3,5-bis (methoxymethoxy)-2-bromo-6-(4-methoxybenzoyl)phenyl]-N-(2-hydroxyethyl)-N-(2-methoxyethyl)acetamide (280 mg, 0.49 mmol) obtained in Example 134, Step 4, using a 4 mol/L solution of hydrogen chloride in 1,4-dioxane (2 mL) and methanol (3 mL).

$^1$H-NMR (CD$_3$OD, 300 MHz) δ (ppm): 7.81-7.78 (m, 2H), 6.95-6.90 (m, 2H), 6.45 (s, 1H), 3.85-3.84 (m, 5H), 3.61 (t, J=5.7 Hz, 1H), 3.53 (t, J=5.1 Hz, 1H), 3.47-3.42 (m, 3H), 3.39-3.28 (m, 3.5H), 3.25-3.21 (m, 2.5H)

APCI-MS (m/z); 482, 484 [M+H]$^+$

EXAMPLE 135

Synthesis of 2-[2-acetyl-3,5-dihydroxy-6-(4-methoxybenzoyl)phenyl]-N-(2-hydroxyethyl)-N-(2-methoxyethyl)acetamide (Compound 136)

(Step 1)

Methyl 3,5-bis (methoxymethoxy)-2-(4-methoxybenzoyl) phenylacetate (0.75 g, 1.9 mmol) obtained in Example 134, Step 2 was dissolved in dichloromethane (20 mL). The resulting solution was cooled to −30° C., and iodine (0.47 g, 1.9 mmol) and [bis(trifluoroacetoxy)iodo]benzene (0.8 g, 1.9 mmol) were successively added thereto in an atmosphere of argon, followed by stirring for 2 hours. To the reaction mixture was added a saturated aqueous solution of sodium thiosulfate, and the mixture was further stirred for one hour, while the temperature was raised to room temperature. To the reaction mixture was added water for liquid separation, and the aqueous layer was extracted with ethyl acetate. The organic layers were combined, dried over anhydrous sodium sulfate, and then concentrated under reduced pressure. The resulting residue was purified by silica gel column chromatography (ethyl acetate/hexane=1/4-1/2) to obtain methyl 3,5-bis(methoxymethoxy)-2-iodo-6-(4-methoxybenzoyl)phenylacetate (0.95 g, 96%).

$^1$H-NMR (CDCl$_3$, 300 MHz) δ (ppm): 7.83-7.80 (m, 2H), 6.93 (s, 1H), 6.92-6.88 (m, 2H), 5.29 ('s, 2H), 5.00 (s, 2H), 3.85 (s, 3H), 3.80 (s, 2H), 3.54 (s, 3H), 3.53 (s, 3H), 3.24 (s, 3H)

APCI-MS (m/z); 531 [M+H]$^+$ (Step 2)

In a manner similar to that in Example 10, Step 1, 3,5-bis(methoxymethoxy)-2-iodo-6-(4-methoxybenzoyl)phenylacetic acid was obtained from methyl 3,5-bis(methoxymethoxy)-2-iodo-6-(4-methoxybenzoyl)phenylacetate (0.94 g; 1.8 mmol) obtained in Example 135, Step 1, using a 2 mol/L aqueous solution of sodium hydroxide (5 mL) and acetonitrile (5 mL).

In a manner similar to that in Example 10, Step 2, 2-[3,5-bis(methoxymethoxy)-2-iodo-6-(4-methoxybenzoyl)phenyl]-N-(2-hydroxyethyl)-N-(2-methoxyethyl)acetamide (0.79 g, 72% in 2 steps) was obtained from 3,5-bis(methoxymethoxy)-2-iodo-6-(4-methoxybenzoyl)phenylacetic acid obtained above, using 1-hydroxybenzotriazole hydrate (0.41 g, 2.7 mmol), 1-(3-dimethylaminopropyl)-3-ethylcarbodiimide hydrochloride (0.51 g, 2.7 mmol), 2-(2-methoxyethylamino)ethanol (0.42 g, 3.5 mmol) obtained in Reference Example 1 and N,N-dimethylformamide (15 mL). $^1$H-NMR (CDCl$_3$, 300 MHz) δ (ppm): 7.87-7.84 (m, 2H), 6.91-6.87 (m, 3H), 5.27 (s, 2H), 4.98 (s, 1H), 4.97 (s, 1H), 3.93-3.84 (m, 8H), 3.54-3.37 (m, 9H), 3.30-3.21 (m, 6H) APCI-MS (m/z); 618 [M+H]$^+$ (Step 3)

2-[3,5-Bis(methoxymethoxy)-2-iodo-6-(4-methoxybenzoyl)phenyl]-N-(2-hydroxyethyl)-N-(2-methoxyethyl)acetamide (0.56 g, 0.91 mmol) obtained in Example 135, Step 2 was dissolved in toluene (10 mL), and ethoxyvinyl tributyltin (0.46 mL, 1.4 mmol) and bis(triphenylphosphine)palladium(II) dichloride (0.05 g, 0.071 mmol) were successively added thereto in an atmosphere of argon. The reaction mixture was stirred for 3 hours under heating and reflux, and then cooled to room temperature. To the mixture was added a saturated aqueous solution of ammonium fluoride, followed by stirring at room temperature for 6 hours. The reaction mixture was filtered through Celite, and the resulting filtrate was extracted with ethyl acetate. The organic layer was dried over anhydrous sodium sulfate and then concentrated under reduced pressure. The resulting residue was dissolved in tetrahydrofuran (10 mL) and a 1 mol/L hydrochloric acid was added thereto with stirring under ice-cooling, followed by stirring at room temperature for 1 hour. The reaction mixture was ice-cooled and neutralized with a saturated aqueous solution of sodium hydrogencarbonate, followed by liquid separation. After the aqueous layer was extracted with ethyl acetate, the organic layers were combined, dried over anhydrous sodium sulfate, and then concentrated under reduced pressure. The resulting residue was dissolved in ethyl acetate (20 mL), and activated carbon (400 mg) was added thereto, followed by stirring at room temperature for 15 hours. The reaction mixture was filtered through Celite, and the obtained filtrate was concentrated under reduced pressure. The resulting residue was purified by silica gel column chromatography (ethyl acetate/methanol=10/0-9/1 to obtain 2-[2-acetyl-3,5-bis(methoxymethoxy)-6-(4-methoxybenzoyl)phenyl]-N-(2-hydroxyethyl)-N-(2-methoxyethyl)acetamide (0.25 g, 51%).

$^1$H-NMR (CDCl$_3$, 300 MHz) δ (ppm): 7.85-7.81 (m, 2H), 6.94-6.88 (m, 3H), 5.25 (s, 2H), 5.02 (s, 1H), 5.01 (s, 1H), 3.85-3.84 (m, 4H), 3.69-3.37 (m, 12H), 3.30-3.21 (m, 6H), 2.59 (s, 1.5H), 2.58 (s, 1.5H)

APCI-MS (m/z); 534 [M+H]$^+$ (Step 4)

In a manner similar to that in Example 59, Step 2, Compound 136 (30 mg, 13%) was obtained from 2-[2-acetyl-3,5-bis(methoxymethoxy)-6-(4-methoxybenzoyl)phenyl]-N-(2-hydroxyethyl)-N-(2-methoxyethyl)acetamide (250 mg, 0.46 mmol) obtained in Example 135, Step 3, using a 4 mol/L solution of hydrogen chloride in 1,4-dioxane (4 mL) and methanol (8 mL).

$^1$H-NMR (CD$_3$OD, 300 MHz) δ (ppm): 7.80-7.77 (m, 2H), 6.95-6.92 (m, 2H), 6.38 (s, 1H), 3.85 (s, 1.5H), 3.84 (s, 1.5H), 3.74 (m, 2H), 3.55-3.36 (m, 4H), 3.35-3.28 (m, 3.5H), 3.18-3.13 (m, 3.5H), 2.52 (s, 1.5H), 2.51 (s, 1.5H)

APCI-MS (m/z); 446 [M+H]$^+$

EXAMPLE 136

Synthesis of 2-{2-[3,4-bis(2-methoxyethoxy)benzoyl]-6-ethyl-3,5-dihydroxyphenyl}-N-bis(2-hydroxyethyl)acetamide (Compound 137)

(Step 1)

In a manner similar to that in Example 101, Step 1, ethyl 3,4-bis(2-methoxyethoxy)benzoate (3.0 g, 95%) was obtained from ethyl 3,4-dihydroxybenzoate (2.0 g, 11 mmol), using 2-bromoethyl methyl ether (2.6 mL, 28 mmol), potassium carbonate (4.5 g, 33 mmol), sodium iodide (0.5 g, 3.4 mmol) and N,N-dimethylformamide (50 mL).

In a manner similar to that in Example 10, Step 1, 3,4-bis(2-methoxyethoxy)benzoic acid (2.0 g, 69%) was obtained from ethyl 3,4-bis(2-methoxyethoxy)benzoate (3.0 g, 11 mmol) obtained above, using a 2 mol/L aqueous solution of sodium hydroxide (10 mL) and acetonitrile (20 mL).

$^1$H-NMR (CD$_3$OD, 300 MHz) δ (ppm): 7.65 (dd, J=8.4, 2.0 Hz, 1H), 7.58 (d, J=2.0 Hz, 1H), 7.03 (d, J=8.4 Hz, 1H), 4.22-4.15 (m, 4H), 3.78-3.74 (m, 4H), 3.48 (s, 3H), 3.42 (s, 3H)

APCI-MS (m/z); 269 [M–H]$^-$ (Step 2)

In a manner similar to that in Example 5, Step 4, methyl 3,5-diallyloxy-2-[3,4-bis(2-methoxyethoxy)benzoyl]-6-ethylphenylacetate (0.48 g, 20%) was obtained from methyl 3,5-diallyloxy-2-ethylphenylacetate (1.3 g, 4.4 mmol) obtained in Example 5, Step 3, using 3,4-bis(2-methoxyethoxy)benzoic acid (1.3 g, 4.8 mmol) obtained in Example 136, Step 1, trifluoroacetic anhydride (0.68 mL, 4.8 mmol) and trifluoroacetic acid (25 mL).

$^1$H-NMR (CD$_3$OD, 300 MHz) δ (ppm): 7.52 (d, J=2.0 Hz, 1H), 7.31 (dd, J=8.4, 2.0 Hz, 1H), 6.83 (d, J=8.4 Hz, 1H), 6.42 (s, 1H), 6.08 (m, 1H), 5.69 (m, 1H), 5.45 (m, 1H), 5.30 (m, 1H), 5.06-4.99 (m, 2H), 4.50 (m, 2H), 4.28 (m, 2H), 4.26-4.16 (m, 4H), 3.83-3.75 (m, 4H), 3.62 (s, 2H), 3.45 (s, 9H), 2.65 (q, J=7.5 Hz, 2H), 1.09 (t, J=7.5 Hz, 3H)

APCI-MS (m/z); 543 [M+H]$^+$ (Step 3)

In a manner similar to that in Example 10, Step 1, 3,5-diallyloxy-2-[3,4-bis(2-methoxyethoxy)benzoyl]-6-ethylphenylacetic acid (0.46 g, 95%) was obtained from methyl 3,5-diallyloxy-2-[3,4-bis(2-methoxyethoxy)-benzoyl]-6- phenylacetate (0.48 g, 0.89 mmol) obtained in Example 136, Step 2, using a 2 mol/L aqueous solution of sodium hydroxide (5 mL) and acetonitrile (10 mL).

$^1$H-NMR (CD$_3$OD, 300 MHz) δ (ppm): 7.52 (d, J=2.0 Hz, 1H), 7.31 (dd, J=8.4, 2.0 Hz, 1H), 6.83 (d, J=8.4 Hz, 1H), 6.42 (s, 1H), 6.08 (m, 1H), 5.69 (m, 1H), 5.45 (m, 1H), 5.30 (m, 1H), 5.06-4.99 (m, 2H), 4.50 (m, 2H), 4.28 (m, 2H), 4.26-4.16 (m, 4H), 3.83-3.75 (m, 4H), 3.62 (s, 2H), 3.45 (s, 6H), 2.65 (q, J=7.5 Hz, 2H), 1.09 (t, J=7.5 Hz, 3H)

APCI-MS (m/z); 543 [M+H]$^+$ (Step 4)

In a manner similar to that in Example 10, Step 2, 2-{3,5-diallyloxy-2-[3,4-bis(2-methoxyethoxy)benzoyl]-6-ethylphenyl}-N,N-bis(2-hydroxyethyl)acetamide was obtained from 3,5-diallyloxy-2-[3,4-bis(2-methoxyethoxy)benzoyl]-6-ethylphenylacetic acid (220 mg, 0.41 mmol) obtained in Example 136, Step 3, using 1-hydroxybenzotriazole hydrate (110 mg, 0.69 mmol), 1-(3-dimethylaminopropyl)-3-ethylcarbodiimide hydrochloride (130 mg, 0.68 mmol), diethanolamine (100 mg, 0.95 mmol) and N,N-dimethylformamide (5 mL).

In a manner similar to that in Example 7, Step 1, Compound 137 (120 mg, 55%) was obtained from 2-{3,5-diallyloxy-2-[3,4-bis(2-methoxyethoxy)benzoyl]-6-ethylphenyl}-N,N-bis(2-hydroxyethyl)acetamide obtained above, using ammonium formate (140 mg, 2.2 mmol), bis(triphenylphosphine)palladium (II) dichloride (30 mg, 0.043 mmol) and 1,4-dioxane (5 mL).

$^1$H-NMR (CD$_3$OD, 300 MHz) δ (ppm): 7.46 (d, J=1.8 Hz, 1H), 7.41 (dd, J=8.4, 1.8 Hz, 1H), 6.95 (d, J=8.4 Hz, 1H), 6.31 (s, 1H), 4.21-4.13 (m, 4H), 3.77-3.72 (m, 4H), 3.68 (s, 2H), 3.59 (t, J=5.8 Hz, 2H), 3.44-3.39 (m, 10H), 3.37-3.27 (m, 2H), 2.54 (q, J=7.5 Hz, 2H), 1.07 (t, J=7.5 Hz, 3H)

APCI-MS (m/z); 536 [M+H]$^+$

EXAMPLE 137

Synthesis of 2-{2-[3,4-bis(2-methoxyethoxy)benzoyl]-3,5-dihydroxy-6-ethylphenyl}-N-(2-hydroxyethyl)-N-(2-methoxy-ethyl)acetamide (Compound 138)

In a manner similar to that in Example 10, Step 2, 2-{3,5-diallyloxy-2-[3,4-bis(2-methoxyethoxy)benzoyl]-6-ethylphenyl}-N-(2-hydroxyethyl)-N-(2-methoxyethyl)acetamide was obtained from 3,5-diallyloxy-2-[3,4-bis(2-methoxyethoxy)benzoyl]-6-ethylphenylacetic acid (220 mg, 0.41 mmol) obtained in Example 136, Step 3, using 1-hydroxybenzotriazole hydrate (110 mg, 0.69 mmol), 1-(3-dimethylaminopropyl)-3-ethylcarbodiimide hydrochloride (130 mg, 0.68 mmol), 2-(2-methoxyethylamino)ethanol (120 mg, 1.0 mmol) obtained in Reference Example 1 and N,N-dimethylformamide (5 mL).

In a manner similar to that in Example 7, Step 1, Compound 138 (120 mg, 53%) was obtained from 2-{3,5-diallyloxy-2-[3,4-bis(2-methoxyethoxy)benzoyl]-6-ethylphenyl}-N-(2-hydroxyethyl)-N-(2-methoxyethyl)acetamide obtained above, using ammonium formate (140 mg, 2.2 mmol), bis(triphenylphosphine)palladium (II) dichloride (30 mg, 0.043 mmol) and 1,4-dioxane (5 mL).

$^1$H-NMR (CD$_3$OD, 300 MHz) δ (ppm): 7.46 (m, 1H), 7.41 (m, 1H), 6.95 (d, J=8.4 Hz, 1H), 6.31 (s, 1H), 4.21-4.13 (m, 4H), 3.77-3.68 (m, 6H), 3.58 (t, J=5.8 Hz, 1H), 3.49 (m, 1H), 3.41-3.38 (m, 9H), 3.35-3.28 (m, 3.5H), 3.15-3.12 (m, 2.5H), 2.53 (q, J=7.5 Hz, 2H), 1.07 (t, J=7.5 Hz, 3H)

APCI-MS (m/z); 550 [M+H]$^+$

EXAMPLE 138

Synthesis of 2-{2-ethyl-3,5-dihydroxy-6-[3-methoxy-4-(2-morpholinoethoxy)benzoyl]phenyl}-N,N-bis(2-methoxyethyl)acetamide hydrochloride (Compound 139)

Compound 125 (110 mg, 0.19 mmol) obtained in Example 124, Step 3 was dissolved in methanol (1.0 mL), and a 10% solution of hydrogen chloride in methanol (1.5 mL, 3.5 mmol) was added thereto with stirring under ice-cooling. The reaction mixture was stirred at room temperature for 30 minutes, and concentrated under reduced pressure. The resulting residue was crystallized from ethanol to obtain Compound 139 (106 mg, 89%).

$^1$H-NMR (DMSO-d$_6$, 300 MHz) δ (ppm): 11.4 (brs, 1H), 9.40 (s, 1H), 9.12 (brs, 1H), 7.37 (d, J=1.8 Hz, 1H), 7.25 (dd, J=8.4, 1.8 Hz, 1H), 7.03 (d, J=8.4 Hz, 1H), 6.35 (s, 1H), 4.48 (brs, 2H), 3.95 (m, 2H), 3.82 (m, 2H), 3.76 (s, 3H), 3.51-3.48 (m, 6H), 3.43-3.30 (m, 4H), 3.23-3.15 (m, 7H), 3.07-3.04 (m 5H), 2.35 (q, J=7.3 Hz, 2H), 0.97 (t, J=7.3 Hz, 3H)

APCI-MS (m/z); 575 [M+H]$^+$

Elemental Analysis: (C$_{30}$H$_{42}$N$_2$O$_9$.HCl.0.5H$_2$O)
Found (%): C, 58.26; H, 7.13; N, 4.41.
Calcd. (%): C, 58.10; H, 7.15; N, 4.52.

EXAMPLE 139

Synthesis of N-(2-dimethylaminoethyl)-2-[2-ethyl-3,5-dihydroxy-6-(4-methoxybenzoyl)phenyl]-N-(3-methoxypropyl)acetamide (Compound 140)

In a manner similar to that in Example 110, Step 2, Compound 140 (0.089 g, 61%) was obtained from 2-ethyl-3,5-dihydroxy-6-(4-methoxybenzoyl)phenylacetic acid (0.10 g, 0.31 mmol) obtained in Example 10, Step 1, using 1-(3-dimethylaminopropyl)-3-ethylcarbodiimide hydrochloride (0.090 g, 0.47 mmol), N-(3-methoxypropyl)-N',N'-dimethylethylenediamine (0.10 g, 0.62 mmol) obtained in Reference Example 10, 1-hydroxybenzotriazole (0.072 g, 0.47 mmol), N-methylmorpholine (0.10 mL, 1.2 mmol) and N,N-dimethylformamide (1.0 mL).

Melting Point: 190-193° C.

$^1$H-NMR (CD$_3$OD, 270 MHz) δ (ppm): 7.78 (d, J=8.9 Hz, 2H), 6.92 (d, J=8.9 Hz, 2H), 6.31 (s, 1H), 3.84 (s, 3H), 3.65 (s, 2H), 3.36-3.15° (m, 9H), 2.55 (q, J=7.3 Hz, 2H), 2.34 (m, 1H), 2.23 (s, 3H), 2.13 (s, 3H), 2.03 (m, 1H), 1.72 (m, 1H), 1.49 (m, 1H), 1.08 (t, J=7.3 Hz, 3H)

APCI-MS (m/z); 473 [M+H]$^+$

Elemental Analysis: (C$_{26}$H$_{36}$N$_2$O$_6$.0.2H$_2$O)
Found (%): C, 65.70; H, 7.71; N, 5.91.
Calcd. (%): C, 65.58; H, 7.71; N, 5.88

EXAMPLE 140

Synthesis of 2-[2-(3,4-dimethoxybenzoyl)-3,5-dihydroxy-6-ethylphenyl]-N-(2-dimethylaminoethyl)-N-(3-methoxypropyl)acetamide (Compound 141)

In a manner similar to that in Example 10, Step 1, Compound 141 (0.087 g, 56%) was obtained from 2-(3,4-dimethoxybenzoyl)-6-ethyl-3,5-dihydroxyphenyl acetic acid (0.11 g, 0.31 mmol) obtained in Example 40, Step 1, using 1-(3-dimethylaminopropyl)-3-ethylcarbodiimide hydrochloride (0.17 g, 0.86 mol), N-(3-methoxypropyl)-N',N'-dimethylethylenediamine (0.18 g, 1.15 mmol) obtained in Reference Example 10, 1-hydroxybenzotriazole (0.13 g, 0.86 mmol), N-methylmorpholine (0.10 mL, 1.2 mmol) and N,N-dimethylformamide (2.0 mL).

Melting Point: 189-191° C.

$^1$H-NMR (CD$_3$OD, 270 MHz) δ (ppm): 7.39-7.46 (m, 2H), 6.96-6.92 (m, 1H), 6.32 (s, 1H), 3.87 (s, 3H), 3.83 (s, 3H), 3.64 (s, 2H), 3.34-3.14 (m, 9H), 2.55 (q, J=7.3 Hz, 2H), 2.32 (m, 1H), 2.22 (s, 3H), 2.11 (s, 3H), 2.00 (m, 1H), 1.70 (m, 1H), 1.49 (m, 1H), 1.07 (t, J=7.3 Hz, 3H)

APCI-MS (m/z); 503 [M+H]$^+$

Elemental Analysis: (C$_{27}$H$_{38}$N$_2$O$_7$)

Found (%): C, 64.24; H, 7.76; N, 5.70.

Calcd. (%): C, 64.52; H, 7.62; N, 5.57

EXAMPLE 141

Synthesis of N-(2-dimethylaminoethyl)-2-[2-ethyl-3,5-dihydroxy-6-(4-methoxybenzoyl)phenyl]-N-(2-methoxyethyl)acetamide hydrochloride (Compound 142)

Compound 11.3 (0.6172 g, 1.346 mmol) obtained in Example 112 was dissolved in ethanol (11 mL). The resulting solution was cooled to 4° C., and a 1.0 mol/L solution of hydrogen chloride in ethanol (1.5 mL) was added thereto, followed by stirring for 20 minutes. The reaction mixture was concentrated under reduced pressure to obtain a quantitative yield of Compound 142.

$^1$H-NMR (CD$_3$OD, 270 MHz) δ (ppm): 7.80 (d, J=9.0 Hz, 2H), 6.97 (d, J=9.0 Hz, 2H), 6.34 (s, 1H), 3.86 (s, 3H), 3.66 (t, J=5.4, 2H), 3.64 (s, 2H), 3.54 (t, J=5.4 Hz, 2H), 3.44 (t, J=4.3 Hz, 2H), 3.33 (s, 3H), 3.25 (t, J=5.7 Hz, 2H), 2.90 (s, 6H), 2.57 (q, J=7.3 Hz, 2H), 1.08 (t, J=7.3 Hz, 3H)

APCI-MS (m/z); 459 [M+H]$^+$

Elemental Analysis: (C$_{25}$H$_{34}$N$_2$O$_6$·HCl·0.9H$_2$O·0.1CH$_3$CH$_2$OH)

Found (%): C, 58.29; H, 7.42; N, 5.84.

Calcd. (%): C, 58.68; H, 7.31; N, 5.43.

EXAMPLE 142

Synthesis of 2-{2-ethyl-3,5-dihydroxy-6-[4-(trifluoromethyl)benzoyl]phenyl}-N,N-bis(2-hydroxyethyl)acetamide (Compound 143)

(Step 1)

In a manner similar to that in Example 88, Step 1, methyl 2-ethyl-3,5-dihydroxy-6-[4-(trifluoromethyl)benzoyl]phenylacetate (2.2 g, 38%) was obtained from methyl 2-ethyl-3,5-dihydroxyphenylacetate (3.1 g, 15 mmol) obtained in Example 7, Step 2, using 4-(trifluoromethyl)benzoyl chloride (3.1 g, 15 mmol) and boron trifluoride diethyl etherate (20 mL).

$^1$H-NMR (CDCl$_3$, 270 MHz) δ (ppm): 7.76 (d, J=7.8 Hz, 2H), 7.67 (d, J=7.8 Hz, 2H), 6.27 (s, 1H), 3.55 (s, 3H), 3.44 (s, 2H), 2.54 (q, J=7.6 Hz, 2H), 1.06 (t, J=7.6 Hz, 3H)

APCI-MS (m/z); 381 [M–H]$^-$ (Step 2)

In a manner similar to that in Example 10, Step 1, 2-ethyl-3,5-dihydroxy-6-[4-(trifluoromethyl)benzoyl]-phenylacetic acid (2.0 g, 99%) was obtained from methyl 2-ethyl-3,5-dihydroxy-6-[4-(trifluoromethyl)benzoyl]phenylacetate (2.2 g, 5.6 mmol) obtained in Example 142, Step 1, using a 2 mol/L aqueous solution of sodium hydroxide (15 mL) and tetrahydrofuran (8 mL).

$^1$H-NMR (CD$_3$OD, 270 MHz) δ (ppm): 7.92 (d, J=7.8 Hz, 2H), 7.70 (d, J=7.8 Hz, 2H), 6.33 (s, 1H), 3.66 (s, 3H), 2.62 (q, J=7.3 Hz, 2H), 1.09 (t, J=7.3 Hz, 3H)

APCI-MS (m/z); 367 [M–H]$^-$ (Step 3)

In a manner similar to that in Example 10, Step 2, Compound 143 (0.38 g, 24%) was obtained from 2-ethyl-3,5-dihydroxy-6-[4-(trifluoromethyl)benzoyl]phenylacetic acid (1.3 g, 3.5 mmol) obtained in Example 142, Step 2, using 1-(3-dimethylaminopropyl)-3-ethylcarbodiimide hydrochloride (0.81 g, 4.2 mmol), diethanolamine (0.55 g, 5.2 mmol) and N,N-dimethylformamide (5 mL).

$^1$H-NMR (CD$_3$OD, 270 MHz) δ (ppm): 7.92 (d, J=8.1 Hz, 2H), 7.68 (d, J=8.1 Hz, 2H), 6.30 (s, 1H), 3.86 (s, 2H), 3.68 (t, J=5.7 Hz, 2H), 3.51 (t, J=5.2 Hz, 2H), 3.43 (t, J=5.2 Hz, 2H), 3.23 (t, J=5.2 Hz, 2H), 2.57 (q, J=7.5 Hz, 2H), 1.08 (t, J=7.5 Hz, 3H)

APCI-MS (m/z); 456 [M+H]$^+$

EXAMPLE 143

Synthesis of 2-{2-ethyl-3,5-dihydroxy-6-[4-(trifluoromethyl)benzoyl]phenyl}-N-(2-hydroxyethyl)-N-(2-methoxyethyl)acetamide (Compound 144)

In a manner similar to that in Example 10, Step 2, Compound 144 (0.45 g, 36%) was obtained from 2-ethyl-3,5-dihydroxy-6-[4-(trifluoromethyl)benzoyl]phenylacetic acid (1.0 g, 2.7 mmol) obtained in Example 142, Step 2, using 1-(3-dimethylaminopropyl)-3-ethylcarbodiimide hydrochloride (0.63 g, 3.3 mmol), 2-(2-methoxyethylamino)ethanol (0.49 g, 4.1 mmol) obtained in Reference Example 1 and N,N-dimethylformamide (10 mL).

$^1$H-NMR (CD$_3$OD, 270 MHz) δ (ppm): 7.91 (d, J=7.8 Hz, 2H), 7.67 (d, J=8.4 Hz, 2H), 6.29 (s, 1H), 3.85 (d, J=3.0 Hz, 2H), 3.67-3.27 (m, 9H), 3.17-3.09 (m, 2H), 2.55 (m, 2H), 1.00 (t, J=7.3 Hz, 3H)

APCI-MS (m/z); 470 [M+H]$^+$

EXAMPLE 144

Synthesis of 2-[2-(3,4-difluorobenzoyl)-6-ethyl-3,5-dihydroxyphenyl]-N,N-bis(2-hydroxyethyl)acetamide (Compound 145)

(Step 1)

In a manner similar to that in Example 88, Step 1, methyl 2-(3,4-difluorobenzoyl)-6-ethyl-3,5-dihydroxyphenylacetate (1.5 g, 28%) was obtained from methyl 2-ethyl-3,5-dihydroxyphenylacetate (3.1 g, 15 mmol) obtained in Example 7, Step 2, using 3,4-difluorobenzoyl chloride (2.6 g, 15 mmol) and boron trifluoride diethyl etherate (20 mL)

$^1$H-NMR (CDCl$_3$, 270 MHz) δ (ppm): 7.79 (brs, 1H), 7.62-7.45 (m, 2H), 7.24 (m, 1H), 6.27 (brs, 1H), 6.19 (s, 1H), 3.62 (s, 3H), 3.47 (s, 2H), 2.54 (q, J=7.6 Hz, 2H), 1.07 (t, J=7.6 Hz, 3H)

APCI-MS (m/z); 349[M–H]$^-$ (Step 2)

In a manner similar to that in Example 10, Step 1, 2-(3,4-difluorobenzoyl)-6-ethyl-3,5-dihydroxyphenylacetic acid (1.1 g, 80%) was obtained from methyl 2-(3,4-difluorobenzoyl)-6-ethyl-3,5-dihydroxyphenylacetate (1.4 g, 4.1 mmol)

obtained in Example 144, Step 1, using a 2 mol/L aqueous solution of sodium hydroxide (10 mL) and tetrahydrofuran (6 mL).

$^1$H-NMR (CD$_3$OD, 270 MHz) δ (ppm): 7.67-7.58 (m, 2H), 7.33-7.30 (m, 1H), 6.33 (s, 1H), 3.60 (s, 2H), 2.61 (q, J=7.6 Hz, 2H), 1.09 (t, J=7.6 Hz, 3H)

APCI-MS (m/z); 335[M−H]$^−$ (Step 3)

In a manner similar to that in Example 10, Step 2, Compound 145 (370 mg, 54%) was obtained from 2-(3,4-difluorobenzoyl)-6-ethyl-3,5-dihydroxyphenylacetic acid (550 mg, 1.6 mmol) obtained in Example 144, Step 2, using 1-(3-dimethylaminopropyl)-3-ethylcarbodiimide hydrochloride (380 mg, 2.0 mmol), diethanolamine (260 mg, 2.5 mmol) and N,N-dimethylformamide (6 mL).

$^1$H-NMR (CD$_3$OD, 300 MHz) δ (ppm): 7.68-7.61 (m, 2H), 7.31 (m, 1H), 6.31 (s, 1H), 3.81 (s, 2H), 3.67 (t, J=4.9 Hz, 2H), 3.51 (t, J=4.9 Hz, 2H), 3.42 (t, J=4.9 Hz, 2H), 3.32 (t, J=4.9 Hz, 2H), 2.56 (q, J=6.7 Hz, 2H), 1.07 (t, J=6.7 Hz, 3H)

APCI-MS (m/z); 424 [M+H]$^+$

EXAMPLE 145

Synthesis of 2-[2-(3,4-difluorobenzoyl)-6-ethyl-3,5-dihydroxyphenyl]-N-(2-hydroxyethyl)-N-(2-methoxyethyl)acetamide (Compound 146)

In a manner similar to that in Example 10, Step 2, Compound 146 (460 mg, 64%) was obtained from 2-(3,4-difluorobenzoyl)-6-ethyl-3,5-dihydroxyphenylacetic acid (560 mg, 1.7 mmol) obtained in Example 144, Step 2, using 1-(3-dimethylaminopropyl)-3-ethylcarbodiimide hydrochloride (380 mg, 2.0 mmol), 2-(2-methoxyethylamino)ethanol (300 mg, 2.5 mmol) obtained in Reference Example 1 and N,N-dimethylformamide (6 mL).

$^1$H-NMR (CD$_3$OD, 300 MHz) δ (ppm): 7.69-7.60 (m, 2H), 7.29-7.26 (m, 1H), 6.31 (s, 1H), 3.81 (s, 2H), 3.66 (t, J=4.9 Hz, 1H), 3.57 (t, J=4.3 Hz, 1H), 3.51-3.17 (m, 9H), 2.55 (m, 2H), 1.00 (t, J=9.7 Hz, 3H)

APCI-MS (m/z); 438 [M+H]$^+$

EXAMPLE 146

Synthesis of 2-{2-ethyl-3,5-dihydroxy-6-[3-methoxy-4-(2-piperidinoethoxy)benzoyl]phenyl}-N,N-bis(2-methoxyethyl)acetamide (Compound 147)

(Step 1)

In a manner similar to that in Example 101, Step 1, 2-{3,5-diallyloxy-2-ethyl-6-[3-methoxy-4-(2-piperidinoethoxy)benzoyl]phenyl}-N,N-bis(2-methoxyethyl)acetamide (175 mg, 97%) was obtained from 2-[3,5-diallyloxy-2-ethyl-6-(4-hydroxy-3-methoxybenzoyl)phenyl]-N,N-bis(2-methoxyethyl)acetamide (150 mg, 0.28 mmol) obtained in Example 124, Step 1, using N-(2-chloroethyl)piperidine hydrochloride (80 mg, 0.44 mmol), potassium carbonate (120 mg, 0.87 mmol) and N,N-dimethylformamide (3 mL).

$^1$H-NMR (CDCl$_3$, 300 MHz) δ (ppm): 7.52 (d, J=1.9 Hz, 1H), 7.38 (dd, J=8.4, 1.9 Hz, 1H), 6.80 (d, J=8.4 Hz, 1H), 6.40 (m, 1H), 6.05 (m, 1H), 5.65 (m, 1H), 5.45 (m, 1H), 5.25 (m, 1H), 5.07-5.00 (m, 2H), 4.55 (m, 2H), 4.36 (m, 2H), 4.18 (t, J=7.2 Hz, 2H), 3.88 (s, 3H), 3.72 (s, 2H), 3.47-3.39 (m, 4H), 3.35 (t, J=5.5 Hz, 2H), 3.29 (s, 3H), 3.20-3.14 (m, 5H), 2.82 (t, J=7.2 Hz, 2H), 2.60 (q, J=7.3 Hz, 2H), 2.56-2.50 (m 4H), 1.64-1.56 (m, 4H), 1.25 (m, 2H), 1.09 (t, J=7.3 Hz, 3H)

APCI-MS (m/z); 653 [M+H]$^+$ (Step 2)

In a manner similar to that in Example 7, Step 1, Compound 147 (1.5 g, 47%) was obtained from 2-{3,5-diallyloxy-2-ethyl-6-[3-methoxy-4-(2-piperidinoethoxy)benzoyl]phenyl}-N,N-bis(2-methoxyethyl)acetamide (175 mg, 0.27 mmol) obtained in Example 146, Step 1, using ammonium formate (70 mg, 1.1 mmol), bis(triphenylphosphine)palladium (II) dichloride (20 mg, 0.029 mmol) and 1,4-dioxane (3 mL).

$^1$H-NMR (CD$_3$OD, 300 MHz) δ (ppm): 7.47 (d, J=1.9 Hz, 1H), 7.40 (dd, J=8.6, 1.9 Hz, 1H), 6.94 (d, J=8.6 Hz, 1H), 6.31 (m, 1H), 4.20 (t, J=5.9 Hz, 2H), 3.92 (s, 3H), 3.70 (s, 2H), 3.47-3.39 (m, 4H), 3.35 (t, J=5.5 Hz, 2H), 3.29 (s, 3H), 3.20-3.14 (m, 5H), 2.82 (t, J=5.5 Hz, 2H), 2.59-2.48 (m, 6H), 1.66-1.58 (m, 4H), 1.48 (m, 2H), 1.07 (t, J=7.3 Hz, 3H)

APCI-MS (m/z); 573 [M+H]$^+$

EXAMPLE 147

Synthesis of 2-(2-ethyl-3,5-dihydroxy-6-{3-methoxy-4-[2-(4-morpholinopiperidino)ethoxy]benzoyl}phenyl)-N,N-bis(2-methoxyethyl)acetamide (Compound 148)

(Step 1)

In a manner similar to that in Example 101, Step 1, 2-{3,5-diallyloxy-2-[4-(2-chloroethoxy)-3-methoxybenzoyl]-6-ethylphenyl}-N,N-bis(2-methoxyethyl)acetamide (46 mg, 83%) was obtained from 2-[3,5-diallyloxy-2-ethyl-6-(4-hydroxy-3-methoxybenzoyl)phenyl]-N,N-bis(2-methoxyethyl)acetamide (50 mg, 0.092 mmol) obtained in Example 124, Step 1, using 1-bromo-2-chloroethane (0.01 mL, 0.12 mmol), potassium carbonate (40 mg, 0.29 mmol) and N,N-dimethylformamide (3 mL).

$^1$H-NMR (CDCl$_3$, 300 MHz) δ (ppm): 7.54 (d, J=2.0 Hz, 1H), 7.40 (dd, J=8.2, 2.0 Hz, 1H), 6.80 (d, J=8.2 Hz, 1H), 6.40 (s, 1H), 6.08 (m, 1H), 5.68 (m, 1H), 5.45 (m, 1H), 5.28 (m, 1H), 5.07-5.00 (m, 2H), 4.55 (m, 2H), 4.36 (m, 2H), 4.28 (t, J=6.3 Hz, 2H), 3.89 (s, 3H), 3.85 (t, J=6.3 Hz, 2H), 3.73 (s, 2H), 3.47-3.40 (m, 4H), 3.34 (t, J=5.6 Hz, 2H), 3.29 (s, 3H), 3.18 (t, J=5.3 Hz, 2H), 3.15 (s, 3H), 2.59 (q, J=7.3 Hz, 2H), 1.09 (t, J=7.3 Hz, 3H)

APCI-MS (m/z); 604 [M+H]$^+$ (Step 2)

2-{3,5-Diallyloxy-2-[4-(2-chloroethoxy)-3-methoxybenzoyl]-6-ethylphenyl}-N,N-bis(2-methoxyethyl)acetamide (45 mg, 0.075 mmol) obtained in Example 147, Step 1 was dissolved in N,N-dimethylformamide. To the solution were successively added potassium carbonate (35 mg, 0.25 mmol), sodium iodide (10 mg, 0.067 mmol) and 4-morpholinopiperidine (20 mg, 0.12 mmol), followed by stirring at 80° C. for 8 hours. To the reaction mixture was added water, and the mixture was extracted with ethyl acetate. The organic layer was washed with a saturated aqueous solution of sodium chloride, dried over anhydrous sodium sulfate, and then concentrated under reduced pressure. The resulting residue was purified by silica gel column chromatography (methanol/chloroform=1/6) to obtain 2-(3,5-diallyloxy-2-ethyl-6-{3-methoxy-4-[2-(4-morpholinopiperidino)ethoxy]benzoyl}phenyl)-N,N-bis(2-methoxyethyliacetamide (43 mg, 78%).

$^1$H-NMR (CDCl$_3$, 270 MHz) δ (ppm): 7.52 (d, J=1.9 Hz, 1H), 7.39 (dd, J=8.6, 1.9 Hz, 1H), 6.80 (d, J=8.6 Hz, 1H), 6.40 (s, 1H), 6.07 (m, 1H), 5.68 (m, 1H), 5.45 (m, 1H), 5.26 (m, 1H), 5.07-5.00 (m, 2H), 4.55 (m, 2H), 4.36 (m, 2H), 4.16 (t, J=6.3 Hz, 2H), 3.88 (s, 3H), 3.75-3.68 (m, 6H), 3.48-3.40 (m, 4H), 3.31 (t, J=5.7 Hz, 2H), 3.15 (s, 3H), 3.18 (t, J=5.4 Hz, 2H), 3.15 (s, 3H), 3.06-3.02 (m, 2H), 2.84 (t, J=6.2 Hz, 2H), 2.64-2.53 (m, 6H), 2.25-2.09 (m, 3H), 1.83-1.79 (m, 4H), 1.58 (m, 2H), 1.09 (t, J=7.3 Hz, 3H)

APCI-MS (m/z); 738 [M+H]$^+$ (Step 3)

In a manner similar to that in Example 7, Step 1, Compound 148 (29 mg, 81%) was obtained from 2-(3,5-diallyloxy-2-ethyl-6-{3-methoxy-4-[2-(4-morpholinopiperidino) ethoxy]benzoyl}phenyl)-N,N-bis(2-methoxyethyl) acetamide (40 mg, 0.054 mmol) obtained in Example 147, Step 2, using ammonium formate (15 mg, 0.24 mmol), bis (triphenylphosphine)palladium (II) dichloride (5 mg, 0.0071 mmol) and 1,4-dioxane (2 mL).

$^1$H-NMR (CD$_3$OD, 300 MHz) δ (ppm): 7.47 (d, J=1.9 Hz, 1H), 7.41 (dd, J=8.4, 1.9 Hz, 1H), 6.94 (d, J=8.4 Hz, 1H), 6.31 (s, 1H), 4.19 (t, J=5.7 Hz, 2H), 3.83 (s, 3H), 3.70-3.67 (m, 6H), 3.47-3.40 (m, 4H), 3.31 (t, J=5.7 Hz, 2H), 3.15 (s, 3H), 3.17-3.13 (m, 5H), 3.09 (brs, 2H), 2.82 (t, J=5.7 Hz, 2H), 2.57-2.48 (m, 6H), 2.21-2.14 (m, 3H), 1.90 (m, 2H), 1.55 (m, 2H), 1.09 (t, J=7.3 Hz, 3H), APCI-MS (m/z); 658 [M+H]$^+$

EXAMPLE 148

Synthesis of 2-{2-ethyl-3,5-dihydroxy-6-[3-methoxy-4-(3-morpholinopropoxy)benzoyl]phenyl}-N,N-bis(2-methoxyethyl)acetamide (Compound 149)

(Step 1)

In a manner similar to that in Example 101, Step 1, 2-{3, 5-diallyloxy-2-[4-(3-chloropropoxy)-3-methoxybenzoyl]-6-ethylphenyl}-N,N-bis(2-methoxyethyl)acetamide (170 mg, 99%) was obtained from 2-[3,5-diallyloxy-2-ethyl-6-(4-hydroxy-3-methoxybenzoyl)phenyl]-N,N-bis(2-methoxyethyl)acetamide (150 mg, 0.28 mmol) obtained in Example 124, Step 1, using 1-bromo-3-chloropropane (0.04 mL, 0.41 mmol), potassium carbonate (120 mg, 0.89 mmol) and N,N-dimethylformamide (3 mL).

$^1$H-NMR (CDCl$_3$, 270 MHz) δ (ppm): 7.53 (d, J=1.9 Hz, 1H), 7.40 (dd, J=8.4, 1.9 Hz, 1H), 6.80 (d, J=8.4 Hz, 1H), 6.41 (s, 1H), 6.07 (m, 1H), 5.69 (m, 1H), 5.45 (m, 1H), 5.28 (m, 1H), 5.07-5.00 (m, 2H), 4.55 (m, 2H), 4.36 (m, 2H), 4.19 (t, J=5.9 Hz, 2H), 3.87 (s, 3H), 3.75 (t, J=6.2 Hz, 2H), 3.72 (s, 2H), 3.47-3.37 (m, 4H), 3.33 (t, J=5.6 Hz, 2H), 3.29 (s, 3H), 3.18 (t, J=5.4 Hz, 2H), 3.15 (s, 3H), 2.59 (q, J=7.3 Hz, 2H), 2.29 (m, 2H), 1.09 (t, J=7.3 Hz, 3H)

APCI-MS (m/z); 618 [M+H]$^+$ (Step 2)

In a manner similar to that in Example 147, Step 2, 2-{3, 5-diallyloxy-2-ethyl-6-[3-methoxy-4-(3-morpholinopropoxy)benzoyl]phenyl}-N,N-bis(2-methoxyethyl)acetamide (170 mg, 99%) was obtained from 2-{3,5-diallyloxy-2-[4-(3-chloropropoxy)-3-methoxybenzoyl]-6-ethylphenyl}-N,N-bis(2-methoxyethyl)acetamide (170 mg, 0.28 mmol) obtained in Example 148, Step 1, using morpholine (0.04 mL, 0.46 mmol), potassium carbonate (120 mg, 0.89 mmol), sodium iodide (50 mg, 0.33 mmol) and N,N-dimethylformamide (3 mL).

$^1$H-NMR (CDCl$_3$, 300 MHz) δ (ppm): 7.52 (d, J=1.6 Hz, 1H), 7.39 (dd, J=7.6, 1.6 Hz, 1H), 6.80 (d, J=7.6 Hz, 1H), 6.41 (s, 1H), 6.08 (m, 1H), 5.68 (m, 1H), 5.45 (m, 1H), 5.28 (m, 1H), 5.07-5.00 (m, 2H), 4.55 (m, 2H), 4.36 (m, 2H), 4.11 (t, J=6.6 Hz, 2H), 3.89 (s, 3H), 3.71-3.68 (m, 6H), 3.47-3.40 (m, 4H), 3.34 (t, J=5.6 Hz, 2H), 3.29 (s, 3H), 3.18 (t, J=5.3 Hz, 2H), 3.15 (s, 3H), 2.61 (q, J=7.3 Hz, 2H), 2.50 (t, J=6.9 Hz, 2H), 2.46-2.43 (m, 4H), 2.03 (m, 2H), 1.09 (t, J=7.3 Hz, 3H)

APCI-MS (m/z); 669 [M+H]$^+$ (Step 3)

In a manner similar to that in Example 7, Step 1, Compound 149 (60 mg, 57%) was obtained from 2-{3,5-diallyloxy-2-ethyl-6-[3-methoxy-4-(3-morpholinopropoxy)benzoyl]phenyl}-N,N-bis(2-methoxyethyl)acetamide (120 mg, 0.18 mmol) obtained in Example 148, Step 2, using ammonium formate (50 mg, 0.79 mmol), bis(triphenylphosphine) palladium (II) dichloride (5 mg, 0.0071 mmol) and 1,4-dioxane (2 mL).

$^1$H-NMR (CDCl$_3$, 300 MHz) δ (ppm): 7.49 (d, J=2.1 Hz, 1H), 7.42 (dd, J=8.4, 2.1 Hz, 1H), 6.95 (d, J=8.4 Hz, 1H), 6.32 (s, 1H), 4.15 (t, J=5.7 Hz, 2H), 3.85 (s, 3H), 3.79 (m, 4H), 3.72 (s, 2H), 3.49-3.43 (m, 4H), 3.34 (t, J=5.2 Hz, 2H), 3.31 (s, 3H), 3.18-3.15 (m, 5H), 2.92-2.85 (m, 6H), 2.50 (t, J=7.3 Hz, 2H), 2.13 (m, 2H), 1.09 (t, J=7.3 Hz, 3H)

APCI-MS (m/z); 589 [M+H]$^+$

EXAMPLE 149

Synthesis of 2-(2-ethyl-3,5-dihydroxy-6-{3-methoxy-4-[2-(4-methylpiperazin-1-yl)-2-oxoethoxy] benzoyl}phenyl)-N,N-bis(2-methoxyethyl)acetamide (Compound 150)

(Step 1)

In a manner similar to that in Example 101, Step 1, 2-{3, 5-diallyloxy-2-ethyl-6-[4-(methoxycarbonylmethoxy)-3-methoxybenzoyl]phenyl}-N,N-bis(2-methoxyethyl)acetamide (170 mg, 99%) was obtained from 2-[3,5-diallyloxy-2-ethyl-6-(4-hydroxy-3-methoxybenzoyl)phenyl]-N,N-bis(2-methoxyethyl)acetamide (50 mg, 0.092 mmol) obtained in Example 124, Step 1, using methyl chloroacetate (0.0-15 mL, 0.17 mmol), potassium carbonate (50 mg, 0.036 mmol) and N,N-dimethylformamide (3 mL).

$^1$H-NMR (CDCl$_3$, 300 MHz) (ppm): 7.54 (d, J=1.8 Hz, 1H), 7.38 (dd, J=8.7, 1.8 Hz, 1H), 6.70 (d, J=8.2 Hz, 1H), 6.40 (s, 1H), 6.08 (m, 1H), 5.68 (m, 1H), 5.45 (m, 1H), 5.28 (m, 1H), 5.07-5.00 (m, 2H), 4.73 (s, 2H), 4.55 (m, 2H), 4.36 (m, 2H), 3.90 (s, 3H), 3.77 (s, 3H), 3.73 (s, 2H), 3.47-3.40 (m, 4H), 3.32 (t, J=5.6 Hz, 2H), 3.29 (s, 3H), 3.21 (t, J=5.3 Hz, 2H), 3.16 (s, 3H), 2.59 (q, J=7.3 Hz, 2H), 1.09 (t, J=7.3 Hz, 3H)

APCI-MS (m/z); 614 [M+H]$^+$ (Step 2)

In a manner similar to that in Example 10, Step 1, 2-{3,5-diallyloxy-6-[4-(carboxymethoxy)-3-methoxybenzoyl]-2-ethylphenyl}-N,N-bis(2-methoxyethyl)acetamide was obtained from 2-{3,5-diallyloxy-2-ethyl-6-[4-(methoxycarbonylmethoxy)-3-methoxybenzoyl]phenyl}-N,N-bis(2-methoxyethyl)acetamide (52 mg, 0.085 mmol) obtained in Example 149, Step 1, using a 2 mol/L aqueous solution of sodium hydroxide (1 mL) and tetrahydrofuran (1 mL).

In a manner similar to that in Example 10, Step 2, 2-(3,5-diallyloxy-2-ethyl-6-{3-methoxy-4-[2-(4-methylpiperazin-1-yl)-2-oxoethoxy]benzoyl}phenyl)-N,N-bis(2-methoxyethyl)acetamide (52 mg, 90% in 2 steps) was obtained from 2-{3,5-diallyloxy-6-[4-(carboxymethoxy)-3-methoxybenzoyl]-2-ethylphenyl}-N,N-bis(2-methoxyethyl)acetamide (450 mg, 1.0 mmol) obtained above, using 1-hydroxybenzotriazole hydrate (20 mg, 0.13 mmol), 1-(3-dimethylaminopropyl)-3-ethylcarbodiimide hydrochloride (25 mg, 0.13 mmol), N-methylpiperidine (0.02 mL, 0.19 mmol) and methylene chloride (1 mL).

¹H-NMR (CDCl₃, 300 MHz) δ (ppm): 7.53 (d, J=2.1 Hz, 1H), 7.38 (dd, J=8.4, 2.1 Hz, 1H), 6.82 (d, J=8.4 Hz, 1H), 6.40 (s, 1H), 6.05 (m, 1H), 5.68 (m, 1H), 5.45 (m, 2H), 5.28 (m, 1H), 5.07-5.00 (m, 2H), 4.76 (s, 2H), 4.55 (m, 2H), 4.36 (m, 2H), 3.88 (s, 3H), 3.71 (s, 2H), 3.68-3.52 (m, 4H), 3.47-3.40 (m, 4H), 3.34 (t, J=5.6 Hz, 2H), 3.29 (s, 3H), 3.23 (t, J=5.3 Hz, 2H), 3.17 (s, 3H), 2.59 (q, J=7.3 Hz, 2H), 2.40-2.35 (m, 4H), 2.20 (s, 3H), 1.09 (t, J=7.3 Hz, 3H)
APCI-MS (m/z); 682 [M+H]⁺

(Step 3)

In a manner similar to that in Example 7, Step 1, Compound 150 (42 mg, 95%) was obtained from 2-(3,5-diallyloxy-2-ethyl-6-{3-methoxy-4-[2-(4-methylpiperazin-1-yl)-2-oxoethoxy]benzoyl}phenyl)-N,N-bis(2-methoxyethyl) acetamide (50 mg, 0.073 mmol) obtained in Example 149, Step 2, using ammonium formate (20 mg, 0.32 mmol), bis(triphenylphosphine)palladium (II) dichloride (5 mg, 0.0071 mmol) and 1,4-dioxane (2 mL).

¹H-NMR (CD₃OD, 300 MHz) δ (ppm): 7.49 (d, J=1.8 Hz, 1H), 7.39 (dd, J=8.7, 1.8 Hz; 1H), 6.90 (d, J=8.7 Hz, 1H), 6.32 (s, 1H), 4.88 (s, 2H), 3.85 (s, 3H), 3.71-3.68 (m, 6H), 3.47-3.40 (m, 4H), 3.34 (t, J=5.6 Hz, 2H), 3.29 (s, 3H), 3.23 (t, J=5.3 Hz, 2H), 3.17 (s, 3H), 2.81-2.74 (m, 4H), 2.52-2.49 (m, 5H), 1.09 (t, J=7.3 Hz, 3H)
APCI-MS (m/z); 602 [M+H]⁺

EXAMPLE 150

Synthesis of 2-[2-ethyl-3,5-dihydroxy-6-(3-thienylcarbonyl)phenyl]-N-(2-hydroxyethyl)-N-(2-methoxyethyl)acetamide (Compound 151)

In a manner similar to that in Example 10, Step 1, Compound 151 (0.60 g, 46%) was obtained from 2-ethyl-3,5-dihydroxy-6-(3-thienylcarbonyl)phenylacetic acid (1.0 g, 3.3 mmol) obtained in Example 73, Step 3, using 1-ethyl-3-(3-dimethylaminopropyl)carbodiimide hydrochloride (1.5 g, 7.8 mmol), 2-(2-methoxyethylamino)ethanol (1.6 g, 13 mmol) obtained in Reference Example 1 and N,N-dimethylformamide (7.0 mL).

¹H-NMR (CD₃OD, 270 MHz) δ (ppm): 7.92 (m, 1H), 7.45 (dd, J=1.1, 5.0 Hz, 1H), 7.35 (m, 1H), 6.31 (s, 1H), 3.73 and 3.71 (s, total 2H), 3.63-3.20 (m, 11H), 2.56-2.47 (m, 2H), 1.06 (t, J=7.4 Hz, 3H)
APCI-MS (m/z); 408 [M+H]⁺
Elemental Analysis: (C₂₀H₂₅NO₆S)
Found (%): C, 59.15; H, 6.24; N, 3.35
Calcd. (%): C, 58.95; H, 6.18; N, 3.44.

EXAMPLE 151

Synthesis of 2-[2-ethyl-6-(3-furylcarbonyl)-3,5-dihydroxyphenyl]-N,N-bis(2-hydroxyethyl)acetamide (Compound 152)

(Step 1)

In a manner similar to that in Example 5, Step 4, methyl 3,5-diallyloxy-2-ethyl-6-(3-furylcarbonyl)phenyl-acetate (1.6 g, 80%) was obtained from methyl 3,5-diallyloxy-2-ethylphenylacetate (1.5 g, 5.0 mmol) obtained in Example 5, Step 3, using 3-furancarboxylic acid (1.1 g, 10 mmol), trifluoroacetic anhydride (1.5 mL, 11 mmol) and trifluoroacetic acid (10 mL).

¹H-NMR (CDCl₃, 300 MHz) δ (ppm): 7.72 (m, 1H), 7.39 (m, 1H), 6.79 (m, 1H), 6.43 (s, 1H), 6.07 (m, 1H), 5.82 (m, 1H), 5.45 (m, 1H), 5.30 (m, 1H), 5.19-5.10 (m, 2H), 4.56 (m, 2H), 4.43 (m, 2H), 3.65 (s, 2H), 3.53 (s, 3H), 2.63 (q, J=7.5 Hz, 2H), 1.08 (t, J=7.5 Hz, 3H)
APCI-MS (m/z); 385 [M+H]⁺

(Step 2)

In a manner similar to that in Example 7, Step 1, methyl 2-ethyl-6-(3-furylcarbonyl)-3,5-dihydroxyphenylacetate (1.1 g, 91%) was obtained from methyl 3,5-diallyloxy-2-ethyl-6-(3-furylcarbonyl)phenylacetate (1.6 g, 4.1 mmol) obtained in Example 151, Step 1, using ammonium formate (1.3 g, 20 mmol), bis(triphenylphosphine)palladium (II) dichloride (0.15 g, 0.21 mmol) and 1,4-dioxane (25 mL).

¹H-NMR (CD₃OD, 300 MHz) δ (ppm): 7.80 (m, 1H), 7.58 (m, 1H), 6.74 (m, 1H), 6.34 (s, 1H), 3.57 (s, 2H), 3.51 (s, 3H), 2.55 (q, J=7.5 Hz, 2H), 1.05 (t, J=7.5 Hz, 3H)
APCI-MS (m/z); 303 [M−H]⁻

(Step 3)

In a manner similar to that in Example 10, Step 1, 2-ethyl-6-(3-furylcarbonyl)-3,5-dihydroxyphenylacetic acid (1.0 g, 86%) was obtained from methyl 2-ethyl-6-(3-furylcarbonyl)-3,5-dihydroxyphenylacetate (1.0 g, 3.3 mmol), using a 2 mol/L aqueous solution of sodium hydroxide (10 mL) and tetrahydrofuran (20 mL).

¹H-NMR (DMSO-d₆, 300 MHz) δ (ppm): 12.1 (brs, 1H), 9.49 (s, 1H), 9.27 (s, 1H), 7.87 (m, 1H), 7.69 (m, 1H), 6.69 (m, 1H), 6.37 (s, 1H), 3.37 (s, 2H), 2.55 (q, J=7.5 Hz, 2H), 1.05 (t, J=7.5 Hz, 3H)
APCI-MS (m/z); 289 [M−H]⁻

(Step 4)

In a manner similar to that in Example 10, Step 2, Compound 152 (26 mg, 15%) was obtained from 2-ethyl-6-(3-furylcarbonyl)-3,5-dihydroxyphenylacetic acid (130 mg, 0.45 mmol) obtained in Example 151, Step 3, using 1-hydroxybenzotriazole hydrate (140 mg, 0.91 mmol), 1-ethyl-3-(3-dimethylaminopropyl)carbodiimide hydrochloride (170 mg, 0.90 mmol), diethanolamine (240 mg, 2.3 mmol) and N,N-dimethylformamide (4 mL).

¹H-NMR (CD₃OD, 300 MHz) δ (ppm): 7.82 (m, 1H), 7.51 (m, 1H), 6.75 (m, 1H), 6.32 (s, 1H), 3.73 (s, 2H), 3.66 (t, J=5.8 Hz, 2H), 3.52-3.48 (m, 4H), 3.37 (t, J=5.7 Hz, 2H), 2.52 (q, J=7.5 Hz, 2H), 1.08 (t, J=7.3 Hz, 3H)
APCI-MS (m/z); 378 [M+H]⁺

EXAMPLE 152

Synthesis of 2-[2-ethyl-6-(3-furylcarbonyl)-3,5-dihydroxyphenyl]-N-(2-hydroxyethyl)-N-(2-methoxyethyl)acetamide (Compound 153)

In a manner similar to that in Example 10, Step 2, Compound 153 (34 mg, 19%) was obtained from 2-ethyl-6-(3-furylcarbonyl)-3,5-dihydroxyphenylacetic acid (130 mg, 0.45 mmol) obtained in Example 151, Step 3, using 1-hydroxybenzotriazole hydrate (140 mg, 0.91 mmol), 1-ethyl-3-(3-dimethylaminopropyl)carbodiimide hydrochloride (170 mg, 0.90 mmol), 2-(2-methoxyethylamino)ethanol (270 mg, 2.3 mmol) obtained in Reference Example 1 and N,N-dimethylformamide (4 mL).

¹H-NMR (CD₃OD, 300 MHz) δ (ppm): 7.82 (m, 1H), 7.51 (m, 1H), 6.75 (m, 1H), 6.32 (s, 1H), 3.75 (s, 2H), 3.64 (t, J=5.7 Hz, 1H), 3.56 (t, J=4.8 Hz, 1H), 3.50-3.40 (m, 4H), 3.40-3.24 (m, 5H), 2.50 (m, 2H), 1.05 (t, J=7.3 Hz, 3H)
APCI-MS (m/z); 392 [M+H]⁺

EXAMPLE 153

Synthesis of 4-{2-[2-ethyl-3,5-dihydroxy-6-(3-thienylcarbonyl)phenyl]acetyl}-1-(2-cyanophenyl)piperazin-2-one (Compound 154)

In a manner similar to that in Example 10, Step 1, Compound 154 (67 mg, 42%) was obtained from 2-ethyl-3,5-dihydroxy-6-(3-thienylcarbonyl)phenylacetic acid (0.10 g, 0.33 mmol) obtained in Example 73, Step 3, using 1-ethyl-3-(3-dimethylaminopropyl)carbodiimide (0.12 g, 0.76 mmol), 1-(2-cyanophenyl)piperazin-2-one hydrochloride (0.17 g, 1.5 mmol) obtained by a method similar to the method described in Tetrahedron Lett., 1998, Vol. 39, p. 7459-7462 and N,N-dimethylformamide (1.0 mL).

Melting Point: 239-242° C.

$^1$H-NMR (CD$_3$OD, 270 MHz) δ (ppm): 7.92-7.40 (m, 7H), 6.35 (s, 1H), 4.34 (s, 1H), 4.11 (s, 1H), 3.91-3.63 (m, 6H), 2.61 (q, J=7.3 Hz, 2H), 1.10 (t, J=7.3 Hz, 3H)

ESI-MS (m/z); 490 [M+H]$^+$

Elemental Analysis: (C$_{26}$H$_{23}$N$_{23}$O$_5$S.0.3H$_2$O)

Found (%): C, 63.02; H, 4.73; N, 8.38

Calcd. (%): C, 63.09; H, 4.81; N, 8.49

EXAMPLE 154

Synthesis of 2-[2-ethyl-3,5-dihydroxy-6-(3-thienylcarbonyl)phenyl]-1-[4-(hydroxymethyl)piperidino]ethanone (Compound 155)

In a manner similar to that in Example 10, Step 1, Compound 155 (44 mg, 30%) was obtained from 2-ethyl-3,5-dihydroxy-6 (3-thienylcarbonyl)phenylacetic acid (0.11 g, 0.36 mmol) obtained in Example 73, Step 3, using 1-ethyl-3-(3-dimethylaminopropyl)carbodiimide hydrochloride (0.16 g, 0.76 mmol), 4-piperidinemethanol (0.17 g, 1.4 mmol), 1-hydroxybenzotriazole hydrate (0.14 g, 0.89 mmol) and N,N-dimethylformamide (1.0 mL).

Melting Point: 142-145° C.

$^1$H-NMR (CD$_3$OD, 270 MHz) δ (ppm): 7.90 (dd, J=1.3, 3.0 Hz, 1H), 7.46 (dd, J=1.3, 5.1 HZ, 1H), 7.37 (dd, J=3.0, 5.1 Hz, 1H), 6.32 (s, 1H), 4.29 (m, 1H), 3.91 (m, 1H), 3.68 (d, J=16.6 Hz, 1H), 3.58 (d, J=16.6 Hz, 2H), 3.33 (s, 2H), 2.98-2.88 (m, 1H), 2.62-2.38 (m, 3H), 1.77-1.55 (m, 3H), 1.07 (t, J=7.3 Hz, 3H), 1.01 (m, 1H), 0.76 (m, 1H.

APCI-MS (m/z); 404 [M+H]$^+$

Elemental Analysis: (C$_{21}$H$_{25}$NO$_5$S.0.2H$_2$O)

Found (%): C, 62.03; H, 6.39; N, 3.44.

Calcd. (%): C, 61.96; H, 6.29; N, 3.44

EXAMPLE 155

Synthesis of 2-[2-ethyl-6-(3-furylcarbonyl)-3,5-dihydroxyphenyl]-N,N-bis(2-methoxyethyl)acetamide (Compound 156)

(Step 1)

In a manner similar to that in Example 10, Step 2, Compound 156 (93 mg, 40%) was obtained from 2-ethyl-6-(3-furylcarbonyl)-3,5-dihydroxyphenylacetic acid (170 mg, 0.58 mmol) obtained in Example 151, Step 3, using 1-hydroxybenzotriazole hydrate (130 mg, 0.85 mmol), 1-ethyl-3-(3-dimethylaminopropyl)carbodiimide hydrochloride (165 mg, 0.86 mmol), bis(2-methoxyethyl)amine (170 mg, 1.4 mmol) and N,N-dimethylformamide (5 mL).

$^1$H-NMR (CD$_3$OD, 300 MHz) δ (ppm): 7.79 (dd, J=1.4, 0.81 Hz, 1H), 7.49 (dd, J=2.2, 1.4 Hz, 1H), 6.75 (dd, J=2.2, 0.81 Hz, 1H), 6.28 (s, 1H), 3.71 (s, 2H), 3.53-3.42 (m, 4H), 3.37 (m, 2H), 3.30 (s, 3H), 3.36-3.30 (m, 2H), 3.19 (s, 3H), 2.46 (q, J=7.5 Hz, 2H), 1.02 (t, J=7.5 Hz, 3H) APCI-MS (m/z); 406 [M+H]$^+$

EXAMPLE 156

Synthesis of 2-[2-(1,3-benzodioxol-5-yl)-6-ethyl-3,5-dihydroxyphenyl]-N,N-bis(2-hydroxyethyl)acetamide (Compound 157)

(Step 1)

In a manner similar to that in Example 5, Step 4, methyl 3,5-diallyloxy-2-(1,3-benzodioxol-5-yl)-6-ethylphenylacetate (0.85 g, 91%) was obtained from methyl 3,5-diallyloxy-2-ethylphenylacetate (0.61 g, 2.1 mmol) obtained in Example 5, Step 3, using piperonylic acid (0.70 g, 4.2 mmol), trifluoroacetic anhydride (0.60 mL, 4.3 mmol) and trifluoroacetic acid (10 mL).

$^1$H-NMR (CDCl$_3$, 300 MHz) δ (ppm): 7.38-7.33 (m, 2H), 6.77 (d, J=8.1 Hz, 1H), 6.43 (s, 1H), 6.07 (m, 1H), 6.01 (s, 2H), 5.60 (m, 1H), 5.47 (m, 1H), 5.30 (m, 1H), 5.09-5.03 (m, 2H), 4.57 (m, 2H), 4.38 (m, 2H), 3.62 (s, 2H), 3.48 (s, 3H), 2.64 (q, J=7.5 Hz, 2H), 1.09 (t, J=7.5 Hz, 3H)

APCI-MS (m/z); 439 [M+H]$^+$ (Step 2)

In a manner similar to that in Example 7, Step 1, methyl 2-(1,3-benzodioxol-5-yl)-6-ethyl-3,5-dihydroxyphenylacetate (0.68 g, 98%) was obtained from methyl 3,5-diallyloxy-2-(1,3-benozdioxol-5-yl)-6-ethylphenylacetate (0.85 g, 1.9 mmol) obtained in Example 156, Step 1; using ammonium formate (0.6 g, 9.5 mmol), bis(triphenylphosphine)palladium (II) dichloride (0.06 g, 0.086 mmol) and 1,4-dioxane (1.5 mL).

$^1$H-NMR (CDOD$_3$, 300 MHz) δ (ppm): 7.33 (dd, J=8.3, 1.5 Hz, 1H), 7.25 (d, J=1.5 Hz, 1H), 6.82 (d, J=8.3 Hz, 1H), 6.33 (s, 1H), 6.02 (s, 2H), 3.53 (s, 2H), 3.46 (s, 3H), 2.57 (q, J=7.5 Hz, 2H), 1.08 (t, J=7.5 Hz, 3H) APCI-MS (m/z); 357 [M−H]

(Step 3)

In a manner similar to that in Example 10, Step 1, 2-(1,3-benzodioxol-5-yl)-6-ethyl-3,5-dihydroxyphenylacetic acid (0.49 g, 73%) was obtained from methyl 2-(1,3-benzodioxol-5-yl)-6-ethyl-3,5-dihydroxyphenylacetate (0.68 g, 1.9 mmol) obtained in Example 156, Step 2, using a 2 mol/L aqueous solution of sodium hydroxide (10 mL) and tetrahydrofuran (10 mL).

$^1$H-NMR (CD$_3$OD, 300 MHz) δ (ppm): 7.38 (dd, J=8.3, 1.5 Hz, 1H), 7.27 (d, J=1.5 Hz, 1H), 6.81 (d, J=8.3 Hz, 1H), 6.33 (s, 1H), 6.02 (s, 2H), 3.50 (s, 2H), 2.57 (q, J=7.5 Hz, 2H), 1.08 (t, J=7.5 Hz, 3H)

APCI-MS (m/z); 343 [M−H]$^−$ (Step 4)

In a manner similar to that in Example 10, Step 2, Compound 157 (30 mg, 20%) was obtained from 2-(1,3-benzodioxol-5-yl)-6-ethyl-3,5-dihydroxyphenylacetic acid (120 mg, 0.35 mmol) obtained in Example 156, Step 3, using 1-hydroxybenzotriazole hydrate (80 mg, 0.52 mmol), 1-ethyl-3-(3-dimethylaminopropyl)carbodiimide hydrochloride (100 mg, 0.52 mmol), diethanolamine (200 mg, 1.9 mmol) and N,N-dimethylformamide (4 mL).

$^1$H-NMR (CD$_3$OD, 300 MHz) δ (ppm): 7.38 (dd, J=8.1, 1.8 Hz, 1H), 7.27 (d, J=1.8 Hz, 1H), 6.80 (d, J=8.1 Hz, 1H), 6.31 (s, 1H), 6.02 (s, 2H), 3.69 (s, 2H), 3.61 (t, J=5.8 Hz, 2H), 3.52-3.48 (m, 4H), 3.37-3.28 (m, 2H), 2.52 (q, J=7.3 Hz, 2H), 1.06 (t, J=7.3 Hz, 3H)

APCI-MS (m/z); 432 [M+H]$^+$

EXAMPLE 157

Synthesis of 2-[2-(1,3-benzodioxol-5-yl)-6-ethyl-3, 5-dihydroxyphenyl]-N-(2-hydroxyethyl)-N-(2-methoxyethyl)acetamide (Compound 158)

In a manner similar to that in Example 10, Step 2, Compound 158 (64 mg, 41%) was obtained from 2-(1,3-benzodioxol-5-yl)-6-ethyl-3,5-dihydroxyphenylacetic acid (120 mg, 0.35 mmol) obtained in Example 156, Step 3, using 1-hydroxybenzotriazole hydrate (80 mg, 0.52 mmol), 1-ethyl-3-(3-dimethylaminopropyl)carbodiimide hydrochloride (100 mg, 0.52 mmol), 2-(2-methoxyethylamino)ethanol (200 mg, 1.7 mmol) obtained in Reference Example 1 and N,N-dimethylformamide (4 mL).

$^1$H-NMR (CD$_3$OD, 300 MHz) δ (ppm): 7.39 (m, 1H), 7.28 (m, 1H), 6.80 (m, 1H), 6.30 (s, 1H), 6.02 (s, 2H), 3.69 (d, J=4.7 Hz, 2H), 3.60 (t, J=5.9 Hz, 1H), 3.50 (m, 1H), 3.45-3.40 (m, 4H), 3.38-3.28 (m, 2.5H), 3.18-3.13 (m, 2.5H), 2.54 (m, 2H), 1.06 (t, J=7.3 Hz, 3H)

APCI-MS (m/z); 446 [M+H]$^+$

REFERENCE EXAMPLE 1

Synthesis of 2-(2-methoxyethylamino)ethanol

2-Methoxyethylamine (87 mL, 1.0 mol) was dissolved in water (25 mL), and 2-chloroethanol (34 mL, 0.50 mol) was added dropwise thereto over 20 minutes. The mixture was stirred at room temperature for 3 hours, followed by further stirring at 90° C. for 1 hour. After the reaction mixture was cooled to room temperature, a 48% aqueous solution of sodium hydroxide was added dropwise thereto over 15 minutes. The reaction mixture was concentrated, and the resulting residue was distilled to obtain 2-(2-methoxyethylamino) ethanol (12 g, 20%).

Boiling Point: 90-100° C. (2.0 mmHg)

$^1$H-NMR (CDCl$_3$, 270 MHz) δ (ppm): 3.64 (t, J=5.2 Hz, 2H), 3.50 (t, J=5.2 Hz, 2H), 3.37 (s, 3H), 2.83-2.78 (m, 4H)

REFERENCE EXAMPLE 2

Synthesis of 3-(2-methoxyethylamino)propanol

In a manner similar to that in Reference Example 1, 3-(2-methoxyethylamino)propanol (4.5 g, 43%) was obtained from 2-methoxyethylamine (21 mL, 0.24 mol), using 3-chloropropanol (6.6 mL, 0.079 mol) and water (3.0 mL). Boiling Point: 89-91° C. (1.0 mmHg)

$^1$H-NMR (CDCl$_3$, 270 MHz) δ (ppm): 3.80 (t, J=5.5 Hz, 2H), 3.47 (t, J=5.1 Hz, 2H), 3.35 (s, 3H), 2.88 (t, J=5.5 Hz, 2H), 2.78 (t, J=5.1 Hz, 2H), 1.70 (m, 2H)

REFERENCE EXAMPLE 3

Synthesis of 2-(3-methoxypropylamino)ethanol

In a manner similar to that in Reference Example 2, 2-(3-methoxypropylamino)ethanol (2.0 g, 33%) was obtained from 3-methoxypropylamine (15 mL, 0.15 mol), using 3-chloroethanol (3.0 mL, 0.045 mol) and water (3.0 mL). Boiling Point: 85-96° C. (1.0 mmHg)

$^1$H-NMR (CDCl$_3$, 300 MHz) δ (ppm): 3.64 (t, J=5.2 Hz, 2H), 3.46 (t, J=6.2 Hz, 2H), 3.34 (s, 3H), 2.79-2.69 (m, 4H), 1.76 (m, 2H)

REFERENCE EXAMPLE 4

Synthesis of 2-(2-morpholinoethylamino)ethanol

A mixture of 2-morpholinoethylchloride hydrochloride (23 g, 0.12 mol) and 2-aminoethanol (22 mL, 0.36 mol) was stirred at 140° C. for 5 hours. After the reaction mixture was cooled to room temperature, water (0.10 L) was added thereto. The resulting aqueous solution was saturated with sodium chloride and extracted with chloroform (100 mL×6). The organic layer was dried over anhydrous sodium sulfate and then concentrated under reduced pressure. The resulting residue was distilled to obtain 2-(2-morpholinoethylamino) ethanol (3.4 g, 16%).

Boiling Point: 160° C. (10 mmHg)

$^1$H-NMR (CDCl$_3$, 270 MHz) δ (ppm): 3.73-3.62 (m, 6H), 2.81-2.72 (m, 4H), 2.51-2.44 (m, 6H)

REFERENCE EXAMPLE 5

Synthesis of N-(2-methoxyethyl)-2-morpholinoethylamine

In a manner similar to that in Reference Example 4, N-(2-methoxyethyl)-2-morpholinoethylamine (7.6 g, 40%) was obtained from 2-morpholinoethylchloride hydrochloride (19 g, 0.10 mol) and 2-methoxyethylamine (26 mL, 0.30 mol). Boiling Point: 78-82° C. (1.0 mmHg)

$^1$H-NMR (CDCl$_3$, 270 MHz) δ (ppm): 3.71 (t, J=4.5 Hz, 4H), 3.50 (t, J=5.2 Hz, 2H), 3.36 (s, 3H), 2.82-2.71 (m, 4H), 2.52-2.43 (m, 6H)

REFERENCE EXAMPLE 6

Synthesis of N,N-diethyl-N'-(2-hydroxyethyl)ethylenediamine

A mixture of 2-(diethylamino)ethylchloride hydrochloride (18 g, 0.11 mol) and 2-aminoethanol (19 mL, 0.32 mol) was stirred at 120° C. for 5 hours. After the reaction mixture was cooled to room temperature, a 1.0 mol/L aqueous solution of sodium hydroxide (40 mL) was added thereto, and the mixture was extracted with chloroform (100 mL×6). The organic layer was dried over anhydrous sodium sulfate and then concentrated under reduced pressure. The resulting residue was distilled to obtain N,N-diethyl-N'-(2-hydroxyethyl)ethylenediamine (7.6 g, 45%).

Boiling Point: 140-152° C. (10 mmHg)

$^1$H-NMR (CDCl$_3$, 270 MHz) δ (ppm): 3.63 (m, 2H), 2.80-2.50 (m, 10H), 1.02 (t, J=7.2 Hz, 6H)

REFERENCE EXAMPLE 7

Synthesis of N,N-diethyl-N'-(2-methoxyethyl)ethylenediamine

In a manner similar to that in Reference Example 6, N,N-diethyl-N'-(2-methoxyethyl)ethylenediamine (7.1 g, 38%) was obtained from 2-(diethylamino)ethylchloride hydrochloride (18 g, 0.10 mol) and 2-methoxyethylamine (26 mL, 0.30 mol).

Boiling Point: 45-50° C. (26 mmHg)
$^1$H-NMR (CDCl$_3$, 270 MHz) δ (ppm): 3.50 (t, J=5.2 Hz, 2H) 3.36 (s, 3H), 2.82-2.48 (m, 10H), 1.01 (t, J=7.2 Hz, 6H)

REFERENCE EXAMPLE 8

Synthesis of N-(2-methoxyethyl)-N',N'-dimethylethylenediamine

In a manner similar to that in Reference Example 6, N-(2-methoxyethyl)-N',N'-dimethylethylenediamine (4.7 g, 32%) was obtained from 2-(dimethylamino)ethylchloride hydrochloride (14 g, 0.10 mol) and 2-methoxyethylamine (26 mL, 0.30 mol).
Boiling Point: 71-74° C. (13 mmHg)
$^1$H-NMR (CDCl$_3$, 270 MHz) δ (ppm): 3.50 (t, J=5.1 Hz, 2H), 3.36 (s, 3H), 2.80 (t, J=5.1 Hz, 2H), 2.71 (t, J=6.2 Hz, 2H), 2.42 (t, J=6.2 Hz, 2H), 2.22 (s, 6H)

REFERENCE EXAMPLE 9

Synthesis of N-(2-methoxyethyl)-N',N'-dimethylpropane-1,3-diamine

In a manner similar to that in Reference Example 6, N-(2-methoxyethyl)-N',N'-dimethylpropane-1,3-diamine (4.1 g, 24%) was obtained from 3-(dimethylamino)propylchloride hydrochloride (17 g, 0.10 mol) and 2-methoxyethylamine (28 mL, 0.32 mol).
Boiling Point: 40° C. (1.0 mmHg)
$^1$H-NMR (CDCl$_3$, 270 MHz) δ (ppm): 3.49 (t, J=5.2 Hz, 2H), 2.78 (t, J=5.2 Hz, 2H), 2.65 (t, J=7.2 Hz, 2H), 2.31 (t, J=7.2 Hz, 2H), 2.21 (s, 6H), 1.67 (m, 2H)

REFERENCE EXAMPLE 10

Synthesis of N-(3-methoxypropyl)-N',N'-dimethylethylenediamine

In a manner similar to that in Reference Example 4, N-(3-methoxypropyl)-N',N'-dimethylethylenediamine (10 g, 42%) was obtained from 2-(dimethylamino)ethylchloride hydrochloride (9.4 g, 0.065 mol) and 3-methoxypropylamine (20 mL, 0.20 mol)
Boiling Point: 80° C. (20 mmHg)
$^1$H-NMR (CDCl$_3$, 270 MHz) δ (ppm): 3.44 (t, J=6.2 Hz, 2H), 3.34 (s, 3H), 2.72-2.66 (m, 4H), 2.41 (t, J=7.2 Hz, 2H), 2.21 (s, 6H), 1.77 (m, 2H)

REFERENCE EXAMPLE 11

Synthesis of 2-(furfurylamino)ethanol (Step 1)
2-Aminoethanol (4.0 mL, 66 mmol) was dissolved in N,N-dimethylformamide (50 mL). After the solution was cooled to −10° C., 2-nitrobenzenesulfonyl chloride (12 g, 52 mmol) and pyridine (4.7 mL, 58 mmol) were added dropwise thereto, followed by stirring for 50 minutes, while the temperature was raised to room temperature. To the reaction mixture was added water (0.20 L), and the mixture was extracted with ethyl acetate (0.10 L×6). The organic layer was dried over anhydrous sodium sulfate and then concentrated under reduced pressure to obtain N-(2-hydroxyethyl)-2-nitrobenzenesulfonamide (10 g, 62%).

$^1$H-NMR (CDCl$_3$, 270 MHz) δ (ppm): 8.12 (m, 1H), 7.84 (m, 1H), 7.78-7.72 (m, 2H), 6.04 (t, J=5.3 Hz, 1H), 3.72 (t, J=5.2 Hz, 2H), 3.24 (m, 2H)

(Step 2)
N-(2-Hydroxyethyl)-2-nitrobenzenesulfonamide (15 g, 60 mmol) obtained in Reference Example 11, Step 1 was dissolved in dichloromethane (50 mL). After the solution was cooled to −10° C., 2,3-dihydro-4H-pyran (22 mL, 0.24 mol) and p-toluenesulfonic acid monohydrate (0.42 g, 2.4 mmol) were gradually added thereto, followed by stirring for 10 minutes. To the reaction mixture was added sodium hydrogencarbonate (1.7 g, 20 mmol), and the mixture was filtered. The obtained filtrate was concentrated under reduced pressure, and the resulting residue was purified by silica gel column chromatography (ethyl acetate/hexane=1/1-1/2) to obtain 2-nitro-N-[2-(tetrahydropyran-2-yloxy)ethyl]benzenesulfonamide (20 g, 100%).
$^1$H-NMR (CDCl$_3$, 270 MHz) δ (ppm): 8.14 (m, 1H), 7.87 (m, 1H), 7.75-7.71 (m, 2H), 6.04 (t, J=5.3 Hz, 1H), 4.46 (brs, 1H), 3.82-3.28 (m, 6H), 1.78-1.49 (m, 6H)

(Step 3)
2-Nitro-N-[2-(tetrahydropyran-2-yloxy)ethyl]benzenesulfonamide (7.8 g, 24 mmol) obtained in Reference Example 11, Step 2 was dissolved in toluene (0.26 L). To the solution were added triphenylphosphine (13 g, 48 mmol), furfuryl alcohol (3.0 mL, 35 mmol) and a 40% solution of diethyl azadicarboxylate in toluene (21 g, 48 mmol), followed by stirring at room temperature for 1 hour. The reaction mixture was concentrated under reduced pressure, and the resulting residue was purified by silica gel column chromatography (ethyl acetate/hexane=1/10-2/1) to obtain a quantitative yield of N-furfuryl-2-nitro-N-[2-(tetrahydropyran-2-yloxy) ethyl] benzenesulfonamide. $^1$H-NMR (CDCl$_3$, 270 MHz) δ (ppm): 7.97 (m, 1H), 7.66-7.60 (m, 3H), 6.45 (brs, 1H), 6.27-6.22 (m, 2H), 4.66 (s, 2H), 4.54 (brs, 1H), 3.86-3.79 (m, 2H), 3.58-3.45 (m, 4H), 1.87-1.51 (m, 6H)

(Step 4)
N-Furfuryl-2-nitro-N-[2-(tetrahydropyran-2-yloxy)ethyl] benzenesulfonamide (10 g, 24 mmol) obtained in Reference Example 11, Step 3 was dissolved in acetonitrile (0.10 L). To the solution were added cesium carbonate (24 g, 74 mmol) and thiophenol (3.0 mL, 29 mmol), followed by stirring for 2 hours, while the temperature was raised from room temperature to 80° C. To the reaction mixture was added water, and the mixture was extracted with ethyl acetate. The organic layer was dried over anhydrous sodium sulfate and then concentrated under reduced pressure. The resulting residue was purified by silica gel column chromatography (ethyl acetate-methanol/ethyl acetate=15/85) to obtain N-[2-(tetrahydropyran-2-yloxy)ethyl]furfurylamine (3.6 g, 65%).
$^1$H-NMR (CDCl$_3$, 270 MHz) δ (ppm): 7.35 (dd, J=0.8, 1.8 Hz, 1H), 6.30 (dd, J=1.8, 3.3 Hz, 1H), 6.18 (d, J=0.8, 3.3 Hz, 1H), 4.58 (brs, 1H), 3.90-3.82 (m, 2H), 3.87 (s, 2H), 3.57-3.46 (m, 2H), 2.85-2.80 (m, 2H), 1.87-1.51 (m, 6H)

(Step 5)
To N-[2-(tetrahydropyran-2-yloxy)ethyl]furfurylamine (0.56 g, 2.5 mmol) obtained in Reference Example 11, Step 4 was added a 10% solution of hydrogen chloride in methanol (5.0 mL), followed by stirring at room temperature for 30 minutes. To the reaction mixture was added potassium carbonate (1.1 g, 7.8 mmol), and the mixture was concentrated under reduced pressure. To the resulting residue was added a saturated aqueous solution of sodium chloride, and the mixture was extracted with ethyl acetate. The organic layer was dried over anhydrous sodium sulfate and then concentrated under reduced pressure. The resulting residue was purified by HP-20 column chromatography (Mitsubishi Chemical Corporation; water-acetonitrile/water=40/60) to obtain 2-(furfurylamino)ethanol (61 mg, 18%).

$^1$H-NMR (CD$_3$OD, 270 MHz) δ (ppm): 7.43 (dd, J=0.8, 2.0 Hz, 1H), 6.34 (dd, J=2.0, 3.2 Hz, 1H), 6.27 (dd, J=0.8, 3.2 Hz, 1H), 3.78 (s, 2H), 3.64 (t, J=5.6 Hz, 2H), 2.71 (t, J=5.6 Hz, 2H)

REFERENCE EXAMPLE 12

Synthesis of 4-(methylsulfonyl)piperidine hydrochloride (Step 1) tert-Butyl 4-hydroxypiperidine-1-carboxylate (2.5 g, 12 mmol) and triethylamine (2.1 mL, 15 mmol) were dissolved in dichloromethane (30 mL). To the solution was added a solution of methanesulfonyl chloride (1.2 mL, 15 mmol) in dichloromethane (10 mL), followed by stirring for 4 hours, while the temperature was raised to room temperature. To the reaction mixture was added water (50 mL), and the mixture was stirred for 30 minutes, followed by liquid separation. The organic layer was washed successively with 0.50 mol/L hydrochloric acid (40 mL×2) and a saturated aqueous solution of sodium hydrogencarbonate (10 mL), dried over anhydrous sodium sulfate, and then concentrated under reduced pressure. To the resulting residue was added a mixed solvent of ethyl acetate and hexane (15 mL, ethyl acetate/hexane=1/2), and the precipitated solid was filtered to obtain tert-butyl 4-(methylsulfonyloxy)piperidine-1-carboxylate (3.1 g, 90%).

$^1$H-NMR (CDCl$_3$, 270 MHz) δ (ppm): 4.88 (m, 1H), 3.75-3.66 (m, 2H), 3.35-3.25 (m, 2H), 3.04 (s, 3H), 2.02-1.75 (m 4H), 1.46 (s, 9H)

(Step 2)

tert-Butyl 4-(methylsulfonyloxy)piperidine-1-carboxylate (2.9 g, 10 mmol) obtained in Reference Example 12, Step 1 was dissolved in N,N-dimethylformamide (15 mL), and sodium thiomethoxide (1.6 g, 23 mmol) was added thereto, followed by stirring at 80° C. for 15 hours. To the reaction mixture was added water (20 mL), and the mixture was extracted with diethyl ether (50 mL×4). The organic layer was dried over anhydrous sodium sulfate and then concentrated under reduced pressure to obtain tert-butyl 4-(methylsulfanyl)piperidine-1-carboxylate.

$^1$H-NMR (CDCl$_3$, 270 MHz) δ (ppm): 4.01-3.87 (m, 3H), 3.49 (m, 1H), 2.95-2.80 (m, 2H), 2.74-2.62 (m, 1H), 2.10 (s, 3H), 2.02-1.75 (m, 2H), 1.46 (s, 9H)

(Step 3)

tert-Butyl 4-(methylsulfanyl)piperidine-1-carboxylate obtained in Reference Example 12, Step 2 was dissolved in methanol (24 mL). After the solution was cooled to 4° C., a solution of Oxone® (13 g, 21 mmol) in water (15 mL) was added thereto, followed by stirring for 4.5 hours. To the reaction mixture was added water (20 mL), and the mixture was extracted with ethyl acetate (60 mL×4). The organic layer was dried over anhydrous sodium sulfate and then concentrated under reduced pressure. The resulting residue was purified by silica gel column chromatography (ethyl acetate/hexane=1/1-ethyl acetate) to obtain tert-butyl 4-(methylsulfonyl)-piperidine-1-carboxylate (2.4 g, 88%).

$^1$H-NMR (CDCl$_3$, 270 MHz) δ (ppm): 4.31 (m, 2H), 3.02-2.92 (m, 1H), 2.85 (s, 3H), 2.80-2.71 (m, 2H), 2.15-2.10 (m, 2H), 1.79-1.65 (m, 2H), 1.46 (s, 9H)

(Step 4)

tert-Butyl 4-(methylsulfonyl)piperidine-1-carboxylate (2.4 g, 9.0 mmol) obtained in Reference Example 12, Step 3 was dissolved in ethyl acetate (16 mL), and a 4.0 mol/L solution of hydrogen chloride in dioxane (12 mL) was added thereto, followed by stirring for 3 hours. The precipitated solid was filtered to obtain 4-(methylsulfonyl)piperidine hydrochloride (1.4 g, 76%).

$^1$H-NMR (DMSO-d$_6$, 270 MHz) δ (ppm): 3.41-3.31 (m, 3H), 2.97 (s, 3H), 2.97-2.82 (m, 2H), 2.18-2.13 (m, 2H), 1.92-1.73 (m, 2H)

INDUSTRIAL APPLICABILITY

The present invention provides Hsp90 family protein inhibitors comprising, as an active ingredient, a benzoyl compound or a prodrug thereof, or a pharmaceutically acceptable salt of said benzoyl compound or said prodrug, and the like.

The invention claimed is:

1. A benzoyl compound represented by general formula (IA):

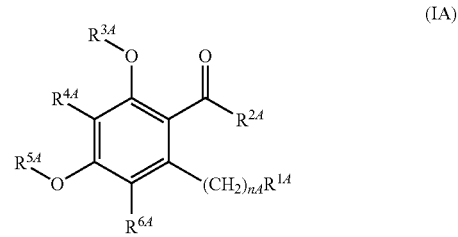

{wherein
nA represents an integer of 1 to 5;
R$^{1A}$ represents substituted or unsubstituted lower alkyl, substituted or unsubstituted lower alkoxy, substituted or unsubstituted cycloalkyl, substituted or unsubstituted lower alkoxycarbonyl, substituted or unsubstituted heterocyclic alkyl, substituted or unsubstituted aryl, CONR$^7$R$^8$ (wherein R$^7$ and R$^8$ independently represent a hydrogen atom, substituted or unsubstituted lower alkyl, substituted or unsubstituted cycloalkyl, substituted or unsubstituted lower alkanoyl, substituted or unsubstituted aryl, a substituted or unsubstituted heterocyclic group, substituted or unsubstituted aralkyl, substituted or unsubstituted heterocyclic alkyl, or substituted or unsubstituted aroyl, or R$^7$ and R$^8$ form a substituted or unsubstituted heterocyclic group together with the adjacent nitrogen atom) or NR$^9$R$^{10}$ (wherein R$^9$ and R$^{10}$ have the same meanings as the above R$^7$ and R$^8$, respectively);
R$^{2A}$ represents substituted or unsubstituted aryl;
R$^{3A}$, R$^{4A}$ and R$^{5A}$ each represent a hydrogen atom; and
R$^{6A}$ represents halogen or lower alkyl, and
wherein (i) substituents in the substituted lower alkyl, the substituted lower alkoxy and the substituted lower alkoxycarbonyl are 1 to 3 substituents which are the same or different selected from the group (A) consisting of hydroxy, oxo, cyano, nitro, carboxy, amino, halogen, substituted or unsubstituted lower alkoxy, cycloalkyl, lower alkanoyl, lower alkoxycarbonyl, lower alkylamino and di-lower alkylamino, wherein substituents in said substituted lower alkoxy are 1 to 3 substituents which are the same or different selected from the group consisting of hydroxy and halogen, and (ii) substituents in the substituted cycloalkyl, the substituted heterocyclic alkyl, the substitued aryl, the substituted lower alkanoyl, the substituted heterocyclic group, the substituted aralkyl, the substituted aroyl and the substituted heterocyclic group formed together with the adjacent nitrogen atom are 1 to 3 substituents which are the same or different selected from the group (B) consisting of hydroxy, halogen, nitro, cyano, amino, carboxy, carbamoyl, substituted or unsubstituted lower alkyl, substituted or unsubstituted lower alkoxy, aralkyloxy, lower alkylsulfonyl, lower alkylsulfanyl, cycloalkyl, lower alkoxycarbonyl, lower alkylamino, di-lower alkylamino, lower alkanoyl, a heterocyclic group, substituted or unsubstituted aryl, substituted or unsubstituted heterocyclic alkyloxy and substituted or unsubstituted heterocyclic carbonylalkyloxy, wherein substituents in said substituted lower alkyl, said substituted lower alkoxy and said substituted aryl are 1 to 3 substituents which are the same or different selected from the group consisting of hydroxy, halogen, lower alkoxy, cyano, lower alkylamino and di-lower alkylamino, and substituents in said substituted heterocyclic alkyloxy and said substituted heterocyclic carbonylalkyloxy are 1 to 3 substituents which are the same or different selected from the group consisting of hydroxy, halogen, lower alkyl, lower alkoxy and a heterocyclic group},
or a pharmaceutically acceptable salt thereof.

2. The benzoyl compound according to claim 1, wherein $R^{2A}$ aryl substituted by 1 to 3 substituents which are the same or different selected from the group (B), or a pharmaceutically acceptable salt thereof.

3. The benzoyl compound according to claim 1 or 2, wherein $R^{1A}$ is $CONR^7R^8$, or a pharmaceutically acceptable salt thereof.

4. The benzoyl compound according to claim 1 or 2, wherein $R^{6A}$ is lower alkyl, or a pharmaceutically acceptable salt thereof.

5. A pharmaceutical composition comprising, as an active ingredient, the benzoyl compound according to claim 4 or a pharmaceutically acceptable salt of said benzoyl compound, together with a pharmaceutically acceptable carrier.

6. The benzoyl compound according to claim 1, wherein nA is 1,
$R^{1A}$ is $CONR^{7a}R^{8a}$ (wherein $R^{7a}$ and $R^{8a}$ independently represent lower alkyl substituted by hydroxy or lower alkoxy), and
$R^{6A}$ is lower alkyl,
or a pharmaceutically acceptable salt thereof.

7. The benzoyl compound according to claim 6, wherein $R^{2A}$ is

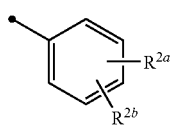

(wherein $R^{2a}$ represents substituted or unsubstituted lower alkoxy, and $R^{2b}$ represents substituted or unsubstituted heterocyclic alkyloxy, wherein substituents in said substituted lower alkoxy are 1 to 3 substituents which are the same or different selected from the group consisting of hydroxy, halogen, lower alkoxy, cyano, lower alkylamino and di-lower alkylamino, and substituents in said substituted heterocyclic alkyloxy are 1 to 3 substituents which are the same or different selected from the group consisting of hydroxy, halogen, lower alkyl, lower alkoxy and a heterocyclic group), or a pharmaceutically acceptable salt thereof.

8. The benzoyl compound according to claim 6, wherein $R^{2A}$ is

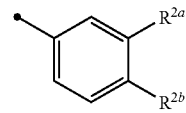

(wherein R represents substituted or unsubstituted lower alkoxy, and $R^{2b}$ represents substituted or unsubstituted heterocyclic alkyloxy, wherein substituents in said substituted lower alkoxy are 1 to 3 substituents which are the same or different selected from the group consisting of hydroxy, halogen, lower alkoxy, cyano, lower alkylamino and di-lower alkylamino, and substituents in said substituted heterocyclic alkyloxy are 1 to 3 substituents which are the same or different selected from the group consisting of hydroxy, halogen, lower alkyl, lower alkoxy and a heterocyclic group), or a pharmaceutically acceptable salt thereof.

9. The benzoyl compound according to claim 6 wherein $R^{2A}$ is

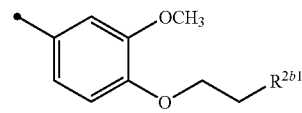

(wherein R represents substituted or unsubstituted morpholino or substituted or unsubstituted piperidino, wherein substituents in said substituted morpholino and said substituted piperidino are 1 to 3 substituents which are the same or different selected from the group consisting of hydroxy, halogen, lower alkyl, lower alkoxy and a heterocyclic group), or a pharmaceutically acceptable salt thereof.

10. A pharmaceutical composition comprising, as an active ingredient, the benzoyl compound according to either one of claims 1 or 2, or a pharmaceutically acceptable salt of said benzoyl compound, together with a pharmaceutically acceptable carrier.

11. A pharmaceutical composition comprising, as an active ingredient, the benzoyl compound according to claim 3, or a pharmaceutically acceptable salt of said benzoyl compound, together with a pharmaceutically acceptable carrier.

12. A pharmaceutical composition comprising, as an active ingredient, the benzoyl compound according to any one of claims 6 to 9, or a pharmaceutically acceptable salt of said benzoyl compound, together with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,538,224 B2 | Page 1 of 14 |
| APPLICATION NO. | : 10/561415 | |
| DATED | : May 26, 2009 | |
| INVENTOR(S) | : Shinji Nara et al. | |

It is certified that error appears in the above-identified patent and that said Letters Patent is hereby corrected as shown below:

ON COVER PAGE [*] NOTICE:

Notice, "This patent is subject to a terminal disclaimer." should be deleted.

COLUMN 2:

Line 39, "(Cell Stress'" should read --(Cell Stress-- and "Vol., 3," should read --Vol. 3,--; and
Line 40, "Vol., 42," should read --Vol. 42,--.

COLUMN 6:

Line 25, "2,4-bis(benzyloxy)-6-(3-oxopentyl)phenyl;" should read --2,4-bis(benzyloxy)-6-(3-oxopentyl)-phenyl;--;
Line 26, "$R^{4A}$ are, each" should read --$R^{4A}$ are each--; and
Line 33, "phenyl]" should read --phenyl,--.

COLUMN 9:

Line 4, "aromatic," should read --aromatic--.

COLUMN 11:

Line 8, "piperiditoalkyl," should read --piperidinoalkyl,--; and
Line 52, "organic" should read --Organic--.

COLUMN 12:

Line 27, "(1999)]" should read --(1999)].--.

COLUMN 15:

Line 5, "agent," should read --agent--;
Line 6, "benziodoxol" should read --benzodioxol--;
Line 9, ""dichloromethane," should read --dichloromethane,--; and
Line 54, "between –20 C." should read --between –20°C.--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 16:

Line 30, "According" should read --according--.

COLUMN 17:

Line 16, "triphenylphosphine" should read --(triphenylphosphine)--.

COLUMN 18:

Line 25, "$R^{1d}$ represents" should read --R represents--; and
Line 53, "with to 5" should read --with 1 to 5--.

COLUMN 19:

Line 51, "material;" should read --material,--.

COLUMN 41:

Line 62, "protien." should read --protein.--.

COLUMN 42:

Line 62, "controls'" should read --controls-- and "which" should read --wherein--; and
Line 63, "compound thereon." should read --compound.--.

COLUMN 43:

Line 41, "treated" should read --treated with--;
Line 54, "Vol., 3," should read --Vol. 3,--; and
Line 55, "Vol., 14," should read --Vol. 14,--.

COLUMN 44:

Line 65, "preferably-0.05" should read --preferably 0.05--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 45:

Line 47, "(4.6 g, 98%). $^1$H-NMR" should read --(4.6 g, 98%) ¶ $^1$H-NMR--.

COLUMN 46:

Line 1, "benzene. $^1$H-NMR" should read --benzene. ¶ $^1$H-NMR--.

COLUMN 47:

Line 3, "3.15 ('s, 3H)" should read --3.15 (s, 3H)--; and
Line 12, "-6 (2-methoxyethyl)" should read -- -6-(2-methoxyethyl)--.

COLUMN 50:

Line 10, "(2-methoxyethyl)" should read --(2-methoxyethyl)- --;
Line 25, "(10' mL)," should read --(10 mL),--; and
Line 44, "270 MHz)." should read --270 MHz)--.

COLUMN 51:

Line 5, "(ddt, J=1.0.6," should read --(ddt, J-10.6,--; and
Line 23, "(30 g, 65%). $^1$H-NMR" should read --(30 g, 65%). ¶ $^1$H-NMR--.

COLUMN 53;

Line 15, "(s, 3H) ESI-MS" should read --(s, 3H) ¶ ESI-MS--.

COLUMN 54:

Line 29, "(0.89 g, 2.4=mol)" should read --(0.89 g, 2.4 mmol)--.

COLUMN 55:

Line 28, "(2'-methoxy-" should read --(2-methoxy- --; and
Line 51, "$^1$H-NMR" should read --¶ $^1$H-NMR--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 56:

Line 54, "(8.0 ml) $^1$H-NMR" should read --(8.0 ml). ¶ $^1$H-NMR--.

COLUMN 57:

Line 28, "97%). $^1$H-NMR" should read --97%). ¶ $^1$H-NMR--;
Line 35, "2-(3,5-diallyloxy 2-" should read --2-(3,5-diallyloxy-2- --; and
Line 39, "(2.0 mL). $^1$H-NMR" should read --(2.0 mL). ¶ $^1$H-NMR--.

COLUMN 58:

Line 4, "0.12 mmol). $^1$H-NMR" should read --0.12 mmol). ¶ $^1$H-NMR--.

COLUMN 60:

Line 23, "anhydrous" should read --over anhydrous-- and "over" should be deleted; and
Line 28, "$^1$HNMR" should read --$^1$H-NMR--.

COLUMN 65:

Line 52, "3H) APCI-MS" should read --3H ¶ APCI-MS--.

COLUMN 67:

Line 14, "(10 mL) $^1$H-NMR" should read --(10 mL) ¶ $^1$H-NMR--.

COLUMN 69:

Line 2, "(1.0 mL)," should read --(1.0 mL).--;
Line 29, "3.42, (brs, 2H)," should read --3.42 (brs, 2H),--;
Line 30, "3H) APCI-MS" should read --3H) ¶ APCI-MS--;
Line 58, "dimethoxybenzoyl" should read --dimethoxybenzoyl)-- and "acid)" should read --acid--; and
Line 59, "phenylacetic acid" should be deleted.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 71:

Line 14, "(1.0 mL). $^1$H-NMR" should read --(1.0 mL). ¶ $^1$H-NMR--; and
Line 56, "46(70" should read --46 (70--.

COLUMN 72:

Line 38, "(1.0 mL). 1H-NMR" should read --(1.0 mL). ¶ $^1$H-NMR--; and
Line 67, "3H) ES-MS" should read --3H) ¶ ES-MS--.

COLUMN 73:

Line 15, "mL)" should read --mL).--;
Line 33, "(25 mL)" should read --(25 mL).--; and
Line 50, "3H)," should read --3H)--.

COLUMN 75:

Line 53, "4.99 (s, 0.2H)," should read --4.99 (s, 2H),--.

COLUMN 76:

Line 25, "3H) ESI-MS" should read --3H) ¶ ESI-MS--.

COLUMN 77:

Line 11, "3H) ESI-MS" should read --3H) ¶ ESI-MS--;
Line 22, "(1.0 mL). $^1$H-NMR" should read --(1.0 mL). ¶ $^1$H-NMR--;
Line 27, "5.07-4.99 (m 2H)" should read --5.07-4.99 (m, 2H)--; and
Line 44, "3H) APCI-MS" should read --3H) ¶ APCI-MS--.

COLUMN 79:

Line 63, "-2-[2-[(2,2-" should read -- -2-{2-[(2,2- --; and
Line 64, "methoxy]-ethyl}" should read --methoxy]ethyl}--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 80:

Line 8, "(1.0 mL). $^1$H-NMR" should read --(1.0 mL). ¶ $^1$H-NMR--; and
Line 51, "(ethyl accetate/hexane 1/9-1/1" should read
--(ethyl acetate/hexane = 1/9-1/1--.

COLUMN 81:

Line 25, "(Step 4)" Insert line space above.

COLUMN 85:

Line 62, "5.2.4 (s, 2H)," should read --5.24 (s, 2H),--.

COLUMN 87:

Line 37, "furyl-ketone" should read --furyl=ketone--;
Line 42, "acetonitrile," should read --acetonitrile--; and
Line 48, "5.30 (dq, J = 0.11," should read --5.30 (dq, J = 11,--.

COLUMN 89:

Line 46, "Elemental Analysis: $(C_{28}H_{25}N_3O_5.0.2H_2O)$" should read
--Elemental Analysis: $(C_{28}H_{25}N_3O_5 \cdot 0.2H_2O)$--; and
Line 58, "dihydroxypheylacetic" should read --dihydroxyphenylacetic--.

COLUMN 90:

Line 20, "acetate. Melting" should read --acetate. ¶ Melting--;
Line 41, "mol)," should read --mmol),--; and
Line 52, "Elemental Analysis: $(C_{28}H_{27}NO_5.0.2H_2O)$" should read
--Elemental Analysis: $(C_{28}H_{27}NO_5 \cdot 0.2H_2O)$--.

COLUMN 91:

Line 37, "(10 mL). $^1$H-NMR" should read --(10 mL). ¶ $^1$H-NMR--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 92:

Line 22, "5 (ppm):" should read --δ (ppm):--.

COLUMN 93:

Line 53, "5.29° (m, 1H)," should read --5.29 (m, 1H),--.

COLUMN 96:

Line 7, "3.3.7 (m, 2H)," should read --3.37 (m, 2H),--.

COLUMN 98:

Line 20, "(3-hydroxy-74-methoxybenzoyl" should read
    --(3-hydroxy-4-methoxybenzoyl--.

COLUMN 100:

Line 37, "(2 mL). $^1$H-NMR" should read --(2 mL). ¶ $^1$H-NMR--.
Line 41, "3H) APCI-MS" should read --3H) ¶ APCI-MS--.

COLUMN 101:

Line 11, "13 mL). $^1$H-NMR" should read --13 mL). ¶ $^1$H-NMR--; and
Line 65, "(3-methylsulfanybenzoyl)" should read
    --(3-methylsulfonylbenzoyl)--.

COLUMN 102:

Line 25, "Hz, 3H) APCL-MS" should read --Hz, 3H) ¶ APCL-MS--.

COLUMN 103:

Line 30, "sulfonyl-benzoyl)" should read --sulfonylbenzoyl)--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 104:

Line 7, "$^1$H-NMR" should read --¶ $^1$H-NMR--.

COLUMN 105:

Line 43, "(5.0 mL). H-NMR" should read --(5.0 mL). ¶ $^1$H-NMR--; and
Line 67, "0.31° mmol)," should read --0.31 mmol),--.

COLUMN 106:

Line 6, "methoxyethyl)" should read --methoxyethyl)- --.
Line 10, "$^1$H-NMR" should read --¶ $^1$H-NMR--; and
Line 66, "$^1$H-NMR" should read --¶ $^1$H-NMR--.

COLUMN 107:

Line 26, "δ (ppm): 7.5.4" should read --δ (ppm): 7.54--; and
Line 59, "$^1$H-NMR" should read --¶ $^1$H-NMR--.

COLUMN 109:

Line 7, "Example 10'," should read --Example 10,--; and
Line 37, "(Step 1) 2-[3,5-Diallyloxy" should read
    --(Step 1) ¶ 2-[3,5-Diallyloxy--.

COLUMN 110:

Line 5, "(3 mL). $^1$H-HMR" should read --(3 mL). ¶ $^1$H-HMR--; and
Line 49, "(310 mg, 0.52 = mmol)" should read --(310 mg, 0.52 mmol)--.

COLUMN 111:

Line 42, "Step 1'," should read --Step 1,--; and
Line 61, "$^1$H-HMR" should read --¶ $^1$H-HMR--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 113:

Line 22, "2-ethyl-6'-" should read --2-ethyl-6- --; and
Line 62, "51%). Melting" should read --51%). ¶ Melting--.

COLUMN 114:

Line 2, "($C_{26}H_{34}N_2O_7.0.2H_2O$)" should read --($C_{26}H_{34}N_2O_7 \cdot 0.2H_2O$)--; and
Line 45, "5.4-4 (m, 1H)," should read --5.44 (m, 1H),--.

COLUMN 115:

Line 44, "($C_{25}H_{34}N_2O_6.0.1H_2O$)" should read --($C_{25}H_{34}N_2O_6 \cdot 0.1H_2O$)--.

COLUMN 116:

Line 56, "-N-(2-(4-morpholinoethyl)acetamide" should read
-- -N-(2-morpholinoethyl)acetamide--.

COLUMN 117:

Line 2, "($C_{28}H_{38}N_2O_8.2.5H_2O$)" should read --($C_{28}H_{38}N_2O_8 \cdot 2.5H_2O$)--.

COLUMN 118:

Line 9, "(m, 3H) APCI-MS" should read --(m, 3H) ¶ APCI-MS--;
Line 10, "($C_{24}H_{31}NO_7.0.2H_2O$)" should read --($C_{24}H_{31}NO_7 \cdot 0.2H_2O$)--;
Line 23, "118-(0.17 g, 42%)" should read --118 (0.17g, 42%)--; and
Line 63, "7.47-7.41 (m, 2H)" should read --7.47-7.41 (m, 2H),--.

COLUMN 119:

Line 2, "($C_{25}H_{33}NO_8.0.3H_2O$)" should read --($C_{25}H_{33}NO_8 \cdot 0.3H_2O$)--.

UNITED STATES PATENT AND TRADEMARK OFFICE
CERTIFICATE OF CORRECTION

PATENT NO.       : 7,538,224 B2
APPLICATION NO.  : 10/561415
DATED            : May 26, 2009
INVENTOR(S)      : Shinji Nara et al.

It is certified that error appears in the above-identified patent and that said Letters Patent is hereby corrected as shown below:

COLUMN 120:

Line 54, "(t, J = 7.3°Hz, 3H)" should read --(t, J = 7.3 Hz, 3H)--.

COLUMN 121:

Line 5, "H-NMR" should read --$^1$H-NMR--.

COLUMN 124:

Line 25, "6.1.1 (m, 1H)," should read --6.11 (m, 1H),--;
Line 38, "Example 126; Step 1," should read --Example 126, Step 1,--; and
Line 49, "($C_{27}H_{38}N_2O_7.0.3H_2O$)" should read --($C_{27}H_{38}N_2O_7 \cdot 0.3H_2O$)--.

COLUMN 125:

Line 26, "3.64 (s, total (2H)," should read --3.64 (s, total 2H),--;
Line 31, "($C_{26}H_{36}N_2O_6.0.3H_2O$)" should read --($C_{26}H_{36}N_2O_6 \cdot 0.3H_2O$)--; and
Line 56, "6.94, (m, 1H)," should read --6.94 (m, 1H),--.

COLUMN 126:

Line 13, "($C_{18}H_{18}O_5.0.3H_2O$)" should read --($C_{18}H_{18}O_5 \cdot 0.3H_2O$)--;
Line 32, "Example 110, Step 11" should read --Example 110, Step 1,--;
Line 58, "2H) 6.95" should read --2H), 6.95-- and "3.8.6 (s, 3H)," should read --3.86 (s, 3H),--; and
Line 64, "($C_{27}H_{38}N_2O_6.2.0H_2O$)" should read --($C_{27}H_{38}N_2O_6 \cdot 2.0H_2O$)--.

COLUMN 127:

Line 35, "2.0 mL). Melting" should read --2.0 mL). ¶ Melting--.
Line 41, "1.12(m, 1H)," should read --1.12 (m, 1H),--.
Line 44, "($C_{28}H_{36}N_2O_7.0.1H_2O$)" should read --($C_{28}H_{36}N_2O_7 \cdot 0.1H_2O$)--.
Line 67, "-5.28 (m, 1H)," should read --5.28 (m, 1H),--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 128:

Line 13, "(2.0 mL). Melting" should read --(2.0 mL). ¶ Melting--;
Line 21, "($C_{22}H_{34}N_2O_6$.0.4$H_2O$)" should read --($C_{22}H_{34}N_2O_6$·0.4$H_2O$)--; and
Line 53, "2.21 (, 1H)," should read --2.21 (m, 1H),--.

COLUMN 131:

Line 4, "resulting," should read --resulting--;
Line 10, "5.29 ('s, 2H)," should read --5.29 (s, 2H),--;
Line 31, "(15 mL). $^1$H-NMR" should read --(15 mL). ¶ $^1$H-NMR--; and
Line 34, "(m, 6H) APCI-MS" should read --(m, 6H) ¶ APCI-MS--.

COLUMN 133:

Line 1, "phenylacetate" should read --ethylphenylacetate--.

COLUMN 134:

Line 28, "($C_{30}H_{42}N_2O_9$.0.HCl.0.5$H_2O$)" should read
    --($C_{30}H_{42}N_2O_9$·0.HCl·0.5$H_2O$)--;
Line 50, "3.36-3.15° (m, 9H)," should read --3.36-3.15 (m, 9H)--; and
Line 55, "($C_{26}H_{36}N_2O_6$.0.2$H_2O$)" should read --($C_{26}H_{36}N_2O_6$·0.2$H_2O$)--.

COLUMN 135:

Line 26, "Compound 11.3" should read --Compound 113--; and
Line 39, "($C_{25}H_{34}N_2O_6$.HCl.0.9$H_2O$.0.1$CH_3$)" should read
    --($C_{25}H_{34}N_2O_6$·HCl·0.9$H_2O$·0.1$CH_3$)--.

COLUMN 137:

Line 37, "3.66(t, J = 4.9" should read --3.66 (t, J = 4.9--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 138:

Line 5, "(175, mg," should read --(175 mg,--; and
Line 61, "(2-methoxyethyliacetamide" should read
--(2-methoxyethyl) acetamide--.

COLUMN 140:

Line 35, "(0.0-15 mL)," should read --(0.015 mL),--; and
Line 38, "(ppm):" should read --$\delta$ (ppm):--.

COLUMN 141:

Line 20, "7.39 (dd, J = 8.7, 1.8 Hz; 1H)," should read --7.39 (dd, J = 8.7,
1.8 Hz, 1H),--; and
Line 58, "phenyl-acetate" should read --phenylacetate--.

COLUMN 142:

Line 13, "H-NMR" should read --$^1$H-NMR--.

COLUMN 143:

Line 21, "($C_{26}H_{23}N_{23}O_5S.0.3H_2O$)" should read --($C_{26}H_{23}N_{23}O_5S\cdot 0.3H_2O$)--;
Line 33, "dihydroxy-6" should read --dihydroxy-6- --; and
Line 48, "($C_{21}H_{25}NO_5S.0.2H_2O$)" should read --($C_{21}H_{25}NO_5S\cdot 0.2H_2O$)--.

COLUMN 144:

Line 5, "3H) APCI-MS" should read --3H) ¶ APCI-MS--;
Line 32, "(1,3-benozdioxo" should read --(1,3-benzodioxo--;
Line 33, "Step 1: using" should read --Step 1, using--;
Line 38, "($CDOD_3$, 300, MHz)" should read --($CDOD_3$, 300 MHz)--;
Line 41, "$H_2$, 3H) APCI-MS" should read --$H_2$, 3H) ¶ APCI-MS--; and
Line 42, "[M-H]" should read --[M-H]$^-$--.

UNITED STATES PATENT AND TRADEMARK OFFICE
CERTIFICATE OF CORRECTION

PATENT NO. : 7,538,224 B2
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 145:

Line 52, "(3.0 mL) Boiling" should read --(3.0 mL) ¶ Boiling--.

COLUMN 146:

Line 32, "Boiling" should read --¶ Boiling--.

COLUMN 147:

Line 45, "0.20 mol)" should read --0.20 mol).--.

COLUMN 148:

Line 34, "benzenesulfonamide. $^1$H-NMR" should read
--benzenesulfonamide. ¶ $^1$H-NMR--.

COLUMN 149:

Line 15, "(Step 1) tert-Butyl" should read --(Step 1) ¶ tert-Butyl--; and
Line 47, "(CDC$_{31}$ 27OMHz)" should read --(CDC$_3$, 270MHz)--.

COLUMN 151:

Line 29, "$R^{2A}$ aryl" should read --$R^{2A}$ is aryl--.

UNITED STATES PATENT AND TRADEMARK OFFICE
CERTIFICATE OF CORRECTION

PATENT NO.        : 7,538,224 B2
APPLICATION NO.   : 10/561415
DATED             : May 26, 2009
INVENTOR(S)       : Shinji Nara et al.

It is certified that error appears in the above-identified patent and that said Letters Patent is hereby corrected as shown below:

COLUMN 152:

Line 18, "(wherein R" should read --(wherein $R^{2A}$--.

Signed and Sealed this

Twentieth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,538,224 B2  Page 1 of 1
APPLICATION NO. : 10/561415
DATED : May 26, 2009
INVENTOR(S) : Shinji Nara et al.

It is certified that error appears in the above-identified patent and that said Letters Patent is hereby corrected as shown below:

COLUMN 42:

Line 62, "were on the same plate wherein" should read --were placed on the same plate as--; and
Line 62, "was placed" should be deleted.

COLUMN 128:

Line 21, "$(C_{22}H_{34}N_2O_6 \cdot 0.4H_2O)$" should read --$(C_{27}H_{34}N_2O_6 \cdot 0.4H_2O)$--.

COLUMN 144:

Line 41, "$H_2$, 3H) ¶ APCI-MS" should read --Hz, 3H) ¶ APCI-MS--.

COLUMN 152:

Line 18, "(wherein $R^{2A}$" should read --(wherein $R^{2a}$--.

Signed and Sealed this

First Day of December, 2009

David J. Kappos
*Director of the United States Patent and Trademark Office*